United States Patent
Nova et al.

(10) Patent No.: US 6,319,668 B1
(45) Date of Patent: *Nov. 20, 2001

(54) METHOD FOR TAGGING AND SCREENING MOLECULES

(75) Inventors: Michael P. Nova, Rancho Santa Fe; Hanan Potash, La Jolla; Xiao-Yi Xiao; Zahra Parandoosh, both of San Diego; Gary S. David, La Jolla, all of CA (US)

(73) Assignee: Discovery Partners International, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/669,252

(22) Filed: Jun. 24, 1996

Related U.S. Application Data

(63) Continuation-in-part of application No. 08/633,410, filed on Jun. 10, 1996, now Pat. No. 6,100,026, which is a continuation-in-part of application No. PCT/US96/06145, filed on Apr. 25, 1996, which is a continuation-in-part of application No. 08/945,053, filed on Oct. 21, 1997, now abandoned, which is a continuation-in-part of application No. 08/639,813, filed on Apr. 2, 1996, now abandoned, which is a continuation-in-part of application No. 08/567,746, filed on Dec. 5, 1995, now Pat. No. 6,025,129, which is a continuation-in-part of application No. 08/538,387, filed on Oct. 3, 1995, now Pat. No. 5,874,214, which is a continuation-in-part of application No. 08/480,147, filed on Jun. 7, 1995, now Pat. No. 5,667,461, and a continuation-in-part of application No. 08/484,486, filed on Jun. 7, 1995, and a continuation-in-part of application No. 08/484,504, filed on Jun. 7, 1995, now Pat. No. 5,751,629, and a continuation-in-part of application No. 08/480,196, filed on Jun. 7, 1995, now Pat. No. 5,925,562, and a continuation-in-part of application No. 08/473,660, filed on Jun. 7, 1995, and application No. 08/480,147, filed on Jun. 7, 1995, now Pat. No. 5,667,461, and application No. 08/484,486, and application No. 08/484,504, and application No. 08/480,196, and application No. 08/473,660, which is a continuation-in-part of application No. 08/428,662, filed on Apr. 25, 1995, now Pat. No. 5,741,462.

(51) Int. Cl.⁷ .............................. C12Q 1/68; G01N 33/53; C12M 1/34; C07H 21/04

(52) U.S. Cl. .......................... 435/6; 435/7.1; 435/287.2; 435/288.7; 530/333; 530/334; 536/24.3; 536/25.3; 365/183; 395/401

(58) Field of Search ............................. 435/6, 5, 7.1–7.9, 435/282.1, 287.2, 288.1, 288.3, 288.4, 288.7; 530/333, 211, 334; 536/24.37, 24.33, 25.3; 585/502; 365/183, 94; 395/401

(56) References Cited

U.S. PATENT DOCUMENTS

| 3,119,099 | 1/1964 | Biernat . |
| 3,692,498 | 9/1972 | Frank et al. . |
| 3,781,120 | 12/1973 | Engelhardt . |
| 3,882,318 | 5/1975 | Mioduski . |

(List continued on next page.)

FOREIGN PATENT DOCUMENTS

| 93 08 204 U1 | 8/1993 | (DE) . |
| 43 10 169 A1 | 9/1993 | (DE) . |
| 43 13 807 A1 | 11/1993 | (DE) . |

(List continued on next page.)

OTHER PUBLICATIONS

Beck–Sickinger et al., "Semiautomated T–Bag Peptide Synthesis Using 9–Fluorenyl–Methoxycarbonyl Strategy and Benzotriazol–1–yl–Tetramethyl–Uronium Tetrafluoroborate Activation", *Peptide Research*, vol. 4, No. 2, Mar.–Apr. 1991, pp. 88–94.

Jung et al., "Multiple Peptide Synthesis Methods and Their Applications", *Angew. Chem. Int. Ed. Engl.*, vol. 31, No. 4, Apr. 1992, pp. 367–383.

Janda, K.D., "Tagged versus untagged libraries: Methods for the generation and screening of combinatorial chemical libraries", *Proc. Natl. Acad. Sci. USA*, vol. 91, Nov. 1994, pp. 10779–10785.

Jurisch, R., "Identifikation: kontaktlos via Hochfrequenz", *Elektronik*, No. 9, 1993, pp. 86–92, Munich, Germany.

Nicolaou et al., "Radiofrequenz–verschlüsselte kombinatorische Chemie", *Angewandte Chemie*, vol. 107, No. 20, Oct. 16, 1995, pp. 2476–2479, Weinheim,DE.

(List continued on next page.)

*Primary Examiner*—Stephanie W. Zitomer
(74) *Attorney, Agent, or Firm*—Kilpatrick Stockton LLP

(57) ABSTRACT

Combinations, called matrices with memories, of matrix materials that are encoded with an optically readable code are provided. The matrix materials are those that are used in as supports in solid phase chemical and biochemical syntheses, immunoassays and hybridization reactions. The matrix materials may additionally include fluophors or other luminescent moieties to produce luminescing matrices with memories. The memories include electronic and optical storage media and also include optical memories, such as bar codes and other machine-readable codes. By virtue of this combination, molecules and biological particles, such as phage and viral particles and cells, that are in proximity or in physical contact with the matrix combination can be labeled by programming the memory with identifying information and can be identified by retrieving the stored information. Combinations of matrix materials, memories, and linked molecules and biological materials are also provided. The combinations have a multiplicity of applications, including combinatorial chemistry, isolation and purification of target macromolecules, capture and detection of macromolecules for analytical purposes, selective removal of contaminants, enzymatic catalysis, cell sorting, drug delivery, chemical modification and other uses. Methods for tagging molecules, biological particles and matrix support materials, immunoassays, receptor binding assays, scintillation proximity assays, non-radioactive proximity assays, and other methods are also provided.

44 Claims, 21 Drawing Sheets

Microfiche Appendix Included
(1 Microfiche, 52 Pages)

U.S. PATENT DOCUMENTS

| | | |
|---|---|---|
| 4,133,642 | 1/1979 | Nosaka et al. . |
| 4,154,795 | 5/1979 | Thorne . |
| 4,855,909 | 8/1989 | Vincent et al. . |
| 4,857,893 | 8/1989 | Carroll . |
| 4,876,668 | 10/1989 | Thakoor et al. . |
| 4,935,875 * | 6/1990 | Shah et al. ........................... 364/497 |
| 5,075,077 | 12/1991 | Durley, III et al. . |
| 5,100,626 | 3/1992 | Levin . |
| 5,120,626 | 6/1992 | Chan et al. . |
| 5,201,728 | 4/1993 | Giampapa . |
| 5,214,409 | 5/1993 | Beigel . |
| 5,253,198 | 10/1993 | Birge et al. . |
| 5,314,829 | 5/1994 | Coles . |
| 5,348,705 | 9/1994 | Koreyasu et al. . |
| 5,474,796 | 12/1995 | Brennan et al. . |
| 5,565,324 | 10/1996 | Still et al. . |
| 5,585,275 | 12/1996 | Hudson et al. . |
| 5,605,662 | 2/1997 | Heller et al. . |
| 5,639,603 | 6/1997 | Dower et al. . |
| 5,641,634 | 6/1997 | Mandecki . |
| 5,708,153 | 1/1998 | Dower et al. . |
| 5,741,462 | 4/1998 | Nova et al. . |
| 5,751,629 | 5/1998 | Nova et al. . |
| 5,770,455 | 6/1998 | Cargill et al. . |
| 5,798,035 | 8/1998 | Kirk et al. . |
| 5,874,214 | 2/1999 | Nova et al. . |
| 5,925,562 | 7/1999 | Nova et al. . |
| 5,961,923 | 10/1999 | Nova et al. . |
| 6,017,496 | 1/2000 | Nova et al. . |
| 6,025,129 | 2/2000 | Nova et al. . |
| 6,087,186 | 7/2000 | Cargill et al. . |
| 6,100,026 | 8/2000 | Nova et al. . |
| 6,136,274 | 10/2000 | Nova et al. . |

FOREIGN PATENT DOCUMENTS

| | | |
|---|---|---|
| 43 06 563 A1 | 9/1994 | (DE) . |
| 94 16 270 U1 | 12/1994 | (DE) . |
| 0 196 174 A2 | 10/1986 | (EP) . |
| 0 410 688 A2 | 10/1991 | (EP) . |
| 0 541 340 A2 | 5/1993 | (EP) . |
| 0 554 955 A1 | 8/1993 | (EP) . |
| 0 378 059 B1 | 9/1993 | (EP) . |
| 0 569 215 A1 | 11/1993 | (EP) . |
| 0 637 750 A1 | 2/1995 | (EP) . |
| 0 640 826 A1 | 3/1995 | (EP) . |
| 2110030 A | 5/1972 | (FR) . |
| 2555744 | 5/1985 | (FR) . |
| 1 423 185 | 1/1976 | (GB) . |
| 2129551 | 5/1984 | (GB) . |
| 2 129 551 A * | 5/1994 | (GB) ................................ 435/7.1 |
| 57 016359 A | 5/1982 | (JP) . |
| 89/08264 | 9/1989 | (WO) . |
| 92/01268 | 1/1992 | (WO) . |
| 92/07093 | 4/1992 | (WO) . |
| 92/13271 | 8/1992 | (WO) . |
| 94/13402 | 6/1994 | (WO) . |
| 97/15390 | 5/1997 | (WO) . |
| 98/11036 | 3/1998 | (WO) . |
| 98/46548 | 10/1998 | (WO) . |
| 98/46549 | 10/1998 | (WO) . |
| 98/46550 | 10/1998 | (WO) . |

OTHER PUBLICATIONS

Moran et al., "Radio Frequency Tag Encoded Combinatorial Library Method for the Discovery of Tripeptide–Substituted Cinnamic Acid Inhibitors of the Protein Tyrosine Phosphatase PTP1B," *J. Am. Chem. Soc.*, 117:10787–10788, 1995.

Brenner, S., "Encoded Combinatorial Chemistry", *Proc. Natl. Acad. Sci. USA*, vol. 89, pp. 5381–5383, Jun. 1992.

* cited by examiner

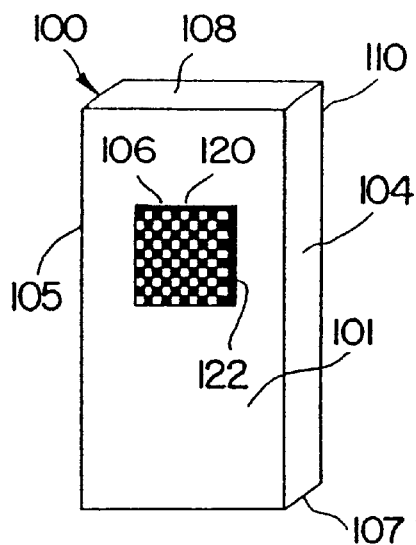
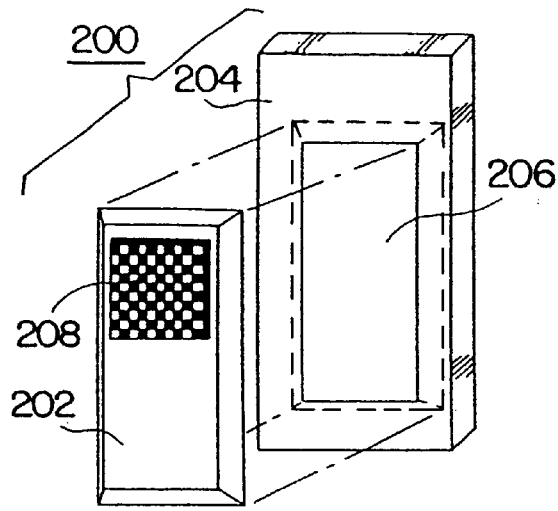
FIG. 22   FIG. 23
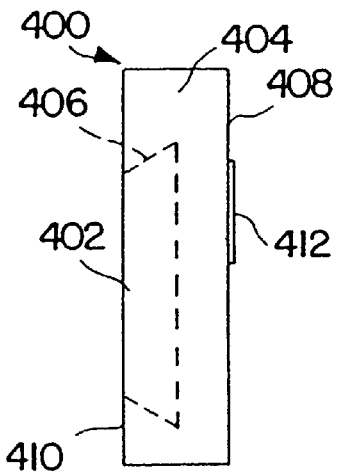 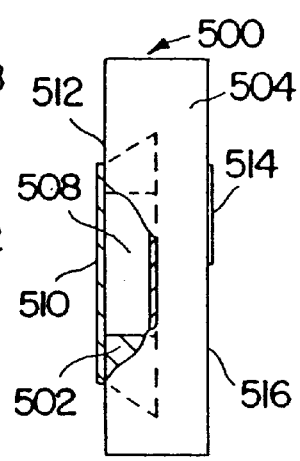 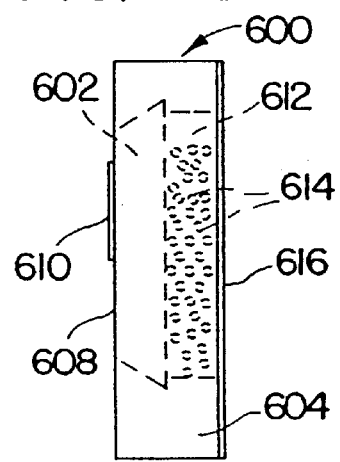
FIG. 25   FIG. 26   FIG. 27
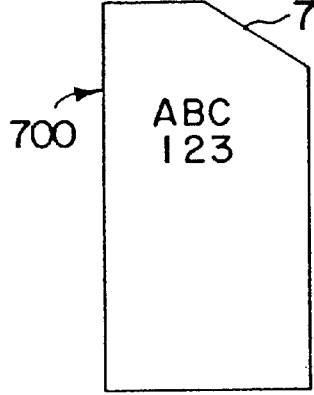 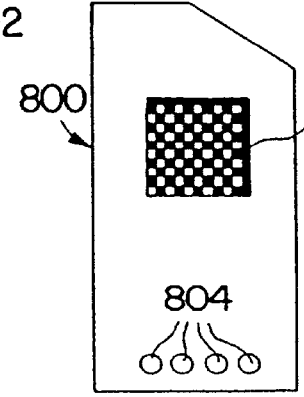 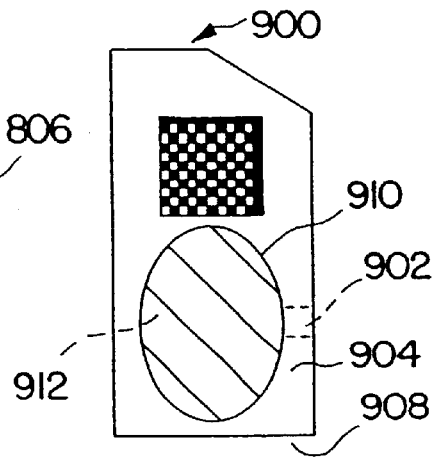
FIG. 28   FIG. 29   FIG. 30

```
                       SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:1:

Leu Ala Gly Asp
1

(2) INFORMATION FOR SEQ ID NO:2:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:2:

Leu Glu Gly Asp
1

(2) INFORMATION FOR SEQ ID NO:3:

(i) SEQUENCE CHARACTERISTICS:
         (A) LENGTH: 4 amino acids
         (B) TYPE: amino acid
         (C) STRANDEDNESS: single
         (D) TOPOLOGY: linear
```

(ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:3:

Ser Ala Gly Asp
  1

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:4:

Ser Glu Gly Asp
  1

(2) INFORMATION FOR SEQ ID NO:5:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:5:

Leu Ala Val Asp
  1

(2) INFORMATION FOR SEQ ID NO:6:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:6:

Leu Glu Val Asp
1

(2) INFORMATION FOR SEQ ID NO:7:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:7:

Ser Ala Val Asp
1

(2) INFORMATION FOR SEQ ID NO:8:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:8:

Ser Glu Val Asp
1

(2) INFORMATION FOR SEQ ID NO:9:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:9:

Leu Ala Gly Phe (2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:10:

Leu Glu Gly Phe
1

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:11:

Ser Ala Gly Phe
1

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:12:

Ser Glu Gly Phe
1

(2) INFORMATION FOR SEQ ID NO:13:

(i) SEQUENCE CHARACTERISTICS:
        (A) LENGTH: 4 amino acids

```
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:13:

Leu Ala Val Phe
 1

(2) INFORMATION FOR SEQ ID NO:14:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Leu Glu Val Phe
 1

(2) INFORMATION FOR SEQ ID NO:15:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:15:

Ser Ala Val Phe
 1

(2) INFORMATION FOR SEQ ID NO:16:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO
```

(iv) ANTI-SENSE: NO (v) FRAGMENT TYPE: internal (vi) ORIGINAL SOURCE:

(xi) SEQUENCE DESCRIPTION: SEQ ID NO:16:

Ser Glu Val Phe
1

(2) INFORMATION FOR SEQ ID NO:17:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:17:

Leu Ala Gly Lys
1

(2) INFORMATION FOR SEQ ID NO:18:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

Leu Glu Gly Lys
1

(2) INFORMATION FOR SEQ ID NO:19:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

```
        (xi) SEQUENCE DESCRIPTION: SEQ ID NO:19:

Ser Ala Gly Lys
1

(2) INFORMATION FOR SEQ ID NO:20:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:20:

Ser Glu Gly Lys
1

(2) INFORMATION FOR SEQ ID NO:21:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:21:

Leu Ala Val Lys
1

(2) INFORMATION FOR SEQ ID NO:22:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:22:

Leu Glu Val Lys
1

(2) INFORMATION FOR SEQ ID NO:23:
```

```
    (i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:23:

Ser Ala Val Lys
1

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:24:

Ser Glu Val Lys
1

(2) INFORMATION FOR SEQ ID NO:25:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:25:

Met Leu Asp Ser Ile Trp Lys Pro Asp Leu
1               5                   10

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: single
        (D) TOPOLOGY: linear
```

```
      (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:26:

Met Leu Asp Ser Gly Trp Lys Pro Asp Leu
  1               5                  10

(2) INFORMATION FOR SEQ ID NO:27:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:27:

Met Leu Asp Ser Ile Trp Lys Pro Asp Ala
  1               5                  10

(2) INFORMATION FOR SEQ ID NO:28:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:28:

Met Leu Asp Ser Ile Trp Lys Phe Asp Leu
  1               5                  10

(2) INFORMATION FOR SEQ ID NO:29:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal
```

(vi) ORIGINAL SOURCE:

(xi) SEQUENCE DESCRIPTION: SEQ ID NO:29:

Met Leu Asp Ser Gly Trp Lys Phe Asp Leu
1               5                   10

(2) INFORMATION FOR SEQ ID NO:30:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:30:

Met Leu Asp Ser Gly Trp Lys Pro Asp Ala
1               5                   10

(2) INFORMATION FOR SEQ ID NO:31:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:31:

Met Leu Asp Ser Ile Trp Lys Phe Asp Ala
1               5                   10

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:32:

Met Leu Asp Ser Gly Trp Lys Phe Asp Ala
1               5                   10

```
(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:33:

Tyr Gly Gly Phe Met
1               5
```

METHOD FOR TAGGING AND SCREENING MOLECULES

RELATED APPLICATIONS

This application is a continuation-in-part of application Ser. No. 08/633,410, filed on Jun. 10, 1996, now issued as U.S. Pat. No. 6,100,026, which is a continuation-in-part of International PCT application No. PCT/US96/06145, filed Apr. 25, 1996, which designates the U.S. and was filed as U.S. national application Ser. No. 08/945,053 on Oct. 21, 1997, now abandoned, and is also a continuation-in-part of application Ser. No. 08/639,813, filed Apr. 2, 1996, now abandoned, which is a continuation-in-part of application Ser. No. 08/567,746, filed Dec. 5, 1995, now issued as U.S. Pat. No. 6,025,129, which is a continuation-in-part of application Ser. No. 08/538,387, filed Oct. 3, 1995, now issued as U.S. Pat. No. 5,874,214, which is a continuation-in-part of each of application Ser. No. 08/480,147, now U.S. Pat. No. 5,667,461 Ser. No. 08/484,486, pending Ser. No. 08/484,504, now issued as U.S. Pat. No. 5,751,629, now U.S. Pat. No. 5,667,461, Ser. No. 08/480,196 now issued as U.S. Pat. No. 5,925,562, and Ser. No. 08/473,660, each filed Jun. 7, 1995 pending, each of which is a continuation-in-part of application Ser. No. 08/428,662, filed Apr. 25, 1995, now issued as U.S. Pat. No. 5,741,462.

The subject matter of each referenced application is incorporated herein by reference in its entirety.

REFERENCE TO COMPUTER APPENDIX

The disclosure of the invention includes a microfiche appendix, referred to herein as "Microfiche Appendix", containing source code for computer programs described herein. The appendix consists of 1 fiche (#1 of 1), with 52 frames.

A portion of the disclosure of this patent document contains material that is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to the application of information and data storage and retrieval technology to molecular tracking and identification and to biological, chemical, immunological and biochemical assays.

BACKGROUND OF THE INVENTION

Automated identification of articles using bar codes in the availability of the integrated circuit technology and computing power at reasonable costs. Such codes are typically used to track and identify consumer goods and other articles of manufacture. One of the first scanners capable of reading a bar code was installed at a supermarket in 1974, and by 1980 more than 90% of all grocery items carried a bar code by 1980. By December 1985, more than 12,000 grocery stores were equipped with scanner checkout systems [See, e.g., Harmon et al. (1989) *Reading Between the Lines-An Introduction to Bar Code Technology*, Helmers Publishing, Inc. 1989]. Bar codes have also been used in other applications, including other inventory control systems and for identification and characterization of responses to mass advertising efforts.

By electro-optically scanning the symbol on an item and generating a corresponding signal, it is possible in an associated computer whose memory has digitally stored therein the full range of items, to compare the signal derived from the scanned symbol with the stored information. When a match is found, the identity of the item and associated information, such as, in the instance of consumer goods, its price. Thus computer technology is exploited to facilitate identification procedures using machine-readable identifiers.

Bar codes are typically read using lasers that scan from left to right, right to left, or in both directions (or other directions) across a field of alternating dark bars and reflective spaces of varying widths. Multiple scans are typically employed to minimize data errors. Because of the multiplicity of bars and spaces required for each alphanumeric character, bar codes generally require a relatively large space to convey a small amount of data. For instance, each character in the bar code system known as Code 39 requires five bars and four spaces. A high density Code 39 field corresponds to only 9.4 characters per inch. Universal Product Codes (UPCs) are another common bar code used primarily in the retail grocery trade and contain a relatively large number of bars and spaces which allow for error checking, parity checking and reduction of errors caused by manual scanning of articles in grocery stores. They accordingly require even larger space for conveyance of character information. The Codabar code, which has been developed by Pitney Bowes and is used in retail price labeling systems and by Federal Express, is a self-checking code. Each character is represented by a stand-alone group of four bars and three interleaving spaces. Federal Express uses an eleven digit Codabar symbol on each airbill to process more than 450,000 packages per night. Other codes use varying bar and space techniques to represent characters. Because of error checking requirements and for other reasons, however, the space required to place a bar code on an article is relatively large.

In addition to the large surface area required for the series of bars and spaces that form a typical bar code symbol, the code must be placed on a background that has a high reflectance level. The high level of contrast, or reflectivity ratio, between the dark bars and the reflective spaces, allows the optical sensor in the reader to discern clearly and dependably the transitions between the bars and spaces in the symbol. Ideally, the printed bar should be observed as perfectly black and the spaces should be perfectly reflective. Because those ideal conditions are seldom possible, the industry typically requires that labeling media reflect at least 70% of incident light energy. Surface reflectivity and thus quality of the media on which the bar code is placed directly affects the successful use of the bar code on that media. Additionally, the media cannot be overly transparent or translucent, since those characteristics can attenuate reflected light. Accordingly, only limited types of highly reflective media may be used for placement of bar codes. Space requirements for bar codes further include a "quiet zone" that surrounds the field of bars and spaces. In many codes, this quiet zone constitutes a border around the code symbol, thus requiring even more space for the bar code.

Bar coding also requires very precise print methods. Assuming that the printing operation is capable of printing the required density to achieve the 70% reflectance ratio, careful attention must be paid to additional major factors that influence the bar code effectiveness. Those include ink spread/shrinkage; ink voids/specks; ink smearing; non-uniformity of ink; bar/space width tolerances; edge roughness and similar factors that must be closely controlled to ensure that the symbol will be easily scannable. In other words, the printer must pay careful attention to using paper or other media that displays the correct absorption properties properly inking the ribbon; carefully controlling hammer pressure; keeping the printhead and paper clean; properly wetting the paper and curing the ink; and maintaining proper adjustment of the printhead control mechanism. These printing details create additional problems and expenses, particularly for placement of bar code symbols on smaller items such as coupons and mail pieces.

"Bar codes" containing an array of marks of any desired size and shape that are arranged in a reference context or frame of one or more columns and one or more rows, together with a reference marker and a reference cue have also been developed [see, U.S. Pat. No. 5,128,528]. The number of rows corresponds to the number of characters contained in the symbology selected for the array. For example, an array that is capable of conveying all the letters of the English language and ten numeral symbols could use 36 rows. The number of columns in the matrix could corresponds to the number of characters desired to be conveyed. The roles of the rows and columns in the reference frame may be reversed if desired. In the preferred embodiment, each column contains one or more dots corresponding to the character which is desired to be conveyed in that column. The reference marker and reference cue may be formed of one shape, of two marks, or according to any other desired arrangement that allows interpretation of the matrix at any desired attitude with respect to the imaging equipment. The reference cue may form a part of the reference marker, or an information dot, if desired.

Thus, there are numerous types of bar codes, codes and methodologies for use available. Bar coding and other coding technology, however, remains to be fully exploited in areas outside the consumer products domain.

Drug Discovery

Drug discovery relies on the ability to identify compounds that interact with a selected target, such as cells, an antibody, receptor, enzyme, transcription factor or the like. Traditional drug discovery relied on collections or "libraries" obtained from proprietary databases of compounds accumulated over many years, natural products, fermentation broths, and rational drug design. Recent advances in molecular biology, chemistry and automation have resulted in the development of rapid, High throughput screening (HTS) protocols to screen these collection. In connection with HTS, methods for generating molecular diversity and for detecting, identifying and quantifying biological or chemical material have been developed. These advances have been facilitated by fundamental developments in chemistry, including the development of highly sensitive analytical methods, solid state chemical synthesis, and sensitive and specific biological assay systems.

Analyses of biological interactions and chemical reactions, however, require the use of labels or tags to track and identify the results of such analyses. Typically biological reactions, such as binding, catalytic, hybridization and signaling reactions, are monitored by labels, such as radioactive, fluorescent, photoabsorptive, luminescent and other such labels, or by direct or indirect enzyme labels. Chemical reactions are also monitored by direct or indirect means, such as by linking the reactions to a second reaction in which a colored, fluorescent, chemiluminescent or other such product results. These analytical methods, however, are often time consuming, tedious and, when practiced in vivo, invasive. In addition, each reaction is typically measured individually, in a separate assay. There is, thus, a need to develop alternative and convenient methods for tracking and identifying analytes in biological interactions and the reactants and products of chemical reactions.

Combinatorial Libraries

The provision and maintenance of compounds to support HTS have become critical. New and innovative methods for the lead generation and lead optimization have emerged to address this need for diversity. Among these methods is combinatorial chemistry, which has become a powerful tool in drug discovery and materials science. Methods and strategies for generating diverse libraries, primarily peptide- and nucleotide-based oligomer libraries, have been developed using molecular biology methods and/or simultaneous chemical synthesis methodologies [see, e.g., Dower et al. (1991) *Annu. Rep. Med. Chem.* 26:271–280; Fodor et al. (1991) *Science* 251:767–773; Jung et al. (1992) *Angew. Chem. Ind. Ed. Engl.* 31:367–383; Zuckerman et al. (1992) *Proc. Natl. Acad. Sci. USA* 89:4505–4509; Scott et al. (1990) *Science* 249:386–390; Devlin et al. (1990) *Science* 249:404–406; Cwirla et al. (1990) *Proc. Natl. Acad. Sci. USA* 87:6378–6382; and Gallop et al. (1994) *J. Medicinal Chemistry* 37:1233–1251]. The resulting combinatorial libraries potentially contain millions of pharmaceutically relevant compounds and that can be screened to identify compounds that exhibit a selected activity.

The libraries fall into roughly three categories: fusion-protein-displayed peptide libraries in which random peptides or proteins are presented on the surface of phage particles or proteins expressed from plasmids; support-bound synthetic chemical libraries in which individual compounds or mixtures of compounds are presented on insoluble matrices, such as resin beads [see, e.g., Lam et al. (1991) *Nature* 354:82–84] and cotton supports [see, e.g., Eichler et al. (1993) *Biochemistry* 32:11035–11041]; and methods in which the compounds are used in solution [see, e.g., Houghten et al. (1991) *Nature* 354:84–86, Houghten et al. (1992) *BioTechniques* 313:412–421; and Scott et al. (1994) *Curr. Opin. Biotechnol.* 5:40–48]. There are numerous examples of synthetic peptide and oligonucleotide combinatorial libraries. The present direction in this area is to produce combinatorial libraries that contain non-peptidic small organic molecules. Such libraries are based on either a basis set of monomers that can be combined to form mixtures of diverse organic molecules or that can be combined to form a library based upon a selected pharmacophore monomer.

There are three critical aspects in any combinatorial library: (i) the chemical units of which the library is composed; (ii) generation and categorization of the library, and (iii) identification of library members that interact with the target of interest, and tracking intermediary synthesis products and the multitude of molecules in a single vessel.

The generation of such libraries often relies on the use of solid phase synthesis methods, as well as solution phase methods, to produce collections containing tens of millions of compounds that can be screened in diagnostically or pharmacologically relevant in vitro assay systems. In generating large numbers of diverse molecules by stepwise synthesis, the resulting library is a complex mixture in which a particular compound is present at very low concentrations, so that it is difficult or impossible to determine its chemical structure. Various methods exist for ordered synthesis by sequential addition of particular moieties, or by identifying molecules based on special positioning on a chip. These methods are cumbersome and ultimately impossible to apply to highly diverse and large libraries. Identification of library members that interact with a target of interest, and tracking intermediary synthesis products and the multitude of molecules in a single vessel is also a problem.

High Throughput Screening

In addition, exploitation of this diversity requires development of methods for rapidly screening compounds. Advances in instrumentation, molecular biology and protein chemistry and the adaptation of biochemical activity screens into microplate formats, has made it possible to screen of large numbers of compounds. Also, because compound screening has been successful in areas of significance for the pharmaceutical industry, high throughput screening (HTS) protocols have assumed importance. Presently, there are hundreds of HTS systems operating throughout the world, which are used, not only for compound screening for drug discovery, but also for immunoassays, cell-based assays and receptor-binding assays.

An essential element of high throughput screening for drug discovery process and areas in which molecules are identified and tracked, is the ability to extract the information made available during synthesis and screening of a library, identification of the active components of intermediary structures, and the reactants and products of assays. While there are several techniques for identification of intermediary products and final products, nanosequencing protocols that provide exact structures are only applicable on mass to naturally occurring linear oligomers such as peptides and amino acids. Mass spectrographic [MS] analysis is sufficiently sensitive to determine the exact mass and fragmentation patterns of individual synthesis steps, but complex analytical mass spectrographic strategies are not readily automated nor conveniently performed. Also, mass spectrographic analysis provides at best simple connectivity information, but no stereoisomeric information, and generally cannot discriminate among isomeric monomers. Another problem with mass spectrographic analysis is that it requires pure compounds; structural determinations on complex mixtures is either difficult or impossible. Finally, mass spectrographic analysis is tedious and time consuming. Thus, although there are a multitude of solutions to the generation of libraries and to screening protocols, there are no ideal solutions to the problems of identification, tracking and categorization.

These problems arise in any screening or analytical process in which large numbers of molecules or biological entities are screened. In any system, once a desired molecule(s) has been isolated, it must be identified. Simple means for identification do not exist. Because of the problems inherent in any labeling procedure, it would be desirable to have alternative means for tracking and quantitating chemical and biological reactions during synthesis and/or screening processes, and for automating such tracking and quantitating.

Therefore, it is an object herein to provide methods for identification, tracking and categorization of the components of complex mixtures of diverse molecules. It is also an object herein to provide products for such identification, tracking and categorization and to provide assays, diagnostics and screening protocols that use such products. It is of particular interest herein to provide means to track and identify compounds and to perform HTS protocols.

SUMMARY OF THE INVENTION

Combinations of matrix materials with programmable data storage or recording devices or other memory means, herein referred to as memories, and assays using these combinations are provided. These combinations are referred to herein as matrices with memories. By virtue of the memory with matrix combination, molecules, such as antigens, antibodies, ligands, proteins and nucleic acids, and biological particles, such as phage and viral particles and cells, that are associated with, such as in proximity to or in physical contact with the matrix combination or linked via information stored in a remote computer, can be electromagnetically tagged by programming the memory with data corresponding to identifying information or can be tagged by imprinting the matrix with identifying information.

Programming and reading the memory is effected remotely, preferably using electromagnetic radiation, particularly radio frequency or radar, or by reading the imprinted information. Memories may also be remote from the matrix, such as instances in which the memory device is precoded with a mark or identifier or the matrix is encoded with a bar code. The identity [i.e., the mark or code] of each device is written to a memory, which may be a computer or a piece of paper or any recording device, and information associated with each matrix is stored in the remote memory and linked to the code or other identifier.

Of particular interest herein are matrices with memories in which the matrices have an engraved coded. These matrices with memories are herein referred to as matrices with codes or optical memory devices [OMDs]. The memories are remote recording devices, such as a remote computer memory in which information associated with the codes is stored. The materials are encoded with identifying information and/or any other information of interest. Synthetic protocols and assays using encoded matrix materials are provided. By virtue of this code on the matrix, molecules, such as antigens, antibodies, ligands, proteins and nucleic acids, and biological particles, such as phage and viral particles and cells, that are associated with, such as in proximity to or in physical contact with the matrix, can be tagged by programming a memory, such as a memory in a computer, with data corresponding to the encoded identifying information. Programming and reading the memory is effected remotely, preferably using electromagnetic radiation, particularly radio frequency or radar. The identity [i.e., the mark or code] of each device is written to a memory, which may be a computer or a piece of paper or any recording device, and information associated with each matrix is stored in the remote memory and linked to the code or other identifier.

The molecules and biological particles that are associated with the matrix combination, such as in proximity to or in physical contact or with the matrix combination, can be identified and the results of the assays determined by retrieving the stored data points from the memories. Querying the memory will identify associated molecules or biological particles that have reacted.

In certain embodiments of the matrices with memories, reactions, assays and other events or external parameters, such as temperature and/or pH, can be monitored because occurrence of a reaction or an event can be detected and such detection sent to the recording device when proximate to the matrix and recorded in the memory.

The combinations provided herein thus have a multiplicity of applications, including combinatorial chemistry, isolation and purification of target macromolecules, capture and detection of macromolecules for analytical purposes, high throughput screening, selective removal of contaminants, enzymatic catalysis, drug delivery, chemical modification, information collection and management and other uses. These combinations are particularly advantageous for use in multianalyte analyses, assays in which a electromagnetic signal is generated by the reactants or products in the assay, for use in homogeneous assays, and for use in multiplexed protocols.

In preferred embodiments, these matrix with memory combinations contain (i) a miniature recording device that includes one or more programmable data storage devices [memories] that can be remotely read and in preferred embodiments also remotely programmed; and (ii) a matrix, such as a particulate support used in chemical syntheses.

The matrix materials [matrices] are any materials that are routinely used in chemical and biochemical synthesis. The matrix materials are typically polymeric materials that are compatible with chemical and biological syntheses and assays, and include, glasses, silicates, celluloses, polystyrenes, polysaccharides, polypropylenes, sand, and synthetic resins and polymers, including acrylamides, particularly cross-linked polymers, cotton, and other such materials. The matrices may be in the form of particles or may be continuous in design, such as a test tube or microplate, 96 well or 384 well or higher density formats or other such microplates and microtiter plates. The matrices may contain one or a plurality of recording devices. For example, each well or selected wells in the microplate include a memory device in contact therewith or embedded therein. The plates may further contain embedded scintillant or a coating of scintillant [such as FlashPlate™, available from DuPont NEN®, and plates available from Packard, Meriden, Conn.]. Automated robotic protocols will incorporate such plates for automated multiplexing [performing a series of coupled synthetic and processing steps, typically, though not necessarily on the same platform, i.e. coupling of the chemistry to the biology] including one or more of the following, synthesis, preferably accompanied by writing to the linked memories to identify linked compounds, screening, including using protocols with matrices with memories, and compound identification by querying the memories of matrices associated with the selected compounds.

The matrices are either particulate of a size that is roughly about 1 to 20 $mm^3$ [or 1–20 mm in its largest dimension], preferably about 10 $mm^3$ or smaller, preferably 1 $mm^3$ or smaller, or a continuous medium, such as a microtiter plate, or other multi-well plate, or plastic or other solid polymeric vial or glass vial or catheter-tube [for drug delivery] or such container or device conventionally used in chemistry and biological syntheses and reactions. In instances in which the matrix is continuous, the data storage device [memory] may be placed in, on, or under the matrix medium or may be embedded in the material of the matrix.

The plates may also include a bar code, particularly the two-dimensional optical bar code provided herein on the base of each well or elsewhere. The two-dimensional bar code or other such code is particularly suited for application to each well in a microplate, such as a microtiter plate, that contain 96, 384, 1536 or higher density formats. The bar code may also be used in combination with modules that are fitted into the frames of 96 wells, or higher density formats [such as those available from NUNC, such as NUNC-Immuno Modules, and also sources, such as COSTAR plate strips, and Octavac Filter Strips]. Separate containers or strips of containers are designed to fit into microplate frames. Each such container may be encoded with a bar code so that, upon removal from the strip, the container, and thereby, its contents or history, may be identified.

In embodiments herein in which the matrices with memories are used in assays, such as scintillation proximity assays [SPA], FP [fluorescence polarization] assays, FET [fluorescent energy transfer] assays, FRET [fluorescent resonance energy transfer] assays and HTRF [homogeneous time-resolved fluorescence] assays, the matrices may be coated with, embedded with or otherwise combined with or in contact with assay material, such as scintillant, fluophore or other fluorescent label. The resulting combinations are called luminescing memories with matrices. When used in SPA formats they are referred to as scintillating matrices with memories and when used in non-radioactive energy transfer formats [such as HTRF] they are referred to as fluorescing memories with matrices.

The recording device used in proximity to the matrix is preferably a miniature device, typically less than 10–20 $mm^3$ [or 10–20 mm in its largest dimension] in size, preferably smaller, such as 1 to 5 mm, that includes at least one data storage unit that includes a remotely programmable and remotely readable, preferably non-volatile, memory. This device with remotely programmable memory is in proximity to, associated with or in contact with the matrix. In particular, the recording device includes a memory device, preferably having memory means, preferably non-volatile, for storing a plurality of data points and means for receiving a transmitted signal that is received by the device and for causing a data point corresponding to the data signal to be permanently stored within the memory means. If needed, the recording device further includes a shell [coating] that is non-reactive with and impervious to any processing steps or solutions in which the combination of matrix with recording device [matrix with memory] is placed, and that is transmissive of read or write signals transmitted to the memory. The device may also include at least one support matrix disposed on an outer surface of the shell for retaining molecules or biological particles. The shell and support matrix may be the same. In such instances, the shell must be treated or derivatized such that molecules, particularly amino acids and nucleic acids, can be linked, preferably either electrostatically or covalently, thereto. Thus, a transponder enclosed in plastic, must be further treated or coated to render it suitable for linkage of the molecule or biological particle.

The data storage device or memory is programmed with or encoded with information that identifies molecules or biological particles, either by their process of preparation, their identity, their batch number, category, physical or chemical properties, combinations of any of such information, or other such identifying information. The molecules or biological particles are in physical contact, direct or indirect, or in proximity with the matrix, which in turn is in physical contact or in the proximity of the recording device that contains the data storage memory. The molecule or biological particle may also be associated, such that a molecule or biological particle that had been linked to or in proximity with a matrix with memory may be identified [i.e., although the matrix particle and biological particle or molecule are not linked or in proximity, the identify of the matrix that had been linked to the molecule or particle is known]. Typically, the matrix is on the surface of the recording device and the molecules and biological particles are in physical contact with the matrix material. In certain embodiments, the memory device may be linked to or in proximity to more than one matrix particle.

The data storage device or memory can also be programmed by virtue of a reaction in proximity to or in the vicinity of the matrix with memory. In particular, the recording devices include memories and also additional components that detect occurrence of external events or to monitor the status of external parameters, such as EM emissions, changes in temperature or pH, ion concentrations and other such solution parameters. For example, recording devices include memories and also include a photodectector can detect the occurrence of fluorescence or other optical emission. Coupling this emission with an amplifier and providing a voltage to permit data storage in the matrix with memory during the reaction by way of, for example an RF signal transmitted to and received by an antenna/rectifier combination within the data storage device or providing voltage sufficient to write to memory from a battery [see, e.g., U.S. Patent No. U.S. Pat. No. 5,350,645 and U.S. Pat. No. 5,089,877], permits occurrence of the emission to be recorded in the memory.

The recording device [containing the memory] is associated with the memory. Typically, the recording device is coated with at least one layer of material, such as a protective polymer or a glass, including polystyrene, heavy metal-free glass, plastic, ceramic, and may be coated with more than one layers of this and other materials. It must be treated to render it suitable for linking molecules or biological particles when it is used as a support. For example, it may be coated with a ceramic or glass that are suitably derivatized or then coated with or linked to the matrix material. Alternatively, the glass or ceramic or other coating may serve as the matrix. In other embodiments the recording device and the matrix material are in proximity, such as in a container of a size approximately that of the device and matrix material. In yet other embodiments the recording device and matrix material are associated, such that the molecule or biological particle that was linked to the matrix or that was in proximity thereto may be identified.

The matrix combinations [the matrices with memories], thus, contain a matrix material, typically in particulate form, in physical contact with a tiny device containing one or more remotely programmable data storage units [memories]. Contact can be effected by placing the recording device with memory on or in the matrix material or in a solution that is in contact with the matrix material or by linking the device, either by direct or indirect covalent or non-covalent interactions, chemical linkages or by other interactions, to the matrix. Alternatively, matrices with memories carry a code, such as a bar code, preferably a two-dimensional bar code, on typically one surface and the memory is remote, such as a memory in a computer or any written record by which the code can be deciphered and information stored and associated therewith.

For example, when the memories are proximate to the matrix, contact can be effected chemically, by chemically coupling the recording device with memory to the matrix, or physically by coating the recording device with the matrix material or another material, by physically inserting or encasing the device in the matrix material, by placing the device onto the matrix or by any other means by which the device can be placed in contact with or in proximity to the matrix material. The contact may be direct or indirect via linkers. The contact may be effected by absorption or adsorption.

Since matrix materials have many known uses in conjunction with molecules and biological particles, there are a multitude of methods known to artisans of skill in this art for linking, joining or physically contacting the molecule or biological particle with the matrix material. In some embodiments, the recording device with data storage unit is placed in a solution or suspension of the molecule or biological particle of interest. In some of such instances, the container, such as the microtiter plate or test tube or other vial, is the matrix material. The recording device is placed in or on the matrix or is embedded, encased or dipped in the matrix material or otherwise place in proximity by enclosing the device and matrix material in a sealed pouch or bag or container [MICROKAN™] fabricated from, preferably, porous material, such as polytetrafluoroethylene [marketed TEFLON® (Trademark, E. I. DuPont)] or polypropylene prepared with pores, that is inert to the reaction of interest and that have pores of size permeable to desired components of the reaction medium.

More than one data storage device may be in proximity to or contact with a matrix particle, or more than one matrix particle may be in contact with on device. For example, microplates, such as microtiter y plates or other such high density format [i.e. 96, 384 1536 or more wells per plate, such as those available from Nunc, Naperville, Ill., Costar, Cambridge Mass., and Millipore, Bedford, Mass.] with the recording device containing the data storage unit [remotely programmable memory] embedded in each well or vials [typically with a 1 ml or smaller capacity] with an embedded recording device may be manufactured.

In a preferred embodiment, the recording device is a semiconductor that is approximately 10 mm or less in its largest dimension and the matrix material is a particle, such as a polystyrene bead. The device and a plurality of particles, referred to as "beads", typically about 1 mg to about 50 mg, but larger size vessels and amounts up to 1000 mg, preferably 50 to about 200 mg, are sealed in chemically inert porous supports, such as polypropylene formed so that it has pores of a selected size that excludes the particles but permits passage of the external medium. For example, a single device and a plurality of particles may be sealed in a porous or semi-permeable inert material to produce a microvessel [such as the MICROKAN™] such as a TEFLON® [polytetra-fluoroethylene] or polypropylene or membrane that is permeable to the components of the medium, or they may be contained in a small closable container that has at least one dimension that is porous or is a semi-permeable tube. Typically such tube, which preferably has an end that can be opened and sealed or closed tightly. These microvessels preferably have a volume of about 200–500 $mm^3$, but can have larger volumes, such as greater than 500 $mm^3$ [or 1000 $mm^3$] at least sufficient to contain at least 200 mg of matrix particles, such as about 500–3000 $mm^3$, such as 1000–2000 or 1000 to 1500, with preferred dimensions of about 1–10 mm in diameter and 5 to 20 mm in height, more preferably about 5 mm by 15 mm, or larger, such as about 1–6 cm by 1–6 cm. The porous wall should be non-collapsible with a pore size in the range of 70 $\mu$M to about 100 $\mu$M, but can be selected to be semi-permeable for selected components of the medium in which the microvessel is placed. The preferred geometry of these combinations is cylindrical. These porous microvessels may be sealed by heat or may be designed to snap or otherwise close. In some embodiments they are designed to be reused. In other embodiments, the microvessel MICROKAN™ with closures may be made out of non-porous material, such as a tube in the conical shape or other geometry.

Also provided herein are tubular devices [or other geometry] in which the recording devise is enclosed in a solid polymer, such as a polypropylene, which is then radiation grafted with selected monomers to produce a surface suitable for chemical synthesis and linkage of molecules or biological particles. These tubular devices [or other geometry] MICROTUBES™ may contain a recording device or may include a code engraved, such as by a laser, or otherwise imprinted on the surface.

Other devices of interest, are polypropylene supports, generally about 5–10 mm in the largest dimension, and preferably a cube or other such shape, that are marked with a code, and tracked using a remote memory. These microvessels can be marked with a code, such as a bar code, alphanumeric code or other mark, for identification, particularly in embodiments in which the memory is not in proximity to the matrix, but is remote therefrom and used to store information regarding each coded vessel.

The combination of matrix with memory is used by contacting it with, linking it to, or placing it in proximity with a molecule or biological particle, such as a virus or phage particle, a bacterium or a cell, to produce a second combination of a matrix with memory and a molecule or biological particle. In certain instances, such combinations of matrix with memory or combination of matrix with memory and molecule or biological particle may be prepared when used or may be prepared before use and packaged or stored as such for futures use. The matrix with memory when linked or proximate to a molecule or biological particle is herein referred to as a microreactor.

The miniature recording device containing the data storage unit(s) with remotely programmable memory, includes, in addition to the remotely programmable memory, means for receiving information for storage in the memory and for retrieving information stored in the memory. Such means is typically an antenna, which also serves to provide power in a passive device when combined with a rectifier circuit to convert received energy, such as RF, into voltage, that can be tuned to a desired electromagnetic frequency to program the memory. Power for operation of the recording device may also be provided by a battery attached directly to the recording device, to create an active device, or by other power sources, including light and chemical reactions, including biological reactions, that generate energy.

Preferred frequencies are any that do not substantially alter the molecular and biological interactions of interest, such as those that are not substantially absorbed by the molecules or biological particles linked to the matrix or in proximity of the matrix, and that do not alter the support properties of the matrix. Radio frequencies are presently preferred, but other frequencies, such as radar, or optical lasers will be used, as long as the selected frequency or optical laser does not interfere with the interactions of the molecules or biological particles of interest. Thus, information in the form of data points corresponding to such information is stored in and retrieved from the data storage device by application of a selected electromagnetic radiation frequency, which preferably is selected to avoid interference from any background electromagnetic radiation.

The preferred miniature recording device for use in the combinations herein is a single substrate of a size preferably less than about 10 to 20 mm$^3$ [or 10–20 mm in its largest dimension], that includes a remotely programmable data storage unit(s) [memory], preferably a non-volatile memory, and an antenna for receiving or transmitting an electromagnetic signal [and in some embodiments for supplying power in passive devices when combined with a rectifier circuit] preferably a radio frequency signal; the antenna, rectifier circuit, memory and other components are preferably integrated onto a single substrate, thereby minimizing the size of the device. An active device, i.e., one that does not rely on external sources for providing voltage for operation of the memory, may include a battery for power, with the battery attached to the substrate, preferably on the surface of the substrate. Vias through the substrate can then provide conduction paths from the battery to the circuitry on the substrate. The device is rapidly or substantially instantaneously programmable, preferably in less than 5 seconds, more preferably in about 1 second, and more preferably in about 50 to 100 milliseconds or less, and most preferably in about 1 millisecond or less. In a passive device that relies upon external transmissions to generate sufficient voltage to operate, write to and read from an electronic recording device, the preferred memory is non-volatile, permanent, and relies on antifuse-based architecture or flash memory. Other memories, such as electrically programmable erasable read only memories [EEPROMs] based upon other architectures also can be used in passive devices. In active recording devices that have batteries to assure continuous power availability, a broader range of memory devices may be used in addition to those identified above. These memory devices include dynamic random access memories [DRAMS, which refer to semiconductor volatile memory devices that allow random input/output of stored information; see, e.g., U.S. Pat. Nos. 5,453,633, 5,451,896, 5,442,584, 5,442,212 and 5,440,511], that permit higher density memories, and EEPROMs.

Containers, such as vials, tubes, microtiter plates, capsules and the like, which are in contact with a recording device that includes a data storage unit with programmable memory are also provided. The container is typically of a size used in immunoassays or hybridization reactions, generally a liter or less, typically less than 100 ml, and often less than about 10 ml in volume. Alternatively the container can be in the form of a plurality of wells, such as a microtiter plate, each well having about 1 to 1.5 ml or less in volume. The container is transmissive to the electromagnetic radiation, such as radio frequencies, infrared wavelengths, radar, ultraviolet wavelengths, microwave frequencies, visible wavelengths, X-rays or laser light, used to program the recording device.

Methods for electromagnetically tagging molecules or biological particles are provided. Such tagging is effected by placing the molecules or biological particles of interest in proximity with the recording device or with the matrix with memory, and programming or encoding the identity of the molecule or synthetic history of the molecules or batch number or other identifying information into the memory. The, thus identified molecule or biological particle is then used in the reaction or assay of interest and tracked by virtue of its linkage to the matrix with memory, its proximity to the matrix with memory or its having been linked or in proximity to the matrix [i.e., its association with], which can be queried at will to identify the molecule or biological particle. The tagging and/or reaction or assay protocols may be automated. Automation may use robotics [see, U.S. Pat. No. 5,463,564, which provides an automated iterative method of drug design].

In particular, methods for tagging constituent members of combinatorial libraries and other libraries or mixtures of diverse molecules and biological particles are provided. These methods involve electromagnetically tagging molecules, particularly constituent members of a library, by contacting the molecules or biological particles or bringing such molecules or particles into proximity with a matrix with memory and programming the memory with retrievable information from which the identity, synthesis history, batch number or other identifying information can be retrieved. The contact is preferably effected by coating, completely or in part, the recording device with memory with the matrix and then linking, directly or via linkers, the molecule or biological particle of interest to the matrix support. The memories can be coated with a protective coating, such as a glass or silicon, which can be readily derivatized for chemical linkage or coupling to the matrix material. In other embodiments, the memories can be coated with matrix, such as for example dipping the memory into the polymer prior to polymerization, and allowing the polymer to polymerize on the surface of the memory.

If the matrices are used for the synthesis of the constituent molecules, the memory of each particle is addressed and the identity of the added component is encoded in the memory at [before, during, or preferably after] each step in the synthesis. At the end of the synthesis, the memory contains a retrievable record of all of the constituents of the resulting molecule, which can then be used, either linked to the support, or following cleavage from the support in an assay or for screening or other such application. If the molecule is cleaved from the support with memory, the memory must remain in proximity to the molecule or must in some manner be traceable [i.e., associated with] to the molecule. Such synthetic steps may be automated.

In preferred embodiments, the matrix with memory with linked molecules [or biological particles] are mixed and reacted with a sample according to a screening or assay protocol, and those that react are isolated. The identity of reacted molecules can then be ascertained by remotely retrieving the information stored in the memory and decoding it to identify the linked molecules.

Compositions containing combinations of matrices with memories and compositions of matrices with memories and molecules or biological particles are also provided. In particular, coded or electronically tagged libraries of oligonucleotides, peptides, proteins, non-peptide organic molecules, phage display, viruses and cells are provided. Particulate matrices, such as polystyrene beads, with attached memories, and continuous matrices, such as microtiter plates or slabs or polymer, with a plurality of embedded or attached memories are provided.

These combinations of matrix materials with memories and combinations of matrices with memories and molecules or biological particles may be used in any application in which support-bound molecules or biological particles are used. Such applications include, but are not limited to diagnostics, such as immunoassays, drug screening assays, combinatorial chemistry protocols and other such uses. These matrices with memories can be used to tag cells for uses in cell sorting, to identify molecules in combinatorial syntheses, to label monoclonal antibodies, to tag constituent members of phage displays, affinity separation procedures, to label DNA and RNA, in nucleic acid amplification reactions [see, e.g., U.S. Pat. No. 5,403,484; U.S. Pat. No. 5,386,024; U.S. Patent No. U.S. Pat. No. 4,683,202 and, for example International PCT Application WO/94 02634, which describes the use of solid supports in connection with nucleic acid amplification methods], to label known compounds, particularly mixtures of known compounds in multianalyte analyses], to thereby identify unknown compounds, or to label or track unknowns and thereby identify the unknown by virtue of reaction with a known. Thus, the matrices with memories are particularly suited for high throughput screening applications and for multianalyte analyses.

Systems and methods for recording and reading or retrieving the information in the data storage devices regarding the identity or synthesis of the molecules or biological particles are also provided. The systems for recording and reading data include: a host computer or other encoder/decoder instrument having a memory for storing data relating to the identity or synthesis of the molecules, and a transmitter means for receiving a data signal and generating a signal for transmitting a data signal; and a recording device that includes a remotely programmable, preferably non-volatile, memory and transmitter means for receiving a data signal and generating at least a transmitted signal and for providing a write signal to the memory in the recording device. The host computer stores transmitted signals from the memories with matrices, and decodes the transmitted information.

In particular, the systems include means for writing to and reading from the memory device to store and identify each of the indicators that identify or track the molecules and biological particles. The systems additionally include the matrix material in physical contact with or proximate to the recording device, and may also include a device for separating matrix particles with memory so that each particle or memory can be separately programmed.

Methods for tagging molecules and biological particles by contacting, either directly or indirectly, a molecule or biological particle with a recording device; transmitting from a host computer or decoder/encoder instrument to the device electromagnetic radiation representative of a data signal corresponding to an indicator that either specifies one of a series of synthetic steps or the identity or other information for identification of the molecule or biological particle, whereby the data point representing the indicator is written into the memory, are provided.

Methods for reading identifying information from recording devices linked to or in contact with or in proximity to or that had been in contact with or proximity to a electromagnetically tagged molecule or electromagnetically tagged biological particles are provided. These methods include the step of exposing the recording device containing the memory in which the data are stored to electromagnetic radiation [EM]; and transmitting to a host computer or decoder/encoder instrument an indicator representative of a the identity of a molecule or biological particle or identification of the molecule or biological particle linked to, in proximity to or associated with the recording device.

One, two, three and N-dimensional arrays of the matrices with memories are also provided. Each memory is programmed with its position in the array. Such arrays may be used for blotting, if each matrix particle is coated on one at least one side with a suitable material, such as nitrocellulose. For blotting, each memory is coated on at least one side with the matrix material and arranged contiguously to adjacent memories to form a substantially continuous sheet. After blotting, the matrix particles may be separated and reacted with the analyte of interest [e.g., a labeled antibody or oligonucleotide or other ligand], after which the physical position of the matrices to which analyte binds may be determined. The amount of bound analyte, as well as the kinetics of the binding reaction, may also be quantified. Southern, Northern, Western, dot blot and other such assays using such arrays are provided. Dimensions beyond three can refer to additional unique identifying parameters, such as batch number, and simultaneous analysis of multiple blots.

Assays that use combinations of (i) a miniature recording device that contains one or more programmable data storage devices [memories] that can be remotely programmed and read; and (ii) a matrix, such as a particulate support used in chemical syntheses, are provided. The remote programming and reading is preferably effected using electromagnetic radiation.

Also provided are scintillation proximity assays, HTRF, FP, FET and FRET assays in which the memories are in proximity with or are in physical contact with the matrix that contains scintillant for detecting proximate radionucleotide signals or fluorescence. In addition, embodiments that include a memory device that also detects occurrence of a reaction are provided.

Molecular libraries, DNA libraries, peptide libraries, biological particle libraries, such as phage display libraries, in which the constituent molecules or biological particles are combined with a solid support matrix that is combined with a data storage unit with a programmable memory are provided.

Affinity purification protocols in which the affinity resin is combined with a recording device containing a data storage unit with a programmable memory are also provided.

Immunological, biochemical, cell biological, molecular biological, microbiological, and chemical assays in which memory with matrix combinations are used are provided. For example immunoassays, such as enzyme linked immunosorbent assays [ELISAs] in which at least one analyte is linked to a solid support matrix that is combined with a recording device containing a data storage unit with a programmable, preferably remotely programmable and non-volatile, memory are provided.

Of particular interest herein, are multiprotocol applications [such as multiplexed assays or coupled synthetic and assay protocols] in which the matrices with memories are used in a series [more than one] of reactions, a series [more than one] of assays, and/or a series of more or more reactions and one or more assays, typically on a single platform or coupled via automated analysis instrumentation. As a result synthesis is coupled to screening.

Methods for engraving bar codes, bar codes and bar-code engraved devices are also provided herein. In particular OMDs are provided and methods for writing to the surface of these devices and reading the engraved symbology are provided. The OMDs are fabricated from a suitable material, such as black, white or colored glass, TEFLON® [polytetrafluoroethylene], polyethylene, high density polyethylene, polypropylene, polystyrene, polyester, ceramic, composites of any of these materials and other such materials. The typical OMD is 10 mm or smaller in its larges dimension and is encoded by direct deposit, dot matrix deposit, direct laser write or dot matrix scan laser write. They may be precoded or coded prior to or even during use. For use in the applications provided herein, at least one surface or a portion of a surface is treated to render it suitable for use as a support, such as by grafting, ion implant, vacuum deposit, oxidation, combinations thereof, suitable derivatization or any other means known to those of skill in the art by which materials are treated to render them suitable for use as supports. The OMDs also have applications as a data pad for recording information about linked molecules or biological particles, or for monitoring storage and location, or in clinical labs for recording relevant information. The OMDs may be in the form of microplates in which each well is encoded or in combination with any instrumentation used in biological and chemical processing and screening.

DESCRIPTION OF THE DRAWINGS

Understanding of the subject matter provided herein will be facilitated by consideration of the detailed description of the preferred embodiments in conjunction with the accompanying drawings, in which like reference numerals refer to like parts and in which:

FIG. 22 is a perspective view of a first embodiment of an optical memory device;

FIG. 23 is an exploded perspective view of a second embodiment of the optical memory device;

FIG. 25 is a side elevation of a third embodiment of the optical memory device;

FIG. 26 is a side elevation of a fourth embodiment of the optical memory device;

FIG. 27 is a side elevation of a fifth embodiment of the optical memory device;

FIG. 28 is a front elevation of a sixth embodiment of the optical memory device;

FIG. 29 is a front elevation of a seventh embodiment of the optical memory device;

FIG. 30 is a front elevation of an eighth embodiment of the optical memory device;

DETAILED DESCRIPTION OF PREFERRED EMBODIMENTS

Definitions

Figure 1:
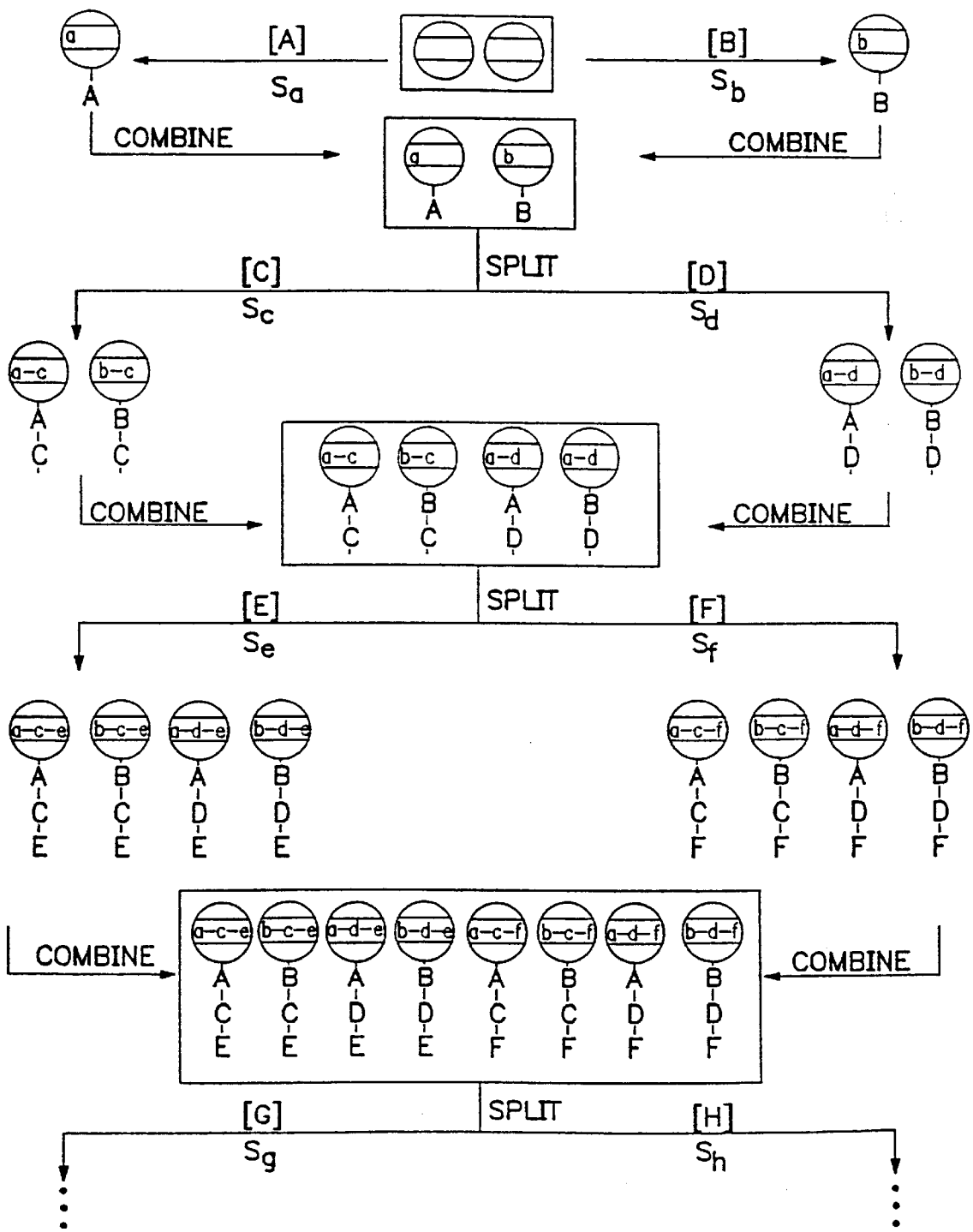
FIG. 1 depicts combinatorial synthesis of chemical libraries on matrix supports with memories. A, B, C . . . represent the chemical building blocks; a, b, c . . . represent the codes stored in memory that correspond to each of A, B, C, . . . , respectively. $S_a$, $S_b$, $S_c$ . . . represent respective signals sent to memory. Alternatively, the matrix supports are OMDs [optical memory devices] that are encoded with symbology associated with information stored in a remote memory, such as a computer. The symbology may be precoded or encoded prior to or during synthesis.

Unless defined otherwise, all technical and scientific terms used herein have the same meaning as is commonly understood by one of skill in the art to which this invention belongs. All patents and publications referred to herein are, unless noted otherwise, incorporated by reference in their entirety.

As used herein, a bar codes refers any array optically readable marks of any desired size and shape that are arranged in a reference context or frame of, preferably, although not necessarily, one or more columns and one or more rows. For purposes herein, the bar code refers to any symbology, not necessary "bar" but may include dots, characters or any symbol or symbols.

As used herein, an optical memory device [OMD] refers to a surface that is encoded with a code, preferably the 2-D bar code provided herein. For use herein, such devices include at least two surfaces, one of which is treated or formed from a matrix material treated to render it suitable for use as a support to which molecules or biological particles are linked, such as in chemical syntheses or as supports in assays, and the other that includes a code that can be optically read and then compared with information in a computer or other memory to interpret its meaning.

As used herein, an optical memory refers to the symbology and the surface on which it is engraved or otherwise imprinted. For purposes herein, an optical memory is distinct from optical recording media that may be appropriate for use in the recording devices and combinations herein include, but are not limited to, optical discs, magneto-optical materials, photochromic materials, photoferroelectric materials, and photoconductive electro-optic materials.

As used herein, symbology refers to the code, such as a bar code, that is engraved or imprinted on the OMD. The symbology is any code known or designed by the user. The symbols are associated with information stored in a remote computer or memory or other such device or means. For example, each OMD can be uniquely identified with an encoded symbology. The process steps or additions or manipulations to the associated molecules or biological particles can be recorded in a remote memory and associated with the code.

As used herein, a matrix refers to any solid or semisolid or insoluble support on which a code is to which the memory device and/or the molecule of interest, typically a biological molecule, organic molecule or biospecific ligand is linked or contacted. Typically a matrix is a substrate material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or other such topology. Matrix materials include any materials that are used as affinity matrices or supports for chemical and biological molecule syntheses and analyses, such as, but are not limited to: polystyrene, polycarbonate, polypropylene, nylon, glass, dextran, chitin, sand, pumice, polytetrafluoroethylene, agarose, polysaccharides, dendrimers, buckyballs, polyacrylamide, Kieselguhr-polyacrlamide non-covalent composite, polystyrene-polyacrylamide covalent composite, polystyrene-PEG [polyethyleneglycol] composite, silicon, rubber, and other materials used as supports for solid phase syntheses, affinity separations and purifications, hybridization reactions, immunoassays and other such applications. The matrix herein may be particulate or may be in the form of a continuous surface, such as a microtiter dish or well, a glass slide, a silicon chip, a nitrocellulose sheet, nylon mesh, or other such materials. When particulate, typically the particles have at least one dimension in the 5–10 mm range or smaller. Such particles, referred collectively herein as "beads", are often, but not necessarily, spherical. Such reference, however, does not constrain the geometry of the matrix, which may be any shape, including random shapes, needles, fibers, elongated, etc. The "beads" may include additional components, such as magnetic or paramagnetic particles [see, e.g., Dyna beads (Dynal, Oslo, Norway)] for separation using magnets, fluophores and other scintillants, as long as the additional components do not interfere with chemical reactions, data entry or retrieval from the memory.

Significantly, it is noted, however, that many surfaces, such as glass, require modification to render them suitable for use as supports. Any such surface must be treated to render it suitable for chemical syntheses or for adsorption of biological particles. Chemical syntheses require a support that not only has the proper surface characteristics (organic solvent wettability, chemical kinetics, etc.), but that also has a high density of functional groups. An untreated glass surface contains only a very small amount [less than 1 nmol/sq. mm] of hydroxy groups. It is also very hydrophilic and not very suitable for reactions in organic media. Therefore, the glass surface has to be modified to achieve high functional group density (~>10 nmol/mm$^2$) and proper hydrophobicity. Thus, as used herein, matrix refers to materials that have been so-treated. Therefore, a transponder in which the memory device is encased in a glass capsule for instance is not usable as is, but must be treated, either by coating at least one surface with a polymer, such as by grafting, derivatizing or otherwise activating the surface.

As used herein, scintillants include, 2,5-diphenyloxazole [PPO], anthracene, 2-(4'-tert-butylphenyl)-5-(4"-biphenyl)-1,3,4-oxadiazole [butyl-PBD]; 1-phenyl-3-mesityl-2-pyrazoline [PMP], with or without frequency shifters, such as 1,4,-bis[5-phenyl(oxazolyl)benzene] [POPOP]; p-bis-o-methylstyrylbenzene [bis-MSB]. Combinations of these fluors, such as PPO and POPOP or PPO and bis-MSB, in suitable solvents, such as benzyltoluene [see, e.g., U.S. Pat. No. 5,410,155], are referred to as scintillation cocktails.

As used herein a luminescent moiety refers to a scintillant or fluorophore used in scintillation proximity assays or in non-radioactive energy transfer assays, such as HTRF assays.

As used herein, fluorescent resonance energy transfer [FRET] is an art-recognized term meaning that one fluorophore [the acceptor] can be promoted to an excited electronic state through quantum mechanical coupling with and receipt of energy from an electronically excited second fluorophore [the donor]. This transfer of energy results in a decrease in visible fluorescence emission by the donor and an increase in fluorescent energy emission by the acceptor. Significant energy transfer can only occur when the donor and acceptor are sufficiently closely positioned since the efficiency of energy transfer is highly dependent upon the distance between donor and acceptor fluorophores.

As used herein, matrix particles refer to matrix materials that are in the form of discrete particles. The particles have any shape and dimensions, but typically have at least one dimension that is 100 mm or less, preferably 50 mm or less, more preferably 10 mm or less, and typically have a size that is 100 mm$^3$ or less, preferably 50 mm$^3$ or less, more preferably 10 mm$^3$ or less, and most preferably 1 mm$^3$ or less. The matrices may also be continuous surfaces, such as microtiter plates [e.g., plates made from polystyrene or polycarbonate or derivatives thereof commercially available from Perkin Elmer Cetus and numerous other sources, and Covalink trays [Nunc], microtiter plate lids or a test tube, such as a 1 ml Eppendorf tube. Matrices that are in the form of containers refers to containers, such as test tubes and microplates and vials that are typically used for solid phase syntheses of combinatorial libraries or as pouches, vessels, bags, and microvessels for screening and diagnostic assays. Thus, a container used for chemical syntheses refers to a container that typically has a volume of about 1 liter, generally 100 ml, and more often 10 ml or less, 5 ml or less, preferably 1 ml or less, and as small as about 50 $\mu$l–500 $\mu$l, such as 100 $\mu$l or 250 $\mu$l. This also refers to multi-well plates, such as microtiter plates 196 well, 384 well or other density format]. Such microtiter plate will typically contain a recording device in, on, or otherwise in contact with in each of a plurality of wells.

As used herein, a matrix with a memory refers to a combination of a matrix with a miniature recording device that stores multiple bits of data by which the matrix may be identified, preferably in a non-volatile memory that can be written to and read from by transmission of electro-magnetic radiation from a remote host, such as a computer. By miniature is meant of a size less than about 10–20 mm$^3$ [or 10–20 mm in the largest dimension]. Preferred memory devices or data storage units are miniature and are preferably smaller than 10–20 mm$^3$ [or 10–20 mm in its largest dimension] dimension, more preferably less than 5 mm$^3$, most preferably about 1 mm$^3$ or smaller.

As used herein, a microreactor refers to combinations of matrices with memories with associated, such as linked or proximate, biological particles or molecules. It is produced, for example, when the molecule is linked thereto or synthesized thereon. It is then used in subsequent protocols, such as immunoassays and scintillation proximity assays.

As used herein, a combination herein called a microvessel [e.g., a microvessel such as those designated presently designated a MICROKAN™] refers to a combination in which a single device [or more than one device] and a plurality of particles are sealed in a porous or semi-permeable inert material, such as polytetrafluoroethylene or polypropylene or membrane that is permeable to the components of the medium, but retains the particles and memory, or are sealed in a small closable container that has at least one dimension that is porous or semi-permeable. Typically such microvessels, which preferably have at least one end that can be opened and sealed or closed tightly, has a volume of about 200–500 mm$^3$, with preferred dimensions of about 1–10 mm in diameter and 5 to 20 mm in height, more preferably about 5 mm by 15 mm. The porous wall should be non-collapsible with a pore size in the range of 70 $\mu$M to about 100 $\mu$M, but can be selected to be semi-permeable for selected components of the reaction medium.

As used herein, a memory is a data storage unit [or medium] with programmable memory, preferably a non-volatile memory; or alternatively is a symbology on a surface, such as a bar code, whose identity and as for which associate information is stored in a remote memory, such as a computer memory.

As used herein, programming refers to the process by which data or information is entered and stored in a memory. A memory that is programmed is a memory that contains retrievable information.

As used herein, remotely programmable, means that the memory can be programmed without direct physical or electrical contact or can be programmed from a distance, typically at least about 10 mm, although shorter distances may also be used, such as instances in which the information comes from surface or proximal reactions or from an adjacent memory or in instances, such as embodiments in which the memories are very close to each other, as in microtiter plate wells or in an array.

As used herein, a recording device [or memory device] is an apparatus that includes the data storage unit with programmable memory, and, if necessary, means for receiving information and for transmitting information that has been recorded. It includes any means needed or used for writing to and reading from the memory. The recording devices intended for use herein, are miniature devices that preferably are smaller than 10–20 mm$^3$ [or 10–20 mm in their largest dimension], and more preferably are closer in size to 1 mm³ or smaller that contain at least one such memory and means for receiving and transmitting data to and from the memory. The data storage device also includes optical memories, such as bar codes, on devices such as OMDs.

As used herein, a data storage unit with programmable memory includes any data storage means having the ability to record multiple discrete bits of data, which discrete bits of data may be individually accessed [read] after one or more recording operations. Thus, a matrix with memory is a combination of a matrix material with a data storage unit.

As used herein, programmable means capable of storing unique data points. Addressable means having unique locations that may be selected for storing the unique data points.

As used herein, reaction verifying and reaction detecting are interchangeable and refer to the combination that also includes elements that detect occurrence of a reaction or event of interest between the associated molecule or biological particle and its environment [i.e., detects occurrence of a reaction, such as ligand binding, by virtue of emission of EM upon reaction or a change in pH or temperature or other parameter].

As used herein, a host computer or decoder/encoder instrument is an instrument that has been programmed with or includes information [i.e., a key] specifying the code used to encode the memory devices. This instrument or one linked thereto transmits the information and signals to the recording device and it, or another instrument, receives the information transmitted from the recording device upon receipt of the appropriate signal. This instrument thus creates the appropriate signal to transmit to the recording device and can interpret transmitted signals. For example, if a "1" is stored at position 1,1 in the memory of the recording device means, upon receipt of this information, this instrument or computer can determine that this means the linked molecule is, for example, a peptide containing alanine at the N-terminus, an organic group, organic molecule, oligonucleotide, or whatever this information has been predetermined to mean. Alternatively, the information sent to and transmitted from the recording device can be encoded into the appropriate form by a person.

As used herein, an electromagnetic tag is a recording device that has a memory that contains unique data points that correspond to information that identifies molecules or biological particles linked to, directly or indirectly, in physical contact with or in proximity [or associated with] to the device. Thus, electromagnetic tagging is the process by which identifying or tracking information is transmitted [by any means and to any recording device memory, including optical and magnetic storage media] to the recording device.

As used herein, proximity means within a very short distance, generally less than 0.5 inch, typically less than 0.2 inches. In particular, stating that the matrix material and memory, or the biological particle or molecule and matrix with memory are in proximity means that, they are at least or at least were in the same reaction vessel or, if the memory is removed from the reaction vessel, the identity of the vessel containing the molecules or biological particles with which the memory was proximate or linked is tracked or otherwise known.

As used herein, associated with means that the memory must remain in proximity to the molecule or biological particle or must in some manner be traceable to the molecule or biological particle. For example, if a molecule is cleaved from the support with memory, the memory must in some manner be identified as having been linked to the cleaved molecule. Thus, a molecule or biological particle that had been linked to or in proximity to a matrix with memory is associated with the matrix or memory if it can be identified by querying the memory.

As used herein, antifuse refers to an electrical device that is initially an open circuit that becomes a closed circuit during programming, thereby providing for non-volatile memory means and, when accompanied by appropriate transceiver and rectification circuitry, permitting remote programming and, hence identification. In practice, an antifuse is a substantially nonconductive structure that is capable of becoming substantially conductive upon application of a predetermined voltage, which exceeds a threshold voltage. An antifuse memory does not require a constant voltage source for refreshing the memory and, therefore, may be incorporated in a passive device. Other memories that may be used include, but are not limited to: EEPROMS, DRAMS and flash memories.

As used herein, flash memory is memory that retains information when power is removed [see, e.g., U.S. Pat. No. 5,452,311, U.S. Pat. No. 5,452,251 and U.S. Pat. No. 5,449,941]. Flash memory can be rewritten by electrically and collectively erasing the stored data, and then by programming.

As used herein, passive device refers to an electrical device which does not have its own voltage source and relies upon a transmitted signal to provide voltage for operation.

As used herein, electromagnetic [EM] radiation refers to radiation understood by skilled artisans to be EM radiation and includes, but is not limited to radio frequency [RF], infrared [IR], visible, ultraviolet [UV], radiation, sonic waves, X-rays, and laser light.

As used herein, information identifying or tracking a biological particle or molecule, refers to any information that identifies the molecule or biological particle, such as, but not limited to the identity particle [i.e. its chemical formula or name], its sequence, its type, its class, its purity, its properties, such as its binding affinity for a particular ligand. Tracking means the ability to follow a molecule or biological particle through synthesis and/or process steps. The memory devices herein store unique indicators that represent any of this information.

As used herein, combinatorial chemistry is a synthetic strategy that produces diverse, usually large, chemical libraries. It is the systematic and repetitive, covalent connection of a set, the basis set, of different monomeric building blocks of varying structure to each other to produce an array of diverse molecules [see, e.g., Gallop et al. (1994) J. Medicinal Chemistry 37:1233–1251]. It also encompasses other chemical modifications, such as cyclizations, eliminations, cleavages, etc., that are carried in manner that generates permutations and thereby collections of diverse molecules.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials.

As used herein, the molecules in the combinations include any molecule, including nucleic acids, amino acids, other biopolymers, and other organic molecules, including peptidomimetics and monomers or polymers of small organic molecular constituents of non-peptidic libraries, that may be identified by the methods here and/or synthesized on matrices with memories as described herein.

As used herein, the term "bio-oligomer" refers to a biopolymer of less than about 100 subunits. A bio-oligomer includes, but is not limited to, a peptide, i.e., containing amino acid subunits. an oligonucleotide, i.e., containing nucleoside subunits, a peptide-oligonucleotide chimera, peptidomimetic, and a polysaccharide.

As used herein, the term "sequences of random monomer subunits" refers to polymers or oligomers containing sequences of monomers in which any monomer subunit may precede or follow any other monomer subunit.

As used herein, the term "library" refers to a collection of substantially random compounds or biological particles expressing random peptides or proteins or to a collection of diverse compounds. Of particular interest are bio-oligomers, biopolymers, or diverse organic compounds or a set of compounds prepared from monomers based on a selected pharmacophore.

As used herein, an analyte is any substance that is analyzed or assayed in the reaction of interest. Thus, analytes include the substrates, products and intermediates in the reaction, as well as the enzymes and cofactors.

As used herein, multianalyte analysis is the ability to measure many analytes in a single specimen or to perform multiple tests from a single specimen. The methods and combinations herein provide means to identify or track individual analytes from among a mixture of such analytes.

As used herein, a fluophore or a fluor is a molecule that readily fluoresces; it is a molecule that emits light following interaction with radiation. The process of fluorescence refers to emission of a photon by a molecule in an excited singlet state. For scintillation assays, combinations of fluors are typically used. A primary fluor that emits light following interaction with radiation and a secondary fluor that shifts the wavelength emitted by the primary fluor to a higher more efficiently detected wavelength.

As used herein, a peptidomimetic is a compound that mimics the conformation and certain stereochemical features of the biologically active form of a particular peptide. In general, peptidomimetics are designed to mimic certain desirable properties of a compound but not the undesirable features, such as flexibility leading to a loss of the biologically active conformation and bond breakdown. For example, methylenethio bioisostere [$CH_2S$] has been used as an amide replacement in enkephalin analogs [see, e.g., Spatola, A. F. *Chemistry and Biochemistry of Amino Acids, Peptides, and Proteins* [Weinstein, B, Ed., Vol. 7, pp. 267–357, Marcel Dekker, New York (1983); and Szelke et al. (1983) *In Peotides: Structure and Function. Proceedings of the Eighth American Peptide Symposium*, Hruby and Rich, Eds., pp. 579–582, Pierce Chemical Co., Rockford, Ill.].

As used herein, complete coupling means that the coupling reaction is driven substantially to completion despite or regardless of the differences in the coupling rates of individual components of the reaction, such as amino acids In addition, the amino acids, or whatever is being coupled, are coupled to substantially all available coupling sites on the solid phase support so that each solid phase support will contain essentially only one species of peptide.

As used herein, the biological activity or bioactivity of a particular compound includes any activity induced, potentiated or influenced by the compound in vivo or in vitro. It also includes the abilities, such as the ability of certain molecules to bind to particular receptors and to induce [or modulate] a functional response. It may be assessed by In vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, substantially pure means sufficiently homogeneous to appear free of readily detectable impurities as determined by standard methods of analysis, such as thin layer chromatography [TLC], mass spectrometry [MS], size exclusion chromatography, gel electrophoresis, particularly agarose and polyacrylamide gel electrophoresis [PAGE] and high performance liquid chromatography [HPLC], used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound [see, e.g., Nogrady (1985) *Medicinal Chemistry A Biochemical Approach*, Oxford University Press, New York, pages 388–392].

As used herein, amino acids refer to the naturally-occurring amino acids and any other non-naturally occurring amino acids, and also the corresponding D-isomers. It is also understood that certain amino acids may be replaced by substantially equivalent non-naturally occurring variants thereof, such as D-Nva, D-Nle, D-Alle, and others listed with the abbreviations below or known to those of skill in this art.

As used herein, hydrophobic amino acids include Ala, Val, Leu, lle, Pro, Phe, Trp, and Met, the non-naturally occurring amino acids and the corresponding D isomers of the hydrophobic amino acids, that have similar hydrophobic properties; the polar amino acids include Gly, Ser, Thr, Cys, Tyr, Asn, Gln, the non-naturally occurring amino acids and the corresponding D isomers of the polar amino acids, that have similar properties, the charged amino acids include Asp, Glu, Lys, Arg, His, the non-naturally occurring amino acids and the corresponding D isomers of these amino acids.

As used herein, Southern, Northern, Western and dot blot procedures refer to those in which DNA, RNA and protein patterns, respectively, are transferred for example, from agarose gels, polyacrylamide gels or other suitable medium that constricts convective motion of molecules, to nitrocellulose membranes or other suitable medium for hybridization or antibody or antigen binding are well known to those of skill in this art [see, e.g., Southern (1975) *J. Mol. Biol.* 98:503–517; Ketner et al. (1976) *Proc. Natl. Acad. Sci. U.S.A.* 73:1102–1106; Towbin et al. (1979) *Proc. Natl. Acad. Sci. U.S.A.* 76:4350].

As used herein, a receptor refers to a molecule that has an affinity for a given ligand. Receptors may be naturally-occurring or synthetic molecules. Receptors may also be referred to in the art as anti-ligands. As used herein, both terms, receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

Examples of receptors and applications using such receptors, include but are not restricted to:

a) enzymes: specific transport proteins or enzymes essential to survival of microorganisms, which could serve as targets for antibiotic [ligand] selection;

b) antibodies: identification of a ligand-binding site on the antibody molecule that combines with the epitope of an antigen of interest may be investigated; determination of a sequence that mimics an antigenic epitope may lead to the development of vaccines of which the immunogen is based on one or more of such sequences or lead to the development of related diagnostic agents or compounds useful in therapeutic treatments such as for auto-immune diseases c) nucleic acids: identification of ligand, such as protein or RNA, binding sites;

d) catalytic polypeptides: polymers, preferably polypeptides, that are capable of promoting a chemical reaction involving the conversion of one or more reactants to one or more products; such polypeptides generally include a binding site specific for at least one reactant or reaction intermediate and an active functionality proximate to the binding site, in which the functionality is capable of chemically modifying the bound reactant [see, e.g., U.S. Pat. No. 5,215,899];

e) hormone receptors: determination of the ligands that bind with high affinity to a receptor is useful in the development of hormone replacement therapies; for example, identification of ligands that bind to such receptors may lead to the development of drugs to control blood pressure; and f) opiate receptors: determination of ligands that bind to the opiate receptors in the brain is useful in the development of less-addictive replacements for morphine and related drugs.

As used herein, antibody includes antibody fragments, such as Fab fragments, which are composed of a light chain and the variable region of a heavy chain.

As used herein, complementary refers to the topological compatibility or matching together of interacting surfaces of a ligand molecule and its receptor. Thus, the receptor and its ligand can be described as complementary, and furthermore, the contact surface characteristics are complementary to each other.

As used herein, a ligand-receptor pair or complex formed when two macromolecules have combined through molecular recognition to form a complex.

As used herein, an epitope refers to a portion of an antigen molecule that is delineated by the area of interaction with the subclass of receptors known as antibodies.

As used herein, a ligand is a molecule that is specifically recognized by a particular receptor. Examples of ligands, include, but are not limited to, agonists and antagonists for cell membrane receptors, toxins and venoms, viral epitopes, hormones [e.g., steroids], hormone receptors, opiates, peptides, enzymes, enzyme substrates, cofactors, drugs, lectins, sugars, oligonucleotides, nucleic acids, oligosaccharides, proteins, and monoclonal antibodies.

As used herein, a sensor is a device or apparatus that monitors external parameters (i.e., conditions), such as ion concentrations, pH, temperatures. Biosensors are sensors that detect biological species. Sensors encompass devices that rely on electrochemical, optical, biological and other such means to monitor the environment.

As used herein, multiplexing refers to performing a series of synthetic and processing steps and/or assaying steps on the same platform [i.e. solid support or matrix] or coupled together as part of the same automated coupled protocol, including one or more of the following, synthesis, preferably accompanied by writing to the linked memories to identify linked compounds, screening, including using protocols with matrices with memories, and compound identification by querying the memories of matrices associated with the selected compounds. Thus, the platform refers system in which all manipulations are performed. In general it means that several protocols are coupled and performed sequentially or simultaneously.

As used herein, a platform refers to the instrumentation or devices in which on which a reaction or series of reactions is(are) performed.

As used herein a protecting group refers to a material that is chemically bound to a monomer unit that may be removed upon selective exposure to an activator such as electromagnetic radiation and, especially ultraviolet and visible light, or that may be selectively cleaved. Examples of protecting groups include, but are not limited to: those containing nitropiperonyl, pyrenylmethoxy-carbonyl, nitroveratryl, nitrobenzyl, dimethyl dimethoxybenzyl, 5-bromo-7-nitroindolinyl, o-hydroxy-alpha-methyl cinnamoyl, and 2-oxymethylene anthraquinone.

Also protected amino acids are readily available to those of skill in this art. For example, Fmoc and Boc protected amino acids can be obtained from Fluka, Bachem, Advanced Chemtech, Sigma, Cambridge Research Biochemical, Bachem, or Peninsula Labs or other chemical companies familiar to those who practice this art.

As used herein, the abbreviations for amino acids and protective groups are in accord with their common usage and the IUPAC-IUB Commission on Biochemical Nomenclature [see, (1972) *Biochem.* 11: 942–944]. Each naturally occurring L-amino acid is identified by the standard three letter code or the standard three letter code with or without the prefix "L-"; the prefix "D-" indicates that the stereoisomeric form of the amino acid is D. For example, as used herein, Fmoc is 9-fluorenylmethoxycarbonyl; BOP is benzotriazol-1-yloxytris(dimethylamino) phosphonium hexafluorophosphate, DCC is dicyclohexylcarbodiimide; DDZ is dimethoxydimethylbenzyloxy; DMT is dimethoxytrityl; FMOC is fluorenylmethyloxycarbonyl; HBTU is 2-(1H-benzotriazol-1-yl)-1,1,3,3-tetramethyluronium; hexafluorophosphate NV is nitroveratryl; NVOC is 6-nitroveratryloxycarbonyl and other photoremovable groups; TFA is trifluoroacetic acid; DMF for N,N-dimethylformamide; Boc is tert-butoxycarbonyl; TFA for trifluoroacetic acid; HF for hydrogen fluoride; HFIP for hexafluoroisopropanol; HPLC for high performance liquid chromatography; FAB-MS for fast atom bombardment mass spectrometry; DCM is dichloromethane, Bom is benzyloxymethyl; Pd/C is palladium catalyst on activated charcoal; DIC is diisopropylcarbodiimide; DCC is N,N'-dicyclohexylcarbodiimide; [For] is formyl; PyBop is benzotriazol-1-yl-oxy-trispyrrolidino-phosphonium hexafluorophosphate; POPOP is 1,4,-bis[5-phenyl(oxazolyl) benzene]; PPO is 2,5-diphenyloxazole; butyl-PBD is [2-(4'-tert-butylphenyl)-5-(4"-biphenyl)-1,3,4-oxadiazole]; PMP is (1-phenyl-3-mesityl-2-pyrazoline) DIEA is diisopropylethylamine; EDIA is ethyidiisopropylethylamine; NMP is N-methylpyrrolidone; NV is nitroveratryl PAL is pyridylalanine; HATU is O(7-azabenzotriaol-1-yl)-1,1,3,3-tetramethyl-uronium hexafluorophosphate; TFA is trifluoracetic acid, THF is tetrahydrofuran; and EDT is 1,2-ethanedithiol.

A. Matrices

Matrices, which are generally insoluble materials used to immobilize ligands and other molecules, have application in many chemical syntheses and separations. Matrices are used in affinity chromatography, in the immobilization of biologically active materials, and during chemical syntheses of biomolecules, including proteins, amino acids and other organic molecules and polymers. The preparation of and use of matrices is well known to those of skill in this art; there are many such materials and preparations thereof known. For example, naturally-occurring matrix materials, such as agarose and cellulose, may be isolated from their respective sources, and processed according to known protocols, and synthetic materials may be prepared in accord with known protocols.

Matrices include any material that can act as a support matrix for attachment of the molecules or biological particles of interest and can be in contact with or proximity to or associated with, preferably encasing or coating, the data storage device with programmable memory. Any matrix composed of material that is compatible with and upon or in which chemical syntheses are performed, including biocompatible polymers, is suitable for use herein. The matrix material should be selected so that it does not interfere with the chemistry or biological reaction of interest during the time which the molecule or particle is linked to, or in proximity therewith [see, e.g., U.S. Pat. No. 4,006,403]. These matrices, thus include any material to which the data storage device with memory can be attached, placed in proximity thereof, impregnated, encased or otherwise connected, linked or physically contacted. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass that is derivatized to render it suitable for use a support, silica gels, polystyrene, gelatin, polyvinyl pyrrolidone, co-polymers of vinyl and acrylamide, polystyrene cross-linked with divinylbenzene or the like [see, Merrifield (1964) Biochemistry 3:1385–1390], polyacrylamides, latex gels, polystyrene, dextran, polyacrylamides, rubber, silicon, plastics, nitrocellulose, celluloses, natural sponges, and many others. It is understood that the matrix materials contemplated are those that are suitable for use a s support matrix for retaining molecules or biological particles during synthesese or reactions.

Among the preferred matrices are polymeric beads, such as the TENTAGEL™ resins and derivatives thereof [sold by Rapp Polymere, Tubingen, Germany; see, U.S. Pat. No. 4,908,405 and U.S. Pat. No. 5,292,814; see, also Butz et al. (1994) *Peotide Res.* 7:20–23; Kleine et al. (1994) *Immunobiol.* 190:53–66; see, also Piskin et al. (1994), Chapter 18 "Nondegradable and Biodegradable Polymeric Particles" in *Diagnostic Biosensor Polymers*, ACS Symp.Series 556, Usmani et al. Eds, American Chemical Society, Washington, D.C.], which are designed for solid phase chemistry and for affinity separations and purifications. See, also Bayer et al. (1994) in *Pept.: Chem., Struct. Biol., Proc. Am. Pept. Symp.*, 13th; Hodges, et al. eds., pp.156–158; Zhang et al. (1993) *Pept.* 1992, *Proc. Eur. Pept. Symp.*, 22nd, Schneider, et al., eds. pp. 432–433; Ilg et al. (1994) *Macromolecules*, pp. 2778–83; Zeppezauer et al. (1993) *Z. Naturforsch., B: Chem. Sci.* 48:1801–1806; Rapp et al. (1992) *Pept. Chem.* 1992, *Proc. Jpn. Symp.*, 2nd, Yanaihara, ed., pp. 7–10; Nokihara et al. (1993) *Shimadzu Hyoron* 50:25–31; Wright et al. (1993) *Tetrahedron Lett.* 34:3373–3376; Bayer et al. (1992) *Poly(Ethylene Glycol) Chem.* Harris, ed., pp. 325–45; Rapp et al. (1990) *Innovation Perspect. Solid Phase Synth. Collect. Pap., Int. Symp.*, 1st, Epton, ed., pp. 205–10; Rapp et al. (1992) *Pept.: Chem. Biol., Proc. Am. Pept. Symp.*, 12th. Smith et al., eds., pp. 529–530; Rapp et al. (1989) *Pept., Proc. Eur. Pent. Sympo.*, 20th, Jung et al., ed.,pp. 199–201; Bayer et al. (1986) *Chem. Pept. Proteins* 3: 3–8; Bayer et al. (1983) *Pept.: Struct. Funct., Proc. Am. Pept. Symp.*, 8th, Hruby et al. eds.,pp. 87–90 for descriptions of preparation of such beads and use thereof in synthetic chemistry. Matrices that are also contemplated for use herein include fluophore-containing or -impregnated matrices, such as microplates and beads [commercially available, for example, from Amersham, Arlington Heights, Ill.; plastic scintillation beads from NE (Nuclear Technology, Inc., San Carlos, Calif.), Packard, Meriden, Conn.]. It is understood that these commercially available materials will be modified by combining them with memories, such as by methods described herein.

Figure 21:
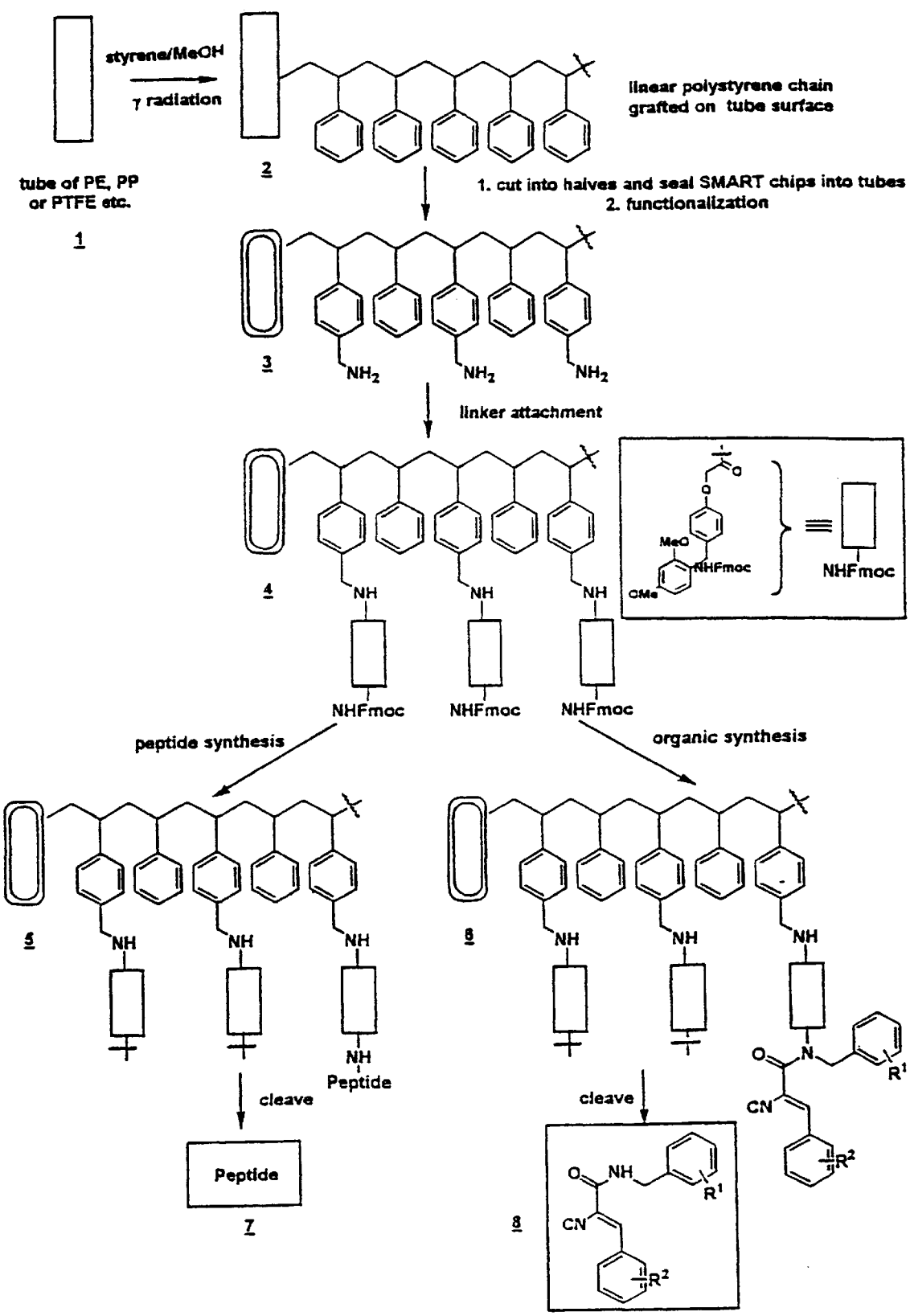
FIG. 21 Show the preparation and use of a tubular microvessel in which the container is radiation grafted with monomers or otherwise activated for use as a support matrix.

The matrix may also be a relatively inert polymer, which can be grafted by ionizing radiation [see, e.g., FIG. 21, which depicts a particular embodiment] to permit attachment of a coating of polystyrene or other such polymer that can be derivatized and used as a support. Radiation grafting of monomers allows a diversity of surface characteristics to be generated on plasmid supports [see, e.g., Maeji et al. (1994) *Reactive Polymers* 22:203–212; and Berg et al. (1989) *J. Am. Chem. Soc.* 111:8024–8026]. For example, radiolytic grafting of monomers, such as vinyl momomers, or mixtures of monomers, to polymers, such as polyethylene and polypropylene, produce composites that have a wide variety of surface characteristics. These methods have been used to graft polymers to insoluble supports for synthesis of peptides and other molecules, and are of particular interest herein. The recording devices, which are often coated with a plastic or other insert material, can be treated with ionizing radiation so that selected monomers can be grafted to render the surface suitable for chemical syntheses.

Where the matrix particles are macroscopic in size, such as about at least 1 mm in at least one dimension, such bead or matrix particle or continuous matrix may contain one or more memories. Where the matrix particles are smaller, such as NE particles [PVT-based plastic scintillator microsphere], which are about 1 to 10 μm in diameter, more than one such particle will generally be associated with one memory. Also, the bead may include additional material, such as scintillant or a fluophore impregnated therein. In preferred embodiments, the solid phase chemistry and subsequent assaying may be performed on the same bead or matrix with memory combination. All procedures, including synthesis on the bead and assaying and analysis, can be automated.

The matrices are typically insoluble substrates that are solid, porous, deformable, or hard, and have any required structure and geometry, including, but not limited to: beads, pellets, disks, capillaries, hollow fibers, needles, solid fibers, random shapes, thin films and membranes. Typically, when the matrix is particulate, the particles are at least about 10–2000 μM, but may be smaller, particularly for use in embodiments in which more than one particle is in proximity to a memory. For purposes herein, the support material will typically encase or be in contact with the data storage device, and, thus, will desirably have at least one dimension on the order of 1 mm [1000 μM] or more, although smaller particles may be contacted with the data storage devices, particularly in embodiments in which more than one matrix particle is associated, linked or in proximity to one memory or matrix with memory, such as the microvessels [see, e.g., FIGS. 11–16]. Each memory will be in associated with, in contact with or proximity to at least one matrix particle, and may be in contact with more than one. As smaller semiconductor and electronic or optical devices become available, the capacity of the memory can be increased and/or the size of the articles can be decreased. For example, presently, 0.5 micron semiconductor devices are available. Integrated circuits 0.25-micron in size have been described and are being developed using a technology called the Complementary Metal Oxide-Semiconductor process (see, e.g., Investor's Business Daily May 30, 1995).

Also of interest herein, are devices that are prepared by inserting the recording device into a "tube" [see, e.g., FIG. 21] or encasing them in an inert material [with respect to the media in which the device will be in contact]. This material is fabricated from a plastic or other inert material. Preferably prior to introducing [and preferably sealing] the recording device inside, the tube or encasing material is treated with ionizing radiation to render the surface suitable for grafting selected monomers, such as styrene [see, e.g., Maeji et al. (1994) *Reactive Polymers* 22:203–212; and Berg et al. (1989) *J. Am. Chem. Soc.* 111:8024–8026].

Recording device(s) is(are) introduced inside the material or the material is wrapped around the device and the resulting matrix with memory "tubes" [MICROTUBES™, see, FIG. 21] are used for chemical synthesis or linkage of selected molecules or biological particles. These "tubes" are preferably synthesized from an inert resin, such as a polypropylene resin [e.g., a Moplen resin, V29G PP resin from Montell, Newark Del., a distributor for Himont, Italy]. Any inert matrix that can then be functionalized or to which derivatizable monomers can be grafted is suitable. Preferably herein, polypropylene tubes are grafted and then formed into tubes or other suitable shape and the recording device inserted inside. These tubes [MICROTUBES™] with grafted monomers are then used as synthesis, and/or for assays or for multiplexed processes, including synthesis and assays or other multistep procedures.

Also larger matrix particles, which advantageously provide ease of handling, may be used and may be in contact with or proximity to more than one memory (i.e., one particle may have a plurality of memories in proximity or linked to it; each memory may programmed with different data regarding the matrix particle, linked molecules, synthesis or assay protocol, etc.]. Thus, so-called macro-beads (Rapp Polymere, Tubingen, Germany), which have a diameter of 2 mm when swollen, or other matrices of such size, are also contemplated for use herein. Particles of such size can be readily manipulated and the memory can be readily impregnated in or on the bead. These beads (available from Rapp) are also advantageous because of their uniformity in size, which is useful when automating the processes for electronically tagging and assaying the beads.

The matrices may also include an inert strip, such as a polytetrafluoroethylene [TEFLON®] strip or other material to which the molecules or biological particles of interest do not adhere, to aid in handling the matrix, such as embodiments in which a matrix with memory and linked molecules or biological particle are introduced into an agar-containing plate for immunoassays or for antibiotic screening.

Selection of the matrices will be governed, at least in part, by their physical and chemical properties, such as solubility, functional groups, mechanical stability, surface area swelling propensity, hydrophobic or hydrophilic properties and intended use.

The data storage device with programmable memory may be coated with a material, such as a glass or a plastic, that can be further derivatized and used as the support or it may be encased, partially or completely, in the matrix material, such as during or prior to polymerization of the material. Such coating may be performed manually or may be automated. The coating can be effected manually or using instruments designed for coating such devices. Instruments for this purpose are available [see, e.g., the Series C3000 systems for dipping available from Specialty Coating Systems, Inc., Indianapolis, Ind.; and the Series CM 2000 systems for spray coating available from Integrated Technologies, Inc. Acushnet, Mass.].

The data storage device with memory may be physically inserted into the matrix material or particle. It also can be manufactured with a coating that is suitable for use as a matrix or that includes regions in the coating that are suitable for use as a matrix. If the matrix material is a porous membrane, it may be placed inside the membrane. It is understood that when the memory device is encased in the matrix or coated with protective material, such matrix or material must be transparent to the signal used to program the memory for writing or reading data. More than one matrix particle may be linked to each data storage device.

In some instances, the data storage device with memory is coated with a polymer, which is then treated to contain an appropriate reactive moiety or in some cases the device may be obtained commercially already containing the reactive moiety, and may thereby serve as the matrix support upon which molecules or biological particles are linked. Materials containing reactive surface moieties such as amino silane linkages, hydroxyl linkages or carboxysilane linkages may be produced by well established surface chemistry techniques involving silanization reactions, or the like. Examples of these materials are those having surface silicon oxide moieties, covalently linked to gamma-aminopropylsilane, and other organic moieties; N-[3-(triethyoxysilyl)propyl]phthelamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art e.g., the TENTAGEL® Resins are available with a multitude of functional groups, and are sold by Rapp Polymere, Tubingen, Germany; see, U.S. Pat. No. 4,908,405 and U.S. Pat. No. 5,292,814; see, also Butz et al. (1994) *Peptide Res.* 7:20–23; Kleine et al. (1994) *Immunobiol.* 190:53–66].

The data storage device with memory, however, generally should not or cannot be exposed to the reaction solution, and, thus, must be coated with at least a thin layer of a glass or ceramic or other protective coating that does not interfere with the operation of the device. These operations include electrical conduction across the device and transmission of remotely transmitted electromagnetic radiation by which data are written and read. It is such coating that may also serve as a matrix upon which the molecules or biological particles may be linked.

The data storage devices with memory may be coated either directly or following coating with a ceramic, glass or other material, may then be coated with agarose, which is heated, the devices are dipped into the agarose, and then cooled to about room temperature. The resulting glass, silica, agarose or other coated memory device, may be used as the matrix supports for chemical syntheses and reactions.

Conventional integrated circuit manufacturing and packaging methods include methods and means for encapsulating integrated circuits to protect the devices from the environment and to facilitate connection to external devices. Also, there are numerous descriptions for the preparation of semiconductor devices and wires, particularly for use as sensors [see, e.g., U.S. Pat. No. 4,933,285; see, also Cass, Ed. (1990) *Biosensors A Practical Approach*, IRL Press at Oxford University Press, Oxford; biosensors are chemosensors an can include a biological detection system, generally biologically active substances, such as enzymes, antibodies, lectins and hormone receptors, which are immobilized on the surface of the sensor electrode or in a thin layer on the sensor electrode; biosensors are sensors that detect biological species], which measure electrochemical solution parameters, such as pH. Despite differences in the components of biosensors and recording devices used herein, certain of the methods for coating electrodes and wires in the biosensor art may be adapted for use herein [see, e.g., U.S. Pat. Nos. 5,342,772, 5,389,534, 5,384,028, 5,296,122, 5,334,880, 5,311,039, 4,777,019, 5,143,854, 5,200,051, 5,212,050, 5,310,686, 5324,591; see, also Usmani et al., ed. (1994) *Diagnostic Biosensor Polymers*, ACS Symposium Series No. 556].

It is, however, emphasized that the combinations herein of matrix with memory are not sensors, which measure external parameters and can include electrodes that must be in contact with the solution such that molecules in solution directly contact the electrode, and which measure solution parameters. Data regarding the combination, particularly the linked or associated biological particle or matrix is written into the memory, and thus records information about itself. Sensors monitor what is going outside of the device. The combinations herein of matrices with memories can be enhanced by addition of sensor elements for the measurement of external conditions, information about the external conditions can be recorded into the combination's memory.

The combinations herein are matrix materials with recording devices that contain data storage units that include remotely programmable memories; the recording devices used in solution must be coated with a material that prevents contact between the recording device and the medium, such as the solution or air or gas [e.g., nitrogen or oxygen or $CO_2$]. The information is introduced into the memory by addressing the memory to record information regarding molecules or biological particles linked thereto. Except in the reaction detecting [verifying] embodiment, in which the memory can be encoded upon reaction of a linked molecule or biological particle, solution parameters are not recorded in the memory.

In certain embodiments herein, the matrices with memories herein, however may be combined with devices or components or biosensors or other such sensor devices and used in connection therewith to monitor solution or external parameters. For example, the combination may be electronically or otherwise linked to a biosensor and information obtained by the biosensor can be encoded in memory, or the combination can transmit information to the biosensor or, when used internally in an animal, to monitor the location of a biosensor or to transmit information from the biosensor. For example, transponder memory devices exemplified herein, include circuitry for measuring and recording solution temperature. These transponders can be modified to read and record pH, instead of or in addition to temperature. Thus, during synthesis or other processing steps of linked or proximate molecules or biological particles, RF or other EM radiation will be used to encode information in the memory and at the same time pH and/or temperature in the external solution can be measured and recorded in the memory.

1. Natural matrix support materials

Naturally-occurring supports include, but are not limited to agarose, other polysaccharides, collagen, celluloses and derivatives thereof, glass, silica, and alumina. Methods for isolation, modification and treatment to render them suitable for use as supports is well known to those of skill in this art [see, eg., Hermanson et al. (1992) *Immobilized Affinity Ligand Techniques*, Academic Press, Inc., San Diego]. Gels, such as agarose, can be readily adapted for use herein. Natural polymers such as polypeptides, proteins and carbohydrates; metalloids, such as silicon and germanium, that have semiconductive properties, as long as they do not interfere with operation of the data storage device may also be adapted for use herein. Also, metals such as platinum, gold, nickel, copper, zinc, tin, palladium, silver, again as long as the combination of the data storage device with memory, matrix support with molecule or biological particle does not interfere with operation of the device with memory, may be adapted for use herein. Other matrices of interest include oxides of the metal and metalloids such as Pt—PtO, Si—SiO, Au—AuO, TiO2, Cu—CuO, and the like. Also compound semiconductors, such as lithium niobate, gallium arsenide and indium-phosphide, and nickel-coated mica surfaces, as used in preparation of molecules for observation in an atomic force microscope [see, e.g., Ill et al. (1993) *Biophys J*. 64:919] may be used as matrices. Methods for preparation of such matrix materials are well known.

For example, U.S. Pat. No. 4,175,183 describes a water insoluble hydroxyalkylated cross-linked regenerated cellulose and a method for its preparation. A method of preparing the product using near stoichiometric proportions of reagents is described. Use of the product directly in gel chromatography and as an intermediate in the preparation of ion exchangers is also described.

2. Synthetic matrices

There are innumerable synthetic matrices and methods for their preparation known to those of skill in this art. Synthetic matrices are typically produced by polymerization of functional matrices, or copolymerization from two or more monomers of from a synthetic monomer and naturally occurring matrix monomer or polymer, such as agarose. Before such polymers solidify, they are contacted with the data storage device with memory, which can be cast into the material or dipped into the material. Alternatively, after preparation of particles or larger synthetic matrices, the recording device containing the data storage unit(s) can be manually inserted into the matrix material. Again, such devices can be pre-coated with glass, ceramic, silica or other suitable material.

Synthetic matrices include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers [see, e.g., Merrifield (1964) Biochemistry 3:1385–1390; Berg et al. (1990) in *Innovation Perspect. Solid Phase Synth. Collect. Pap.*, Int. Symp., 1st, Epton, Roger (Ed), pp. 453–459; Berg et al. (1989) in *Pept., Proc. Eur. Pept. Symp.*, 20th, Jung, G. et al. (Eds), pp. 196–198; Berg et al. (1989) *J. Am. Chem. Soc.* 111:8024–8026; Kent et al. (1979) *Isr. J. Chem.* 17:243–247; Kent et al. (1978) *J. Org. Chem.* 43:2845–2852; Mitchell et al. (1976) *Tetrahedron Lett.* 42:3795–3798; U.S. Pat. No. 4,507,230; U.S. Pat. No. 4,006,117; and U.S. Pat. No. 5,389,449]. Methods for preparation of such matrices are well-known to those of skill in this art.

Synthetic matrices include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethylacrylate, polypropylene-co-methyl acrylate, polyethylene-co-vinyl acetate, polypropylene-co-vinyl acetate, and those containing acid anhydride groups such as polyethylene-co-maleic anhydride, polypropylene-co-maleic anhydride and the like. Liposomes have also been used as solid supports for affinity purifications [Powell et al. (1989) *Biotechnol. Bioeng.* 15 33:173].

For example, U.S. Pat. No. 5,403,750, describes the preparation of polyurethane-based polymers. U.S. Pat. No. 4,241,537 describes a plant growth medium containing a hydrophilic polyurethane gel composition prepared from chain-extended polyols; random copolymerization is preferred with up to 50% propylene oxide units so that the prepolymer will be a liquid at room temperature. U.S. Pat. No. 3,939,123 describes lightly crosslinked polyurethane polymers of isocyanate terminated prepolymers containing poly(ethyleneoxy) glycols with up to 35% of a poly (propyleneoxy) glycol or a poly(butyleneoxy) glycol. In producing these polymers, an organic polyamine is used as a crosslinking agent.

Other matrices and preparation thereof are described in U.S. Pat. Nos. 4,177,038, 4,175,183, 4,439,585, 4,485,227, 4,569,981, 5,092,992, 5,334,640, 5,328,603.

U.S. Pat. No. 4,162,355 describes a polymer suitable for use in affinity chromatography, which is a polymer of an aminimide and a vinyl compound having at least one pendant halo-methyl group. An amine ligand, which affords sites for binding in affinity chromatography is coupled to the polymer by reaction with a portion of the pendant halomethyl groups and the remainder of the pendant halo-methyl groups are reacted with an amine containing a pendant hydrophilic group. A method of coating a substrate with this polymer is also described. An exemplary aminimide is 1,1-dimethyl-1-(2-hydroxyoctyl)amine methacrylamide and vinyl compound is a chloromethyl styrene.

U.S. Pat. No. 4,171,412 describes specific matrices based on hydrophilic polymeric gels, preferably of a macroporous character, which carry covalently bonded D-amino acids or peptides that contain D-amino acid units. The basic support is prepared by copolymerization of hydroxyalkyl esters or hydroxyalkylamides of acrylic and methacrylic acid with crosslinking acrylate or methacrylate comonomers are modified by the reaction with diamines, aminoacids or dicarboxylic acids and the resulting carboxyterminal or aminoterminal groups are condensed with D-analogs of aminoacids or peptides. The peptide containing D-aminoacids also can be synthesized stepwise on the surface of the carrier.

U.S. Pat. No. 4,178,439 describes a cationic ion exchanger and a method for preparation thereof. U.S. Pat. No. 4,180,524 describes chemical syntheses on a silica support.

Immobilized Artificial Membranes [IAMs; see, eg., U.S. Pat. Nos. 4,931,498 and 4,927,879] may also be used. IAMs mimic cell membrane environments and may be used to bind molecules that preferentially associate with cell membranes [see, e.g., Pidgeon et al. (1990) *Enzyme Microb. Technol.* 12:149].

3. Immobilization and activation

Numerous methods have been developed for the immobilization of proteins and other biomolecules onto solid or liquid supports [see, e.g., Mosbach (1976) *Methods in Enzymology* 44; Weetall (1975) *Immobilized Enzymes, Antigens, Antibodies, and Peptides*; and Kennedy et al. (1983) *Solid Phase Biochemistry, Analytical and Synthetic Aspects*, Scouten, ed., pp. 253–391; see, generally, *Affinity Techniques. Enzyme Purification: Part B. Methods in Enzymology*, Vol. 34, ed. W. B. Jakoby, M. Wilchek, Acad. Press, N.Y. (1974); *Immobilized Biochemicals and Affinity Chromatography, Advances in Experimental Medicine and Biology*, vol. 42, ed. R. Dunlap, Plenum Press, N.Y. (1974)].

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art [see, eq, the PIERCE CATALOG, ImmunoTechnology Catalog & Handbook, 1992–1993, which describes the preparation of and use of such reagents and provides a commercial source for such reagents; and Wong (1993) *Chemistry of Protein Conjugation and Cross Linking*, CRC Press; see, also DeWitt et al. (1993) *Proc. Natl. Acad. Sci. U.S.A.* 90:6909; Zuckermann et al. (1992) *J. Am. Chem. Soc.* 114:10646; Kurth et al (1994) *J. Am. Chem. Soc.* 116:2661; Ellman et al. (1994) *Proc. Natl. Acad. Sci. U.S.A.* 91:4708; Sucholeiki (1994) *Tetrahedron Lttrs.* 35:7307; and Su-Sun Wang (1976) *J. Org. Chem.* 41:3258; Padwa et al. (1971) *J. Org. Chem.* 41:3550 and Vedejs et al. (1984) *J. Org. Chem.* 49:575, which describe photosensitive linkers].

To effect immobilization, a solution of the protein or other biomolecule is contacted with a support material such as alumina, carbon, an ion-exchange resin, cellulose, glass or a ceramic. Fluorocarbon polymers have been used as supports to which biomolecules have been attached by adsorption [see, U.S. Pat. No. 3,843,443; Published International PCT Application WO/86 03840].

A large variety of methods are known for attaching biological molecules, including proteins and nucleic acids, molecules to solid supports [see. e.g., U.S. Pat. No. 5,451, 683]. For example, U.S. Pat. No. 4,681,870 describes a method for introducing free amino or carboxyl groups onto a silica matrix. These groups may subsequently be covalently linked to other groups, such as a protein or other anti-ligand, in the presence of a carbodiimide. Alternatively, a silica matrix may be activated by treatment with a cyanogen halide under alkaline conditions. The anti-ligand is covalently attached to the surface upon addition to the activated surface. Another method involves modification of a polymer surface through the successive application of multiple layers of biotin, avidin and extenders [see, e.g., U.S. Pat. No. 4,282,287]; other methods involve photoactivation in which a polypeptide chain is attached to a solid substrate by incorporating a light-sensitive unnatural amino acid group into the polypeptide chain and exposing the product to low-energy ultraviolet light [see, e.g., U.S. Pat. No. 4,762,881]. Oligonucleotides have also been attached using a photochemically active reagents, such as a psoralen compound, and a coupling agent, which attaches the photoreagent to the substrate [see, e.g., U.S. Pat. No. 4,542,102 and U.S. Pat. No. 4,562,157]. Photoactivation of the photoreagent binds a nucleic acid molecule to the substrate to give a surface-bound probe.

Covalent binding of the protein or other biomolecule or organic molecule or biological particle to chemically activated solid matrix supports such as glass, synthetic polymers, and cross-linked polysaccharides is a more frequently used immobilization technique. The molecule or biological particle may be directly linked to the matrix support or linked via linker, such as a metal [see, e.g., U.S. Pat. No. 4,179,402; and Smith et al. (1992) *Methods: A Companion to Methods in Enz.* 4:73–78]. An example of this method is the cyanogen bromide activation of polysaccharide supports, such as agarose. The use of perfluorocarbon polymer-based supports for enzyme immobilization and affinity chromatography is described in U.S. Pat. No. 4,885,250]. In this method the biomolecule is first modified by reaction with a perfluoroalkylating agent such as perfluorooctylpropylisocyanate described in U.S. Pat. No. 4,954,444. Then, the modified protein is adsorbed onto the fluorocarbon support to effect immobilization.

The activation and use of matrices are well known and may be effected by any such known methods [see, e.g., Hermanson et al. (1992) *Immobilized Affinity Ligand Techniques*, Academic Press, Inc., San Diego]. For example, the coupling of the amino acids may be accomplished by techniques familiar to those in the art and provided, for example, in Stewart and Young, 1984, *Solid Phase Synthesis*, Second Edition, Pierce Chemical Co., Rockford.

Molecules may also be attached to matrices through kinetically inert metal ion linkages, such as Co(III), using, for example, native metal binding sites on the molecules, such as IgG binding sequences, or genetically modified proteins that bind metal ions [see, e.g., Smith et al. (1992) *Methods: A Companion to Methods in Enzymology* 4, 73 (1992); III et al. (1993) *Biophys J.* 64:919: Loetscher et al. (1992) *J. Chromatography* 595:113–199; U.S. Pat. No. 5,443,816; Hale (1995) *Analytical Biochem.* 231:46–49].

Other suitable methods for linking molecules and biological particles to solid supports are well known to those of skill in this art [see, e.g., U.S. Pat. No. 5,416,193]. These linkers include linkers that are suitable for chemically linking molecules, such as proteins and nucleic acid, to supports include, but are not limited to, disulfide bonds, thioether bonds, hindered disulfide bonds, and covalent bonds between free reactive groups, such as amine and thiol groups. These bonds can be produced using heterobifunctional reagents to produce reactive thiol groups on one or both of the moieties and then reacting the thiol groups on one moiety with reactive thiol groups or amine groups to which reactive maleimido groups or thiol groups can be attached on the other. Other linkers include, acid cleavable linkers, such as bismaleimideothoxy propane, acid labile-transferring conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (see, Batra et al. (1993) *Molecular Immunol.* 30:379–386).

Presently preferred linkages are direct linkages effected by adsorbing the molecule or biological particle to the surface of the matrix. Other preferred linkages are photocleavable linkages that can be activated by exposure to light [see, e.g., Baldwin et al. (1995) *J. Am. Chem. Soc.* 117:5588; Goldmacher et al. (1992) *Bioconj. Chem.* 3:104–107, which linkers are herein incorporated by reference]. The photocleavable linker is selected such that the cleaving wavelength that does not damage linked moieties. Photocleavable linkers are linkers that are cleaved upon exposure to light [see, e.g., Hazum et al. (1981) in *Pept., Proc. Eur. Pept. Symp.*, 16th, Brunfeldt, K (Ed), pp. 105–110, which describes the use of a nitrobenzyl group as a photocleavable protective group for cysteine; Yen et al. (1989) *Makromol. Chem* 190:69–82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3:104–107, which describes a cross-linker and reagent that undergoes photolytic degradation upon exposure to near UV light (350 nm); and Senter et al. (1985) *Photochem. Photobiol* 42:231–237, which describes nitrobenzyloxycarbonyl chloride cross linking reagents that produce photocleavable linkages]. Other linkers include fluoride labile linkers [see, e.g., Rodolph et al. (1995) *J. Am. Chem. Soc.* 117:57121, and acid labile linkers [see, e.g., Kick et al. (1995) *J. Med. Chem.* 38:1427]. The selected linker will depend upon the particular application and, if needed, may be empirically selected.

B. Optically Encoded Memory Devices

The matrices or strips attached thereto may be encoded with a preprogrammed identifying bar code, such as an optical bar code that will be encoded on the matrix and read by laser. Such pre-coded devices may be used in embodiments in which parameters, such as location in an automated synthesizer, are monitored. The identity of a product or reactant determined by its location or path, which is monitored by reading the chip in each device and storing such information in a remote computer.

Thus, it is contemplated herein, that the memory is not proximate to the matrix, but is separate, such a memory in a remote computer or other recording device. In these embodiments, the matrices are marked with a unique code or mark of any sort. The identity of each mark is saved in the remote memory, and then, each time something is done to a molecule or biological particle linked to each matrix, the information regarding such event is recorded and associated with the coded identity. After completion of, for example, a synthetic protocol, each matrix is examined or read to identify the code. Retrieving information that from the remote memory that is stored with the identifying code will permit identification or retrieval of any other saved information regarding the matrix.

For example, simple codes, including bar codes, alphanumeric characters or other visually or identifiable codes or marks on matrices are also contemplated for use herein. When bar codes or other precoded devices are used, the information can be written to an associated but remote memory, such as a computer or even a piece of paper. The computer stores the bar code that a identifies a matrix particle or other code and information relating to the molecule or biological particle linked to the matrix or other relevant information regarding the linked materials or synthesis or assay. Instead of writing to an on-board memory, information is encoded in a remote memory that stores information regarding the precoded identity of each matrix with bar code and linked molecules or biological particles. Thus, the precoded information is associated with, for example, the identity of the linked molecule or a component thereof, or a position (such as X-Y coordinates in a grid). This information is transmitted to a memory for later retrieval. Each treatment or synthetic step that is performed on the linked molecule or biological particle is transmitted to the remote memory and associated with the precoded ID.

For example, an amino acid is linked to a matrix particle that is encoded with or marked with a bar code or even a letter such as "A" or other coded mark. The identity the amino acid linked to the matrix particle "A" is recorded into a memory. This particle is mixed with other particles, each with a unique identifier or mark, and this mixture is then treated to a synthetic step. Each particle is individually scanned or viewed to see what mark is on each particle and the remote memory is written to describe the synthetic step, which is then associated with each unique identifier in the memory, such as the computer or piece of paper. Thus, in the remote memory the original amino acid linked to particle A is stored. After the synthetic step, the identify of the next amino acid is stored in the memory associated with "A" as is the identity of the next amino acid added. At the end of the synthesis, the history of each particle can be read by scanning the particle or visually looking at the particle and noting its bar code or mark, such as A. The remote memory is then queried to determine what amino acids are linked to the particle identified as "A" [see, e.g., FIG. 20].

Figure 20:
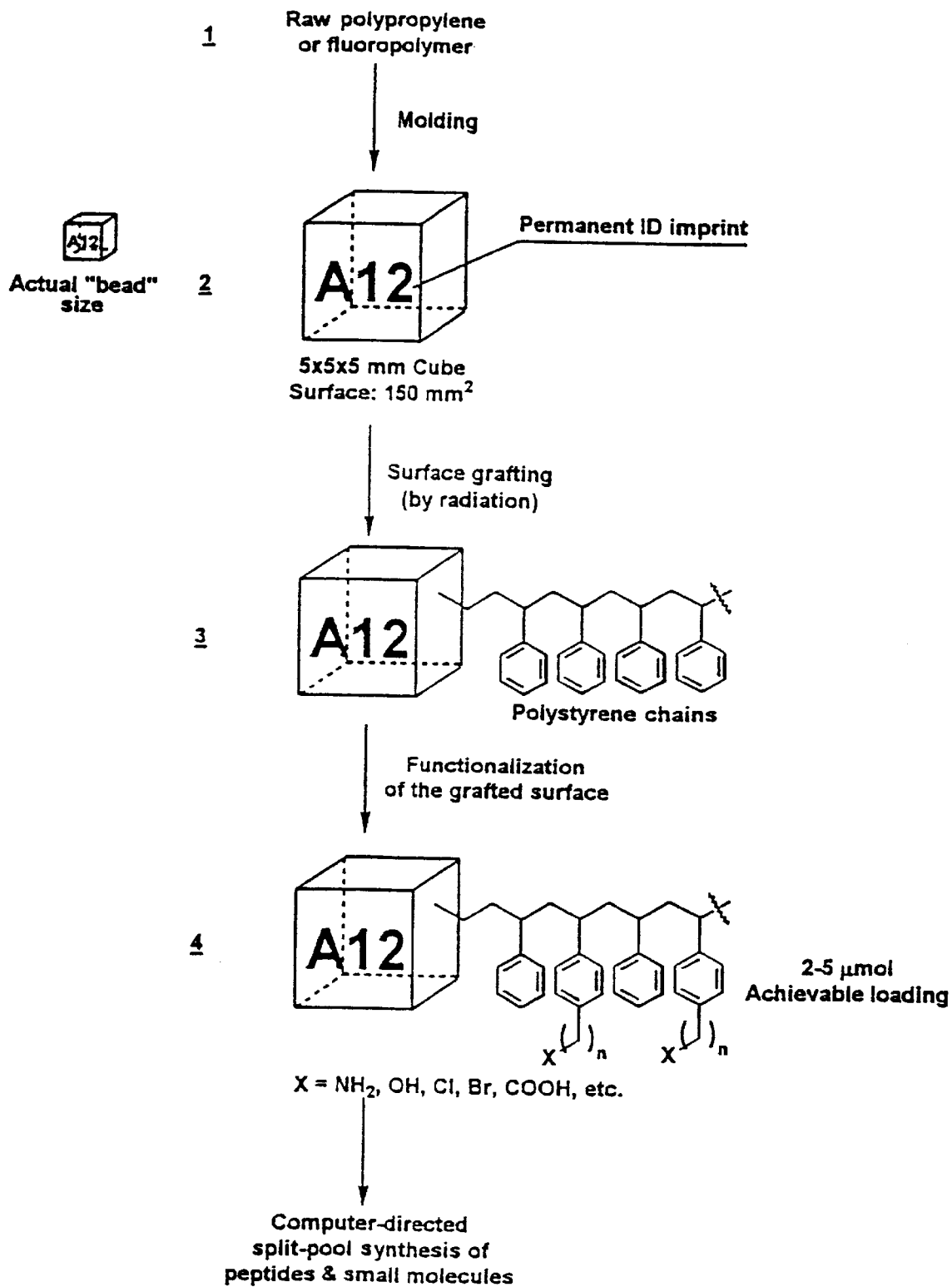
FIG. 20 Coded macro "beads" for efficient combinatorial synthesis.

For example, many combinatorial libraries contain a relatively small number of discrete compounds [$10^2$–$10^4$] in a conveniently manipulable quantity, rather than millions of members in minute quantities. These small libraries are ideal for use with the methods and matrices with memories herein. They may also be used in methods in which the memory is not in proximity to the matrix, but is a remote memory, such as a computer or a table of information stored even on paper. The system depicted in FIG. 20 is ideal for use in these methods.

Polypropylene or other inert polymer, including fluoropolymers or scintillating polymers are molded into a convenient geometry and size, such an approximately 5 mm×5 mm×5 mm cube [or smaller or larger] with a unique identifying code imprinted, preferably permanently, on one side of each cube. If, for example, a three element code is used, based on all digits (0 to 9) and all letters of the alphabet, a collection of 46,666 unique three element codes are available for imprinting on the cubes.

The cubes are surface grafted with a selected monomer [or mixture of monomer], such as styrene. Functionalization of the resulting polymer provides a relatively large surface area for chemical syntheses and subsequent assaying [on a single platform]. For example, a 5×5×5 mm$^3$ cube has a surface area of 150 mm$^2$, which is equivalent to about 2–5 µmol achievable loading, which is about 1–2.5 mg of compounds with a molecular weight of about 500. A simple computer program or protocol can direct split and pool during synthesis and the information regarding each building block of the linked molecules on each cube conveniently recorded in the memory [i.e., computer] at each step in the synthesis.

Since the cubes [herein called MACROCUBES™ or MACROBEADS™] are relatively large, they can be read by the eye or any suitable device during synthesis and the associated data can be manually entered into a computer or even written down. The cubes can include scintillant or fluorophore or label and used in any of the assay formats described herein or otherwise known to those of skill in the art.

For example, with reference to FIG. 20, polypropylene, polyethylene or fluophore raw material [any such material described herein, particularly the Moplen resin e.g., V29G PP resin from Montell, Newark Del., a distributor for Himont, Italy] 1 is molded, preferably into a cube, preferably about 5×5×5 mm$^3$ and engraved, using any suitable imprinting method, with a code, preferably a three element alphanumeric code, on one side. The cube can be weighted or molded so that it all cubes will orient in the same direction. The engraved cubes 2 are then surface-grafted 3 and functionalized using methods described herein or known to those of skill in this art, to produce cubes [MACROBEADS™ or MACROCUBES™] or devices any selected geometry 4.

Encoded Memory Devices with Two-dimensional Bar Codes Matrices with Optical Memories In another exemplary embodiment, illustrated in FIG. 22, the optical memory device ["OMD"] 100 is a preferably a rectangular parallelepiped that provides a broad face upon which encoded information can be inscribed. Any geometry that is suitable for a particular application and that provides at least one surface for encoding information. The OMDs may also be containers used for chemical synthesis, such as microtiter plates, tubes, tubes adapted for use with microtiter-type plates. The two-dimensional bar code described herein is ideally suited for incorporation onto the outside surface of each well of a microtiter plate or on the outside of a small test tube or other such tube, particularly, tubes intended for use with a microplate frame, such as those available from NUNC and COSTAR. This two-dimensional bar code as wells as the method for reading and writing may also be used to track and identify other laboratory equipment, such as chromatography tubes, test tubes, beakers, flasks and other such items.

The OMDs may also be fabricated as tubes, such as the MICROTUBES™ provided herein. When used with such tubular devices, they will be engraved on the outer surface, preferably the top or bottom of the device.

The material of which the OMDs are fabricated will depend upon the monitored processes. The materials that may be used include, but are not limited to, black, white or colored glass, TEFLON®, polyethylene, high density polyethylene, polypropylene, polystyrene, polyester, ceramic, such as alumina or zirconia, metal, or any composite of the above materials or any material that is physically or chemically structured to produce optical contrast as the result of exposure to the write process, which is described below. For use in the methods herein, these materials may be suitable or at least one surface there may have been treated to render them suitable for retaining molecules and biological particles for use as matrices as described herein.

For the first exemplary embodiment of OMD 100 shown in FIG. 22, if the OMD is formed from a ceramic material, it may have exemplary dimensions of 280 mil (L)×140 mil (W)×50 mil (T) [7 mm×3.5 mm×1.3 mm]. The dimensions of the face can be varied as needed to provide the appropriate size for recording data, providing sufficient chemical binding surface area, and to facilitate handling. The presently preferred minimum size for use with commercial feeding systems is on the order of 0.5 mm×0.5 mm×0.5 mm.

If the OMD 100 is formed from polypropylene, it may have exemplary dimensions of 280 mil (L)×140 mil (W)× 100 mil (T) [7 mm×3.5 mm×2.6 mm], although smaller dimensions are contemplated. Since OMDs made from polypropylene may be read by transmission of light through the device, the thickness must be sufficiently thin to permit transmission of light through the OMD, except where there are darkened areas of a bar code symbol. Where reflected light is to be used, as with the ceramic OMDs, thickness need not be so limited.

For OMDs used for chemical binding or other processes for which surfaces must be specially prepared in order to assure adsorption or absorption or any means of binding of molecules or biological particles, it may be desirable to separate the binding surfaces from the data storage surface 101. In this case, one or more of sides 104 and 105, bottom 107, top 108, and back 110 may be treated to enhance binding using radiation, mechanical or chemical abrasion, or other processes as appropriate. By segregation of the binding and information surfaces, possible activation or modification of certain bound compounds by the high intensity light source used in the write process is avoided. In addition, degradation of the bar code contrast may be less on a surface that is not derivatized for binding.

If needed, segregation of the binding and information surfaces can be achieved by coating portions of the OMD with films formed from a dielectric material such as polyethylene, MYLAR, TEFLON®, KAPTON, polycarbonate, or, preferably, the para-xylylene polymers sold under the trade name Parylene [see, e.g., U.S. Pat. Nos. 3,288,728, 3,342,754 and 3,429,739], or any other such materials that are commonly used in the electronics industry to passivate electronic components and circuit boards, and as a coating for medical devices, especially implants, catheters, probes and needles. [Parylene is the trade name for members of a series of polymers which are commercially available from Specialty Coating Systems, Inc., of Indianapolis, Ind. and originally from Union Carbide Corporation, Greenville, S.C., see, U.S. Pat. Nos. 3,288,728, 3,342,754 and Gorham 3,429,739; see, also brochures distributed by the manufacturer, entitled "Parylene Conformal Coatings Specifications and Properties" (© 1984, Specialty Coating Systems, Inc.), and "Parylene, A Biostable Coating for Medical Applications" (© 1984, Specialty Coating Systems, Inc.]. These polymers provide a conformal biostable coating which electrically and chemically isolates the protected surface from its environment.

The Parylene or other such polymeric coating can be treated to form a chemically functional substrate by methods such as beta or gamma radiation, and mechanical or chemical roughening. Alternatively, polystyrene microspheres can be bonded [glued or welded] to selected surface(s) of the OMD, either on the Parylene or similar coating, or directly to the ceramic or polypropylene.

The encoded information may be stored in any optically writable and readable format. As shown printed on data storage surface 101, symbologies 106 are two-dimensional bar codes, which can be stacked rows of one-dimensional bar codes, checkerboards, or dot matrices. Other symbologies that can be used include one-dimensional bar codes, target codes, alphanumeric characters or other optically readable characters which are well known in the art. [See, e.g., Wang, et al. (1990) *A High Density Two Dimensional Bar Code SPIE Proceedings* Vol. 1384, High-Speed Inspection Architectures, Bar Coding, and Character Recognition, pp. 169–175; Martin (1991) *Unique Symbol for Marking and Tracking Very Small Semiconductor Products, SPIE Proceedings* Vol. 1598, Lasers in Microelectronic Manufacturing, pp. 206–220.]

In the exemplary embodiment, the two-dimensional bar code [e.g., symbol 106] includes an orientation indicator in the form of solid black lines across the top 120 and down the right side 122 of the symbol. Upon acquisition of the image of the symbol by the image sensing means, the image processor will utilize the orientation indicator to provide information about the rotation of the OMD relative to the sensor, and can compensate in its software by rotating the image to the appropriate orientation for decoding the image. Other types of orientation indicators as are known in the art, such as those described in the above-identified references relating to bar codes, may also be used such that physical precise orientation of the OMD within the read area is not critical. For reflection-type readers, it is only necessary for the OMD to be right side up and the symbol is fully within the field of view of the detector, so that the symbol 106 is exposed to the image sensor. Even where reading is accomplished by transmission of light through the OMD, as in certain polypropylene embodiments, an orientation indicator in the symbol in combination with a distinctive physical or optical feature, such as described below, can provide information sufficient to determine whether the OMD is face up or face down so that appropriate compensation, such as reversal of the image, can be performed by the software in order to enable decoding.

An alternative means for recording and reading information involves the formation of a magnetic film on at least a portion of the surface of the OMD. Creation of thin magnetic films by sputtering, electroplating, or other deposition techniques are well known in magnetic recording technology. [See, e.g.,Chapter 11, "Tape and Disk Materials" from *The Complete Handbook of Magnetic Recording*, 3rd Edition, by Finn Jorgenson, Tab Books, 1988.] Recording and reading of data on the magnetic film can utilize conventional magnetic recording techniques.

The OMD 200 of FIG. 23 is a variation on the embodiment of FIG. 22 that provides a information recording section that is formed from a separate material from that of the binding surface(s) [i.e., the chemistry surface(s) or the surface(s) to which molecules or biological particles are linked]. In this embodiment, the OMD contains two sections that are linked together. Here, OMD 200 is formed from the assembly of information unit 202 and binding unit 204, with unit 202 fitting within a cavity or well 206 formed in unit 204. This embodiment provides the advantage of selecting the optimal material for each of the binding and recording processes, and also permits the information unit 202 to be assembled with the binding unit 204 after the binding unit has been treated to enhance adhesion. For example, binding unit 204 can be formed from a polymer, e.g., polypropylene, functionalized by radiation and/or chemical processes, or can be modified by bonding polystyrene microspheres to its surface(s). Information unit 202 can be formed from plastic, ceramic or glass, and mounted within well 206 by adhesive or other bonding process, or may simply be press fit into the well. Since pre-treatment of the binding unit to enhance binding could possibly discolor the information unit, or otherwise make it less readable by modifying the surface, e.g., pitting or etching, separate formation could be advantageous. The outer dimensions of unit 202 are preferably selected to closely fit the inside dimensions of well 206 to prevent the intrusion of chemicals, or even air, into spaces between the units. In the illustrated example, unit 204 has outer dimensions of 280 mil (L)×140 mil (W)×100 mil (T) [7 mm×3.5 mm×2.6 mm] and unit 202 has maximum dimensions of 210 mil (L)×115 mil (W)×50 mil (T) 15.3 mm×2.9 mm×1.3 mm]. Since, as shown, the sides of unit 202 are beveled to form a trapezoidal cross-section to conform to a corresponding shape of the well 206, and also to assist in forming a tight seal between the two units, the actual exposed face of the information unit is on the order of 105 mil×200 mil [2.7 mm×5 mm]. When the two units are assembled, the combined face surface of the information and binding units are preferably flush. As can be seen, the encoded information, shown as a two-dimensional bar code symbol 208, is inscribed on information unit 202 only. With regard to the magnetic recording alternative method, the use of a separate information unit is ideal since it would generally be preferred to avoid exposure of magnetic recording media to the radiation or corrosive chemicals used for enhancement of the binding process.

Variations on the two-part OMD of FIG. 23 are illustrated in FIGS. 25–27. In FIG. 25, OMD 400 is illustrated where insert unit 402 is the binding unit formed, for example, from polymer functionalized by radiation and/or derivatized by suitable chemical processes or grafted to render the surface suitable for binding biological particles and molecules. Base unit 404, which may be formed from plastic, polymer, ceramic or glass, has a well 406 corresponding to the exterior shape of the binding unit 402, so that they will interfit closely. The encoded information, shown, again, as a two-dimensional bar code symbol 412, is inscribed on the back 408 of base unit 404, opposite the face 410 at which binding unit 402 is exposed.

In FIG. 26 [an embodiment of a microvessel], insert unit 502 has a cavity 508 covered by mesh 510 [porous material] for retaining particles but permitting chemical materials and biological particles to pass through, to form OMD 500. The chemicals pass through mesh 510 to be within cavity 508, or some material contained therein, such as microspheres, or are retained on the strands of mesh 510. As in the embodiment of FIG. 25, base unit 504, which is encoded with the symbology, receives the binding [chemistry] unit so that it is exposed on one face 512, with the encoded information 514 located on the opposite face 516.

In the embodiment of FIG. 27, insert unit 602 is formed from polypropylene or ceramic or other suitable material and provides the information storage face 608 for writing symbology, preferably a bar code symbol 610 on OMD 600. Base unit 604 provides the means for binding of chemical materials, which contains cavity 612 which is filled with microspheres 614 and covered with polypropylene screen 616 or other suitable porous material. The base material is preferably polypropylene or other such material. In this embodiment, the information storage face 608 is on the opposite side of the OMD from the screen 616.

In yet another embodiment, OMD 700, which is illustrated in FIG. 28, an orientation indicator is provided in the form of a notched or cut-corner 702. In this embodiment, the corner cut-out 702 will provide information as to the rotation and inversion of OMD 700, since, even if the OMD is face down, it will be apparent due to the unique outline of the face. The use of a physically detectable orientation indicator allows the handling equipment to readily detect improper positioning, for example, by placement of mechanical or optical edge detectors within the handling system. An improperly positioned OMD can be removed from the imaging position and placed back at the entry point into the reading handler, or mechanical means, such as a retractable blade, can be provided to flip the OMD over if it is presented face down within the field of view of the reader. An alternative symbology 706 is illustrated which is, in this case, an alphanumeric code, which can be read and decoded using known optical character recognition (OCR) techniques.

Other types of orientation indicators that can be used include chamfers, holes and protrusions. Several different and distinctive shapes can be included on a single OMD to assist in orientation, positioning and separation of the OMDs. For example, a group of OMDs can have a cut corner for orientation of each OMD, with some of those OMDs having a tab extending from one of its sides, so that those with tabs can be separated from those without tabs, which facilitates division of the group for diversion to different containers.

Additional test media can be included in the OMD in the embodiment of FIG. 29. Here, the OMD 800 has a plurality of wells or recesses 804 into which can be placed gels, beads, or the like for retaining additional chemical [molecules] or biological materials [biological particles], and/or chemical, biological or temperature sensors, or other such devices. Where such materials are placed in the wells 804, the bar code symbol 806 can include information about the nature of these materials.

The embodiment of FIG. 30 is a variation on that of FIG. 29. Here, the OMD 900 is partially hollow, and a plug 902 is formed in the side to permit access to the cavity 912. The front 904 and/or back 908 walls of the OMD have a mesh insert 910 which provides limited access to the cavity 912 in the OMD. A chemically- or biologically-functional material [biolgocial particle or molecule], or microspheres, for example, can be placed within the cavity 912 through plug 902 so that it is exposed to the chemical or biological materials to which the OMD is exposed without allowing direct contact between the material in the cavity and the environment in which the OMD is placed. The mesh [porous material] 910 can be polypropylene or other such suitable polymer, and of a size that makes it semi-permeable, admitting the external solution without allowing the interior material to escape. Generally, the pore size will be within the range of 20 $\mu$m to 200 $\mu$m.

Reading and Writing to Matrices with Optical Memories

Figure 24:
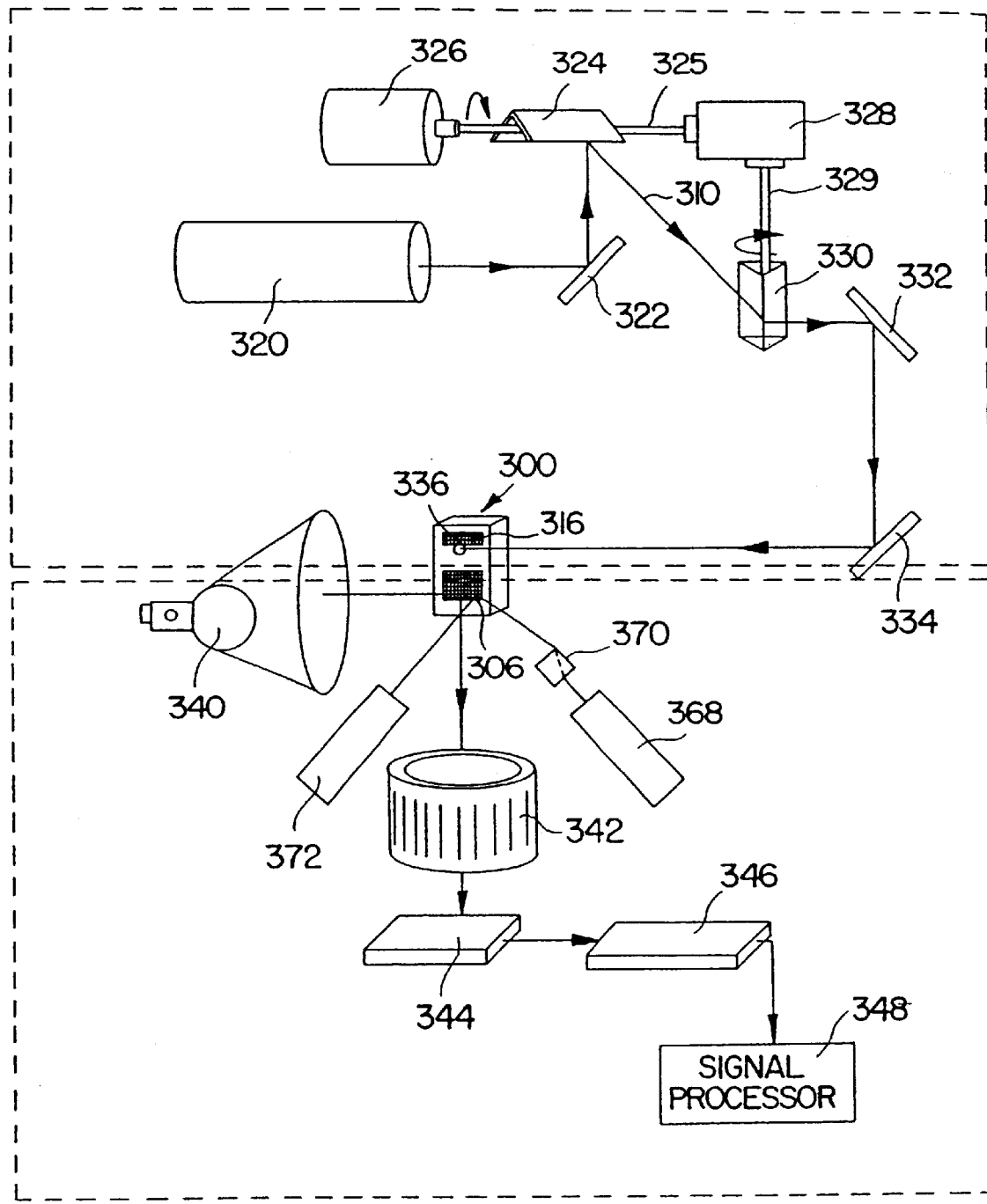
FIG. 24 is a diagrammatic view of the optical write and read for the optical memory devices.

An exemplary read/write system is illustrated in FIG. 24. The write system includes laser 320, mirror 322, and prism 324 mounted on drive shaft 325 connected at a first end to drive motor 326. Drive shaft 325 is connected at its second end to geared linkage 328 which rotates drive shaft 329 and prism 330 in synchrony with prism 324. The beam emitted by laser 320 follows optical path 310 to mirror 322, where it is reflected toward prism 324. Prism 324 rotates to scan the beam along the y-axis, i.e., up and down, so that the beam effectively shifts top to bottom by reflection from the prism faces in succession as it rotates. This beam is similarly scanned along the x-axis from left to right by reflection from the faces of prism 330 in succession as prism 330 rotates. Either or both prisms can be replaced with rotating or oscillating mirrors to achieve the same scanning pattern, in a manner similar to the scanning mechanisms used in conventional laser-based bar code scanners. See, e.g., U.S. Pat. No. 4,387,297 to Swartz, et al., entitled "Portable Laser Scanning System and Scanning Methods", and U.S. Pat. No.

4,409,470 to Shepard, et aL, entitled "Narrow Bodied, Single- and Twin-Windowed Portable Laser Scanning Head for Reading Bar Code Symbols", the disclosures of which are incorporated herein by reference. Mirrors 332 and 334 provide means for directing the beam toward the OMD 300 at the appropriate level, and, thus, are positioned in consideration of the guide means, so that the beam impinges upon the desired recording surface.

As illustrated in FIG. 24, OMD 300 has already been inscribed during an earlier process step, evidenced by the fact that symbology 306 is present and complete. Also as illustrated, symbology 316 is currently being written by the progression of laser spot 336 across the write surface, as scanned by prisms 324 and 330. The contrasting dark and light areas of the symbologies 306,316 are created by pulsing the laser 320 according to a signal provided by system controller 338.

In an exemplary embodiment, laser 320 is a $CO_2$ laser, which emits light in the infrared at a wavelength of 10.6 µm. The writing process is accomplished by using a sufficiently high power beam to burn the surface of the OMD, formed of ceramic, white polypropylene or the like, to produce a dark carbon build-up corresponding to the dark lines of the symbology on the lighter colored background. The exemplary laser power is 25 W, with a spot size of 0.03 mm, burning a dot in the write surface of 0.13 mm, to create a two-dimensional bar code using a dot matrix pattern. Mirrors 322, 332 and 334, and prisms 324 and 330 must be coated with an appropriate IR-reflective film to avoid damage to the optics by the laser. In read systems which utilize transmission of light through the OMD, the carbon build-up will block the light, appearing as darkened areas to a sensor on the opposite side of the OMD from the light source. In read systems which utilize back-reflection, the carbon build-up will absorb light, while the other areas will reflect the light, again creating a contrast between the inscribed and untouched areas of the surface.

Since the IR write beam is not visible, it may be desirable to use an optically-visible laser 336, for example, He—Ne or a diode laser which emits within the visible spectrum, or other focussed light source, to emit a beam along optical path 310 to permit visual alignment. Optically-visible laser 339 may also be used as a proximity detector to send a signal to the system controller to indicate the presence of the OMD in the write position to trigger the write process, either by reflection or by blocked transmission using conventional optical sensors. Alternatively, a separate optical detector system may also be used to detect and indicate the presence of an OMD in the write or read position.

For OMDs formed from glass or ceramic, a beam from a $CO_2$ laser can be used to etch the glass to produce contrasting lines by modifying the surface finish of the glass. For example, the glass can be frosted or otherwise roughened, which may assist in the binding of compounds, and which has a reduced reflectivity. Upon exposure to the high power write beam, the glass surface is partly flowed, i.e., partly melted, so that a smooth, highly reflective surface remains after the surface cools. Contrast between the frosted and flowed glass can be enhanced for reading by selecting a read wavelength which maximizes the differences in reflectivity between the two surface finishes.

Other types of lasers which may be used include neodymium-YAG [yttrium-aluminum-garnet], excimer, or any other laser capable of emitting a sufficiently high power beam to modify the material surface to produce an optically-readable contrast. Alternative lasers for the writing process include diode lasers, such as those made by Coherent, Inc. of Santa Barbara, Calif. Among those that are suitable are Model No. S-98-2000C-200-C, T or H, which emit light at 980 nm with a CW power of 2000 mW, Model No. B1-81-10C-19-30-A or W, which emit light at 808 nm with a CW power of 10,000 mW, or Model No. B1-81-15C-19-30-A or W, which emit light at 808 nm with a CW power of 15,000 mW.

Selection of the laser will depend on the material of which the OMDs are formed. For example, if an optically-reactive material is encased within a transparent glass or plastic shell, any laser capable of inducing the readable change in the optically-reactive material would be acceptable. Photochemically-reactive media, such as that disclosed for the "Optical Data Storage System" which is the subject of U.S. Pat. No. 5,136,572 to Bradley, incorporated herein by reference, can be selectively activated and read by use of wavelength tunable diode lasers, such that a lesser power and/or visible light laser can be used with a more reactive recording media.

Figure 32:
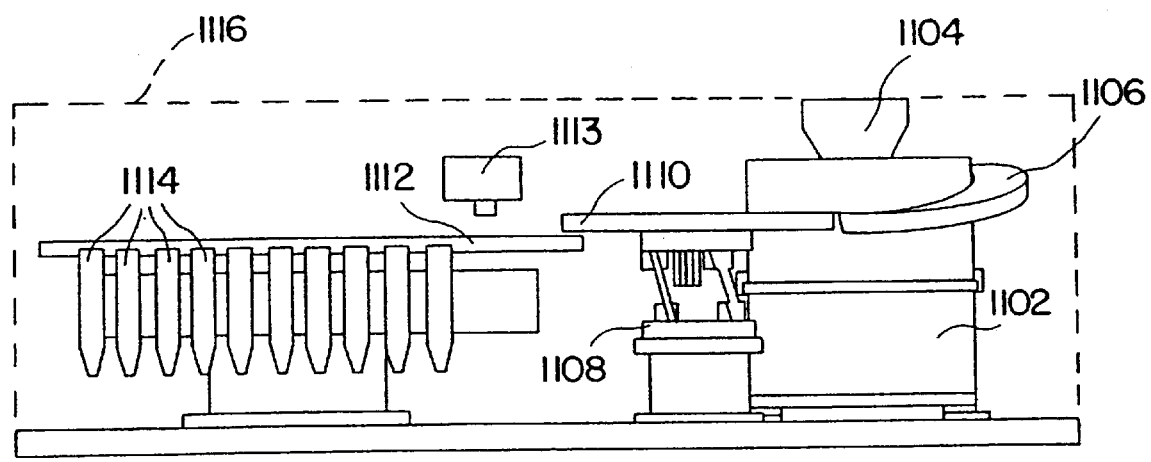
FIG. 32 is a diagrammatic view of an exemplary handling system for feeding, reading and distributing the optical memory devices.

The range of movement of the laser spot 336 is limited, generally to the area of the write surface, so that the OMDs must be moved past a target area within which laser spot 336 is projected. Movement of the OMDs can be achieved by one or more sets of conveyor belts 370, chutes or guide rollers, each of which can be fed by a commercial-type centrifugal feeder, such as those available from Hoppmann Corporation of Chantilly, Va. and Kirchlintein, Germany. Feeders of this type are known in industry for mass handling of parts and products, including foods, pharmaceuticals, containers and hardware. Linear and vibratory feeders are also known and may be used for handling the OMDs. An exemplary handling system is illustrated in FIG. 32 and will be discussed in more detail below.

Included in the proximity location process to detect the presence of an OMD within the write position can be a detector 372 for locating the next available area on the write surface for writing. In the example illustrated in FIG. 24, for a write surface having four available locations, position #1 is already filled with symbology 306, and position #2 is in the process of being filled with symbology 316. A light source 368, such as a visible laser, emits a beam which is directed by scanning optics 370 toward the write surface of the OMD. As the write surface is scanned by the beam, the next available area detector 372 can look sequentially at each OMD as its presence is detected, first at position #1, then at subsequent positions until it finds an area on which no symbology is written, i.e., no contrasting markings are detected, or a "white" area of a pre-determined width is detected which is wider than the "quiet Zone" which is commonly included in bar codes. [See, e.g., Wang, et al., "A High Density Two Dimensional Bar Code," SPIE Proceedings Vol. 1384, High-Speed Inspection Architectures, Bar Coding, and Character Recognition (1990) pp. 169–175.] This location process permits multiple uses of OMDs, and takes into consideration that some OMDs may be exposed to a greater number of process steps than others before being combined into the string in which they are presently included.

The detector 372 can also be used for indication of the presence of OMDs to be read. In the case of reading, the detector 372 can also be used to identify the presence of all symbologies to be scanned for reading, which is particularly important if a laser beam or other relatively narrow beam of light is scanned over the written surface to read the symbology. Where an incoherent light source is used to simply flood the entire write surface with light, such as a lamp 340, the ability to detect the presence of individual symbologies is not critical, since the entire write surface will be viewed and recorded at once using frame grabbing techniques.

During the read process, after the presence of an OMD is indicated, the lamp 340 is activated to illuminate the write surface. The light reflected from the surface is modulated by the symbology printed thereon due to the selective reflection and absorption of the contrasting areas. Optics 342, which will typically be an assembly of lenses and filters, which remove stray light, focus the reflected light onto detector 344. Selection of optics can be performed in a manner similar to that disclosed in U.S. Pat. No. 5,354,977 of Roustaei, incorporated herein by reference, which describes an optical bar code scanner using a CCD [charge-coupled device] detector and associated optics. In the same reference, a detailed description of CCD detectors for use in bar code scanners is provided, as well as steps for processing the signal generated by the CCD detector.

In the exemplary embodiment illustrated in FIG. 24, the CCD detector 344 comprises an array of discrete devices, each of which is a "pixel", capable of storing charge impinging upon it representative of reflected light from the write surface, then reading out the charge as a serial analog waveform. A typical CCD array for bar code scanning has 2048 pixels, however, CCD arrays of other dimensions may be used. In the preferred embodiment, a CCD array of 640×480 pixels is used. Using the CCD array, a "snap shot" of the OMD surface is created using known image or frame grabbing techniques, and an analog electrical representative of the snap shot is conducted to the signal processing function 348 within the system controller, which includes an analog-to-digital converter, to convert the signal into an output of the data written on the OMD.

In a preferred embodiment, the detector is a commercially-available, PC-interfaceable CCD camera sold under the trademark QuickCam™ by Connectix Corporation of San Mateo, Calif., which has a resolution of 640×480 pixels. Any other such camera may be used. The camera has a manually-adjustable focus lens, but image acquisition is otherwise controlled by the system controller 348, which, as part of its software, initializes the camera for frame grabbing. Any such PC-interfaceable CCD camera with a similar or better resolution may be used.

For example, other types of detector arrays are known within the bar code scanning technology, including CMOS sensors, such as described in the article entitled "CMOS in camera", *IEE Review*, May 1994, p. 111, incorporated by reference, which are also capable of generating "snap shots" of the data written on the OMD and could be used in place of the CCD detector array 344.

Processing of the image grabbed by the image detector is a significant aspect of the system in that it provides the flexibility to manipulate the image to enhance readability. The steps of the exemplary image processor are provided in the flow diagram of FIG. 31, and the image signal generated by the detector is checked for completeness, validity and orientation, among other things. As discussed above, if systems where physical orientation and positioning of the OMD is not assured by the handling hardware, one aspect of the image processing software is to determine skew or rotation of the image as seen by the detector.

Figure 31:
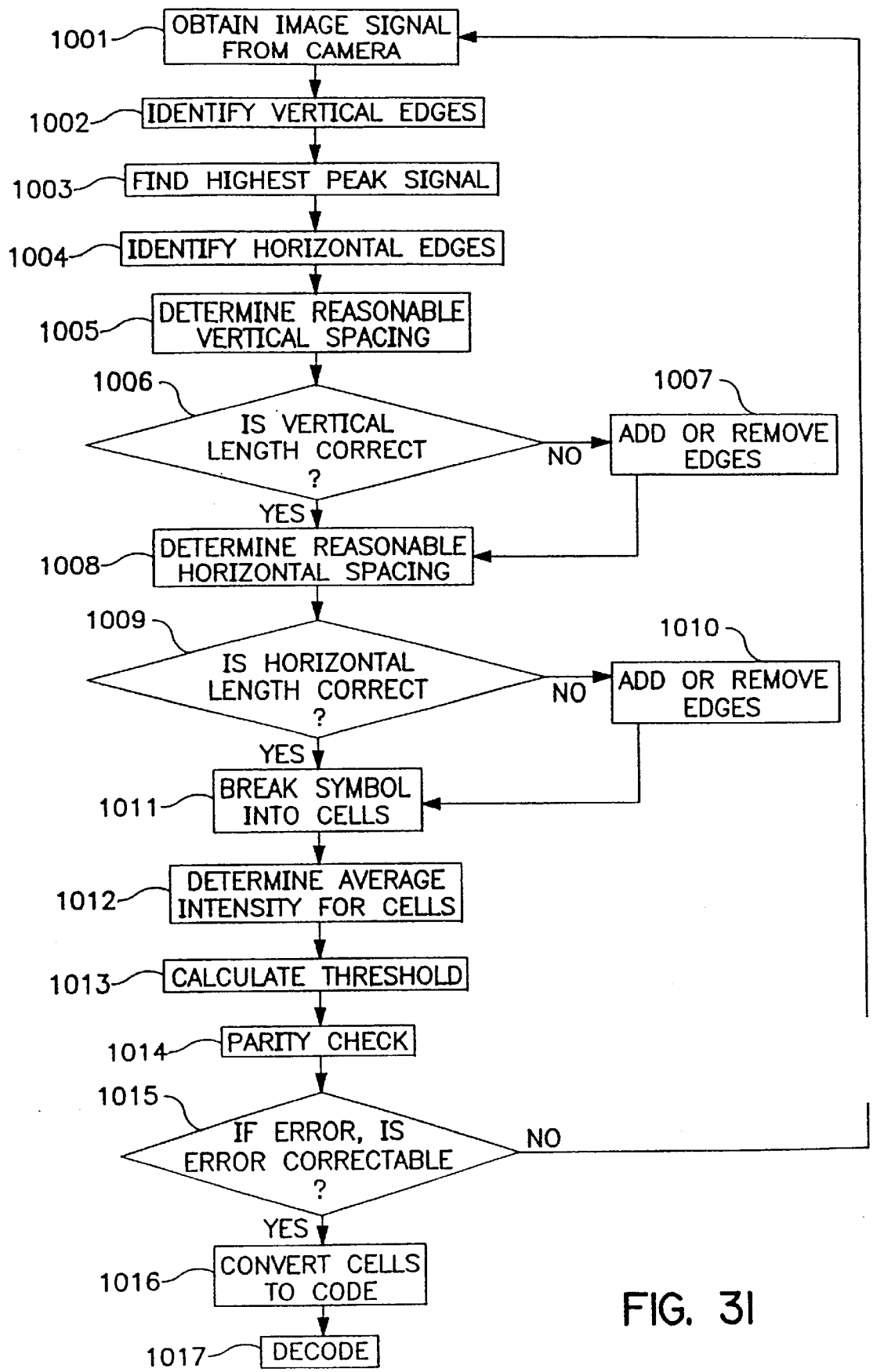
FIG. 31 is a flow diagram of the image processing sequence for a two-dimensional bar code on an optical memory device.

The following steps are provided in detail in the system processor's software, the code for which is provided as a Microfiche Appendix, and a portion of which is depicted in the flow diagram of FIG. 31. [Note that the actual image obtained from the camera can be displayed on a system monitor as it is being modified to permit decoding.] First, after obtaining the image from the camera [step 1001], in steps 1002 and 1003, the edges of the symbol in the vertical direction are identified, looking for the highest peak signal to provide a reference, then the horizontal edges are found [step 1004]. Knowing the boundaries of the symbol, the reasonable spacing is determined [step 1005] to correct for missing or extra vertical edges using a neural network approach. Based on the reasonable spacing, it is determined if the length of the vertical edge is appropriate [step 1006]; if not, adjustments are made by adding or removing edges [step 1007]. A similar procedure is used for the horizontal edges [steps 1008–1010], allowing skew to be determined. Having determined the orientation and spacing of the symbol, the symbol is broken into sections [step 1011], or cells, and the average intensity for each cell is determined [step 1012] to permit calculation of the threshold [step 1013] for distinguishing a dark from a light area of the code. Following this, parity checks are performed [step 1014] to provide an indication of whether the complete symbol was detected, i.e., the correct number of bits was obtained, or whether the signal was corrupted. In the preferred embodiment, 17 bits of the data contained within the two-dimensional bar code are dedicated to parity checking. At this point, if a corrupted signal is indicated, and the error is not corrected [step 1015], rather than proceeding with an attempt to decode, the image processor initiates a new scan of the symbol [step 1001]. If the signal is good, the cells are converted to code [step 1016] which is decoded [step 1017].

The image processing system converts the stored image into a series of rows [and columns for two-dimensional codes] containing binary data, with dark lines indicating highs, or ones, and white lines indicating lows, or zeroes [or vice versa]. To enhance accuracy, a number of processing steps may be performed, and the resulting data can be the average of all processing steps for that particular image.

Although efforts are taken initially to avoid modification of the surface on which the information is written, because each OMD is presumably being subjected to a significant number of process steps, the appearance of the symbol may degrade with time due to accumulation of chemicals or surface roughening, resulting in decreased contrast between the light and dark lines of the code. This issue can be addressed with software, which can compensate for the deterioration of the symbol. In a preferred embodiment, the software includes neural network algorithms which can be trained to learn the specific cumulative effects of chemical processing and compensate by either recalibrating the detector, for example, to increase the exposure time, to modify the illumination, to increase the number of verification decode steps used for averaging, or to adjust the threshold between "dark" and "light". Two appropriate commercially-available neural network programs are Thinks™ and ThinksPro™ [published by Logical Designs Consulting, Inc. La Jolla, Calif.; see, U.S. Pat. No. 5,371, 809], which are designed to run on personal computers, and provides numerous different and well known training algorithms and methods. Other neural network software products are commercially available, including Neural Works Professional™ by NeuralWare, NeuroShell2™ by Ward Systems, BrainMaker Professional™ by California Scientific, and Neural Net Tool Kit™ by Math Works. Each could be used for training of the signal processor to compensate for degraded contrast in the symbol, and selection of the appropriate program or creation of an appropriate program would be within the level of skill in the art.

FIG. 32 provides a diagram of an exemplary handling system for separating and reading and/or writing to an OMD, particularly those in the shape of a parallelopiped. Such handlers are commercially avaiable [e.g., from Hoppmann Corporation, Chantilly, Va., see, U.S. Pat. Nos. 5,333,716, 5,236,077, 5,145,051, 4,848,559 4,828,100, 4,821,920, 4,723,661 and 4,305,496]. The OMDs are placed in vibratory feeder 1102 by way of supply hopper 1104. Vibratory feeder 1102 includes rings and ramps [not shown] which support the OMDs as they move within the feeder, driven by the feeder's vibration in a direction toward exit chute 1106. An orientation rim, bar, or other feature [not shown] may be included in the internal ramps or exit chute to rotate the OMDs when a physical orientation indicator, such as the cut corner, is provided. Exit chute 1106 feeds the OMDs to ramp 1110 of linear feeder 1108. The reciprocating motion of the ramp 1110 causes the OMDs to move forward [to the left in the figure] toward walking beam 1112 and within the field of view of camera 1114. [Where a write operation is to be performed, the write laser and optics can be positioned in place of or nearby the camera.] Movement of the walking beam 1112 is stepped so as to pause advance motion of the OMD to allow writing and/or reading of the appropriate information.

After completion of the writing or reading step, the OMD is advanced along the walking beam 1112 toward one or more vials or flasks 1114 containing chemical or biological solutions. Ramps [not shown] leading from the walking beam to the vials or flasks 1114 can be selected by opening gates, or by tilting the walking beam 1112 in front of the selected vial, thus feeding the OMD into the desired vial for the next process step. The vials or flasks 1114 can be fixed within a tray or rack that allows it to be removed after the processing has finished so that the OMDs can be dumped into the hopper of the same or another feeder to repeat the above steps for handling, writing, reading, and distributing the OMDs to the next process step.

It may be desirable to include a protective enclosure 1116, such as a polycarbonate and polyphenylene oxide resins, preferably the polycarbonate resin sold under the name LEXAN™ [the well known polycarbonate resin commercially available from General Electric Corp, Waterford, N.Y., or MERLON™ made by Mobey Chemical Co., Pittsburg, Pa.] or the resin sold under the trademan NORYL [from General Electric Corp] other such polymer such as polyethylene, lucite, bakelite and other such resins that have high tensile and impact strength over a broad temperature range, are virtually shatter-proof and are extrudable as transparent sheets, over the handling system to prevent contamination of the OMDs and solutions as well as for the safety of the system operator.

C. Data Storage Units with Memory

In embodiments in which OMDs are used, the programmable devices are remote memories, such as computers into which information regarding the encoded information and linked molecules and biological particles is stored. The OMDs are read/write devices or are precoded devices.

For use with the matrices in which the memory, rather than a code, is linked to the device, any remotely programmable data storage device that can be linked to or used in proximity to the solid supports and molecules and biological particles as described herein is intended for use herein. Preferred devices are rapidly and readily programmable using penetrating electromagnetic radiation, such as radio frequency or visible light lasers, operate with relatively low power, have fast access [preferably 1 sec or less, more preferably $10^2$–$10^3$ sec], and are remotely programmable so that information can be stored or programmed and later retrieved from a distance, as permitted by the form of the electromagnetic signal used for transmission. Presently preferred devices are on the order of 1–10 mm in the largest dimension and are remotely programmable using RF or radar.

Recording devices may be active, which contain a power source, such as a battery, and passive, which does not include a power source. In a passive device, which has no independent power source, the transmitter/receiver system, which transfers the data between the recording device and a host computer and which is preferably integrated on the same substrate as the memory, also supplies the power to program and retrieve the data stored in the memory. This is effected by integrating a rectifier circuit onto the substrate to convert the received signal into an operating voltage.

Alternatively, an active device can include a battery [see, e.g., U.S. Pat. No. 5,442,940, U.S. Pat. No. 5,350,645, U.S. Pat. No. 5,212,315, U.S. Pat. No. 5,029,214, U.S. Pat. No. 4,960,983] to supply the power to provide an operating voltage to the memory device. When a battery is used the memory can be an EEPROM, a DRAM, or other erasable memory requiring continuous power to retain information. It may be desirable to combine the antenna/rectifier circuit combination with a battery to create a passive/active device, with the voltages supplied by each source supplementing each other. For example, the transmitted signal could provide the voltage for writing and reading, while the battery, in addition to supplementing this voltage, provides a refresh voltage for a DRAM memory so that data is retained when the transmitted signal is removed.

The remotely programmable device can be programmed sequentially to be uniquely identifiable during and after stepwise synthesis of macromolecules or before, or during, or after selection of screened molecules. In certain embodiments herein, the data storage units are information carriers in which the functions of writing data and reading the recorded data are empowered by an electromagnetic signal generated and modulated by a remote host controller. Thus, the data storage devices are inactive, except when exposed to the appropriate electromagnetic signal. In an alternative embodiment, the devices may be optically or magnetically programmable read/write devices.

1. Electromagnetically programmable devices

The programmable devices intended for use herein, include any device that can record or store data. A preferred device will be remotely programmable and will be small, typically on the order of 10–20 mm³ [or 10–20 mm in its largest dimension] or, preferably smaller. Any means for remote programming and data storage, including semiconductors and optical storage media are intended for use herein.

Also intended for use herein, are commercially available precoded devices, such as identification and tracking devices for animals and merchandise, such those used with and as security systems [see, e.g., U.S. Pat. Nos. 4,652,528, 5,044, 623, 5,099,226, 5,218,343, 5,323,704, 4,333,072, 4,321,069, 4,318,658, 5,121,748, 5,214,409, 5,235,326, 5,257,011 and 5,266,926], and devices used to tag animals. These devices may also be programmable using an RF signal. These device can be modified, such as by folding it, to change geometry to render them more suitable for use in the methods herein. Of particular interest herein are devices sold by BioMedic Data Systems, Inc, NJ [see, e.g., the IPTT-100 purchased from BioMedic Data Systems, Inc., Maywood, N.J.; see, also U.S. Pat. Nos. 5,422,636, 5,420,579, 5,262,772, 5,252, 962, 5,250,962, and see, also, U.S. application Ser. No. 08/322,644, filed Oct. 13, 1994]. ID tags available from IDTAG™ Inc, particularly the IDT150 read/write transponder [ITDAG™ Ltd. Bracknell, Berks RG12 3XQ, UK, fabricated using standard procedures and the method for coil winding, bonding and packaging described in International PCT application Nos. WO95/33246, WO95/16270, WO94/24642, WO93/12513, WO92/15105, WO91/16718; see, also U.S. Pat. Nos. 5,223,851 and 5,281,855] are also preferred herein. The IDT150 is a CMOS device that provides a kilobit of EEROM. This transponder also includes a 32 bit fixed code serial number that uniquely identifies each chip. The IDTAG™ transponder transmits data to a transceiver system by amplitude modulating its coil and generating an EM field. It receives data and commands from a transceiver by demodulating the field received by the coil and decoding the commands. The transponder derives its power source from a frequency emitted in the signal from the reader, to which the transponder emits a response. A smaller version [that has 16 bit EEROM] and is about 11 mm×4 mm×3 mm of this transponder is also among preferred devices. These transponders are packaged in glass or polystyrene or other such material.

In a preferred embodiment herein, the data storage unit includes a semiconductor chip with integrated circuits formed thereon including a memory and its supporting circuitry. These devices can be written to and interrogated from a distance. A radio frequency transmitter/receiver system supplies power to program and retrieve data. In particular, the data storage unit preferably includes a programmable read only semi-conductor memory [PROM], preferably a non-volatile memory or other memory that can store data for future retrieval, that will have information describing or identifying the molecules or biological particles linked to or in proximity to the matrix. This information either identifies the molecule or biological particles including a phage and viral particles, bacteria, cells and fragments thereof, provides a history of the synthesis of the molecule, or provides information, such as a batch number, quality control data, reaction number, and/or identity of the linked entity. The memory is programmed, before, during or, preferably, after, each step of synthesis and can thereafter be read, thereby identifying the molecule or its components and order of addition, or process of synthesis.

While many well known read only memory devices use fuse structures that are selectively "blown" to store data points, with a fuse located at each possible data address in an array, among the devices of interest herein are those that rely on antifuse programming technology, in which short circuits are selectively created through an insulating layer separating word and bit lines in an array. Due to the relatively low level of voltage supplied by the transmitted signal when the memory device is passive, antifuse memories are readily used because of the lower voltage requirements for writing.

Thus, suitable memory devices, are about 1–20 mm in the smallest dimension [or smaller], are rapidly programmable [1 sec, preferably 1 sec or less], can be interrogated from a distance [distances of about a centimenter up to about an inch are presently preferred], and are programmable using electromagnetic radiation, preferably frequencies, such as those within the radio frequency range, that do not alter the assessed activities and physical properties of the molecules and biological particles of interest.

Devices that rely on other programmable volatile memories are also intended for use herein. For example, a battery may be used as to supply the power to provide an operating voltage to the memory device. When a battery is used the memory can be an EEPROM, a DRAM, or other erasable memory requiring continuous power to retain information. It may be advantageous to combine the antenna/rectifier circuitry with a battery to create a passive/active device, in which the voltages supplied by each source supplement each other. For example, the transmitted signal could provide the voltage for writing and reading, while the battery, in addition to supplementing this write/read voltage, provides a refresh voltage for a DRAM memory so that data is retained when the transmitted signal is removed.

a. Antifuses

An antifuse contains a layer of antifuse material sandwiched between two conductive electrodes. The antifuse device is initially an open circuited device in its unprogrammed state and can be irreversibly converted into an essentially short circuited device by the application of a programming voltage across the two electrodes to disrupt the antifuse material and create a low resistance current path between the two electrodes.

An exemplary antifuse structure for use herein is formed by defining a word line of heavily N-doped polysilicon on an insulating substrate, depositing an antifuse layer of lightly N-doped semiconductor over the polysilicon, and defining a metal address [or bit] line upon and in electrical contact with the antifuse layer. The semiconductor material used for the antifuse layer is typically selected from among silicon, germanium, carbon and alpha-tin. The properties of the semiconductor material are such that the material is essentially non-conductive as long as the voltage across it does not exceed a threshold level. Once the threshold voltage is exceeded, a conductive filament is formed through the semiconductor so that the resistance between the metal and polysilicon lines at the points at which they cross irreversibly switches from a high resistance state to a relatively low resistance state.

To program or change the resistance of the antifuse from a very high level [greater than 100,000,000 ohms] to a low level [less than 1000 ohms], a voltage of sufficiently high electrical field strength is placed across the antifuse film to create a short circuit. The voltage level required to induce breakdown is determined by the level of dopant in the antifuse layer. As breakdown occurs electrical current will flow through one small region of the film. The current is limited by the resistance of the filament itself as well as any series resistance of conductive layers or logic devices [transistors] in series with the antifuse.

Examples of the antifuse and its use as a memory cell within a Read-Only Memory are discussed in Roesner et al., "Apparatus and Method of Use of Radio frequency Identification Tags", U.S. application Ser. No. 08/379,923, filed Jan. 27, 1995, Roesner, "Method of Fabricating a High Density Programmable Read-Only Memory", U.S. Pat. No. 4,796,074 (1989) and Roesner, "Electrically Programmable Read-Only Memory Stacked above a Semiconductor Substrate", U.S. Pat. No. 4,442,507 (1984). A preferred antifuse is described in U.S. Pat. No. 5,095,362. "Method for reducing resistance for programmed antifuse" (1992) [see, also U.S. Pat. No. 5,412,593 and 5,384,481].

U.S. Pat. No. 5,095,362 provides a method for fabricating a layer of programmable material within an antifuse that exhibits relatively lower than normal resistance in its programmed state and also provides a semiconductor device containing an antifuse film of the type composed of semiconductor material having a first electrical state that is characterized by high electrical resistivity and a second electrical state that is characterized by low electrical resistivity.

The means for selectively decreasing resistivity includes nonactivated conductive dopants that are ion implanted within the otherwise highly resistive semiconductor material. The dopants as implanted are in a nonactivated state so that the dopants do not enhance the conduction of carriers in the film. Once activated, the dopants enhance the conduction of carriers in the film. Activation of the dopants occurs upon application of a threshold voltage across a predetermined and selected portion of the material in which the dopants are disposed. The selected portion is defined by the crossover point of selected word and bit [or address] lines. The dopants are N-type, selected from among antimony, phosphorous, arsenic, and others to provide additional charge carriers. The implant dosage is used to determine the threshold voltage level that will be required to induce formation of the conductive filament. P-type dopants, such as boron, may also be used to affect a change in programming voltage.

b. A Recording Device with Non-volatile, such as Anti-fuse-based, Memory

Figure 5:
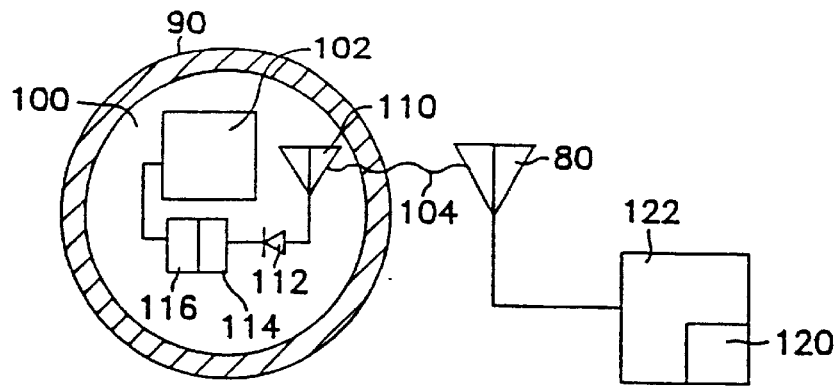
FIG. 5 is a block diagram of the data storage means and supporting electrical components of a preferred embodiment.

FIG. 5 depicts a recording device containing a non-volatile electrically-programmable read-only memory [ROM] 102 that utilizes antifuse technology [or EEPROM or other suitable memory] is combined on a single substrate 100 with a thin-film planar antenna 110 for receiving/transmitting an RF signal 104, a rectifier 112 for deriving a voltage from a received radio frequency [RF] signal, an analog-to-digital converter [ADC] 114 for converting the voltage into a digital signal for storage of data in the memory, and a digital-to-analog converter [DAC] 116 for converting the digital data into a voltage signal for transmission back to the host computer is provided. A single substrate 100 is preferred to provide the smallest possible chip, and to facilitate encapsulation of the chip with a protective, polymer shell [or shell+matrix or matrix material] 90. Shell 90 must be non-reactive with and impervious to the various processes that the recording device is being used to track in order to assure the integrity of the memory device components on the chip. Materials for the shell include any such materials that are known to those of skill in the art [see, es, Hiroshi et.al., eds. (1995) *Polymeric Materials for Microelectronic Applications: Science and Technology*, ACS Symposium Series No. 579], including glasses, ceramics, plastics and other inert coatings.

Based on current semiconductor integrated circuit fabrication process capabilities, in a preferred embodiment the finished chip on which all of the listed components are integrated is on the order of 1 mm×1 mm [~40 mils×40 mils], with a memory capacity of about 1024 bits, but can have greater or lesser capacity as required or desired. Greater memory capacity, where needed, and smaller chips, however, will be preferred. The chip may be larger to accommodate more memory if desired, or may be smaller as design rules permit smaller transistors and higher device densities, i.e., greater memory capacity.

The antifuse ROM structure described herein, and the method for fabricating the same, are based upon the teachings of U.S. Pat. No. 4,424,579, issued Jan. 3, 1984, U.S. Pat. No. 4,442,507, issued Apr. 10, 1984, U.S. Pat. No. 4,796,074, issued Jan. 3, 1989, and U.S. Pat. No. 5,095,362, issued Mar. 10, 1992, all of Roesner, U.S. Pat. No. 4,598,386, issued Jul. 1, 1986, of Roesner et al., and U.S. Pat. No. 5,148,256, issued Sep. 15, 1992 and U.S. Pat. No. 5,296,722, issued Mar. 22, 1994, both of Potash, et al and also U.S. application Ser. No. 08/379,923, filed Jan. 27, 1995, to Roesner et al., all of which are incorporated herein by reference.

In an antifuse-type memory device, the individual memory cells are arranged in arrays of orthogonal conductive word and bit lines to obtain the smallest possible memory array size. For example, for 1024 bits of memory, there are 32 word lines and 32 bit lines for a square array. Memories with greater capacity may also be used. Schottky diodes are formed generally corresponding to the points at which the word and bit lines cross. The word and bit lines are separated by an undoped or lightly-doped semiconductor layer with interstitial doping. The semiconductor layer may also be amorphous silicon with implanted dopants in a nonactivated state. Each of these crossover points is a memory cell and is the equivalent of a programmable switch in series with a Schottky diode. Data are stored by the switch being ON or OFF. As fabricated, an antifuse memory device has all of its switches in the OFF state. A switch is turned on by applying a voltage in excess of a pre-determined threshold voltage to one of the word lines while setting a selected bit line to a low logic level. The threshold voltage is determined by the impedance of the semiconductor layer, i.e., its doping level. According to the process for fabricating the antifuse memory of the preferred embodiment, the impedance can be less than 200 ohms with a threshold voltage for programming as low as 3 volts. Since in the embodiment described herein the programming voltage is provided solely by the rectified RF signal, a low threshold is preferred. Application of voltage exceeding the threshold activates the interstitial dopant in the semiconducting film at the point corresponding to the cross-over between the two lines, causing a short between the word and bit lines and irreversibly turning on that particular switch or memory cell. Address decoders, as are known in the art, are used to selectively address the word and bit lines for purposes of both writing information to and reading stored information from the memory array. [See, e.g., U.S. Pat. Nos. 5,033,623, 5,099,226, 5,105,190, 5,218,343, 5,323,704]. Exemplary means for decoding information to be stored in memory and to be read from memory are provided in U.S. Pat. No. 4,442,507 and U.S. Pat. No. 4,598,386.

Information to be written into the memory need not be detailed since the data stored in the memory is primarily acting as an identification marker that is traceable to a more detailed record stored in the host computer memory 120, independent of the memory associated with the matrix support or tagged molecule or biological particle. In this manner, the RF signal from transmitter 80 that is used to provide the power and the signal to the matrix particle memory need only address a single memory cell to indicate that a nascent oligomer linked to or in proximity to the memory device has been subjected to a given process step or to identify a molecule or biological particle. In other words, a conventional "push-pull" type of address decoder, where only one bit line and one word line are driven high and low, respectively, at any given time, may be used. Thus, a sophisticated memory addressing system need not be provided on the matrix particle memory chip, and shift registers may be used to control memory addressing. Alternatively, a microprocessor which is mask-programmed during the fabrication process for controlling an address bus which connects the ADC 114 and the DAC 116 to the memory array may also be built onto the same substrate on which the memory and other components are integrated. Other integrated means for selectively addressing locations within the memory are known and will be apparent to the practitioner skilled in the art.

As described above, antifuse memories are well known in the art. These memories include structures in which the word and bit lines may both be made of either N+polysilicon or metal [aluminum or aluminum-silicon], separated by silicon dioxide ($SiO_2$), silicon nitride ($Si_3N_4$), combinations thereof, or amorphous silicon alone or in combination with SiO$_2$ and/or Si$_3$N$_4$. In each case, a short circuit is created at locations in the antifuse material corresponding to the crossover location of selected word and bit lines by applying a voltage in excess of a pre-determined threshold voltage.

Examples of alternate means for forming an antifuse memory are provided in the following U.S. Pat. No. 5,248,632, issued Sep. 28, 1993, of Tung et al.; U.S. Pat. No. 5,250,459, issued Oct. 5, 1993, of Lee, U.S. Pat. No. 5,282,158, issued Jan. 25, 1994, of Lee; U.S. Pat. No. 5,290,734, issued Mar. 1, 1994, of Boardman, et al.; U.S. Pat. No. 5,300,456, issued Apr. 5, 1994, of Tigelaar et al.; U.S. Pat. No. 5,311,039, issued May 10, 1994, of Kimura, et al.; U.S. Pat. No. 5,316,971, issued May 31, 1994, of Chiang et al.; U.S. Pat. No. 5,322,812, issued Jun. 21, 1994, of Dixit, et al.; U.S. Pat. No. 5,334,880, issued Aug. 2, 1994, of Abadeer, et al., and others.

Generally for use in the methods herein, non-volatility of the memory or the ability to lock or prevent erasure is preferred since power is applied to the chip only when it is subjected to the RF or other transmission signal for reading or reading and writing. Further considerations are the voltage levels required for writing into memory, since the threshold voltage must be less than the maximum voltage of the rectified RF signal in order to assure that sufficient voltage is always available during the writing process. The write voltage may be enhanced by supplementing the RF-supplied voltage with optically-generated voltage, such as a photocell. Photocells on semiconductor substrates are well known in the art and could be easily integrated onto the chip. A laser or other light source could be readily included in the write apparatus to illuminate the chip coincident with transmission of the RF write signal. Similarly, other forms of electromagnetic radiation may be used to provide additional power, if needed.

Although antifuse memories are not designed to be erasable, it may be desirable to re-use the devices if the memory becomes full. In such instances, conventional electrically programmable erasable read only memories [EEPROMs] may be used instead. Since EEPROMs require higher write voltage levels, it may be desirable to supplement the RF-supplied voltage as described above. In EEPROMs, stored data can be erased by exposing the device to UV light.

Signal rectifier 112 may be one or more Schottky diode(s), making it readily incorporated into the fabrication process used for the memory array. Other means for signal rectification may be used as are known. The ADC 114 and DAC 116 are well-known devices and are readily integrated onto the substrate 100 using the fabrication process described in the references for the memory array. Radio frequency modulation techniques, which are known in the art, for example, pulse code modulation, may be adapted to permit direct digital transmission, in which case the ADC and DAC may not be required.

Antenna 110 is formed during the fabrication process using conventional photolithographic techniques to provide one or more metal structures, such as aluminum, to receive a pre-determined wavelength RF transmission. The antenna may be a simple straight line half-wave antenna which is created by patterning a structure during the second metal process steps so that the structure has a length equal to one-half of the wavelength of the selected RF transmission frequency in free space. Another option for formation of the antenna is as a small loop, either on a dedicated portion of the chip, or encircling the other components of the chip, also formed during the second metal step of the fabrication process. It is noted that, in a typical semiconductor fabrication process, such as would be compatible with the preferred antifuse memory, the first and second metal steps include depositing a layer of aluminum, then patterning the aluminum photolithographically followed by a plasma etch to define the desired features. Except where vias are formed, the two metal layers are separated by a dielectric film. Dipole antennas may be formed by patterning the second metal in a similar manner, with the dimensions of the antenna being selected for the appropriate RF frequency. The two metal layers may also be used to form a microstrip antenna structure by selecting the dielectric film between the metal layers such that it has a dielectric constant and thickness appropriate so that the microstrip is resonant at one-half of the RF wavelength. [The first metal layer provides the ground plane.] The metal structures, which may be square patches, circles, lines, or other geometries, are defined photolithographically during the normal masking steps of the first and second metal processes. Other antenna structures which can be configured as a thin film device for integration onto a common substrate with the memory structure and other components may be used and will be apparent to those skilled in the art. Similarly, a resonant circuit [inductor-capacitor] can be readily integrated onto the chip, with the resonant circuit being tuned to the RF carrier signal of the transmitter.

Frequency tuning of either an antenna or resonant circuit can provide additional coding capability. For example, a first group of memory devices can be tuned to receive a carrier wave of a first RF frequency, e.g., $f_1$, and a second group could be tuned to receive a second frequency $f_2$, and so on. The separate carrier frequencies could provide additional means for tracking or providing information to the devices, even if the groups become intermixed.

The RF antenna may, in an alternate embodiment, be formed external to the semiconductor substrate. In this configuration, a separate conductive wire, which acts as an antenna, will be attached to a bond pad formed on the chip using methods known to those skilled in the art. The wire will then be stabilized when the chip is encased in the protective shell, so that the antenna extends at some angle to the chip.

Also, as an alternative to signal transmission via RF, the antifuse or other semiconductor memory and supporting circuitry can receive the addressing commands and device power by optical transmission. In this embodiment, the RF antenna 110 would be replaced by a photocell that generates sufficient write voltage to exceed the threshold voltage. For the addressing commands, the RF transmitter 80 is replaced by a light source, and the commands may be transmitted digitally by pulsing the optical transmitter, which can be a laser, flash lamp or other high intensity light source. It is noted that the light intensity must be sufficient to generate adequate voltage, either singly or in conjunction with a second power generating device, in the photocell to write into memory, but not so high that it damages the metal interconnect on the chip. With digital data transmission analog-to-digital and digital-to-analog conversion circuitry can be eliminated.

C. Other Memory Devices and or Encoded Devices [OMDS]

In addition to antifuse memory devices, other types of electrically-programmable read-only memories, preferably non-volatile memories, which are known in the art, may be used [see, e.g., U.S. Pat. No. 5,335,219]. Chips, such as those sold by Actel, Mosaic, Lattice Semiconductor, AVID, Anicare, Destron, Rayethon, Altera, ICT, Xilinix, Intel and Signetics [see, e.g., U.S. Pat. Nos. 4,652,528, 5,044,623, 5,099,226, 5,218,343, 5,323,704, 4,333,072, 4,321,069, 4,318,658, 5,121,748, 5,214,409, 5,235,326, 5,257,011 and 5,266,926] may be used herein. Preprogrammed remotely addressable identification tags, such as those used for tracking objects or animals [see, e.g., U.S. Pat. Nos. 5,257,011, 5,235,326, 5,226,926, 5,214,409, 4,333,072, available from AVID, Norco, Calif.; see, also U.S. Pat. Nos. 5,218,189, 5,416,486, 4,952,928, 5,359,250] and remotely writable versions thereof are also contemplated for use herein. Preprogrammed tags may be used in embodiments, such as those in which tracking of linked molecules is desired.

d. Pre-coded Memory Devices

Alternatively, the matrices or strips attached thereto may be encoded with a pre-programmed identifying bar code, such as an optical bar code that will be encoded on the matrix and read by laser. Such pre-coded devices may be used in embodiments in which parameters, such as location in an automated synthesizer, are monitored. The identity of a product or reactant determined by its location or path, which is monitored by reading the chip in each device and storing such information in a remote computer. Read/write tags such as the IPTT-100 [BioMedic Data Systems, Inc., Maywood, N.J.; see, also U.S. Pat. Nos. 5,422,636, 5,420,579, 5,262,772, 5,252,962, 5,250,962, and U.S. application Ser. No. 08/322,644] are also contemplated for use herein.

Among the particularly preferred devices are the chips [particularly, the IPTT-100, Bio Medic Data Systems, Inc., Maywood, N.J.; see, also U.S. Pat. Nos. 5,422,636, 5,420,579, 5,262,772, 5,252,962 and 5,250,962 and U.S. application Ser. No. 08/322,644,] that can be remotely encoded and remotely read. These devices, such as the IPTT-100 transponders that are about 8 mm long, include a recording device, an EEPROM, a passive transponder for receiving an input signal and transmitting an output signal in response. In some embodiments here, the devices are modified for use herein by altering the geometry. They are folded in half and the antenna wrapped around the resulting folded structure. This permits convenient insertion into the microvessels and formation of other combinations.

These devices include a power antenna means [see, e.g., U.S. Pat. No. 5,250,944 and U.S. Pat. No. 5,420,579] for receiving the input signal, frequency generator and modulator means for receiving the input signal the receive antenna means and for generating the output signal. The output signal has a frequency different from the input frequency, outputs the output signal in response the input signal. The input signal having a first frequency, the output signal has a second frequency that is a multiple of the first frequency, and is greater that the first frequency. It also includes a transmitting antenna means for receiving the output signal from the frequency generator and modulator means and that transmit the output signal. Data are stored within the transponder within a reprogrammable memory circuit that is programmed by the user [see, e.g., U.S. Pat. No. 5,422,636 and EP 0 526 173 A3]. A transponder scanner for scanning and programming the transponder is also available [Bio Medic Data Systems Inc. DAS-5001 CONSOLE™ System, e.g., U.S. Pat. No. 5,252,962 and U.S. Pat. No. 5,262,772].

Another such device is a 4 mm chip with an onboard antenna and an EEPROM [Dimensional Technology International, Germany]. This device can also be written to and read from remotely.

Also, ID tags available from IDTAG™ Inc, particularly the IDT150 read/write transponder [ITDAG™ Ltd. Bracknell, Berks RG12 3XQ, UK], discussed above, are also preferred herein.

2. Optically or magnetically programmed devices

In addition to electrically-programmable means for storing information on the matrix particles, optical or magnetic means may be used. One example of an optical storage means is provided in U.S. Pat. No. 5,136,572, issued Aug. 4, 1992, of Bradley, which is incorporated herein by reference. Here, an array of stabilized diode lasers emits fixed wavelengths, each laser emitting light at a different wavelength. Alternatively, a tunable diode laser or a tunable dye laser, each of which is capable of emitting light across a relatively wide band of wavelengths, may be used. The recording medium is photochemically active so that exposure to laser light of the appropriate wavelength will form spectral holes.

Figure 7:
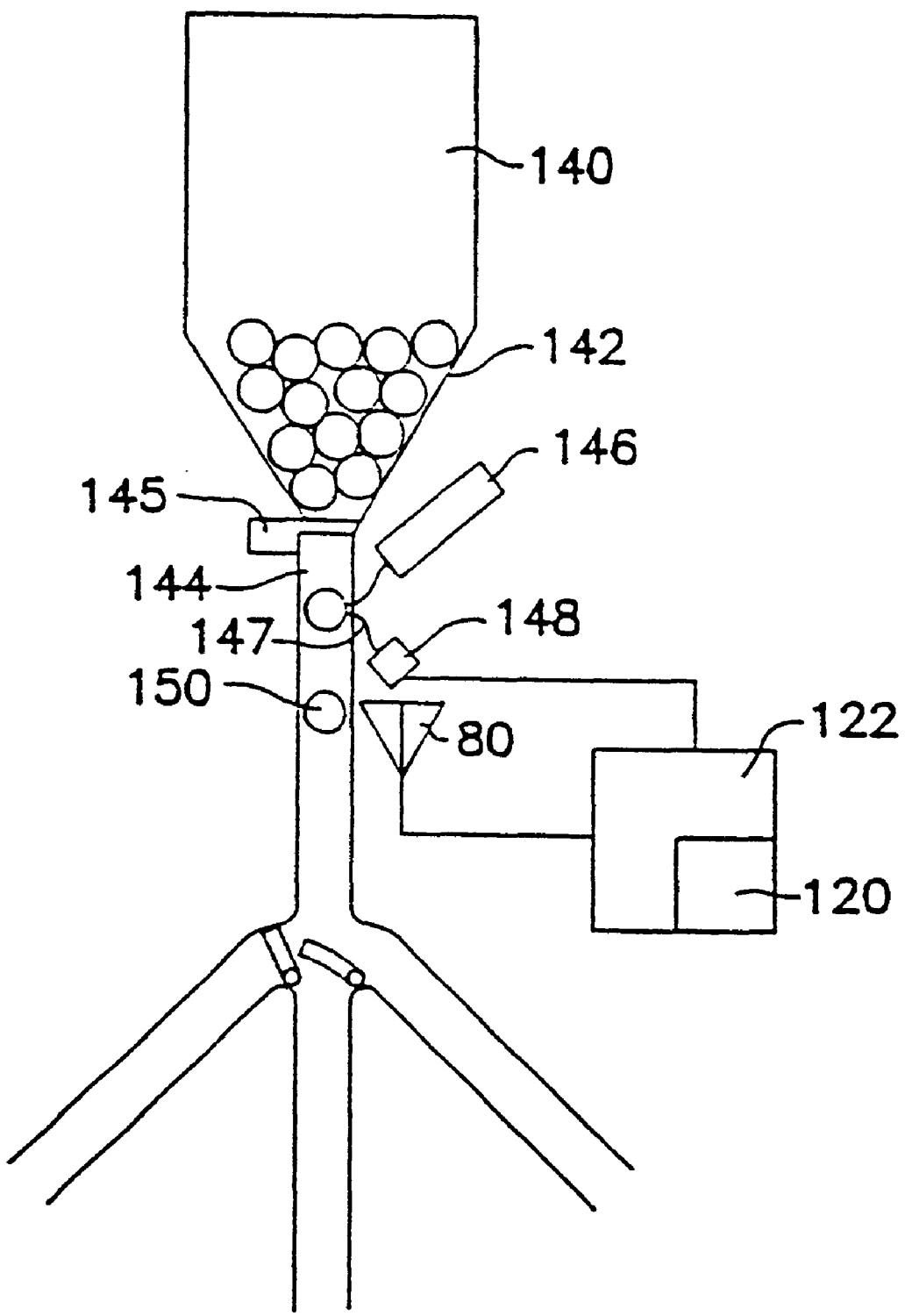
FIG. 7 is an illustration of an exemplary apparatus for separating the matrix particles with memories for individual exposure to an EM signal.
Figure 8:
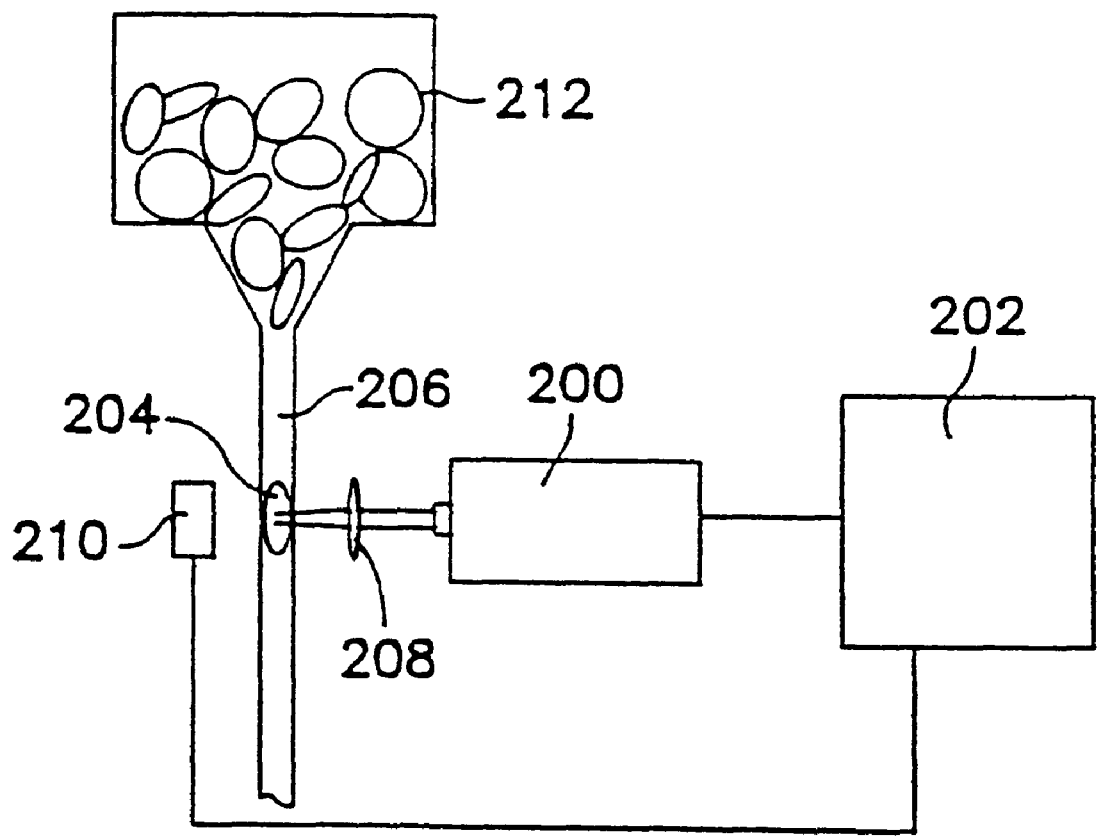
FIG. 8 is an illustration of a second exemplary embodiment of an apparatus for separating matrix particles for individual exposure to an optical signal.

As illustrated In FIG. 8, an optical write/read system is configured similar to that of the embodiment of FIG. 7, with a vessel 212 containing a number of the particles which are separated and oriented by passing through a constricted outlet into a write read path 206 that has an optically-transparent tube [i.e., optically transparent to the required wavelength(s)] with a cross-section which orients the particles as required to expose the memory surface to the laser 200 which is capable of emitting a plurality of discrete, stable wavelengths. Gating and detection similar to that described for the previous embodiment may be used and are not shown. Computer 202 controls the tuning of laser 200 so that it emits light at a unique wavelength to record a data point. Memory within computer 202 stores a record indicating which process step corresponds to which wavelength. For example, for process A, wavelength $\lambda_1$, e.g., 630 nm [red], for process C, $\lambda_2$, e.g., 550 nm [yellow], and for process E, $\lambda_3$, e.g., 480 nm [blue], etc. The recording medium 204 is configured to permit orientation to repeatably expose the recording side of the medium to the laser beam each time it passes through tube 206. One possible configuration, as illustrated here, is a disc.

To write onto the recording medium 204, the laser 200 emits light of the selected wavelength to form a spectral hole in the medium. The light is focussed by lens 208 to illuminate a spot on recording medium 204. The laser power must be sufficient to form the spectral hole. For reading, the same wavelength is selected at a lower power. Only this wavelength will pass through the spectral hole, where it is detected by detector 210, which provides a signal to computer 202 indicative of the recorded wavelength. Because different wavelengths are used, multiple spectral holes can be superimposed so that the recording medium can be very small for purposes of tagging. To provide ah analogy to the electrical memory embodiments, each different wavelength of light corresponds to an address, so that each laser writes one bit of data. If a large number of different steps are to performed for which each requires a unique data point, the recording media will need to be sufficiently sensitive, and the lasers well-stabilized, to vary only within a narrow band to assure that each bit recorded in the media is distinguishable. Since only a single bit of information is required to tag the particle at any given step, the creation of a single spectral hole at a specific wavelength is capable of providing all of the information needed. The host computer then makes a record associating the process performed with a particular laser wavelength.

For reading, the same wavelength laser that was used to create the spectral hole will be the only light transmitted through the hole. Since the spectral holes cannot be altered except by a laser having sufficient power to create additional holes, this type of memory is effectively non-volatile. Further, the recording medium itself does not have any operations occurring within its structure, as is the case in electrical memories, so its structure is quite simple. Since the recording medium is photochemically active, it must be well encased within an optically transmissive [to the active optical wavelength(s)], inert material to prevent reaction with the various processing substances while still permitting the laser light to impinge upon the medium. In many cases, the photochemical recording media may be erased by exposure to broad spectrum light, allowing the memory to be reused.

Writing techniques can also include the formation of pits in the medium. To read these pits, the detector 210 with be positioned on the same side of the write/read tube 206 as the laser 200 to detect light reflected back from the medium. Other types of optical data storage and recording media may be used as are known in the art. For example, optical discs, which are typically plastic-encapsulated metals, such as aluminum, may be miniaturized, and written to and read from using conventional optical disc technology. In such a system, the miniature discs must be aligned in a planar fashion to permit writing and reading. A modification of the funnel system, described above, will include a flattened tube to insure the proper orientation. Alternatively, the discs can be magnetically oriented. Other optical recording media that may be appropriate for use in the recording devices and combinations herein include, but are not limited to, magneto-optical materials, which provide the advantage of erasability, photochromic materials, photoferroelectric materials, photoconductive electro-optic materials, all of which utilize polarized light for writing and/or reading, as is known in the art. When using any form of optical recording, however, considerations must be made to insure that the selected wavelength of light will not affect or interfere with reactions of the molecules or biological particles linked to or in proximity to matrix particles.

Three Dimensional Optical Memories

Another device that is suitable for use in the matrix with memory combinations are optical memories that employ rhodopsins, particularly bacteriorhodopsin [BR], or other photochromic substances that change between two light absorbing states in response to light of each of two wavelengths [see, e.g., U.S. Pat. Nos. 5,346,789, 5,253,198 and 5,228,001; see, also Birge (1990) *Ann. Rev. Phys. Chem* 41:683–733]. These substances, particularly BR, exhibit useful photochromic and optoelectrical properties. BR, for example, has extremely large optical nonlinearities, and is capable of producing photoinduced electrical signals whose polarity depends on the prior exposure of the material to light of various wavelengths as well as on the wavelength of the light used to induce the signal. There properties are useful for information storage and computation. Numerous applications of this material have been designed, including its use as an ultrafast photosignal detector, its use for dynamic holographic recording, and its use for data storage, which is of interest herein.

The rhodopsins include the visual rhodopsins, which are responsible for the conversion of light into nerve impulses in the image resolving eyes of mollusks, anthropods, and vertebrates, and also bacteriorhodopsin [BR]. These proteins also include a class of proteins that serve photosynthetic and phototactic functions. The best known BR is the only protein found in nature in a crystalline membrane, called the "purple membrane" of *Halobacterium Halobium*. This membrane converts light into energy via photon-activated transmembrane proton pumping. Upon the absorption of light, the BR molecule undergoes several structural transformations in a well-defined photocycle in which energy is stored in a proton gradient formed upon absorption of light energy. This proton gradient is subsequently utilized to synthesize energy-rich ATP.

The structural changes that occur in the process of light-induced proton pumping of BR are reflected in alterations of the absorption spectra of the molecule. These changes are cyclic, and under usual physiological conditions bring the molecule back to its initial BR state after the absorption of light in about 10 milliseconds. In less than a picosecond after BR absorbs a photon, the BR produces an intermediate, known as the "J" state, which has a red-shifted absorption maximum. This is the only light-driven event in the photocycle; the rest of the steps are thermally driven processes that occur naturally. The first form, or state, following the photon-induced step is called "K", which represents the first form of light-activated BR that can be stabilized by reducing the temperature to 90° K. This form occurs about 3 picoseconds after the J intermediate at room temperature. Two microseconds later there occurs an "L" intermediate state which is, in turn, followed in 50 microseconds by an "M" intermediate state.

There are two important properties associated with all of the intermediate states of this material. The first is their ability to be photochemically converted back to the basic BR state. Under conditions where a particular intermediate is made stable, illumination with light at a wavelength corresponding to the absorption of the intermediate state in question results in regeneration of the BR state. In addition, the BR state and intermediates exhibit large two-photon absorption processes which can be used to induce interconversions among different states.

The second important property is light-induced vectorial charge transport within the molecule. In an oriented BR film, such a charge transport can be detected as an electric signal. The electrical polarity of the signal depends on the physical orientation of molecules within the material as well as on the photochemical reaction induced. The latter effect is due to the dependence of charge transport direction on which intermediates [including the BR state] are involved in the photochemical reaction of interest. For example, the polarity of an electrical signal associated with one BR photochemical reaction is opposite to that associated with a second BR photochemical reaction. The latter reaction can be induced by light with a wavelength around 412 nm and is completed in 200 ns.

In addition to the large quantum yields and distinct absorptions of BR and M, the BR molecule [and purple membrane] has several intrinsic properties of importance in optics. First, this molecule exhibits a large two-photon absorption cross section. Second, the crystalline nature and adaptation to high salt environments makes the purple membrane very resistant to degeneration by environmental perturbations and thus, unlike other biological materials, it does not require special storage. Dry films of purple membrane have been stored for several years without degradation. Furthermore, the molecule is very resistant to photochemical degradation.

Thus, numerous optical devices, including recording devices have been designed that use BR or other rhodopsin as the recording medium [see, e.g., U.S. Pat. Nos. 5,346,789, 5,253,198 and 5,228,001; see, also Birge (1990) *Ann. Rev. Phys. Chem* 41:683–733]. Such recording devices may be employed in the methods and combinations provided herein.

Event-detecting Embodiment

Figure 9:
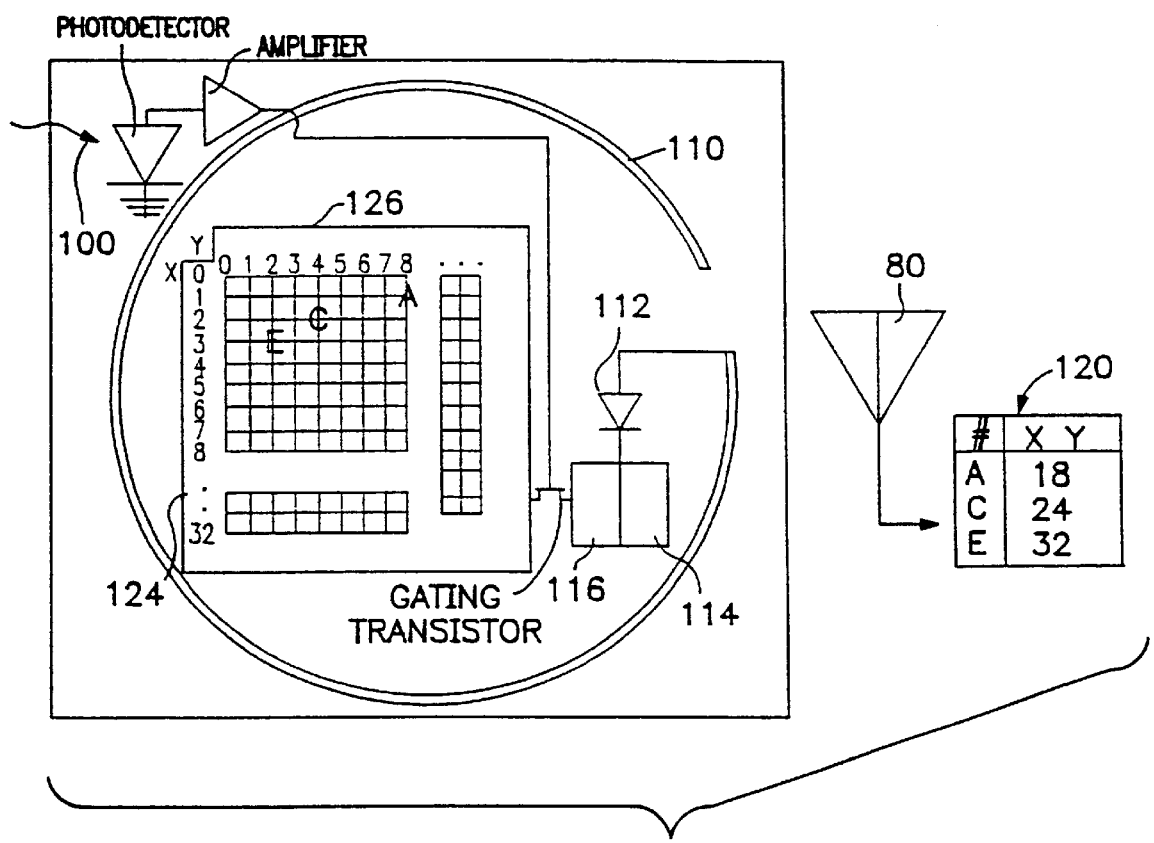
FIG. 9 is a diagrammatic view of the memory array within the recording device, the corresponding data stored in the host computer memory, and included photodetector with amplifier and gating transistor.

Another embodiment of the combinations herein utilizes a recording device that can detect the occurrence of a reaction or event or the status of any external parameter, such as pH or temperature, and record a such occurrence or parameter in the memory. Any of the above devices may be modified to permit such detection. For example, the chip with the antifuse memory array with decoder, rectifier components and RF antenna, can be modified by addition of a photodetector and accompanying amplifier components as shown in FIG. 9. The photodetector will be selected so that it is sensitive to the frequencies of expected photoemissions from reactions of interest. To maintain the chip's passive operation, the photodetector circuitry may use voltage supplied by the same RF signal that is used to write other data to memory, so that no detection of photoemission will occur unless RF or other power is applied to provide bias and drain voltage. If an active device is used, the power supplied by the battery can provide operational voltage to the photodetector circuitry, independent of any transmitted signal. The voltage supplied by the photodetector can be used in a number of different ways. For example:

1) The threshold voltage for writing to memory will exceed the voltage supplied by the RF signal, which will still contain the address information. In order to write, additional voltage must be provided by the photodetector so that the sum of the voltages exceeds the threshold. ($V_{RF} < V_T < V_{RF} + V_{PD}$). This permits the RF supplied voltage to go to the correct address, however, no writing will occur unless a photoemission has been detected by the detector. Therefore, there will be no record of exposure to a particular process step unless a sufficient reaction has occurred to generate the required photoemission. Since the address signal can still get to the memory array without the extra voltage, reading of recorded data can be achieved without any special circuitry. If the memory device is an active device, a similar mechanism can be used in which only the sum of the voltages is sufficient to record an occurrence.

2) The threshold voltage for writing to memory will be provided by the RF signal alone, and the RF signal will include address information. ($V_T < V_{RF}$). However, unless voltage from the photodetector is supplied to a "gating" transistor, access to the memory array is prevented so that no writing occurs unless a photoemission is detected. (This embodiment is illustrated.) This will require a special provision for opening the gate during read operations to permit access to the memory array. Since the gating transistor will conduct a signal only in the event of photoemission, this embodiment will work equally well with passive and active memory devices.

3) The RF signal provides sufficient voltage to exceed the threshold voltage. ($V_T < V_{RF}$). Voltage from the photodetector is used to create a write potential difference at an additional address location which is carried in the RF signal. For example, if the RF signal is addressing column 3, row 3, column 32 could be connected only to the photodetector circuit's output so that, when a photoemission occurs, the write signal will create antifuses [or in the case of EEPROM, standard fuses] at addresses 3,3 and 32,3. If no photoemission occurs, only address 3,3 will have an antifuse formed, providing a record of exposure of the matrix to a particular process step even without the occurrence of a detectable reaction. Special provisions, such as software within the host computer in combination with mask-programmed interconnections within the decode circuitry of the memory device, must be made to assure that more than one column in a single row of the array is polled during read operations so that both memory locations are read.

In addition to the above-described methods for recording the occurrence of photo-emitting reactions, the photodetector, while still integrated on the same substrate with the basic memory matrix for recording transmitted signals, can be connected to its own independent memory matrix. In this embodiment, the photodetector's memory matrix can be connected to separate transceiver circuitry with an antenna tuned to a different frequency from that of the basic memory. During the read operation, the memory device will be exposed to two different radio frequency signals, one for the basic memory, the other for the photodetection circuit memory. If only the photoemission information is required, only the corresponding frequency signal need be provided during the read operation.

Depending on the type of energy release that occurs during a reaction, other types of sensors may be used in addition to photodetectors or in place thereof. In addition changes in ion concentration may also be detected. Many such sensors will be capable of generating an electrical signal that can be used as described above for the photodetectors. These sensing devices may also be incorporated onto the substrate and electrically connected to the memory device, providing data points within the device's memory under the appropriate write conditions. For example, temperature sensing elements can be made from semiconductor liquid crystal and fluorescent crystals, and addition to conventional thermocouples created by placing two different metals in contact at the detection point. It is also possible to include radiation, pH and $pCO_2$ sensors in a similar manner, using materials that respond to the detected variables by generating a voltage potential that can be conducted to the memory device and recorded.

The reaction-detecting embodiment may be advantageously used in assays, such as the SPA, HTRF, FET, FRET and FP assays described below. In these assays, reaction, such as receptor binding, produces a detectable signal, such as light, in the matrix. If a matrix with memory with a photodetection circuit is used, occurrence of the binding reaction will be recorded in memory.

3. Reading and writing to memory a. Embodiments Using a Proximate Memory, such as a Non-volatile Memory Device The operation of programming the memory to record the process steps to which the linked or adjacent matrix particle or support and linked or proximate molecule or biological particle is exposed involves placing the memory device reasonably close [a distance on the order of about 1 inch [25.4 mm] is presently contemplated, but longer distances should be possible and shorter distances are also contemplated [suitable distances can be determined empirically] to RF transmitter 80. The RF transmitter 80 emits a carrier wave modulated by a signal generated by host computer 122 using conventional RF technology. The carrier wave itself can provide the power to the generate the programming voltage and the operating voltage for the various devices via the rectifier, while the modulation signal provides the address instructions.

Figure 6:
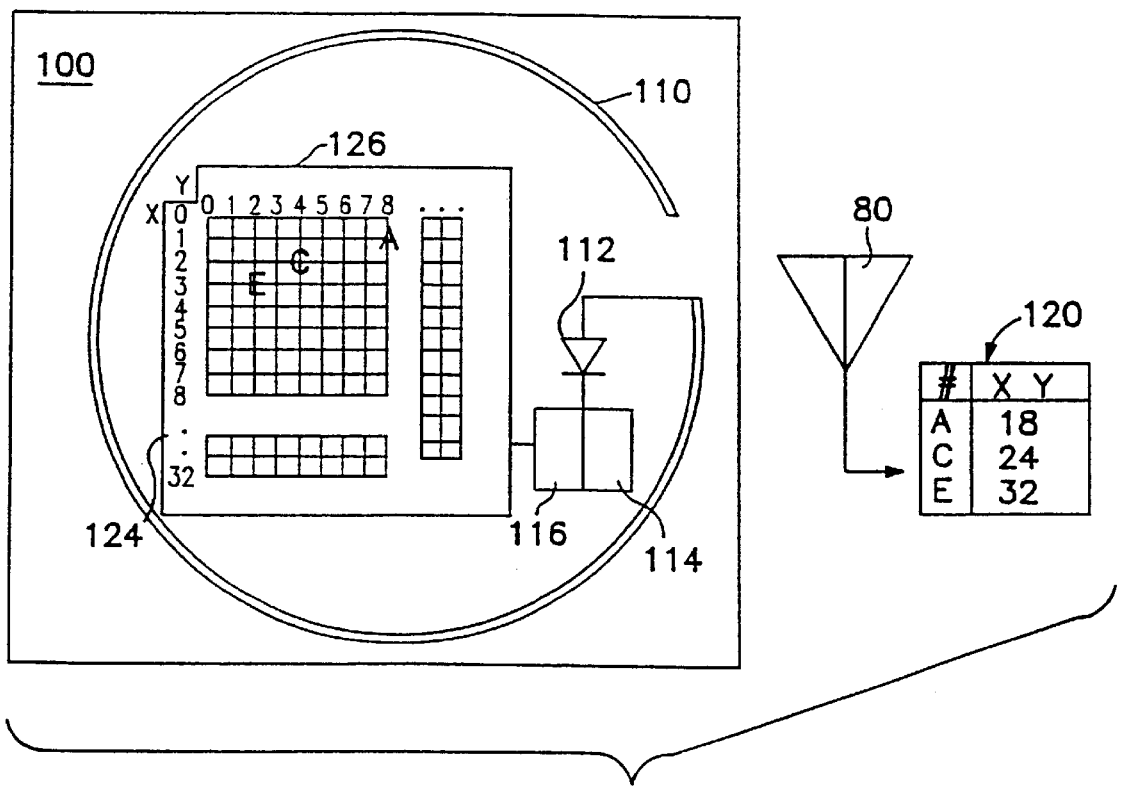
FIG. 6 is a diagrammatic view of the memory array within the recording device, and the corresponding data stored in the host computer memory.

As stated previously, since the memory only has to be "tagged" to record the exposure of the proximate or linked molecule or biological particle to a given process, the address signal only has to carry information to turn on a single memory location, while the host computer 122 stores into memory 120 the information linking the process information with the single memory location that was "tagged" to record exposure to the process step. Referring to FIG. 1, in which chemical building blocks A, C, and E are added to a molecule linked to a matrix with memory, and to FIG. 6, an illustrative example of how information is written onto a particle is provided in Table 1.

TABLE 1

| PROCESS STEP | X-REGISTER ADDRESS | Y-REGISTER ADDRESS |
|---|---|---|
| A | 1 | 8 |
| C | 2 | 4 |
| E | 3 | 2 |

For the step in which A is added, the address signal would increment the x-register 124 one location and increment the y-register 126 eight locations, and then apply the programming voltage. The activation of this switch is indicated by an "A" at the selected address, although the actual value stored will be a binary "1", indicating ON. [As described, for example, in U.S. Pat. No. 4,424,579; the manner in which the programming voltage is applied depends on whether the decoders have depletion or enhancement transistors.] The host computer 122 would write into its memory 120 that for process A, the x- ,y- address is 1,8. Upon removal of the RF signal after recording process A, the voltage is removed and the registers would reset to 0. For the step in which C is added, the address signal would increment the x-register 124 two locations and the y-register 126 four locations, then apply the programming voltage, as indicated by the letter "C". The host computer 120 would similarly record in memory that an indication of exposure to process C would be found at x-,y- address 2,4. Again, upon removal of the RF signal, the registers reset to 0 so that when the matrix particle's memory is again exposed to RF following addition of block E, the registers increment 3 and 2 locations, respectively, and the programming voltage is applied to turn on the switch, indicated by "E". Desirably all processing steps are automated.

After processing is completed, to read the information that has been recorded in the memory of the data storage unit, the host computer 122 will inquire into the identity of the particle by generating a command signal to the registers to select the appropriate address locations to determine whether the switch is on or off. If the switch is on, i.e., a voltage drop occurs at that point, the computer will create a record that the particle received a particular process step. Alternatively, the host computer can generate an inquiry signal to sequentially look at all memory locations to determine which switches have been turned on, recording all locations at which voltage drops occurred. The computer will then compare the "on" locations to the process steps stored in its memory to identify the steps through which the subject particle was processed.

If desired, individual particles can be identified by reserving certain memory locations for identification only, for example, the first two rows of the x-register. In this case, particles will be passed separately through the RF signal while the x-register is incremented to turn on switches at address locations 0,0, 1,0, 2,0, etc. With individual identification, the host computer 122 can first generate a signal to query a matrix particle memory to determine its identity, then write the information with regard to the process performed, saving the process and particle information in the host computer memory 120.

Ideally, the tagging of particles which are exposed to a particular process would be performed in the process vessel containing all of the particles. The presence, however, of a large number of particles may result in interference or result in an inability to generate a sufficiently high voltage for programming all of the particles simultaneously. This might be remedied by providing an exposure of prolonged duration, e.g., several minutes, while stirring the vessel contents to provide the greatest opportunity for all particles to receive exposure to the RF signal. On the other hand, since each particle will need to be read individually, a mechanism for separating the particles may be used in both write and read operations. Also, in instances in which each particle will have a different molecule attached, each particle memory must be addressed separately.

b. Embodiments Using OMDs

When precoded OMDs are used, each OMD (or group thereof) has a unique identifier is optically scanned and entered into a remote memory. Thereafter, after each synthesis, processing or assaying step, information regarding such for each device identified by its encoded symbology is entered into a remote memory. Upon completion of the synthesis, processing, assay or other protocol, each device can be scanned and identified. Reference to the information stored in the remote memory provides information regarding the linked molecules or biological particles or the assay or other information. When read/write OMDs are used, identifying symbology is encoded on the device and the decrypting information is stored in a remote memory.

D. The Combinations and Preparation Thereof

Combinations of a miniature recording device that contains or is a data storage unit linked to or in proximity with matrices or supports used in chemical and biotechnical applications, such as combinatorial chemistry, peptide synthesis, nucleic acid synthesis, nucleic acid amplification methods, organic template chemistry, nucleic acid sequencing, screening for drugs, particularly high throughput screening, phage display screening, cell sorting, drug delivery, tracking of biological particles and other such methods, are provided. These combinations of matrix material with data storage unit [or recording device including the unit] are herein referred to as matrices with memories. These combinations have a multiplicity of applications, including combinatorial chemistry, isolation and purification of target macromolecules, capture and detection of macromolecules for analytical purposes, high throughput screening protocols, selective removal of contaminants, enzymatic catalysis, drug delivery, chemical modification, scintillation proximity assays, FET, FRET and HTRF assays, immunoassays, receptor binding assays, drug screening assays, information collection and management and other uses. These combinations are particularly advantageous for use in multianalyte analyses. These combinations may also be advantageously used in assays in which a electromagnetic signal is generated by the reactants or products in the assay. These combinations may be used in conjunction with or may include a sensor element, such as an element that measures a solution parameter, such as pH. Change in such parameter, which is recorded in the memory will indicate a reaction event of interest, such as induction of activity of a receptor or ion channel, has occurred. The combination of matrix with memory is also advantageously used in multiplex protocols, such as those in which a molecule is synthesized on the matrix, its identity recorded in the matrix, the resulting combination is used in an assay or in a hybridization reaction. Occurrence of the reaction can be detected externally, such as in a scintillation counter, or can be detected by a sensor that writes to the memory in the matrix. Thus, combinations of matrix materials, memories, and linked or proximate molecules and biological materials and assays using such combinations are provided.

The combinations contain (i) a miniature recording device that contains one or more programmable data storage devices [memories] that can be remotely read and in preferred embodiments also remotely programmed; and (ii) a matrix as described above, such as a particulate support used in chemical syntheses. The remote programming and reading is preferably effected using electromagnetic radiation, particularly radio frequency or radar. Depending upon the application the combinations will include additional elements, such as scintillants, photodetectors, pH sensors and/or other sensors, and other such elements.

1. Preparation of matrix-memory combinations

In preferred embodiments, the recording device is cast in a selected matrix material during manufacture. Alternatively, the devices can be physically inserted into the matrix material, the deformable gel-like materials, or can be placed on the matrix material and attached by a connector, such as a plastic or wax or other such material. Alternatively, the device or device(s) may be included in an inert container in proximity to or in contact with matrix material.

2. Non-linked matrix-memory combinations

The recording device with memory can be placed onto the inner surface of a vessel, such as a microtiter plate or vial or tube in which the reaction steps are conducted. Alternatively, the device can be incorporated into the vessel material, such into the a wall of each microtiter well or vial or tube in which the reaction is conducted. As long as the molecules or biological particles remain associated with the well, tube or vial, their identity can be tracked. Also of interest herein are the multiwell "chips" [such as those available from Orchid Biocomputer, Inc. Princeton, N.J., see, e.g., U.S. Pat. Nos. 5,047,371, 4,952,531, 5,043,222, 5,277,724, 5,256,469 and Prabhu et al. (1992) *Proc. SPIE-Int. Soc. Opt. Eng.* 1847 NUMBER: Proceedings of the 1992 International Symposium on Microelectronics, pp.601–6], that are silicone based chips that contain 10,000 microscopic wells connected by hair-thin glass tubes to tiny reservoirs containing reagents for synthesis of compounds in each well. Each well can be marked with a code and the code associated with the identity of the synthesized compound in each well. Ultimately, a readable or read/write memory may be incorporated into each well, thus permitting rapid and ready identification of the contents of each well.

In a particularly preferred embodiment, one or more recording devices with memory and matrix particles are sealed in a porous non-reactive material, such as polypropylene or TEFLON net, with a pore size smaller than the particle size of the matrix and the device. Typically one device per about 1 to 50 mg, preferably 5 to 30, more preferably 5 to 20 mg of matrix material, or in some embodiments up to gram, generally 50 to 250 mg, preferably 150 mg to about 200 mg, and one device is sealed in a porous vessel a microvessel [MICROKAN™]. The amount of matrix material is a function of the size of the device and the application in which the resulting matrix with memory is used, and, if necessary can be empirically determined. Generally, smaller sizes are desired, and the amount of material will depend upon the size of the selected recording device.

The resulting microvessels are then encoded, reactions, such as synthetic reactions, performed, and read, and if desired used in desired assays or other methods.

3. Preparation of matrix-memory-molecule or biological particle combinations

In certain embodiments, combinations of matrices with memories and biological particle combinations are prepared. For example, libraries [e.g., bacteria or bacteriophage, or other virus particles or other particles that contain genetic coding information or other information] can be prepared on the matrices with memories, and stored as such for future use or antibodies can be linked to the matrices with memories and stored for future use.

4. Combinations for use in proximity assays

In other embodiments the memory or recording device is coated or encapsulated in a medium, such as a gel, that contains one or more fluophors or one or more scintillants, such as 2,5-diphenyloxazole [PPO] and/or 1,4-bis-[5-phenyl-(oxazolyl)]benzene [POPOP] or FlexiScint [a gel with scintillant available from Packard, Meriden, Conn.] or yttrium silicates. Any fluophore or scintillant or scintillation cocktail known to those of skill in the art may be used. The gel coated or encased device is then coated with a matrix suitable, such as glass or polystyrene, for the intended application or application(s). The resulting device is particularly suitable for use as a matrix for synthesis of libraries and subsequent use thereof in scintillation proximity assays.

Similar combinations in non-radioactive energy transfer proximity assays, such as HTRF, FP, FET and FRET assays, which are described below. These luminescence assays are based on energy transfer between a donor luminescent label, such as a rare earth metal cryptate [e.g., Eu trisbipyridine diamine (EuTBP) or Tb tribipyridine diamine (TbTBP)] and an acceptor luminescent label, such as, when the donor is EuTBP, allopycocyanin (APC), allophycocyanin B, phycocyanin C or phycocyanin R, and when the donor is TbTBP, a rhodamine, thiomine, phycocyanin R, phycoerythrocyanin, phycoerythrin C, phycoerythrin B or phycoerythrin R. Instead of including a scintillant in the combination, a suitable fluorescent material, such as allopycocyanin (APC), allophycocyanin B, phycocyanin C, phycocyanin R; rhodamine, thiomine, phycocyanin R, phycoerythrocyanin, phycoerythrin C, phycoerythrin B or phycoerythrin R is included. Alternatively, a fluorescent material, such a europium cryptate is incorporated in the combination.

5. 2-D Bar codes, other symbologies and application thereof

Any application and combination described herein in which a recording device in proximity with a matrix may include a code or symbology in place of or in addition to the recording device. The information associated with the code is stored in a remote recording device, such as a computer. Thus, by electro-optically scanning the symbol on the combination and generating a corresponding signal, it is possible in an associated computer whose memory has digitally stored therein the full range of codes, to compare the signal derived from the scanned symbol with the stored information. When a match is found, the identity of the item and associated information, such as the identity of the linked molecule or biological particle or the synthetic steps or assay protocol, can be retrieved.

The symbology can be engraved on any matrix used as a solid support for chemical syntheses, reactions, assays and other uses set forth herein, for identification and tracking of the linked or proximate biological particles and molecules. Particularly preferred is the two-dimensional bar code and system used therewith for reading and writing the codes on matrix materials.

6. Other variations and embodiments

The combination of matrix particle with memory may be further linked, such as by welding using a laser or heat, to an inert carrier or other support, such as a TEFLON strip. This strip, which can be of any convenient size, such as 1 to 10 mm by about 10 to 100 $\mu$M will render the combination easy to use and manipulate. For example, these memories with strips can be introduced into 10 cm culture dishes and used in assays, such as immunoassays, or they can be used to introduce bacteria or phage into cultures and used in selection assays. The strip may be encoded or impregnated with a bar code to further provide identifying information.

Microplates containing a recording device in one or a plurality of wells are provided. The plates may further contain embedded scintillant or a coating of scintillant [such as FlashPlate™, available from DuPont NEN®, and plates available from Packard, Meriden, Conn.] FLASHPLATE™ is a 96 well microplate that is precoated with plastic scintillant for detection of β-emitting isotopes, such as $^{125}$I, $^{3}$H, $^{35}$S, $^{14}$C and 33P. A molecule is immobilized or synthesized in each well of the plate, each memory is programmed with the identify of each molecule in each well. The immobilized molecule on the surface of the well captures a radiolabeled ligand in solution results in detection of the bound radioactivity. These plates can be used for a variety of radioimmunoassays [RIAs], radioreceptor assays [RRAs], nucleic acid/protein binding assays, enzymatic assays and cell-based assays, in which cells are grown on the plates.

Figure 19:
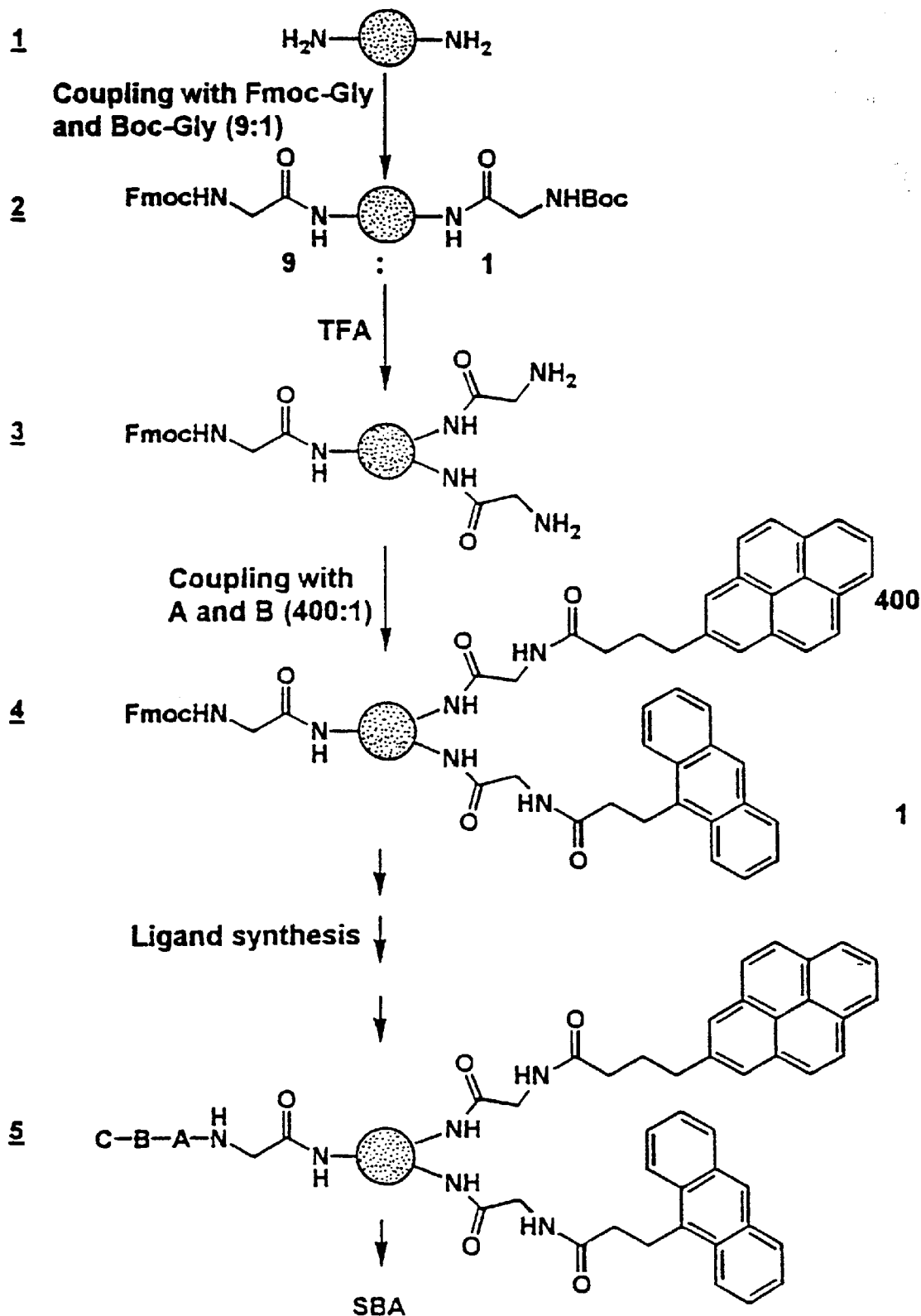
FIG. 19 shows fluorescent solid supports: application in solid phase synthesis of direct SPA.

Another embodiment is depicted in FIG. 19. The reactive sites, such as amines, on a support matrix [1 in the FIGURE] in combination with a memory [a MICROKAN™, a MICROTUBE™, a MACROBEAD™, a MICROCUBE™ or other matrix with memory combination] are differentiated by reacting them with a selected reation of Fmoc-glycine and Boc-glycine, thereby producing a differentiated support [2]. The Boc groups gropus on 2 are then deprotected with a suitable agent such as TFA, to produce 3. The resulting free amine groups are coupled with a fluophore [or mixture A and B, to produce a fluorescent support 4, which can be used in subsequent syntheses or for linkage of desired molecules or biological particles, and then used in fluorescence assays and SPAs.

E. The Recording and Reading and Systems

Systems for recording and reading information are provided. The systems include a host computer or decoder/encoder instrument, a transmitter, a receiver and the data storage device. The systems also can include a funnel-like device or the like for use in separating and/or tagging single memory devices. In practice, an EM signal, preferably a radio frequency signal is transmitted to the data storage device. The antenna or other receiver means in the device detects the signal and transmits it to the memory, whereby the data are written to the memory and stored in a memory location.

Mixtures of the matrix with memory-linked molecules or biological particles may be exposed to the EM signal, or each matrix with memory [either before, after or during linkage of the biological particles or molecules] may be individually exposed, using a device, such as that depicted herein, to the EM signal. Each matrix with memory, as discussed below, will be linked to a plurality of molecules or biological particles, which may be identical or substantially identical or a mixture of molecules or biological particles depending, upon the application and protocol in which the matrix with memory and linked [or proximate] molecules or biological particles is used. The memory can be programmed with data regarding such parameters.

The location of the data, which when read and transmitted to the host computer or decoder/encoder instrument, corresponds to identifying information about linked or proximate molecules or biological particles. The host computer or decoder/encoder instrument can either identify the location of the data for interpretation by a human or another computer or the host computer or the decoder/encoder can be programmed with a key to interpret or decode the data and thereby identify the linked molecule or biological particle.

As discussed above, the presently preferred system for use is the IPTT-100 transponder and DAS-5001 CONSOLE™ [Bio Medic Data Systems, Inc., Maywood, N.J.; see, e.g., U.S. Pat. Nos. 5,422,636, 5,420,579, 5,262,772, 5,252,962 and 5,250,962, 5,252,962 and 5,262,772].

These systems may be automated or may be manual.

Manual system

Figure 17:
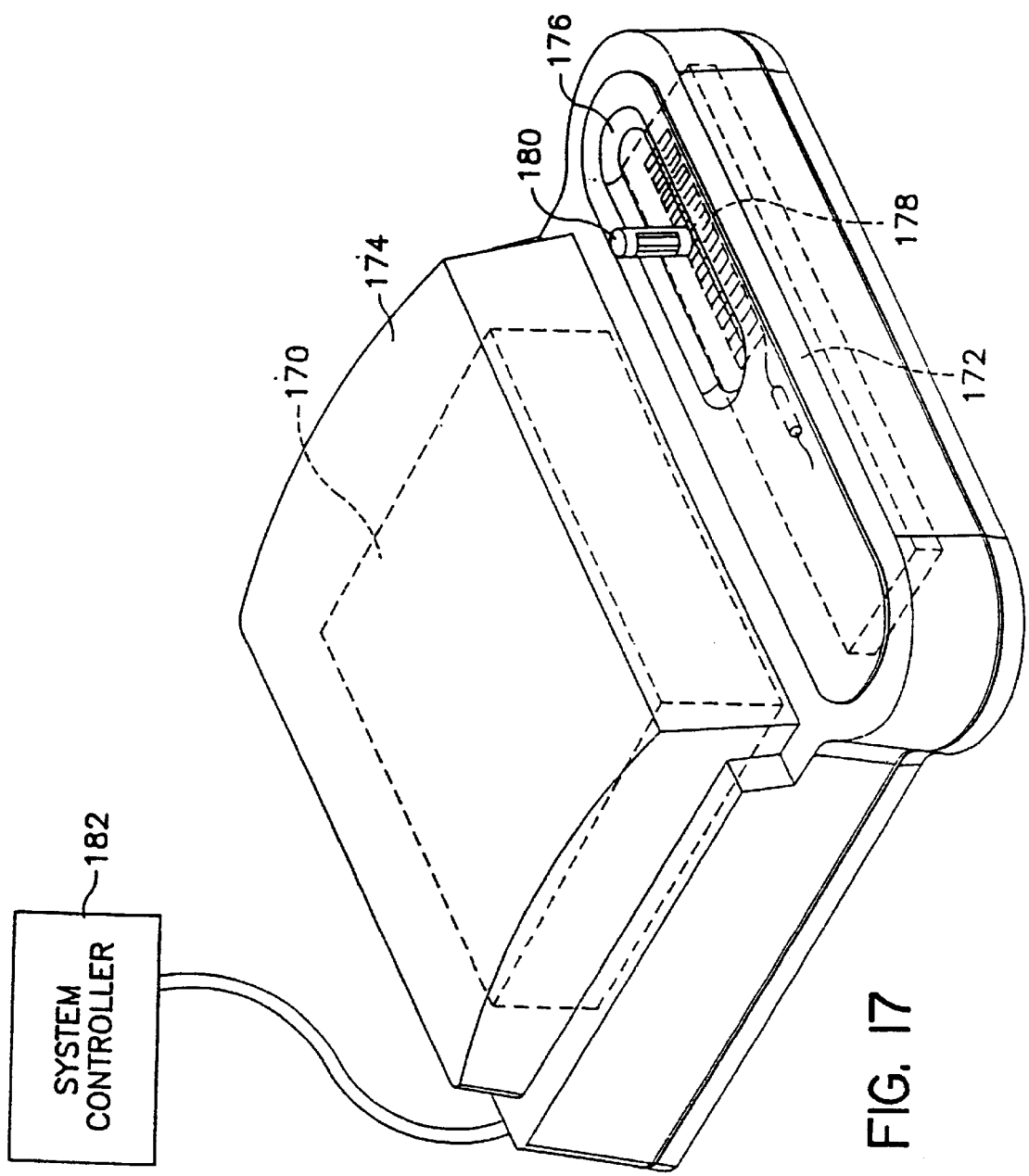
FIG. 17 is a perspective view of an exemplary write/read station.
Figure 18:
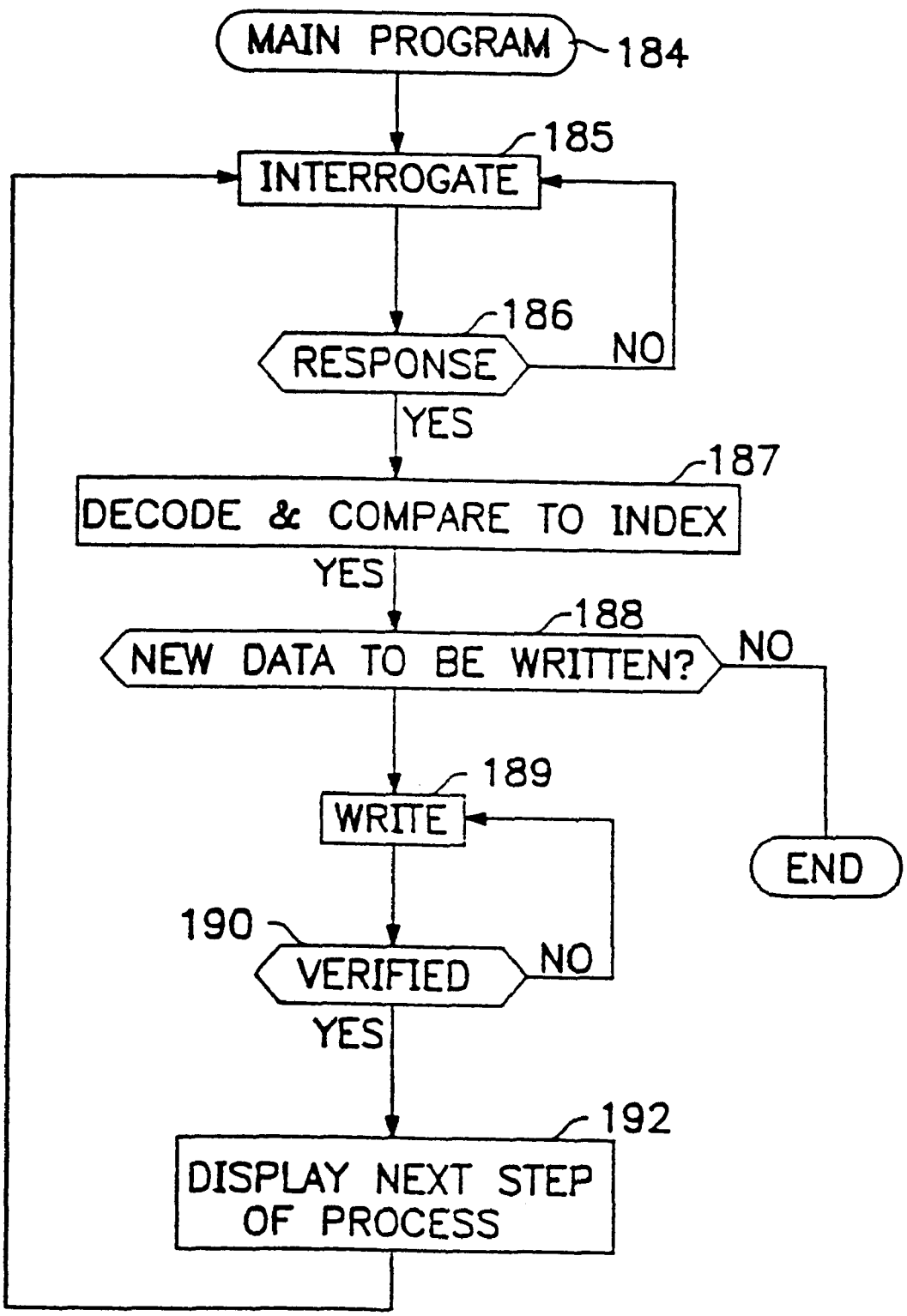
FIG. 18 is a flow diagram of the operation of the system of FIG. 17.

The presently preferred manual system includes a transponder, particularly the BMDS transponder described below or an IDTAG™ transponder, described above, and uses the corresponding reading and writing device, which has been reconfigured and repackaged, such as in FIG. 17, described in the EXAMPLES An example of the operation of the system of FIG. 17 is illustrated in FIG. 18 and described in EXAMPLE 4. Briefly, the user manually places a microvessel 180 within the recessed area 176 so that the interrogation signal 185 provides a response to the controllers indicating the presence on the microvessel, and information is read from or written to the transponder.

This will include microvessels, such as MICROKANS™ or MICROTUBES™, read/writer hardware [such as that available from BMDS or IDTAG™] connected to a PC and software running on the PC that performs a user interface and system control function. The software is designed to facilitate the a number of aspects of synthetic combinatorial chemistry libraries, including: organization, planning and design, synthesis compound formula determination, molecular weight computation, reporting of plans, status and results.

In particular, for each chemical library, the software creates a data base file. This file contains all of the information pertinent to the library, including chemical building blocks to be used, the design of the library in terms of steps and splits, and what synthesis has been performed. This file oriented approach allows many different chemical library projects to be conducted simultaneously. The software allows the user to specify what chemical building blocks are to be used and their molecular weights. The user specifies the number of steps, the number of "splits" at each step, and what chemical building blocks are to be used at each split. The user may also enter the name of the pharmacophore and its molecular weight. Additionally, the user may specify graphical chemical diagrams for the building blocks and the pharmacophore. This information is useful in displaying resulting compounds. The software records all of the above "design" information. It computes and displays the size of the library. It may also predict the range of molecular weights of the resulting compounds.

For example, the user specifies that there will be eight chemical building blocks. Their names are entered, and the user enters a unique letter codes for each: A, B, C, D, E, F, G and H. The user specifies that there will be three steps. Step one will have four splits, appending the A, B, C and D building blocks. Step two will also have four splits, adding the B, D, E and H building blocks. Step three will have six splits, adding the B, C, D, E, F and G building blocks. The software computes that the library will contain 96 (4×6×5= 96) unique compounds. With the planning and design completed, the software helps the user perform the synthesis steps. This is done in concert with the reader/writer hardware transceiver or a scanner, such as the BMDS-DAS 5003] or a similar device available form IDTAG Ltd [Bracknell, Berks RG12 3XQ, UK] and devices, such as the MICROKAN™ or MICROTUBE™ microvessel with memory devices. Before the synthesis begins, the microvessels are filled with polymer resin. The microvessel devices are, one at a time placed upon the scanner. The device and software reads the contents of the data encoded in the recording device, transponder, such as the BMDS tag or the IDTAG™ tag, contained in each microvessi. The software, chooses which building block shall be added to the compound contained in each microvessel. It directs the transceiver to write encoded data to the transponder, indicating which building block this is. The software displays a message which directs the user to place the microvessel in the appropriate reaction vessel so that the chosen building block will be added. This process is repeated a plurality of times with each microvessel and for each synthetic step the planned steps of the library.

The software then uses the scanner to read a tag and receive its encoded information. Using the user-entered compound names stored in the library's data base, the software translates the encoded information into the names of the chemical building blocks. The software can also display compounds graphically, using the graphical information specified by the user. The software calculates the molecular weight of compounds from the data provided for the pharmacophore and building blocks. The software facilitates the recording of progress through the above process. The software generates displays and reports which illustrate this and all of the above planning, design, compound data, and graphical representations of compounds.

F. Tools and Applications Using Matrices with Memories

1. Tools

The matrix with memory and associated system as described herein is the basic tool that can be used in a multitude of applications, including any reaction that incorporates a functionally specific (i.e. in the reaction) interaction, such as receptor binding. This tool is then combined with existing technologies or can be modified to produce additional tools.

For example, the matrix with memory combination, can be designed as a single analyte test or as a multianalyte test and also as a multiplexed assay that is readily automated. The ability to add one or a mixture of matrices with memories, each with linked or proximate molecule or biological particle to a sample, provides that ability to simultaneously determine multiple analytes and to also avoid multiple pipetting steps. The ability to add a matrix with memory and linked molecules or particles with additional reagents, such as scintillants, provides the ability to multiplex assays.

As discussed herein, in one preferred embodiment the matrices are particulate and include adsorbed, absorbed, or otherwise linked or proximate, molecules, such as peptides or oligonucleotides, or biological particles, such as cells. Assays using such particulate memories with matrices may be conduced "on bead" or "off bead". On bead assays are suitable for multianalyte assays in which mixtures of matrices with linked molecules are used and screened against a labeled known. Off bead assays may also be performed; in these instances the identity of the linked molecule or biological particle must be known prior to cleavage or the molecule or biological particle must be in some manner associated with the memory.

In other embodiments the matrices with memories use matrices that are continuous, such as microplates, and include a plurality of memories, preferably one memory/well. Of particular interest herein are matrices, such as Flash Plates™ [NEN, Dupont], that are coated or impregnated with scintillant or fluophore or other luminescent moiety or combination thereof, modified by including a memory in each well. The resulting matrix with memory is herein referred to as a luminescing matrix with memory. Other formats of interest that can be modified by including a memory in a matrix include the Multiscreen Assay System [Millipore] and gel permeation technology. Again it is noted that the memories may be replaced with or supplemented with engraved code, preferably at the base of each well [outer surface preferred] that is either precoded or added prior to or during use. The memory, in these instances, is then remote from the matrix.

Preferred plates are those that contain a microplate type frame and removable wells or strips. Each well or strip can contain a memory and/or can be engraved with a code.

2. Scintillation proximity assays (SPAs) and scintillant-containing matrices with memories Scintillation proximity assays are well known in the art [see, e.g., U.S. Pat. No. 4,271,139; U.S. Pat. No. 4,382,074; U.S. Pat. No. 4,687,636; U.S. Pat. No. 4,568,649; U.S. Pat. No. 4,388,296; U.S. Pat. No. 5,246,869; International PCT Application No. WO 94/26413; International PCT Application No. WO 90/03844; European Patent Application No. 0 556 005 A1; European Patent Application No. 0 301 769 A1; Hart et al. (1979) *Molec. Immunol.* 16:265–267; Udenfriend et al. (1985) *Proc. Natl. Acad. Sci. U.S.A.* 82:8672–8676; Nelson et al. (1987) *Analyt. Biochem* 165:287–293; Heath, et al. (1991) *Methodol. Surv. Biochem. Anal.* 21:193–194; Mattingly et al. (1995) *J. Memb. Sci.* 98:275–280; Pernelle (1993) *Biochemistry* 32:11682–116878; Bosworth et al. (1989) *Nature* 341:167–168; and Hart et al. (1989) *Nature* 341:265]. Beads [particles] and other formats, such as plates and membranes have been developed.

SPA assays refer to homogeneous assays in which quantifiable light energy produced and is related to the amount of radioactively labelled products in the medium. The light is produced by a scintillant that is incorporated or impregnated or otherwise a part of a support matrix. The support matrix is coated with a receptor, ligand or other capture molecule that can specifically bind to a radiolabeled analyte, such as a ligand.

a. Matrices

Typically, SPA uses fluomicrospheres, such as diphenyloxazole-latex, polyacrylamide-containing a fluophore, and polyvinyltoluene [PVT] plastic scintillator beads, and they are prepared for use by adsorbing compounds into the matrix. Also fluomicrospheres based on organic phosphors have been developed. Microplates made from scintillation plastic, such as PVT, have also been used [see, e.g., International PCT Application No. WO 90/03844]. Numerous other formats are presently available, and any format may be modified for use herein by including one or more recording devices.

Typically the fluomicrospheres or plates are coated with acceptor molecules, such as receptors or antibodies to which ligand binds selectively and reversibly. Initially these assays were performed using glass beads containing fluors and functionalized with recognition groups for binding specific ligands [or receptors], such as organic molecules, proteins, antibodies, and other such molecules. Generally the support bodies used in these assays are prepared by forming a porous amorphous microscopic particle, referred to as a bead [see, e.g., European Patent Application No.0 154,734 and International PCT Application No. WO 91/08489]. The bead is formed from a matrix material such as acrylamide, acrylic acid, polymers of styrene, agar, agarose, polystyrene, and other such materials, such as those set forth above. Cyanogen bromide has been incorporated into the bead into to provide moieties for linkage of capture molecules or biological particles to the surface. Scintillant material is impregnated or incorporated into the bead by precipitation or other suitable method. Alternatively, the matrices are formed from scintillating material [see, e.g., International PCT Application No. WO 91/08489, which is based on U.S. application Ser. No. 07/444,297; see, also U.S. Pat. No. 5,198,670], such as yttrium silicates and other glasses, which when activated or doped respond as scintillators. Dopants include Mn, Cu, Pb, Sn, Au, Ag, Sm, and Ce. These materials can be formed into particles or into continuous matrices. For purposes herein, the are used to coat, encase or otherwise be in contact with one or a plurality of recording devices.

Assays are conducted in normal assay buffers and requires the use of a ligand labelled with an isotope, such as $^3$H and $^{125}$I, that emits low-energy radiation that is readily dissipated easily an aqueous medium. Because $^3$H β particles and $^{125}$I Auger electrons have average energies of 6 and 35 keV, respectively, their energies are absorbed by the aqueous solutions within very small distances (~4 μm for $^3$H β particles and 35 μm for $^{125}$I Auger electrons). Thus, in a typical reaction of 0.1 ml to 0.4 ml the majority of unbound labelled ligands will be too far from the fluomicrosphere to activate the fluor. Bound ligands, however, will be in sufficiently close proximity to the fluomicrospheres to allow the emitted energy to activate the fluor and produce light. As a result bound ligands produce light, but free ligands do not. Thus, assay beads emit light when they are exposed to the radioactive energy from the label bound to the beads through the antigen-antibody linkage, but the unreacted radioactive species in solution is too far from the bead to elicit light. The light from the beads will be measured in a liquid scintillation counter and will be a measure of the bound label.

Matricses with memories for use in scintillation proximity assays [SPA] are prepared by associating a memory [or engraved or printed code or symbology] with a matrix that includes a scintillant. In the most simple embodiment, matrix particles with scintillant [fluomicrospheres] are purchased from Amersham, Packard, NE Technologies [(formerly Nuclear Enterprises, Inc.) San Carlos, Calif.] or other such source and are associated with a memory, such as by including one or more of such beads in a MICROKAN™ microvessel with a recording device. Typically, such beads as purchased are derivatized and coated with selected moieties, such as streptavidin, protein A, biotin, wheat germ agglutinin [WGA], and polylysine. Also available are inorganic fluomicrospheres based on cerium-doped yttrium silicate or polyvinyltoluene (PVT). These contain scintillant and may be coated and derivatized.

Alternatively, small particles of PVT impregnated with scintillant are used to coat recording devices, such as the IPTT-100 devices [Bio Medic Data Systems, Inc., Maywood, N.J.; see, also U.S. Pat. Nos. 5,422,636, 5,420, 579, 5,262,772, 5,252,962, 5,250,962, 5,074,318, and RE 34,936] that have been coated with a protective material, such as polystyrene, TEFLON, a ceramic or anything that does not interfere with the reading and writing EM frequency(ies). Such PVT particles may be manufactured or purchased from commercial sources such as NE TECHNOLOGY, INC. [e.g., catalog # 191A, 1–10 μm particles]. These particles are mixed with agarose or acrylamide, styrene, vinyl or other suitable monomer that will polymerize or gel to form a layer of this material, which is coated on polystyrene or other protective layer on the recording device. The thickness of the layers may be empirically determined, but they must be sufficiently thin for the scintillant to detect proximate radiolabels. To make the resulting particles resistant to chemical reaction they may be coated with polymers such as polyvinyltoluene or polystyrene, which can then be further derivatized for linkage and/or synthesis of molecules and biological particles. The resulting beads are herein called luminescing-matrices with memories, and when used in SPA formats are herein referred to as scintillating matrices with memories.

The scintillating matrices with memories beads can be formed by manufacturing a bead containing a recording device and including scintillant, such as 2,5-diphenyloxazole [PPO] and/or 1,4-bis-[5-phenyl-(oxazolyl)]benzene [POPOP] as a coating. These particles or beads are then coated with derivatized polyvinyl benzene or other suitable matrix on which organic synthesis, protein synthesis or other synthesis can be performed or to which organic molecules, proteins, nucleic acids, biological particles or other such materials can be attached. Attachment may be effected using any of the methods known to those of skill in the art, including methods described herein, and include covalent, non-covalent, direct and indirect linkages.

Alternatively or additionally, each bead may be engraved with a code. Preferably the beads are of such geometry that they can be readily oriented for reading.

Molecules, such as ligands or receptors or biological particles are covalently coupled thereto, and their identity is recorded in the memory. Alternatively, molecules, such as small organics, peptides and oligonucleoties, are synthesized on the beads as described herein so that history of synthesis and/or identity of the linked molecule is recorded in the memory. The resulting matrices with memory particles with linked molecules or biological particles may be used in any application in which SPA is appropriate. Such applications, include, but are not limited to: radioimmunoassays, receptor binding assays, enzyme assays and cell biochemistry assays.

For use herein, the beads, plates and membranes are either combined with a recording device or a plurality of devices, or the materials used in preparing the beads, plates or membranes is used to coat, encase or contact a recording device and/or engraved with a code. Thus, microvessels [MICROKANS™] containing SPA beads coated with a molecule or biological particle of interest; microplates impregnated with or coated with scintillant, and recording devices otherwise coated with, impregnated with or contacted with scintillant are provided.

To increase photon yield and remove the possibility of loss of fluor, derivatized fluomicrospheres based on yttrium silicate, that is doped selectively with rare earth elements to facilitate production of light with optimum emission characteristics for photomultipliers and electronic circuitry have been developed [see, e.g., European Patent Application No. 0 378 059 B1; U.S. Pat. No. 5,246,869]. In practice, solid scintillant fibers, such as cerium-loaded glass or based on rare earths, such as yttrium silicate, are formed into a matrix. The glasses may also include activators, such as terbium, europium or lithium. Alternatively, the fiber matrix may be made from a scintillant loaded polymer, such as polyvinyltoluene. Molecules and biological particles can be adsorbed to the resulting matrix.

For use herein, these fibers may be combined in a microvessel with a recording device [i.e., to form a MICROKAN™]. Alternatively, the fibers are used to coat a recording device or to coat or form a microplate containing recording devices in each well. The resulting combinations are used as supports for synthesis of molecules or for linking biological particles or molecules. The identity and/or location and/or other information about the particles is encoded in the memory and the resulting combinations are used in scintillation proximity assays.

Scintillation plates [e.g., FlashPlates™, NEN Dupont, and other such plates] and membranes have also been developed [see, Mattingly et al. (1995) *J. Memb. Sci.* 98:275–280] that may be modified by including a memory for use as described herein. The membranes, which can contain polysulfone resin M.W. 752 kD, polyvinylpyrrolidone MW 40 kDA, sulfonated polysulfone, fluor, such as p-bis-o-methylstyrylbenzene, POP and POPOP, may be prepared as described by Mattingly, but used to coat, encase or contact a recording device. Thus, instead of applying the polymer solution to a glass plate the polymer solution is applied to the recording device, which, if need is pre-coated with a protective coating, such as a glass, TEFLON or other such coating.

Further, as shown in the Examples, the recording device may be coated with glass, etched and the coated with a layer of scintillant. The scintillant may be formed from a polymer, such as polyacrylamide, gelatin, agarose or other suitable material, containing fluorophores, a scintillation cocktail, FlexiScint [Packard Instrument Co., Inc., Downers Grove, Ill.] NE Technology beads [see, e.g., U.S. Pat. No. 4,588,698 for a description of the preparation of such mixtures]. Alternatively, microplates that contain recording devices in one or more wells may be coated with or impregnated with a scintillant or microplates containing scintillant plastic may be manufactured with recording devices in each well. If necessary, the resulting bead, particle or continuous matrix, such as a microplate, may be coated with a thin layer polystyrene, TEFLON or other suitable material. In all embodiments it is critical that the scintillant be in sufficient proximity to the linked molecule or biological particle to detect proximate radioactivity upon interaction of labeled molecules or labeled particles with the linked molecule or biological particle.

The resulting scintillating matrices may be used in any application for which scintillation proximity assays are used. These include, ligand identification, single assays, multianalyte assays, including multi-ligand and multi-receptor assays, radioimmunoassays [RIAs], enzyme assays, and cell biochemistry assays [see, e.g., International PCT Application No. WO 93/19175, U.S. Pat. No. 5,430,150, Whitford et al. (1991) *Phytochemical Analysis* 2:134–136; Fenwick et al. (1994) *Anal. Proc. Including Anal. Commun.* 31:103–106; Skinner et al. (1994) *Anal. Biochem.* 223:259–265; Matsumura et al. (1992) *Life Sciences* 51:1603–1611; Cook et al. (1991) *Structure and Function of the Aspartic Proteinases*, Dunn, ed., Penum Press, NY, pp. 525–528; Bazendale et al. in (1990) *Advances in Prostaglandin, Thromboxane and Leukotriene Research*, Vol. 21, Samuelsson et al., eds., Raven Press, NY, pp 302–306].

b. Assays (1) Receptor Binding Assays

Scintillating matrices with memories beads can be used, for example, in assays screening test compounds as agonists or antagonists of receptors or ion channels or other such cell surface protein. Test compounds of interest are synthesized on the beads or linked thereto, the identity of the linked compounds is encoded in the memory either during or following synthesis, linkage or coating. The scintillating matrices with memories are then incubated with radiolabeled [$^{125}$I, $^3$H, or other suitable radiolabel] receptor of interest and counted in a liquid scintillation counter. When radiolabeled receptor binds to any of the structure(s) synthesized or linked to the bead, the radioisotope is in sufficient proximity to the bead to stimulate the scintillant to emit light. In contrast By contrast, if a receptor does not bind, less or no radioactivity is associated with the bead, and consequently less light is emitted. Thus, at equilibrium, the presence of molecules that are able to bind the receptor may be detected. When the reading is completed, the memory in each bead that emits light [or more light than a control] queried and the host computer, decoder/encoder, or scanner can interpret the memory in the bead and identify the active ligand.

(a) Multi-ligand Assay

Mixtures of scintillating matrices with memories with a variety of linked ligands, which were synthesized on the matrices or linked thereto and their identities encoded in each memory, are incubated with a single receptor. The memory in each light-emitting scintillating matrix with memory is queried and the identity of the binding ligand is determined.

(b) Multi-receptor Assays

Similar to conventional indirect or competitive receptor binding assays that are based on the competition between unlabelled ligand and a fixed quantity of radiolabeled ligand for a limited number of binding sites, the scintillating matrices with memories permit the simultaneous screening of a number of ligands for a number of receptor subtypes.

Mixtures of receptor coated beads [one receptor type/per bead; each memory encoded with the identity of the linked receptor] are reacted with labeled ligands specific for each receptor. After the reaction has reached equilibrium, all beads that emit light are reacted with a test compound. Beads that no longer emit light are read.

For example receptor isoforms, such as retinoic acid receptor isoforms, are each linked to a different batch of scintillating matrix with memory beads, and the identity of each isoform is encoded in the memories of linked matrices. After addition of the radiolabeled ligand(s), such as $^3$H-retinoic acid, a sample of test compounds [natural, synthetic, combinatorial, etc.] is added to the reaction mixture, mixed and incubated for sufficient time to allow the reaction to reach equilibrium. The radiolabeled ligand binds to its receptor, which has been covalently linked to the bead and which the emitted short range electrons will excite the fluophor or scintillant in the beads, producing light. When unlabelled ligand from test mixture is added, if it displaces the labeled ligand it will diminish or stop the fluorescent light signal. At the end of incubation period, the tube can be measured in a liquid scintillation counter to demonstrate if any of the test material reacted with receptor family. Positive samples [reduced or no fluorescence] will be further analyzed for receptor subtyping by querying their memories with the RF detector. In preferred embodiments, each bead will be read and with a fluorescence detector and RF scanner. Those that have a reduced fluorescent signal will be identified and the linked receptor determined by the results from querying the memory.

The same concept can be used to screen for ligands for a number of receptors. In one example, FGF receptor, EGF receptor, and PDGF receptor are each covalently linked to a different batch of scintillating matrix with memory beads. The identity of each receptor is encoded in each memory. After addition of the $^{125}$I-ligands [$^{125}$I-FGF, $^{125}$I-EGF, and $^{125}$I-PDGF] a sample of test compounds [natural, synthetic, combinatorial, etc.) is added to the tube containing $^{125}$I-ligand-receptor-beads, m mixed and incubated for sufficient time to allow the reaction to reach equilibrium. The radiolabeled ligands bind to their respective receptors receptor that been covalently linked to the bead. By virtue of proximity of the label to the bead, the emitted short range electrons will excite the fluophor in the beads. When unlabelled ligand from test mixture is added, if it displaces the any of the labeled ligand it will diminish or stop the fluorescent signal. At the end of incubation period, the tube can be measured in a liquid scintillation counter to demonstrate if any of the test material reacted with the selected receptor family. Positive samples will be further analyzed for receptor type by passing the resulting complexes measuring the fluorescence of each bead and querying the memories by exposing them to RF or the selected EM radiation. The specificity of test ligand is determined by identifying beads with reduced fluorescence that and determining the identity of the linked receptor by querying the memory.

(c) Other formats

Microspheres, generally polystyrene typically about 0.3 $\mu$m–3.9 $\mu$m, are synthesized with scintillant inside can either be purchased or prepared by covalently linking scintillant to the monomer prior to polymerization of the polystyrene or other material. They can then be derivatized [or purchased with with chemical functional groups], such as —COOH, and —CH$_2$OH. Selected compounds or libraries are synthesized on the resulting microspheres linked via the functional groups, as described herein, or receptor, such as radiolabeled receptor, can be coated on the microsphere. The resulting "bead" with linked compounds, can used in a variety of SPA and related assays, including immunoassays, receptor binding assays, protein:protein interaction assays, and other such assays in which the ligands linked to the scintillant-containing microspheres are reacted with memories with matrices that are coated with a selected receptor.

For example, $^{125}$I-labeled receptor is passively coated on the memory with matrix and then mixed with ligand that is linked to a the scintillant-containing microspheres. Upon binding the radioisotope into is brought into close proximity to the scintillant in which effective energy transfer from the $\beta$ particle will occur, resulting in emission of light.

Alternatively, the memory with matrix [containing scintillant] can also be coated with $^3$H-containing polymer on which the biological target [i.e., receptor, protein, antibody, antigen] can be linked [via adsorption or via a functional group]. Binding of the ligand brings the scintillant into close proximity to the label, resulting in light emission.

(2) Cell-based Assays

Cell-based assays, which are fundamental for understanding of the biochemical events in cells, have been used with increasing frequency in biology, pharmacology, toxicology, genetics, and oncology [see, e.g., Benjamin et al. (1992) *Mol. Cell. Boil.* 12:2730–2738] Such cell lines may be constructed or purchased [see, e.g., the Pro-Box Kit available from Xenometrix, Boulder Colo.; see, also International PCT Application No. WO 94/7208 cell lines]. Established cell lines, primary cell culture, reporter gene systems in recombinant cells, cells transfected with gene of interest, and recombinant mammalian cell lines have been used to set up cell-based assays. For example Xenometrix, Inc. [Boulder, Colo.] provides kits for screening compounds for toxicological endpoints and metabolic profiles using bacteria and human cell lines. Screening is effected by assessing activation of regulatory elements of stress genes fused to reporter genes in bacteria, human liver or colon cell lines and provide information on the cytotoxicity and permeability of test compounds.

In any drug discovery program, cell-based assays offer a broad range of potential targets as well as information on cytotoxicity and permeability. The ability to test large numbers of compounds quickly and efficiently provides a competitive advantage in pharmaceutical lead identification.

High throughput screening with cell-based assays is often limited by the need to use separation, wash, and disruptive processes that compromise the functional integrity of the cells and performance of the assay. Homogeneous or mix-and-measure type assays simplify investigation of various biochemical events in whole cells and have been developed using scintillation microplates [see, e.g., International PCT Application No. WO 94/26413, which describes scintillant plates that are adapted for attachment and/or growth of cells and proximity assays using such cells]. In certain embodiment herein, cell lines such as those described in International PCT Application No. WO 94/17208 are be plated on scintillant plates, and screened against compounds synthesized on matrices with memories. Matrices with memories encoded with the identity of the linked molecule will be introduced into the plates, the linkages cleaved and the effects of the compounds assessed. Positive compounds will be identified by querying the associated memory.

The scintillant base plate is preferably optically transparent to selected wavelengths that allow cells in culture to be viewed using an inverted phase contrast microscope, and permit the material to transmit light at a given wavelength with maximum efficiency. In addition the base retains its optical properties even after exposure to incident beta radiation from radioisotopes as well as under stringent radiation conditions required for sterilization of the plates. The base plate can be composed of any such optically transparent material containing scintillant, e.g., a scintillant glass based on lanthanide metal compounds. Typically, the base plate is composed of any plastic material, generally formed from monomer units that include phenyl or naphthyl moieties in order to absorb incident radiation energy from radionuclides which are in close proximity with the surface. Preferably the plastic base plate is composed of polystyrene or polyvinyltoluene, into which the scintillant is incorporated. The scintillant includes, but is not limited to: aromatic hydrocarbons such as p-terphenyl, p-quaterphenyl and their derivatives, as well as derivatives of the oxazoles and 1,3,4-oxadiazoles, such as 2-(4-t-butylphenyl)-5-(4-biphenyl)-1,3,4-oxadiazole and 2,5-diphenyloxazole. Also included in the polymeric composition may be a wavelength shifter such as 1,4-bis(5-phenyl-2-oxazolyl)benzene, 9,10-diphenylanthracene, 1,4-bis(2-methylstyryl)-benzene, and other such compounds. The function of the wavelength shifter is to absorb the light emitted by the scintillant substance and re-emit longer wavelength light which is a better match to the photo-sensitive detectors used in scintillation counters. Other scintillant substances and polymer bodies containing them are known to those of skill in this art [see, e.g., European Patent Application No. 0 556 005 A1].

The scintillant substances can be incorporated into the plastic material of the base by a variety of methods. For example, the scintillators may be dissolved into the monomer mix prior to polymerization, so that they are distributed evenly throughout the resultant polymer. Alternatively the scintillant substances may be dissolved in a solution of the polymer and the solvent removed to leave a homogeneous mixture. The base plate of disc may be bonded to the main body of the well or array of wells, which itself may be composed of a plastic material including polystyrene, polyvinyltoluene, or other such polymers. In the case of the multi-well array, the body of the plate may be made opaque, i.e., non-transparent and internally reflective, in order to completely exclude transmission of light and hence minimize "cross-talk." This is accomplished by incorporating into the plastic at the polymerization stage a white dye or pigment, for example, titanium dioxide. Bonding of the base plate to the main body of the device can be accomplished by any suitable bonding technique, for example, heat welding, injection molding or ultrasonic welding.

For example, a 96-well plate is constructed to the standard dimensions of 96-well microtiter plates 12.8 cm×8.6 cm×1.45 cm with wells in an array of 8 rows of 12 wells each. The main body of the plate is constructed by injection molding of polystyrene containing a loading of white titanium oxide pigment at 12%. At this stage, the wells of the microtiter plate are cylindrical tubes with no closed end. A base plate is formed by injection molding of polystyrene containing 2-(4-t-butylphenyl)-5-(4-biphenyl)-1,3,4oxadiazole (2%) and 9,10-diphenylanthracene (0.5%). The base plate has been silk screen printed with a grid array to further reduce crosstalk. The base plate is then fused in a separate operation to the body by ultrasonic welding, such that the grid array overlies the portions of the microtiter plate between the wells.

A 24-well device is constructed to the dimensions 12.8× 8.6×1.4 cm with 24 wells in an array of 4 rows of 6 wells. The main body of the plate [not including the base of each well] is constructed by injection molding of polystyrene containing 12% white titanium oxide pigment. The base 24 of each well is injection molded with polystyrene containing 2-(4-t-butylphenyl)-5-(4-biphenylyl)-1,3,4-oxadizaole [2%] and 9,10-diphenylanthracene [0.5%]. The heat from the injected base plastic results in fusion to the main body giving an optically transparent base to the well.

The plates may contain multiple wells that are continuous or that are each discontinuous from the other wells in the array, or they may be single vessels that have, for example, an open top, side walls and an optically transparent scintillant plastic base sealed around the lower edge of the side walls.

In another format the plate, is a single well or tube. The tube may be constructed from a hollow cylinder made from optically transparent plastic material and a circular, scintillant containing, plastic disc. The two components are welded together so as to form a single well or tube suitable for growing cells in culture. As in the plate format, bonding of the circular base plate to the cylindrical portion is achieved by any conventional bonding technique, such as ultrasonic welding. The single well or tube may be any convenient size, suitable for scintillation counting. In use, the single well may either be counted as an insert in a scintillation vial, or alternatively as an insert in a scintillation vial, or alternatively as an insert in a multi-well plate of a flat bed scintillation counter. In this latter case, the main body of the multi-well plate would need to be opaque for reasons given earlier.

The various formats are selected according to use. They may be used for growing cells and studying cellular biochemical processes in living cells or cell fragments. The 96-well plate is a standard format used in experimental cell biology and one that is suitable for use in a flat bed scintillation counter [e.g., Wallac Microbeta or Packard Top Count]. In the multi-well format, it is an advantage to be able to prevent "cross talk" between different wells of the plate that may be used for monitoring different biological processes using different amounts or types of radioisotope. Therefore the main body of the plate can be made from opaque plastic material. The 24-well plate format is commonly used for cell culture. This type of plate is also suitable for counting in a flat bed scintillation counter. The dimensions of the wells will be larger.

As an alternative format, the transparent, scintillant containing plastic disc is made to be of suitable dimensions so as to fit into the bottom of a counting vessel. The counting vessel is made from non-scintillant containing material such as glass or plastic and should be sterile in order to allow cells to grow and the corresponding cellular metabolic processes to continue. Cells are first cultured on the disc, which is then transferred to the counting vessel for the purposes of monitoring cellular biochemical processes.

The culture of cells on the scintillation plastic base plate of the wells (or the disc) involves the use of standard cell culture procedures, e.g, cells are cultured in a sterile environment at 37° C. in an incubator containing a humidified 95% air/5% $CO_2$ atmosphere. Various cell culture media may be used including media containing undefined biological fluids such as fetal calf serum, or media which is fully defined and serum-free. For example, MCDB 153 is a selective medium for the culture of human keratinocytes [Tsao et al. (1982) *J. Cell. Physiol.* 110:219–229].

These plates are suitable for use with any adherent cell type that can be cultured on standard tissue culture plasticware, including culture of primary cells, normal and transformed cells derived from recognized sources species and tissue sources. In addition, cells that have been transfected with the recombinant genes may also be cultured using the invention. There are established protocols available for the culture of many of these diverse cell types [see, e.g., Freshney et al. (1987) *Culture of Animal Cells: A Manual of Basic Technique*, 2nd Edition, Alan R. Liss Inc.]. These protocols may require the use of specialized coatings and selective media to enable cell growth and the expression of specialized cellular functions.

The scintillating base plate or disc, like all plastic tissue culture ware, requires surface modification in order to be adapted for the attachment and/or growth of cells. Treatment can involves the use of high voltage plasma discharge, a well established method for creating a negatively charged plastic surface [see, e.g., Amstein et al. (1975) *J. Clinical Microbiol.* 2:46–54]. Cell attachment, growth and the expression of specialized functions can be further improved by applying a range of additional coatings to the culture surface of the device. These can include: (i) positively or negatively charged chemical coatings such as poly-lysine or other biopolymers [McKeehan et al. (1976) *J. Cell Biol.* 71:727–734 (1976)]; (ii) components of the extracellular matrix including collagen, laminin, fibronectin [see, e.g., Kleinman et al. (1987) *Anal. Biochem.* 166:1–13]; and (iii) naturally secreted extracellular matrix laid down by cells cultured on the plastic surface [Freshney et al. et al. (1987) *Culture of Animal Cells: A Manual of Basic Technique*, 2nd Edition, Alan R. Liss Inc.]. Furthermore, the scintillating base plate may be coated with agents, such as lectins, or adhesion molecules for attachment of cell membranes or cell types that normally grow in suspension. Methods for the coating of plasticware with such agents are known [see, e.g., Boldt et al. (1979) *J. Immunol.* 123:808].

In addition, the surface of the scintillating layer may be coated with living or dead cells, cellular material, or other coatings of biological relevance. The interaction of radiolabeled living cells, or other structures with this layer can be monitored with time allowing processes such as binding, movement to or from or through the layer to be measured.

Virtually all types of biological molecules can be studied. A any molecule or complex of molecules that interact with the cell surface or that can be taken up, transported and metabolized by the cells, can be examined using real time analysis. Examples of biomolecules will include receptor ligands, protein and lipid metabolite precursors (e.g., amino acids, fatty acids), nucleosides and any molecule that can be radiolabeled. This would also include ions such as calcium, potassium, sodium and chloride, that are functionally important in cellular homeostasis, and which exist as radioactive isotopes. Furthermore, viruses and bacteria and other cell types, which can be radiolabeled as intact moieties, can be examined for their interaction with monolayer adherent cells grown in the scintillant well format.

The type of radioactive isotope that can be used with this system will typically include any of the group of isotopes that emit electrons having a mean range up to 2000 $\mu$m in aqueous medium. These will include isotopes commonly used in biochemistry such as [$^3$H], [$^{125}$I], [$^{14}$C], [$^{35}$S], [$^{45}$Ca], [$^{33}$p], and [$^{32}$p], but does not preclude the use of other isotopes, such as [$^{55}$Fe], [$^{109}$Cd] and [$^{51}$Cr] that also emit electrons within this range. The wide utility of the invention for isotopes of different emission energy is due to the fact that the current formats envisaged would allow changes to the thickness of the layer containing a scintillant substance, thereby ensuring that all the electron energy is absorbed by the scintillant substance. Furthermore, crosstalk correction software is available which can be utilized with all high energy emitters. Applications using these plates include protein synthesis, $Ca^{2+}$ transport, receptor-ligand binding, cell adhesion, sugar transport and metabolism, hormonal stimulation, growth factor regulation and stimulation of motility, thymidine transport, and protein synthesis.

For use in accord with the methods herein, the scintillant plates can include a memory in each well, or alternatively, memory with matrix-linked compounds will be added to each well. The recording device with memory may be impregnated or encased or placed in wells of the plate, typically during manufacture. In preferred embodiments, however, the memories are added to the wells with adsorbed or linked molecules.

In one embodiment, matrices with memories with linked molecules are introduced into scintillant plates in which cells have been cultured [see, e.g., International PCT Application No. WO 94/26413]. For example, cells will be plated on the transparent scintillant base 96-well microplate that permits examination of cells in culture by inverted phase contrast microscope and permits the material to transmit light at a given wavelength with maximum efficiency. Matrices with memories to which test compounds linked by preferably a photocleaveable linker are added to the wells. The identity of each test compound is encoded in the memory of the matrix during synthesis if the compound is synthesized on the matrix with memory or when the compound is linked to the matrix.

Following addition of matrix with memory to the well and release of chemical entities synthesized on the beads by exposure to light or other procedures, the effects of the chemical released from the beads on the selected biochemical events, such as signal transduction, cell proliferation, protein or DNA synthesis, in the cells can be assessed. In this format receptor binding events include, but are not limited to: whole cell receptor-ligand binding [agonist or antagonist], thymidine or uridine transport, protein synthesis (using, for example, labeled cysteine, methionine, leucine or proline], hormone and growth factor induced stimulation and motility, and calcium uptake.

In another embodiment, the memories are included in the plates either placed in the plates or manufactured in the wells of the plates. In these formats, the identities of the contents of the well is encoded into the memory. Of course it is understood, that the information encoded and selection of encased or added memories depends upon the selected protocol.

In another format, cells will be plated on the tissue culture plate, after transferring the matrices with memories and release of compounds synthesized on the beads in the well. Cytostatic, cytotoxic and proliferative effects of the compounds will be measured using colorimetric [MTT, XTT, MTS, Alamar blue, and Sulforhodamine B], fluorimetric [carboxyfluorescein diacetate], or chemiluminescent reagents [i.e., CytoLite™, Packard Instruments, which is used in a homogeneous luminescent assay for cell proliferation, cell toxicity and multi-drug resistance].

For example, cells that have been stably or transiently transfected with a specific gene reporter construct containing an inducible promoter operatively linked to a reporter gene that encodes an indicator protein can be calorimetrically monitored for promoter induction. Cells will be plated on the tissue culture 96-well microtiter plate and after addition of memories with matrices in the wells and release of chemical entities synthesized on the matrices, the effect of the compound released from the beads on the gene expression will be assessed. The Cytosensor Microphysiometer [Molecular Devices] evaluates cellular responses that are mediated by G protein-linked receptors, tyrosine kinase-linked receptors, and ligand-gated ion channels. It measures extracellular pH to assess profiles of compounds assessed for the ability to modulate activities of any of the these cell surface proteins by detecting secretion of acid metabolites as a result of altered metabolic states, particularly changes in metabolic rate. Receptor activation requires use of ATP and other energy resources of the cell thereby leading to increased in cellular metabolic rate. For embodiments herein, the memories with matrices, particularly those modified for measuring pH, and including linked test compounds, can be used to track and identify the added test compound added and also to detect changes in pH, thereby identifying linked molecules that modulate receptor activities.

3. Memories with matrices for non-radioactive energy transfer proximity assays

Non-radioactive energy transfer reactions, such as FET or FRET, FP and HTRF assays, are homogeneous luminescence assays based on energy transfer are carried out between a donor luminescent label and an acceptor label [see, e.g., Cardullo et al. (1988) *Proc. Natl. Acad. Sci. U.S.A.* 85:8790–8794; Peerce et al. (1986) *Proc. Natl. Acad. Sci. U.S.A.* 83:8092–8096; U.S. Pat. No. 4,777,128; U.S. Pat. No. 5,162,508; U.S. Pat. No. 4,927,923; U.S. Pat. No. 5,279,943; and International PCT Application No. WO 92/01225]. The donor label is usually a rare earth metal cryptate, particularly europium trisbipyridine diamine [EuTBP] or terbium trisbipyridine diamine [TbTBP] and an acceptor luminescent, presently fluorescent, label. When the donor is EuTBP, the acceptor is preferably allopycocyanin [APC], allophycocyanin B, phycocyanin C or phycocyanin R, and when the donor is TbTBP, the acceptor is a rhodamine, thiomine, phycocyanin R, phycoerythrocyanin, phycoerythrin C, phycoerythrin B or phycoerythrin R.

Energy transfer between such donors and acceptors is highly efficient, giving an amplified signal and thereby improving the precision and sensitivity of the assay. Within distances characteristic of interactions between biological molecules, the excitation of a fluorescent label (donor) is transferred non radiatively to a second fluorescent label (acceptor). When using europium cryptate as the donor, APC, a phycobiliprotein of 5 kDa, is presently the preferred acceptor because it has high molar absorptivity at the cryptate emission wavelength providing a high transfer efficiency, emission in a spectral range in which the cryptate signal is insignificant, emission that is not quenched by presence of sera, and a high quantum yield. When using $Eu^{3+}$ cryptate as donor, an amplification of emitted fluorescence is obtained by measuring APC emission.

The rare earth cryptates are formed by the inclusion of a luminescence lanthanide ion in the cavity of a macropolycyclic ligand containing 2,2'-biphyridine groups as light absorbers [see, e.g., U.S. Pat. No. 5,162,508; U.S. Pat. No. 4,927,923; U.S. Pat. No. 5,279,943; and International PCT Application No. WO 92/01225]. Preferably the $Eu3^+$ tris-bypryidine diamine derivative, although the acceptor may be used as the label, is cross-linked to antigens, antibodies, proteins, peptides, and oligonucleotides and other molecules of interest.

For use herein, matrices with memories are prepared that incorporate either the donor or, preferably the acceptor, into or on the matrix. In practice, as with the scintillating matrices with memories, the matrices may be of any format, i.e. particulate, or continuous, and used in any assay described above for the scintillating matrices. For example, the recording device is coated with a protective coating, such as glass or polystyrene. If the coating is glass it can be etched. As with preparation of the scintillating matrices with memories, compositions containing the donor or preferably acceptor, such as APC, and typically a polymer or gel, are coated on the recording device or the device is mixed with the composition to produce a fluorescing matrix with memory. To make these matrices resistant to chemical reaction, if needed, they may be coated with polymers such as polyvinylbenzene or polystyrene. Molecules, such as the constituents of combinatorial libraries, are synthesized on the fluorescing matrices with memories, or molecules or biological particles are linked thereto, the identity of the synthesized molecules or linked molecules or biological particles is encoded in memory, and the resulting matrices with memories employed in any suitable assay, including any of those described for the scintillating memories with matrices. In particular, these homogeneous assays using long-lived fluorescence rare earth cryptates and amplification by non radiative energy transfer have been adapted to use in numerous assays including assays employing ligand receptor interaction, signal transduction, transcription factors (protein-protein interaction), enzyme substrate assays and DNA hybridization and analysis [see, Nowak (1993) *Science* 270:368; see, also, Velculescu et al. (1995) *Science* 270:484–487, and Schena et al. (1995) *Science* 270:467–470, which describe methods quantitative and simultaneous analysis of a large number of transcripts that are particularly suited for modification using matrices with memories]. Each of these assays may be modified using the fluorescing matrices with memories provided herein.

For example, a receptor will be labeled with a europium cryptate [where the matrices with memories incorporate, for example allophycocyanin (APC)] or will be labeled with APC, where the matrices incorporate a europium cryptate. After mixing receptor and mixtures of matrices with different ligands, the mixture is exposed to laser excitation at 337 nm, and, if reaction has occurred, typical signals of europium cryptate and APC over background are emitted. Measurement with an interference filter centered at 665 nm selects the signal of the APC labeled receptor from that of europium cryptate labeled ligand on the beads. If particulate, the memories of matrices that emit at 665, can be queried to identify linked ligands.

4. Other applications using memories with matrices and luminescing memories with matrices a. Natural Product Screening In the past, the vast majority of mainline pharmaceuticals have been isolated form natural products such as plants, bacteria, fungus, and marine microorganisms. Natural products include microbials, botanicals, animal and marine products. Extracts of such sources are screened for desired activities and products. Selected products include enzymes [e.g., hyaluronidase], industrial chemicals [a, petroleum emulsifying agents], and antibiotics [e.g., penicillin]. It is generally considered that a wealth of new agents still exist within the natural products pool. Large mixtures of natural products, even within a fermentation broth, can be screened using the matrices with memory combinations linked, for example, to peptides, such as antigens or antibody fragments or receptors, of selected and known sequences or specificities, or to other biologically active compounds, such as neurotransmitters, cell surface receptors, enzymes, or any other identified biological target of interest. Mixtures of these peptides linked to memory matrices can be introduced into the natural product mixture. Individual binding matrices, detected by an indicator, such as a fluorometric dye, can be isolated and the memory queried to determine which linked molecule or biological particle is bound to a natural product.

b. Immunoassays and Immunodiagnostics

The combinations and methods provided herein represent major advances in immunodiagnotics. Immunoassays [such as ELISAs, RIAs and EIAs (enzyme immunoassays)] are used to detect and quantify antigens or antibodies.

(1) Immunoassays

Immunoassays detect or quantify very small concentrations of analytes in biological samples. Many immunoassays use solid supports in which antigen or antibody is covalently, non-covalently, or otherwise, such as via a linker, attached to a solid support matrix. The support-bound antigen or antibody is then used as an analyte in the assay. As with nucleic acid analysis, the resulting antibody-antigen complexes or other complexes, depending upon the format used, rely on radiolabels or enzyme labels to detect such complexes.

The use of antibodies to detect and/or quantitate reagents ["antigens"] in blood or other body fluids has been widely practiced for many years. Two methods have been most broadly adopted. The first such procedure is the competitive binding assay, in which conditions of limiting antibody are established such that only a fraction [usually 30–50%] of a labeled [e.g., radioisotope, fluophore or enzyme] antigen can bind to the amount of antibody in the assay medium. Under those conditions, the addition of unlabeled antigen [e.g., in a serum sample to be tested] then competes with the labeled antigen for the limiting antibody binding sites and reduces the amount of labeled antigen that can bind. The degree to which the labeled antigen is able to bind is inversely proportional to the amount of unlabeled antigen present. By separating the antibody-bound from the unbound labeled antigen and then determining the amount of labeled reagent present, the amount of unlabeled antigen in the sample [e.g., serum] can be determined.

As an alternative to the competitive binding assay, in the labeled antibody, or "immunometric" assay also known as "sandwich" assay], an antigen present in the assay fluid is specifically bound to a solid substrate and the amount of antigen bound is then detected by a labeled antibody [see, e.g., Miles et al. (1968) *Nature* 29:186–189; U.S. Pat. No. 3,867,517; U.S. Pat. No. 4,376,110]. Using monoclonal antibodies two-site immunometric assays are available [see, e.g., U.S. Pat. No. 4,376,110]. The "sandwich" assay has been broadly adopted in clinical medicine. With increasing interest in "panels" of diagnostic tests, in which a number of different antigens in a fluid are measured, the need to carry out each immunoassay separately becomes a serious limitation of current quantitative assay technology.

Some semi-quantitative detection systems have been developed [see, e.g., Buechler et al. (1992) *Clin. Chem.* 38:1678–1684; and U.S. Pat. No. 5,089,391] for use with immunoassays, but no good technologies yet exist to carefully quantitate a large number of analytes simultaneously [see, e.g., Ekins et al. (1990) *J. Clin. Immunoassay* 13:169–181] or to rapidly and conveniently track, identify and quantitate detected analytes.

The methods and memories with matrices provided herein provide a means to quantitate a large number of analytes simultaneously and to rapidly and conveniently track, identify and quantitate detected analytes.

(2) Multianalyte immunoassays

The combinations of matrix with memories provided herein permits the simultaneous assay of large numbers of analytes in any format. In general, the sample that contains an analyte, such as a ligand or any substance of interest, to be detected or quantitated, is incubated with and bound to a protein, such as receptor or antibody, or nucleic acid or other molecule to which the analyte of interest binds. In one embodiment, the protein or nucleic acid or other molecule to which the analyte of interest binds has been linked to a matrix with memory prior to incubation; in another embodiment, complex of analyte or ligand and protein, nucleic acid or other molecule to which the analyte of interest binds is linked to the matrix with memory after the incubation; and in a third embodiment, incubation to form complexes and attachment of the complexes to the matrix with memory are simultaneous. In any embodiment, attachment is effected, for example, by direct covalent attachment, by kinetically inert attachment, by noncovalent linkage, or by indirect linkage, such as through a second binding reaction [i.e., biotinavidin, Protein A-antibody, antibody-hapten, hybridization to form nucleic acid duplexes of oligonucleotides, and other such reactions and interactions]. The complexes are detected and quantitated on the solid phase by virtue of a label, such as radiolabel, fluorescent label, luminophore label, enzyme label or any other such label. The information that is encoded in the matrix with memory depends upon the selected embodiment. If, for example, the target molecule, such as the protein or receptor is bound to the solid phase, prior to complexation, the identity of the receptor and/or source of the receptor may be encoded in the memory in the matrix.

For example, the combinations provided herein are particularly suitable for analyses of multianalytes in a fluid, and particularly for multianalyte immunoassays. In one example, monoclonal antibodies very specific for carcinoembryonic antigen [CEA], prostate specific antigen [PSA], CA-125, alphafetoprotein [AFP], TGF-β, IL-2, IL-8 and IL-10 are each covalently attached to a different batch of matrices with memories using well-established procedures and matrices for solid phase antibody assays. Each antibody-matrix with memory complex is given a specific identification tag, as described herein.

A sample of serum from a patient to be screened for the presence or concentration of these antigens is added to a tube containing two of each antibody-matrix with memory complex [a total of 16 beads, or duplicates of each kind of bead]. A mixture of monoclonal antibodies, previously conjugated to fluorescent dyes, such as fluorescein or phenyl-EDTA-Eu chelate, reactive with different epitopes on each of the antigens is then added. The tubes are then sealed and the contents are mixed for sufficient time [typically one hour] to allow any antigens present to bind to their specific antibody-matrix with memory-antigen complex to produce antibody-matrix with memory-antigen-labeled antibody complexes. At the end of the time period, these resulting complexes are briefly rinsed and passed through an apparatus, such as that set forth in FIG. 7, but with an additional light source. As each complex passes through a light source, such as a laser emitting at the excitation wavelength of fluorescein, about 494 nm, or 340 nm for the Eu chelate complex, its fluorescence is measured and quantitated by reading the emitted photons at about 518 nm for fluorescein or 613 nm for phenyl-EDTA-Eu, and as its identity is determined by the specific signal received by the RF detector. In this manner, eight different antigens are simultaneously detected and quantitated in duplicate.

In another embodiment, the electromagnetically tagged matrices with recorded information regarding linked antibodies can be used with other multianalyte assays, such as those described by Ekins et al. [(1990) *J. Clin. Immunoassay* 13:169–181; see, also International PCT Applications Nos. 89/01157 and 93/08472, and U.S. Pat. Nos. 4,745,072, 5,171,695 and 5,304,498]. These methods rely on the use of small concentrations of sensor-antibodies within a few $\mu m^2$ area. Individual memories with matrices, or an array of memories embedded in a matrix are used. Different antibodies are linked to each memory, which is programmed to record the identity of the linked antibody. Alternatively, the antibody can be linked, and its identity or binding sites identified, and the information recorded in the memory. Linkage of the antibodies can be effected by any method known to those of skill in this art, but is preferably effected using cobalt-iminodiacetate coated memories [see, Hale (1995) *Analytical Biochem.* 231:46–49, which describes means for immobilization of antibodies to cobalt-iminodiacetate resin] mediated linkage particularly advantageous. Antibodies that are reversibly bound to a cobalt-iminodiacetate resin are attached in exchange insert manner when the cobalt is oxidized from the +2 to +3 state. In this state the antibodies are not removed by metal chelating regents, high salt, detergents or chaotropic agents. They are only removed by reducing agents. In addition, since the metal binding site in antibodies is in the C-terminus heavy chain, antibodies so-bound are oriented with the combining site directed away from the resin.

In particular antibodies are linked to the matrices with memories. The matrices are either in particulate form or in the form of a slab with an array of recording devices linked to the matrices or microtiter dish or the like with a recording device in each well. Antibodies are then linked either to each matrix particle or to discrete "microspots" on the slab or in the microtiter wells. In one application, prior to use of these matrices with memories, they are bound to a relatively low affinity anti-idiotype antibody [or other species that specifically recognizes the antibody binding site, such as a single chain antibody or peptidomimetic] labeled with a fluophore [e.g., Texas Red, acridine, fluorescein, ellipticine, rhodamine, Lissamine rhodamine B, Malachite Green, erythrosin, tetramethylrhodamine, eosin, pyrene, anthracene, methidium, ethydium, phenanthroline, 4-dimethylaminonaphthalene, quinoxaline, 2-dimethylaminonaphthalene, 7-dimethylamino-4-methylcoumarin, 7-dimethylaminocoumarin, 7-hydroxy-4-methylcoumarin, 7-hydroxycoumarin, 7-methoxycoumarin, 7-acetoxycoumarin, 7-diethylamino-3-phenyl-4-methylcoumarin, isoluminol, benzophenone, dansyl, dabsyl, mansyl, sulfo rhodamine, 4-acetamido-4'-stilbene-2,2'-disulfonic acid disodium salt, 4-benzamido-4'-stilbene-2,2'-disulfonic acid disodium salt] to measure the concentration of and number of available binding sites present on each matrix with memory particle or each microspot, which information is then encoded into each memory for each microspot or each particle [see, Ekins et al. (1990) *J. Clin. Immunoassay* 13:169–181]. These low affinity antibodies are then eluted, and the matrices can be dried and stored until used.

Alternatively or additionally, the memories in the particles or at each microspot could be programmed with the identity or specificity of the linked antibody, so that after reaction with the test sample and identification of complexed antibodies, the presence and concentration of particular analytes in the sample can be determined. They can be used for multianalyte analyses as described above.

After reaction with the test sample, the matrices with memories are reacted with a second antibody, preferably, although not necessarily, labeled with a different label, such as a different fluophore, such as fluorescein. After this incubation, the microspots or each matrix particle is read by passing the particle through a laser scanner [such as a confocal microscope, see, e.g., Ekins et al. (1990) *J. Clin. Immunoassay* 13:169–181; see also U.S. Pat. No. 5,342,633] to determine the fluorescence intensity. The memories at each spot or linked to each particle are queried to determine the total number of available binding sites, thereby permitting calculation of the ratio of occupied to unoccupied binding sites.

Equilibrium dialysis and modifications thereof has been used to study the interaction of antibody or receptor or other protein or nucleic acid with low molecular weight dialyzable molecules that bind to the antibody or receptor or other protein or nucleic acid. For applications herein, the antibody, receptor, protein or nucleic acid is linked to solid support (matrix with memory) and is incubated with the ligand.

In particular, this method may be used for analysis of multiple binding agents [receptors], linked to matrices with memories, that compete for available ligand, which is present in limiting concentration. After reaction, the matrices with memories linked to the binding agents [receptors] with the greatest amount of bound ligand, are the binding agents [receptors] that have the greatest affinity for the ligand.

The use of matrices with memories also permits simultaneous determination of $K_a$ values of multiple binding agents [receptors] or have multiple ligands. For example, a low concentration of labeled ligand is mixed with a batch of different antibodies bound to matrices with memories. The mixture is flowed through a reader [i.e., a Coulter counter or other such instrument that reads RF and the label] could simultaneously measure the ligand [by virtue of the label] and identity of each linked binding agent [or linked ligand] as the chip is read. After the reaction equilibrium [determined by monitoring progress of the reaction] labeled ligand is added and the process of reading label and the chips repeated. This process is repeated until all binding sites on the binding agent [or ligand] approach saturation, thereby permitting calculation of $K_a$ values and binding sites that were available.

c. Selection of Antibodies and Other Screening Methods (1) Antibody selection

In hybridoma preparation and selection, fused cells are plated into, 5 for example, microtiter wells with the matrices with memory-tagged antibody binding reagent [such as protein A or Co-chelate [see, e.g., Smith et al. (1992) *Methods: A Companion to Methods in Enzymology* 4, 73 (1992); Ill et al. (1993) *Biophys J*. 64:919; Loetscher et al. (1992) *J. Chromatography* 595:113–199; U.S. Pat. No. 5,443,816; Hale (1995) *Analytical Biochem*. 231:46–49]. The solid phase is removed, pooled and processed batchwise to identify the cells that produce antibodies that are the greatest binders [see, e.g., U.S. Pat. No. 5,324,633 for methods and device for measuring the binding affinity of a receptor to a ligand; or the above method by which phage libraries are screened for highest $K_A$ phage, i.e., limiting labeled antigen].

(2) Antibody panning

Memories with matrices with antibody attached thereto [e.g., particularly embodiments in which the matrix is a plate] may be used in antibody panning [see, e.g., Wysocki et al. (1978) *Proc. Natl. Acad. Sci. U.S.A*. 75:2844–48; Basch et al. (1983) *J. Immunol. Methods* 56:269; Thiele et al. (1986) *J. Immunol*. 136:1038–1048; Mage et al. (1981) *Eur. J. Immunol*. 11:226; Mage et al. (1977) *J. Immunol. Methods* 15:47–56; see, also, U.S. Pat. Nos. 5,217,870 and 5,087,570, for descriptions of the panning method]. Antibody panning was developed as a means to fractionate lymphocytes on the basis of surface phenotype based on the ability of antibody molecules to adsorb onto polystyrene surfaces and retain the ability to bind antigen. Originally [Wysocki et al. (1978) *Proc. Natl. Acad. Sci. U.S.A*. 75:2844–2848] polystyrene dishes coated with antibodies specific for cell surface antigens and permit cells to bind to the dishes, thereby fractionating cells. In embodiments herein, polystyrene or other suitable matrix is associated with a memory device and coated with an antibody, whose identity is recorded in the memory. Mixtures of these antibody coated memories with matrices can be mixed with cells, and multiple cell types can be sorted and identified by querying the memories to which cells have bound.

d. Phage Display

Phage, viruses, bacteria and other such manipulable hosts and vectors [referred to as biological particles] can be modified to express selected antigens [peptides or polypeptides] on their surfaces by, for example, inserting DNA encoding the antigen into the host or vector genome, at a site such as in the DNA encoding the coat protein, such that upon expression the antigen [peptide or polypeptide] is presented on the surface of the virus, phage or bacterial host. Libraries of such particles that express diverse or families of proteins on their surfaces have been prepared. The resulting library is then screened with a targeted antigen [receptor or ligand] and those viruses with the highest affinity for the targeted antigen [receptor or ligand] are selected [see, e.g., U.S. Pat. Nos. 5,403,484, 5,395,750, 5,382,513, 5,316,922, 5,288,622, 5,223,409, 5,223,408 and 5,348,867].

Libraries of antibodies expressed on the surfaces of such packages have been prepared from spleens of immunized and unimmunized animals and from humans. In the embodiment in which a library of phage displaying antibodies from unimmunized human spleens is prepared, it is often of interest to screen this library against a large number of different antigens to identify a number of useful human antibodies for medical applications. Phage displaying antibody binding sites derived from single or small numbers of spleen cells can be separately produced, expanded into large batches, and bound to matrices with memories, such as programmable PROM or EEPROM memories, and identified according to phage batch number recorded in the memory. Each antigen can then be exposed to a large number of different phage-containing memory devices, and those that bind the antigen can be identified by one of several means, including radiolabeled, fluorescent labeled, enzyme labeled or alternate (e.g., mouse) tagged antibody labeled antigen. The encoded information in the thus identified phage-containing devices, relates to the batch of phage reactive with the antigen.

Libraries can also be prepared that contain modified binding sites or synthetic antibodies. DNA molecules, each encoding proteins containing a family of similar potential binding domains and a structural signal calling for the display of the protein on the outer surface of a selected viral or bacterial or other package, such as a bacterial cell, bacterial spore, phage, or virus are introduced into the bacterial host, virus or phage. The protein is expressed and the potential binding domain is displayed on the outer surface of the particle. The cells or viruses bearing the binding domains to which target molecules bind are isolated and amplified, and then are characterized. In one embodiment, one or more of these successful binding domains is used as a model for the design of a new family of potential binding domains, and the process is repeated until a novel binding domain having a desired affinity for the target molecule is obtained. For example, libraries of de novo synthesized synthetic antibody library containing antibody fragments expressed on the surface have been prepared. DNA encoding synthetic antibodies, which have the structure of antibodies, specifically Fab or Fv fragments, and contain randomized binding sequences that may correspond in length to hypervariable regions [CDRs] can be inserted into such vectors and screened with an antigen of choice.

Synthetic binding site libraries can be manipulated and modified for use in combinatorial type approaches in which the heavy and light chain variable regions are shuffled and exchanged between synthetic antibodies in order to affect specificities and affinities. This enables the production of antibodies that bind to a selected antigen with a selected affinity. The approach of constructing synthetic single chain antibodies is directly applicable to constructing synthetic Fab fragments which can also be easily displayed and screened. The diversity of the synthetic antibody libraries can be increased by altering the chain lengths of the CDRs and also by incorporating changes in the framework regions that may affect antibody affinity. In addition, alternative libraries can be generated with varying degrees of randomness or diversity by limiting the amount of degeneracy at certain positions within the CDRs. The synthetic binding site can be modified further by varying the chain lengths of the CDRs and adjusting amino acids at defined positions in the CDRs or the framework region which may affect affinities. Antibodies identified from the synthetic antibody library can easily be manipulated to adjust their affinity and or effector functions. In addition, the synthetic antibody library is amenable to use in other combinatorial type approaches. Also, nucleic acid amplification techniques have made it possible to engineer humanized antibodies and to clone the immunoglobulin [antibody] repertoire of an immunized mouse from spleen cells into phage expression vectors and identify expressed antibody fragments specific to the antigen used for immunization [see, e.g., U.S. Pat. No. 5,395,750].

The phage or other particles, containing libraries of modified binding sites, can be prepared in batches and linked to matrices that identify the DNA that has been inserted into the phage. The matrices are then mixed and screened with labeled antigen [e.g, fluorescent or enzymatic] or hapten, using an assay carried out with limiting quantities of the antigen, thereby selecting for higher affinity phage. Thus, libraries of phage linked to matrix particles with memories can be prepared. The matrices are encoded to identify the batch number of the phage, a sublibrary, or to identify a unique sequence of nucleotides or amino acids in the antibody or antibody fragment expressed on its surface. The library is then screened with labeled antigens. The antigens are labeled with enzyme labels or radiolabels or with the antigen bound with a second binding reagent, such as a second antibody specific for a second epitope to which a fluorescent antigen binds.

Following identification of antigen bound phage, the matrix particle can be queried and the identity of the phage or expressed surface protein or peptide determined. The resulting information represents a profile of the sequence that binds to the antigen. This information can be analyzed using methods known to those of skill in this art.

e. Anti-microbial Assays and Mutagenicity Assays

Compounds are synthesized or linked to matrix with memory. The linkage is preferably a photocleavable linkage or other readily cleavable linkage. The matrices with memories with linked compounds, whose identities are programmed into each memory are the placed on, for example, 10-cm culture plates, containing different bacteria, fungi, or other microorganism. After release of the test compounds the anti-microbial effects of the chemical will be assessed by looking for lysis or other indicia of anti-microbial activity. In preferred embodiments, arrays of memories with matrices can be introduced into plates. The memories are encoded with the identity of the linked or associated test compound and the position on the array.

The AMES test is the most widely used mutagen/ carcinogen screening assay [see, e.g., Ames et al. (1975) *Mutation Res.* 31:347–364; Ames et al. (1973) *Proc. Natl. Acad. Sci. U.S.A.* 70:782–786.; Maron et al., (1983) *Mutation Research* 113:173; Ames (1971) in *Chemical Mutagens. Principles and Methods for their Detection*, Vol. 1, Plenum Press, NY, pp 267–282]. This test uses several unique strains of *Salmonella typhimurium* that are histidine-dependent for growth and that lack the usual DNA repair enzymes. The frequency of normal mutations that render the bacteria independent of histidine [i.e., the frequency of spontaneous revertants] is low. The test evaluates the impact of a compound on this revertant frequency. Because some substances are converted to a mutagen by metabolic action, the compound to be tested is mixed with the bacteria on agar plates along with the liver extract. The liver extract serves to mimic metabolic action in an animal. Control plates have only the bacteria and the extract. The mixtures are allowed to incubate. Growth of bacteria is checked by counting colonies. A test is positive where the number of colonies on the plates with mixtures containing a test compound significantly exceeds the number on the corresponding control plates.

A second type of Ames test [see, International PCT Application No. WO 95110629, which is based on U.S. application Ser. No. 08/011,617; and Gee et al. (1994) *Proc. Natl. Acad. Sci. U.S.A.* 91:11606–11610; commercially avail from Xenometrix, Boulder Colo.] is of interest herein. This test provides a panel of *Salmonella typhimurium* strains for use as a detection system for mutagens that also identifies mutagenic changes. Although a direct descendant of the traditional Ames Salmonella reverse mutation assay in concept, the Ames II assay provides the means to rapidly screen for base mutations through the use of a mixture of six different Salmonella strains.

These new strains carry his mutations listed in the table below. All are deleted for uvrB and are deficient therefore in excision repair. In addition, all six have lipopolysaccharide [rfa] mutations rendering them more permeable, and all contain the pKM$^{101}$ plasmid conferring enhanced mutability.

| STRAIN | BASE CHANGE | MUTATION |
|---|---|---|
| TA7001 | A:T → G:C | hisG1775 |
| TA7002 | T:A → A:T | hisC9138 |
| TA7003 | T:A → G:C | hisG9074 |
| TA7004 | G:C → A:T | hisG9133 |
| TA7005 | G:C → A:T | hisG9130 |
| TA7006 | G:C → C:G | hisC9070 |

These strains, which revert at similar spontaneous frequencies [approximately 1 to $10 \times 10^8$] can be exposed and plated separately for determining mutational spectra, or mixed and exposed together to assess broad mutagenic potential. The assay takes 3 days from start to finish and can be performed in 96 well- or 384 well-microtiter plates. Revertant colonies are scored using bromo-creosol purple indicator dye in the growth medium. The mixed strains can be assayed first as part of a rapid screening program. Since this six strain mixture is slightly less sensitive than individual strains tested alone, compounds which are negative for the mix can be retested using all six strains. For all but the weakest mutagens, the Ames II strain mixture appears to be capable of detecting reversion events even if only one strain is induced to revert. The mixed strains provide a means to perform rapid initial screening for genotoxins, while the battery of base-specific tester strains permit mutational spectra analysis.

As modified herein, the test compounds are linked to matrices with memories, that have been encoded with the identity of the test compounds. The assays can be performed on multiple test compounds simultaneously using arrays of matrices with memories or multiple matrices with memories encoded with the identity of the linked test compound and the array position or plate number into which the compound is introduced.

f. Hybridization Assays and Reactions (1) Hybridization reactions

It is often desirable to detect or quantify very small concentrations of nucleic acids in biological samples. Typically, to perform such measurements, the nucleic acid in the sample [i.e., the target nucleic acid] is hybridized to a detection oligonucleotide. In order to obtain a detectable signal proportional to the concentration of the target nucleic acid, either the target nucleic acid in the sample or the detection oligonucleotide is associated with a signal generating reporter element, such as a radioactive atom, a chromogenic or fluorogenic molecule, or an enzyme [such as alkaline phosphatase] that catalyzes a reaction that produces a detectable product. Numerous methods are available for detecting and quantifying the signal.

Following hybridization of a detection oligonucleotide with a target, the resulting signal-generating hybrid molecules must be separated from unreacted target and detection oligonucleotides. In order to do so, many of the commonly used assays immobilize the target nucleic acids or detection oligonucleotides on solid supports. Presently available solid supports to which oligonucleotides are linked include nitrocellulose or nylon membranes, activated agarose supports, diazotized cellulose supports and non-porous polystyrene latex solid microspheres. Linkage to a solid support permits fractionation and subsequent identification of the hybridized nucleic acids, since the target nucleic acid may be directly captured by oligonucleotides immobilized on solid supports. More frequently, so-called "sandwich" hybridization systems are used. These systems employ a capture oligonucleotide covalently or otherwise attached to a solid support for capturing detection oligonucleotide-target nucleic acid adducts formed in solution [see, e.g., EP 276,302 and Gingeras et al. (1989) Proc. Natl. Acad. Sci. USA 86:1173]. Solid supports with linked oligonucleotides are also used in methods of affinity purification. Following hybridization or affinity purification, however, if identification of the linked molecule or biological material is required, the resulting complexes or hybrids or compounds must be subjected to analyses, such as sequencing. The combinations and methods herein eliminate the need for such analyses.

Use of matrices with memories in place of the solid support matrices used in the prior hybridization methods permits rapid identification of hybridizing molecules. The identity of the linked oligonucleotide is written or encoded into the memory. After reaction, hybrids are identified, such as by radioactivity or separation, and the identify of hybridizing molecules are determined by querying the memories.

(2) Hybridization assays

Mixtures nucleic acid probes linked to the matrices with memories can be used for screening in assays that heretofore had to be done with one probe at a time or with mixtures of probes followed by sequencing the hybridizing probes. There are numerous examples of such assays [see, e.g., U.S. Pat. No. 5,292,874, "Nucleic acid probes to *Staghylococcus aureus*" to Milliman, and U.S. Pat. No. 5,232,831, "Nucleic acid probes to *Streptococcus pyogenes*" to Milliman, et al.; see, also, U.S. Pat. Nos. 5,216,143, 5,284,747 5,352,579 and 5,374,718]. For example, U.S. Pat. No. 5,232,831 provides probes for the detection of particular Streptococcus species from among related species and methods using the probes. These probes are based on regions of Streptococcus rRNA that are not conserved among related Streptococcus species. Particular species are identified by hybridizing with mixtures of probes and ascertaining which probe(s) hybridize. By virtue of the instant matrices with memories, following hybridization, the identity of the hybridizing probes can be determined by querying the memories, and thereby identifying the hybridizing probe.

g. Combinatorial Libraries and Other Libraries and Screening Methododologies

The combinations of matrices with memories are applicable to virtually any synthetic scheme and library preparation and screening protocol. These include, those discussed herein, and also methodologies and devices, such as the Chiron "pin" technology [see, e.g., International PCT application No.WO 94/11388; Geysen et al. (1985) *Proc. Natl. Acad. Sci. U.S.A.* 82:178; and Geysen et al. (1987) *J. Immunol. Meth.* 102:259–274] which relies on a support composed of annular synthesis components that have an active surface for synthesis of a modular polymer and an inert support rod that is positioned axially to the annular synthesis components. This pin technology was developed fo rthe simultaneous synthesis of multiple peptides. In particular the peptides are synthesized on polyacrylic acid grafted on the tip of polyethylene pins, typically arranged in a microtiter format. Amino acid coupling is effected by immersing the pins in a microtiter plate. The resulting peptides remain bound to the pins and can be resused.

As provided herein, "pins" may be linked to a memory or recording device, preferably encasing the device, or each pin may be coded and the code and the identity of the associated linked molecule(s) stored in a remote memory. As a result it will not be necessary to physically array the pins, rather the pins can be removed and mixed or sorted.

Also of interest herein, are DIVERSOMER™ technology libraries produced by simultaneous parallel sythesis schemes for production of nonoligomeric chemical diversity

[see, e.g., U.S. Pat. No. 5,424,483; Hobbs DeWitt et al. (1994) *Drug Devel. Res.* 33:116–124; Czarnik et al. (1994) *Polym. Prepr.* 35:985; Stankovic et al. (1994) in *Innovation Perspect. Solid Phase Synth. Collect. Pap., Int. Symp.*, 3rd Epton, R. (Ed), pp. 391–6; DeWitt et al. (1994) *Drug Dev. Res.* 33:116–124; Hobbs DeWitt et al. (1993) *Proc. Natl. Acad. Sci. U.S.A.* 90:6909–6913]. In this technology a starting material is bonded to a solid phase, such as a matrix metraial, and is subsequently treated with reagents in a stepwise fashion. Because the products are linked to the solid support, multistep syntheses can be automated and multiple reactions can be performed simultaneously to produce libraries of small molecules. This technology can be readily improved by combining the matrices with memories or encoding the matrix supports in accord with the methods herein.

The matrices with memories, either those with memories in proximity or those in which the matrix includes a code stored in a remote memory, can be used in virtually any combinatorial library protocol. These protocols or methodologies and libraries, include but are not limited to those described in any of following references: Zuckermann et al. (1994) *J. Med. Chem.* 37:2678; Martin et al. (1995) *J. Med. Chem.* 38:1431; Campbell et al. (1995) *J. Am. Chem. Soc.* 117:5381; Salmon et al. (1993) *Proc. Natl. Acad. Sci. U.S.A.* 90:11708; Patek et al. (1994) *Tetrahedron Lett.* 35:9169; Patek et al. (1995) *Tetrahedron Lett.* 36:2227; Hobbs DeWitt et al. (1993) *Proc. Natl. Acad. Sci. U.S.A.* 90:6906; Baldwin et al. (1995) *J. Am. Chem. Soc.* 117:5588; and any others.

h. Nucleic Acid Sequencing

Methods of DNA sequencing based on hybridization of DNA fragments with a complete set of fixed length oligonucleotides [usually 8-mers] that are immobilized individually as dots in a 2-dimensional matrix is sufficient for computer-assisted reconstruction of the sequences of fragments up to 200 bases long [International PCT Application WO 92/10588]. The nucleic acid probes are of a length shorter than a target, which is hybridized to the probes under conditions such that only those probes having an exact complementary sequence are hybridized maximally, but those with mismatches in specific locations hybridize with a reduced affinity, as can be determined by conditions necessary to dissociate the pairs of hybrids. Alignment of overlapping sequences from the hybridizing probes reconstructs the complement of the target [see, EP 0 535 242 A1, International PCT Application WO 95/00530, and Khrapko et al. (1989) *FEBS Lttrs.* 256:118–122]. The target fragment with the sequence of interest is hybridized, generally under highly stringent conditions that tolerate no mismatches or as described below a selected number of mismatches, with mixtures of oligonucleotides [typically a mixture of octomers of all possible sequences] that are each immobilized on a matrix with memory that is encoded with the sequence of the probe. Upon hybridization, hybridizing probes are identified by routine methods, such as OD or using labeled probe, and the sequences of the hybridizing probes can be determined by retrieving the sequences from the linked memories. When hybridization is carried out under conditions in which no mismatches are tolerated, the sequence of the target can then be determined by aligning overlapping sequences of the hybridizing probes.

Previous methods used to accomplish this process have incorporated microscopic arrays of nucleotide oligomers synthesized on small silicon based chips. It is difficult to synthesize such arrays and quality control the large number of spots on each chip [about 64,000 spots for 8-mer oligonucleotides, that number necessary to accomplish sequencing by hybridization].

In the present method, each oligomer is independently synthesized on a batch of individual chips, those chips are tested for accuracy and purity of their respective oligomers, then one chip from each batch is added to a large pool containing oligomers having all possible sequences. After hybridization in batch mode with the gene segment to be sequenced, usually amplified by a method such as PCR, using appropriate primers, and labeled with a detectable [such as fluorescent] tag, the chips can be passed through a detector, such as described above for processing multiplexed assays, including multiplexed immunoassays, and the degree of binding to each oligomer can be determined. After exposing the batch to varying degrees of dissociating conditions, the devices can again be assayed for degree of binding, and the strength of binding to related sequences will relate the sequence of the gene segment [see, e.g., International PCT Application WO 95/00530].

Figure 33:
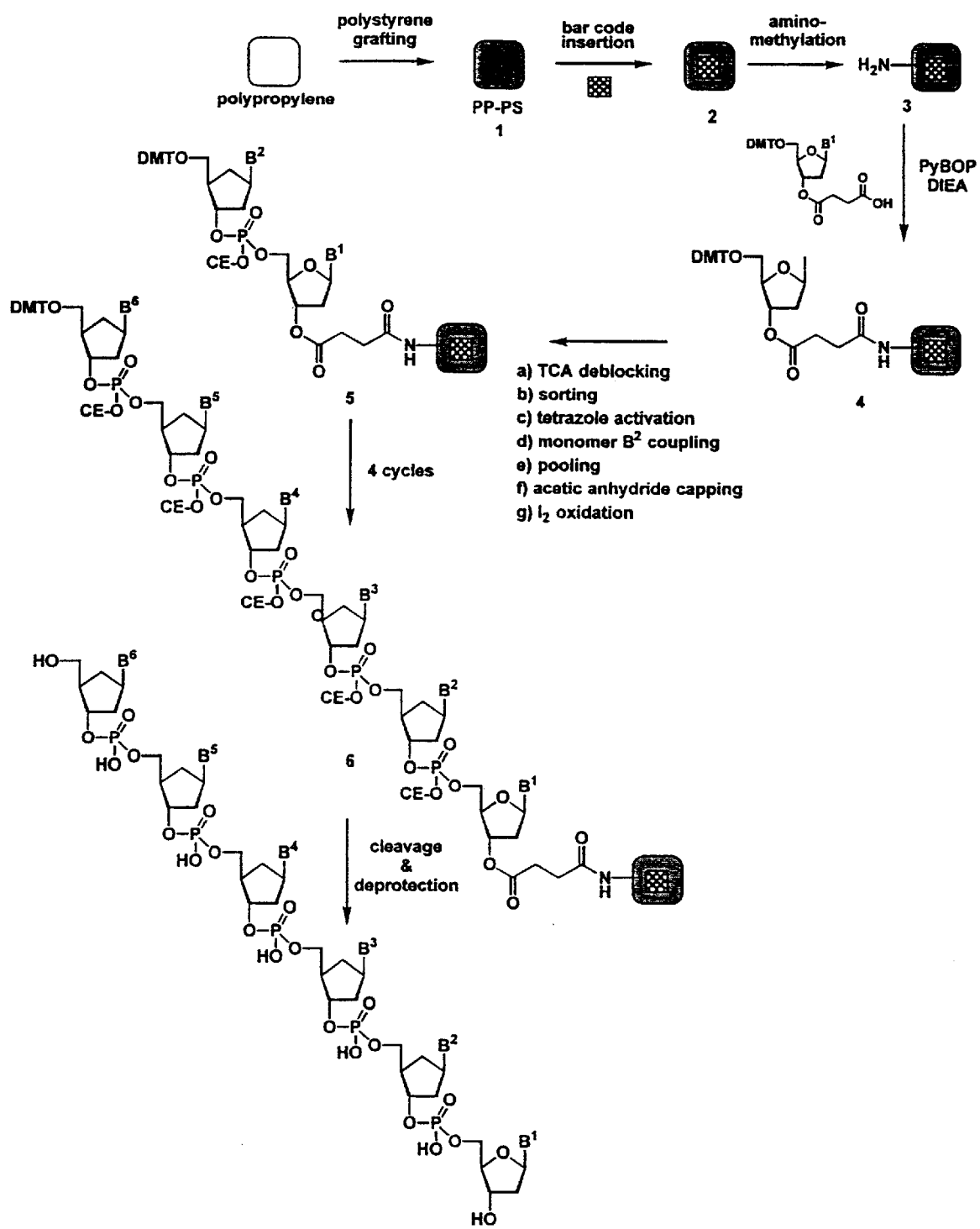
FIG. 33 depicts an oligonucleotide hexamer library using the optical memory device. Each B$^n$ refers to a nucleoside base, and the resulting library, where n=6, will contain 4096 unique members [$4^6$=4096].

An exemplary method for synthesizing an oligonucleotide library, preferably hexamers or octomers, for use in sequencing methods, or other methods, is set forth in the EXAMPLES and depicted in FIG. 33, in which the oligonucleotides are synthesized on optical memory devices that are each uniquely encoded either before, during or after synthesis with a code. The identity of the oligomer associated with each code is stored in a remote memory, generally a computer. Other memory with matrices, such as the MICROTUBES™ and MICROKANS™ and other such combination, may be used in place of the optical memory devices In particular this library of microreactors [oligonucleotides-linked to memory with matrix] can be used in methods for DNA sequencing by primer walking using capillary electorphoresis and ultrathin slab gels for separation [see, e.g., Ruiz-Martinez et al. (1996) *Biotechniques* 20:1058–1069; Kieleczawa et al. (1992) *Science* 258:1787–1791; McCombie et al. (1994) *BioTechniques* 17:574–57901. Such methods rely on the use of oligonucleotide libraries, containing all permutations of pentamer or hexamers, which are used as primers. The identity of each oligonucleotide will be encoded in the associated memory or stored in the proximate or linked memory. A synthetic protocol is depicted in FIG. 33.

i. Separations, Physical Mapping and Measurements of Kinetics of Binding and Binding Affinities Multiple blots [i.e., Western, Northern, Southern and/or dot blots] may be simultaneously reacted and processed. Each memory, in the form of a rectangle or other suitable, is linked or coated on one surface with material, such as nitrocellulose, to which or the analyte of interest binds or with which it reacts. The chips are arranged in an array, such as in strips that can be formed into rectangles or suitable other shapes, circles, or in other geometries, and the respective x-y coordinate or other position-identifying coordinate (s), and, if needed, sheet number and/or other identifying information, is programmed into each memory. Alternatively, they may be programmed with this identification, then positioned robotically or manually into an array configuration. They are preferably linked together, such as by reversible glue, or placing them in agarose, or by any suitable method as long as the reactive surface is not disturbed. Following transfer of the material, such as transfer of protein from a Western Blot, nucleic acid from a Southern or Northern blot, dot blots, replica plated bacterial culture, or viral plaques, the memories are separated and mixed for reaction with a traditionally labeled, such as a fluorescent label, detection nucleic acid, protein, antibody or receptor of interest. Complexes are identified, and their origin in the blot determined by retrieving the stored information in each chip. Quantitation may also be effected based on the amount of label bound.

A series of appropriately activated matrices with memories are arranged in an array, one or, preferably two dimensional. In one configuration, each chip is pre-programmed and placed in a specific location that is entered into its memory, such as an x-y coordinate. At least one surface of the memory with matrix is treated so that the transferred reagent binds. For example, a piece of nitrocellulose can be fixed to one side of the memory device. The resulting array is then contacted with a separation medium whereby each reagent of interest is transferred to and bound to the end of the matrix with memory such that the reagent location is known. The matrices are separated and pooled; multiple arrays may be pooled as long as source information is recorded in each memory. All matrices with memories are then contacted with detection agents that specifically bind to reagents in the mixture. The matrices with memories are passed through a reading device, either after an incubation for end point determinations or continuously for kinetic measurements. The reading device comprises a device that can detect labels such as fluorescence, and a reader, such as an RF reader, that can query the memory and identify each matrix. The rate of binding and maximum binding and identify of bound reagents can be determined. Dot blots, for example, can be used in hybridoma analysis to identify clones that secrete antibodies of desired reactivity and to determine the relative affinities of antibodies secreted by different cell lines. Matrices with memories that are activated to bind immunoglobulins and with on-board information specifying their relative locations in the array are dipped in an array into the wells of microplates containing hybridoma cells. After incubation, they are withdrawn, rinsed, removed and exposed to labeled antigen. Matrices of desired specificity and affinity are selected and read thereby identifying the original wells containing the hybridoma cells that produce the selected antibodies.

In other embodiments, the transfer medium [i.e., the nitrocellulose or other such medium] may be part of the surface of the chip or array of chips that can bind to the separated species subsequent to separation. For example, the separation system, such as the agarose or polyacrylamide gel, can be included on the surface(s) of the matrix with memories in the array. After separation the surface will be activated with a photactivatable linker or suitable activating agent to thereby covalently link, such as by a photoflash, the separated molecules to the matrices in the array.

Alternatively, each matrix with memory may have one or more specific binding agents, such as an antibody or nucleic acid probe, attached (adsorbed, absorbed, or otherwise in physical contact) to matrix with memory. The matrix with memory and linked binding agent is then contacted with a medium containing the target(s). After contacting, which permits binding of any targets to which the linked binding agents specifically bind, the matrix with memory is processed to identify memories with matrices to which target has specifically bound via interaction with the binding agent. For example, the (1) the target is labeled, thereby permitted direct detection of complexes; (2) the memory with matrix is then contacted with a developing agent, such as a second antibody or detection probe, whereby binding agent-target complexes are detected; or (3) the detection agent is present during the reaction, such as non-specifically attached to the matrix with memory or by other method [thin film, coated on the matrix with memory, coated on nitrocellulose].

Such support bound analytes may also be used to analyze the kinetics of binding by continuously passing the supports through a label reading device during the reaction, and identify the labeled complexes.

The binding agents can be eluted, either in a kinetically readable manner or in batch. In addition, since the recording devices may also include components that record reaction conditions, such as temperature and pH, kinetics, which are temperature and pH dependent, may be accurately calculated.

After elution, the support bound analytes may be identified to analyze kinetics of binding to the binding agent. Such binding and elution protocols may also be adapted to affinity purification methodologies.

j. Cell Sorting

The devices herein may also be used in methods of cell sorting. For example, the memory with matrix combinations are linked to selected antigens, information regarding the antigens is encoded into the memories, the resulting combinations are used in multi-analyte analyses of cells.

It is possible to identify a profile of cells exhibiting different surface markers [antigens, for example, or other ligands or receptor molecules] by using combinations of labeled and matrix memory-bound binding agents.

In one embodiment, each agent, such as an antibody, capable of binding specifically to one of many different surface markers is bound to a different matrix with a memory. The nature of the recognized marker is recorded in the memory of each matrix-binding agent complex, and the mixture of binding-agent-matrix memory complexes is reacted with a mixture of cells. The cell-matrix complexes that result from binding agents attaching cells to the surfaces of the respective matrices are then reacted with a labeled [for example, fluorescent] reagent or mixture of reagents which also reacts with the cells. These labeled reagents can be the same or different from those coupled to the memory matrices. When the matrices are passed through a reader [to read the label and the memory], those that have bound cells can be identified and if necessary isolated. This application is particularly useful for screening for rare cells, for example stem cells in a bone marrow or peripheral lymphocyte sample, for detecting tumor cells in a bone marrow sample to be used for autologous transplantation, or for fetal cells in a maternal circulation.

In these embodiments, the memory with matrices herein can be counted and read with instruments, such as a device that operates on the principles of a Coulter counter, that are designed to count cells or particles. In using a Coulter Counter, a suspension of cells or particles is sucked through a minute hole in a glass tube. One electrode is placed within the tube and another is outside of the tube in the suspension. The passage of a particle through the hole temporarily interrupts the current; the number of interruptions is determined by a conventional scaling unit.

For use herein, such instruments are modified by including an RF reader [or other reader if another frequency or memory means is selected] so that the identity of the particle or cell [or antigen on the cell or other encoded information] can be determined as the particle or cell passes through the hole and interrupts the current, and also, if needed, a means to detect label, such as fluorescent label. As the particle passes through the hole the RF reader will read the memory in the matrix that is linked to the particle. The particles also may be counted concurrently with the determination of the identity of the particle. Among the applications of this device and method, is a means to sort multiple types of cells at once.

k. Drug Delivery and Detecting Changes in Internal Conditions in the Body

Memories may also be combined with biocompatible supports and polymers that are used internally in the bodies of animals, such as drug delivery devices [see, e.g, U.S. Pat. Nos. 5,447,533, 5,443,953, 5,383,873, 5,366,733, 5,324,324, 5,236,355, 5,114,719, 4,786,277, 4,779,806, 4,705,503, 4,702,732, 4,657,543, 4,542,025, 4,530,840, 4,450,150 and 4,351,337] or other biocompatible support [see, U.S. Pat. No. 5,217,743 and U.S. Pat. No. 4,973,493, which provide methods for enhancing the biocompatibility of matrix polymers]. Such biocompatible polymers include matrices of poly(ethylene-co-vinyl acetate) and matrices of a polyanhydride copolymer of a stearic acid dimer and sebacic acid [see, e.g., Sherwood et al. (1992) *Bio/Technology* 10:1446–1449].

The biocompatible drug delivery device in combination with the memory is introduced into the body. The device, generally by virtue of combination with a biosensor or other sensor, also monitors pH, temperature, electrolyte concentrations and other such physiological parameters and in response to preprogrammed changes, directs the drug delivery device to release or not release drugs or can be queried, whereby the change is detected and drug delivered or administered.

Alternatively, the device provided in combination with a biocompatible support and biosensor, such that the information determined by the biosensor can be stored in the device memory. The combination of device and biosensor is introduced into the body and is used to monitor internal conditions, such as glucose level, which level is written to memory. The internal condition, such as glucose level, electrolytes, particularly potassium, pH, hormone levels, and other such level, can then be determined by querying the device.

In one embodiment, the device, preferably one containing a volatile memory that is read to and written using RF, linked to a biosensor [see, e.g., U.S. Pat. No. 5,384,028 which provides a biosensor with a data memory that stores data] that can detect a change in an internal condition, such as glucose or electrolyte, and store or report that change via RF to the linked matrix with memory, which records such change as a data point in the memory, which can then be queried. The animal is then scanned with RF and the presence of the data point is indicative of a change. Thus, instead of sampling the body fluid, the memory with matrix with linked biosensor is introduced into a site in the body, and can be queried externally. For example, the sensor can be embedded under the skin and scanned periodically, or the scanner is worn on the body, such as on the wrist, and the matrix with memory either periodically, intermittently, or continuously sends signals; the scanner is linked to an infusion device and automatically, when triggered triggers infusion or alters infusion rate.

l. Multiplexed or Coupled Protocols in Which the Synthesis Steps [the chemistry] is Coupled to Subsequent Uses of the Synthesized Molecules Multiplexed or multiple step processes in which compounds are synthesized and then assayed without any intermediate identification steps are provided herein. Since the memories with matrices permit identification of linked or proximate or associated molecules or biological particles, there is no need to identify such molecules or biological particles during any preparative and subsequent assaying steps or processing steps. Thus, the chemistry [synthesis] can be directly coupled to the biology [assaying, screening or any other application disclosed herein]. For purposes herein this coupling is referred to as multiplexing. Thus, high speed synthesis can be coupled to high throughput screening protocols.

G. Applications of the Memories with Matrices and Luminescing Matrices with Memories in Combinatorial Syntheses and Preparation of Libraries Libraries of diverse molecules are critical for identification of new pharmaceuticals. A diversity library has three components: solid support matrix, linker and synthetic target. The support is a matrix material as described herein that is stable to a wide range of reaction conditoins and solvents; the linker is selectively cleavable and does not leave a functionalized appendage on the synthetic target; and the target is synthesized in high yield and purity. For use herein, the diversity library further includes a memory or recording device in combination with the support matrix. The memory is linked, encased, in proximity with or otherwise associate with each matrix particle, whereby the identify of synthesized targets is written into the memory.

The matrices with memories are linked to molecules and particles that are components of libraries to electronically tagged combinatorial libraries. Particularly preferred libraries are the combinatorial libraries that containing matrices with memories that employ radio frequencies for reading and writing.

1. Oligomer and polypeptide libraries a. Bio-oligomer Libraries

One exemplary method for generating a library [see, U.S. Pat. No. 5,382,513] involves repeating the steps of (1) providing at least two aliquots of a solid phase support; separately introducing a set of subunits to the aliquots of the solid phase support; completely coupling the subunit to substantially all sites of the solid phase support to form a solid phase support/new subunit combination, assessing the completeness of coupling and if necessary, forcing the reaction to completeness; thoroughly mixing the aliquots of solid phase support/new subunit combination; and, after repeating the foregoing steps the desired number of times, removing protecting groups such that the bio-oligomer remains linked to the solid phase support. In one embodiment, the subunit may be an amino acid, and the bio-oligomer may be a peptide. In another embodiment, the subunit may be a nucleoside and the bio-oligomer may be an oligonucleotide. In a further embodiment, the nucleoside is deoxyribonucleic acid; in yet another embodiment, the nucleoside is ribonucleic acid. In a further embodiment, the subunit may be an amino acid, oligosaccharide, oligoglycosides or a nucleoside, and the bio-oligomer may be a peptide-oligonucleotide chimera or other chimera. Each solid phase support is attached to a single bio-oligomer species and all possible combinations of monomer [or multimers in certain embodiments] subunits of which the bio-oligomers are composed are included in the collection.

In practicing this method herein, the support matrix has a recording device with programmable memory, encased, linked or otherwise attached to the matrix material, and at each step in the synthesis the support matrix to which the nascent polymer is attached is programmed to record the identity of the subunit that is added. At the completion of synthesis of each biopolymer, the resulting biopolymers linked to the supports are mixed.

After mixing an acceptor molecule or substrate molecule of interest is added. The acceptor molecule is one that recognizes and binds to one or more solid phase matrices with memory/bio-oligomer species within the mixture or the substrate molecule will undergo a chemical reaction catalyzed by one or more solid phase matrix with memory/bio-oligomer species within the library. The resulting combinations that bind to the acceptor molecule or catalyze reaction are selected. The memory in the matrix-memory combination is read and the identity of the active bio-oligomer species is determined.

b. Split Bead Sequential Syntheses

Figure 2:
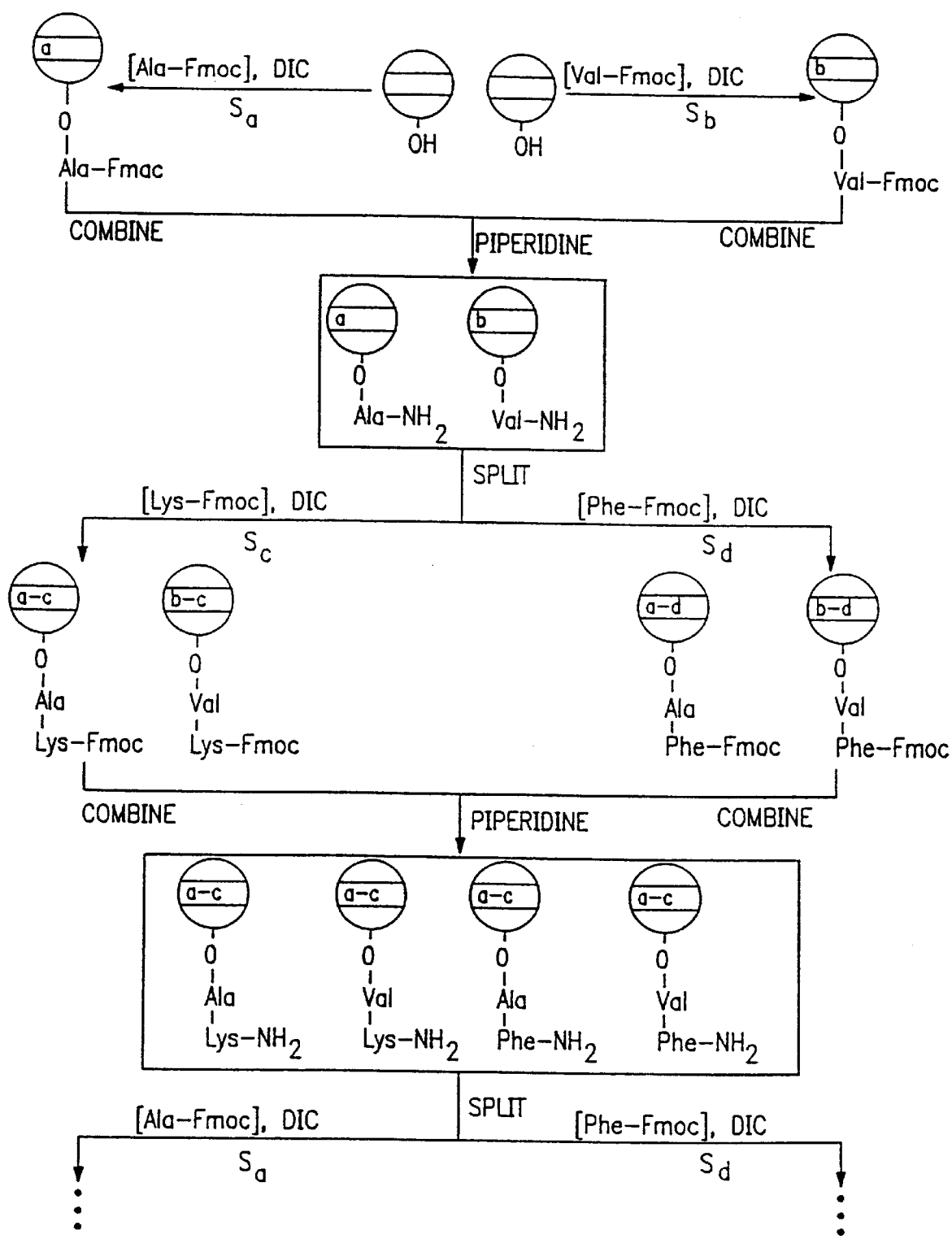
FIG. 2 depicts combinatorial synthesis of peptides on a matrix with memory. Each amino acid has a corresponding code, a,b, c . . . , in the matrix memory, and L represents a Linker between the memory device and the pharmacophore. Again as in FIG. 1, the matrix supports may be engraved with a code or symbology associated with information stored in a remote memory.
Figure 3:
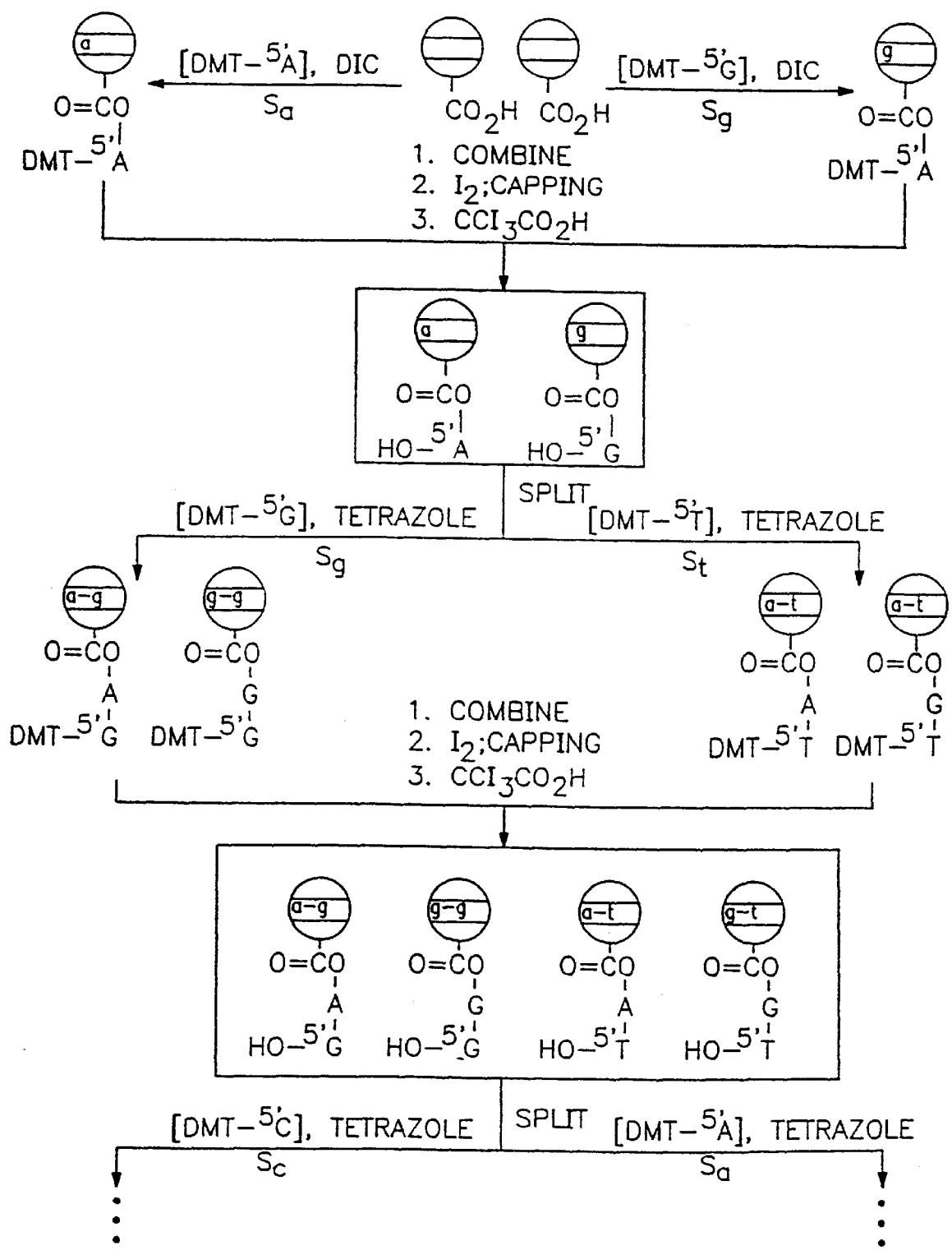
FIG. 3 depicts combinatorial synthesis of oligonucleotides on matrix supports with memories. A, G, T and C represent nucleotides, and a, g, t, and c represent the electronic codes stored in memory that correspond to each of A, G T and C, respectively. The phosphoramidite method of oligonucleotide synthesis is performed by methods known to those of skill in the art [see, e.g., Brown et al. (1991) "Modern machine-aided methods of oligodeoxyribonucleotide synthesis" in Oligonucleotides Analogues EDITOR: Eckstein, Fritz (Ed), IRL, Oxford, UK., pp. 1–24, esp. pp. 471. As in FIGS. 1 and 2, the matrix may alternatively, or additionally, have symbology engraved thereon.
Figure 4:
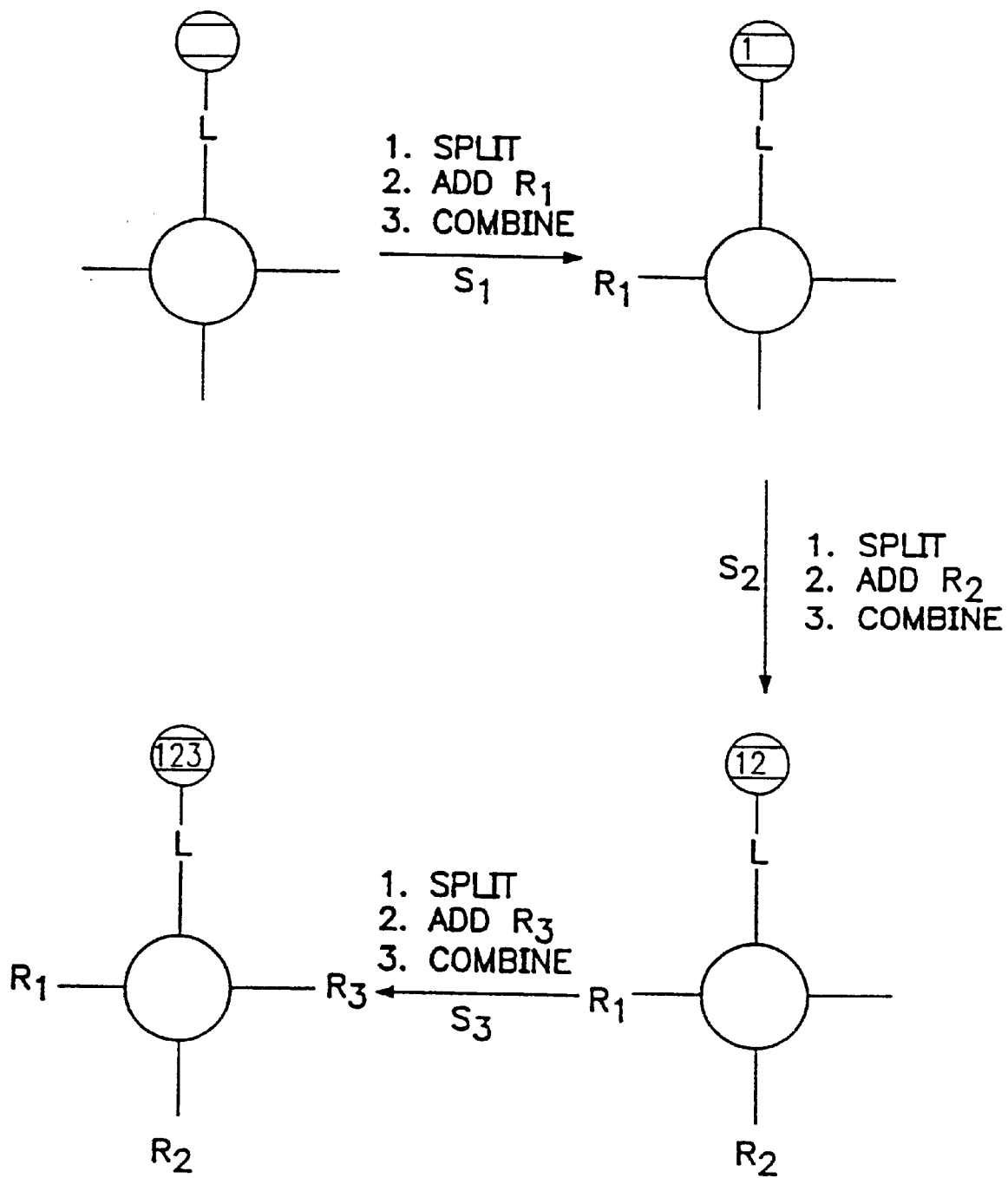
FIG. 4 depicts generation of a chemical library, such as a library of organic molecules, in which $R_1$, $R_2$, $R_3$ are substituents on selected molecule, such as a pharmacophore monomer, each identified with a different signal, depicted as 1, 2, or 3, from the classes $S_1$, $S_2$, $S_3$, respectively. The circle represents an organic pharmacophore. If $R_1$–$R_3$ are the same, and selected from among the same 50 choices, then the complete library contains $50^3$=125,000 members. If $R_1$–$R_3$ selected from among different sets of choices, then the resulting library has correspondingly more members. Each optical memory device can be encoded with information that represents the $R_n$ added and class $[S_n]$ thereby providing a unique code for each library member. As in FIGS. 1–3, the matrix may be engraved with symbology, such as a two-dimensional bar code.

Various schemes for split bead syntheses of polymers [FIG. 1], peptides [FIG. 2], nucleic acids [FIG. 3] and organic molecules based on a pharmacophore monomer [FIG. 4] are provided. Selected matrices with memory particles are placed in a suitable separation system, such as a funnel [see, FIG. 5]. After each synthetic step, each particle is scanned [i.e., read] as it passes the RF transmitter, and information identifying the added component or class of components is stored in memory. For each type of synthesis a code can be programmed [i.e., a 1 at position 1,1 in the memory could, for example, represent alanine at the first position in the peptide]. A host computer or decoder/encoder is programmed to send the appropriate signal to a transmitter that results in the appropriate information stored in the memory [i e for alanine as amino acid 1, a 1 stored at position 1,1]. When read, the host computer or decoder/encoder can interpret the signal read from and transmitted from the memory.

In an exemplary embodiment, a selected number of beads [i.e., particulate matrices with memories [matrix particles linked to recording devices], typically at least $10^3$, more often $10^4$, and desirably at least $10^5$ or more up to and perhaps exceeding $10^{15}$, are selected or prepared. The beads are then divided into groups, depending upon the number of choices for the first component of the molecule. They are divided into a number of containers equal to or less than [for pooled screening, nested libraries or the other such methods] the number of choices. The containers can be microtiter wells, Merrifield synthesis vessels, columns, test tubes, gels, etc. The appropriate reagents and monomer are added to each container and the beads in the first container are scanned with electromagnetic with radiation, preferably high frequency radio waves, to transmit information and encode the memory to identify the first monomer. The beads in the second container are so treated. The beads are then combined and separated according to the combinatorial protocol, and at each stage of added monomer each separate group is labeled by inputting data specific to the monomer. At the end of the synthesis protocol each bead has an oligomer attached and information identifying the oligomer stored in memory in a form that can be retrieved and decoded to reveal the identity of each oligomer.

An 8-member decapeptide library was designed, synthesized, and screened against an antibody specifically generated against one of the library members using the matrices with memories. Rapid and clean encoding and decoding of structural information using radio frequency signals, coupling of combinatorial chemical synthesis to biological assay protocols, and potential to sense and measure biodata using suitable biosensors, such as a temperature thermistor or pH electrode, embedded within the devices have been demonstrated. The "split and pool" method [see, e.g., Furka et al. (19910 *Int. J. Pept. Protein Res.* 37:487–493; Lam et al. (1991) *Nature* 354:82–84; and Sebestyén et al. (1993) *Bioorg. Med. Chem. Lett.* 3:413–418] was used to generate the library. An ELISA [see e.g., Harlow et al. (1988) *Antibodies, a laboratory manual*, Cold Spring Harbor, N.Y.] was used to screen the library for the peptide specific for the antibody.

2. "Nested" combinatorial library protocols

In this type of protocol libraries of sublibraries are screened, and a sublibrary selected for further screening [see, e.g., Zuckermann et al. (1994) *J. Med. Chem.* 37:2678–2685; and Zuckermann et al. (1992) *J. Am. Chem. Soc.* 114:10646–10647]. In this method, three sets of monomers were chosen from commercially available monomers, a set of four aromatic hydrophobic monomers, a set of three hydroxylic monomers, a set of seventeen diverse monomers, and three N-termini were selected. The selection was based on an analysis of the target receptor and known ligands. A library containing eighteen mixtures, generated from the six permutations of the three monomer sets, times three N-termini was prepared. Each mixture of all combinations of the three sets of amines, four sets of hydrophobic monomers and seventeen diverse monomers was then assayed. The most potent mixture was selected for deconvolution by synthesis of pools of combinatorial mixtures of the components of the selected pool. This process was repeated, until individual compounds were selected.

Tagging the mixtures with the matrices with memories will greatly simplify the above protocol. Instead of screening each mixture separately, each matrix particle with memory will be prepared with sets of the compounds, analogous to the mixtures of compounds. The resulting matrix particles with memories and linked compounds can be combined and then assayed. As with any of the methods provided herein, the linked compounds [molecules or biological particles] can be cleaved from the matrix with memory prior to assaying or anytime thereafter, as long as the cleaved molecules remain in proximity to the device or in some manner can be identified as the molecules or particles that were linked to the device. The matrix particle (s) with memories that exhibit the highest affinity [bind the greatest amount of sample at equilibrium] are selected and identified by querying the memory to identify the group of compounds. This group of compounds is then deconvoluted and further screened by repeating this process, on or off the matrices with memories, until high affinity compounds are selected.

3. Other combinatorial protocols

The matrices with memories provided herein may be used as supports in any synthetic scheme and for any protocol, including protocols for synthesis of solid state materials. Combinatorial approaches have been developed for parallel synthesis of libraries of solid state materials [see, e.g., Xiang et al. (1995) *Science* 268:1738–1740]. In particular, arrays containing different combinations, stoichiometries, and deposition sequences of inorganics, such as $BaCO_3$, $BiO_3$, $CaO$, $CuO$, $PbO$, $SrCO_3$ and $Y_2O_3$, for screening as superconductors have been prepared. These arrays may be combined with memories that identify position and the array and/or deposited material.

The following examples are included for illustrative purposes only and are not intended to limit the scope of the invention.

EXAMPLE 1

Formulation of a Polystyrene Polymer on Glass and Derivatization of Polystyrene

A glass surface of any conformation [beads for exemplification purposes (1)] that contain a selected memory device that coat the device or that can be used in proximity to the device or subsequently linked to the device is coated with a layer of polystyrene that is derivatized so that it contains a cleavable linker, such as an acid cleavable linker. To effect such coating a bead, for example, is coated with a layer of a solution of styrene, chloromethylated styrene, divinyl benzene, benzoyl peroxide [88/10/1/1/, molar ratio] and heated at 70° C. for 24 h. The result is a cross-linked chloromethylated polystyrene on glass (2). Treatment of (2) with ammonia [2 M in 1,4-dioxane, overnight] produces aminomethylated coated beads (3). The amino group on (3) is coupled with polyethylene glycol dicarboxymethyl ether (4) [n≈20] under standard conditions [PyBop/DIEA] to yield carboxylic acid derivatized beads (5). Coupling of (5) with modified PAL [PAL is pyridylalanine] linker (6) under the same conditions produces a bead that is coated with polystyrene that has an acid cleavable linker (7).

Inc., Maywood, N.J.; see, also U.S. Pat. Nos. 5,422,636, 5,420,579, 5,262,772, 5,252,962, 5,250,962, 5,074,318, and RE 34,936].

The memory device is a transponder [IPTT-100, Bio Medic Data Systems, Inc., Maywood, N.J.] that includes a remotely addressable memory [EEPROM]. The transponder receives, stores and emits radio frequency signals of different frequencies so that it can be remotely programmed with information regarding synthetic steps and the constituents of linked or proximate molecules or biological particles. These

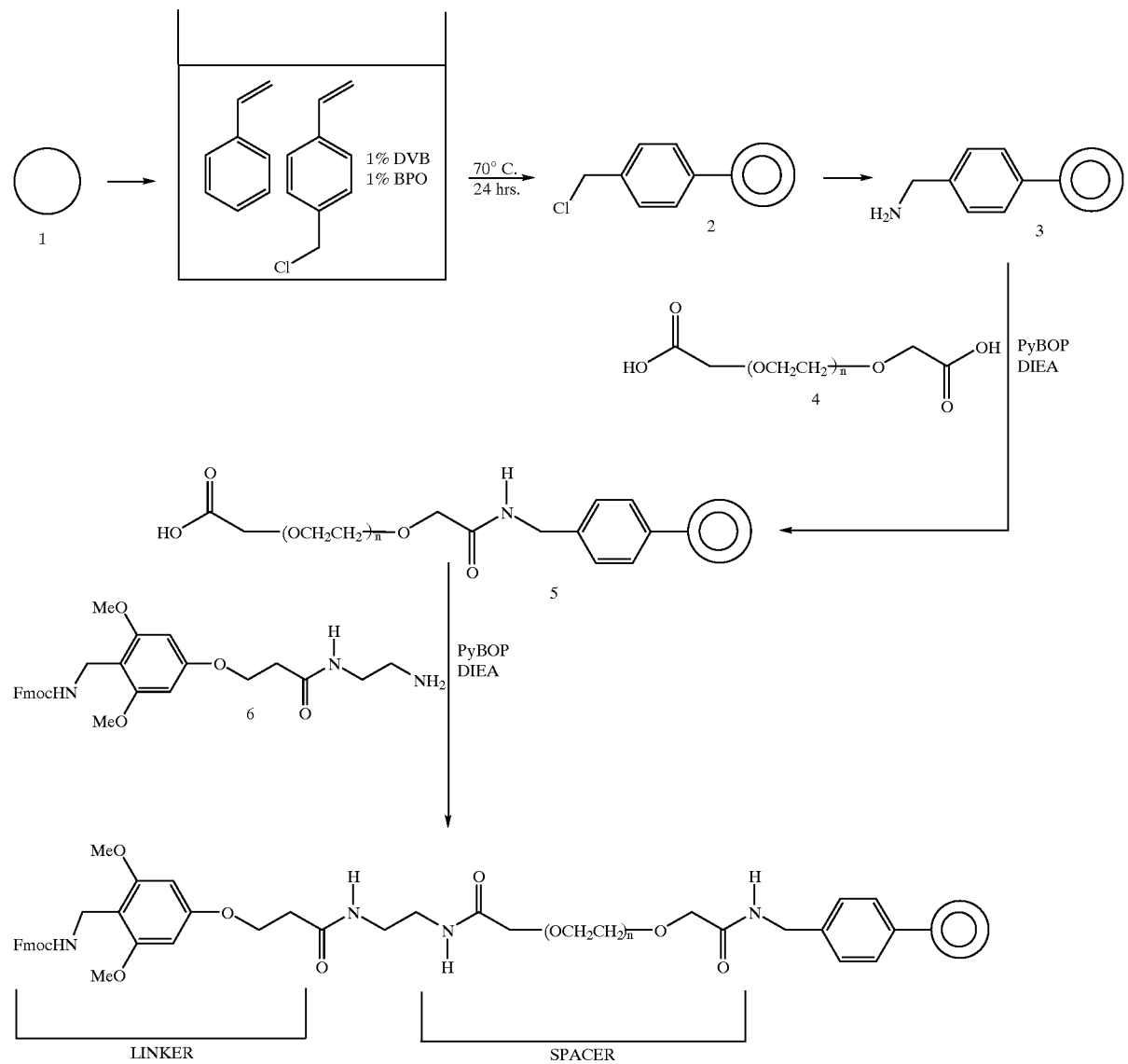

The resulting coated beads with memories are then used as solid support for molecular syntheses or for linkage of any desired substrate.

EXAMPLE 2

Construction of a Matrix with Memory

A matrix with memory was constructed from (a) and (b) as follows:

(a) A small (8×1×1 mm) semiconductor memory device [the IPTT-100 purchased from Bio Medic Data Systems, devices are designed to operate without a battery, relying on the energy generated by the radio frequency pulses used in the encoding process. Also, it is important to note that additional sensors such as temperature [as in this case], pH, or concentration measuring devices can be installed. The resulting combinations are capable of withstanding most reagents and conditions used in synthetic organic chemistry, including temperatures from −78 to 150° C.

The transponder was encoded and read with a device that emits and reads RF frequencies [Bio Medic Data Systems Inc. DAS-5001 CONSOLE™ System, see, also U.S. Pat. No. 5,252,962].

These memory devices include EEPROM (Electrical, Erasable, rogrammable, Read-Only Memory) "flash" unit and a temperature sensing device able to accept or emit information at any time. At each step of the combinatorial "split and pool" sequence, encoding information is sent from a distance in the form of radio frequency pulses at 145 kHz and stored until decoding is needed. When needed the radio frequency signals are retrieved using a specially assembled apparatus capable of reading the radio frequency code from a distance [DAS-5001 CONSOLE™ from Bio Medic Data Systems, Inc., Maywood, N.J.; see, e.g., U.S. Pat. Nos. 5,422,636, 5,420,579, 5,262,772, 5,252,962 and 5,250,962, 5,252,962 and 5,262,772].

(b) TENTAGEL™polymer beads carrying an acid-cleavable linker [TENTAGEL S Am cat # S30 022, RAPP Polymer, Tubingen, Germany].

(c) A chemically inert surrounding porous support [polypropylene AA, SPECTRUM, Houston, Tex.].

One transponder and about 20 mg of the derivatized TENTAGEL™ beads have been sealed in a small lof a size just sufficient to hold the beads and transponder] porous polypropylene microvessel [see, Examples 3 and 4].

EXAMPLE 3

Microvessels

A. FIGS. 11–13

Figure 11:
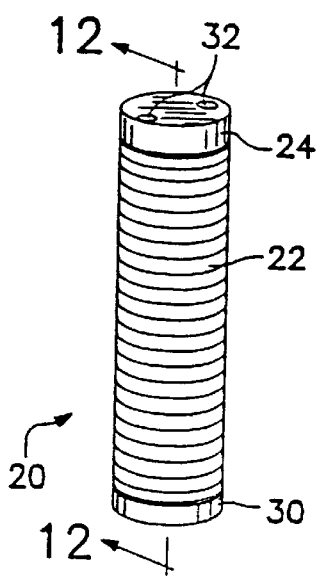
FIG. 11 is a side elevation of a preferred embodiment of a microvessel.
Figure 13:
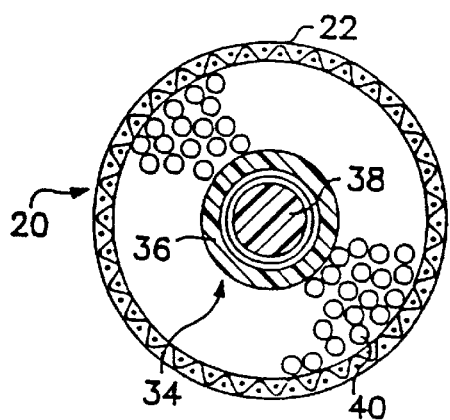
FIG. 13 is a sectional view taken along line 13—13 of FIG. 12.
Figure 12:
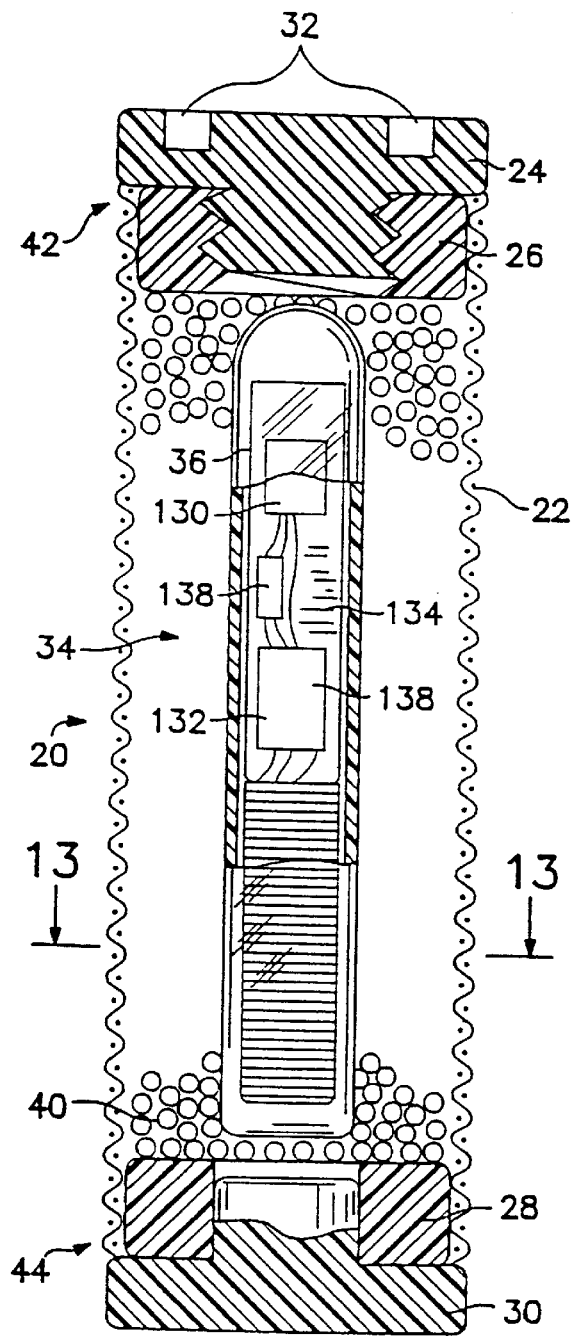
FIG. 12 is a sectional view, with portions cut away, taken along line 12—12 of FIG. 11.

FIGS. 11–13 illustrate an embodiment of a microvessel 20 provided herein. The microvessel 20 is a generally elongated body with walls 22 of porous or semi-permeable non-reactive material which are sealed at both ends with one or more solid-material cap assemblies 42, 44. The microvessel 20 retains particulate matrix materials 40 and can, as depicted in the Figure, contain one or more recording devices 34. In the preferred embodiment illustrated in FIGS. 11–13, the recording device includes a shell 36 that is impervious to the processing steps or solutions with which the microvessel may come into contact, but which permits transmission of electromagnetic signals, including radiofrequency, magnetic or optical signals, to and from the recording media of the recording device.

The preferred microvessel 20 is generally cylindrically shaped and has two solid-material cap assemblies 42, 44. The cap assemblies may be formed of any material that is non-reactive with the solutions with which the microvessel will come into contact. Such appropriate materials include, for example, plastic, TEFLON, polytetrafluoroethylene (hereinafter, PTFE) or polypropylene. Each cap assembly 42, 44 preferably includes a support base 26, 28, respectively, and an end cap 24, 30, respectively. Each support base 26, 28 is permanently attached to the walls 22 of the vessel by known means such as bonding with appropriate adhesives or heat treatment, either by heat-shrinking the wall material onto the lower portions of the support bases 26, 28, or by fusing the wall material with the support base material.

Preferably, at least one of the caps 24, 30 is removably attached to its cap base 26, for example by providing complementary threads on the support base and the end cap so that the end cap can be screwed into the support base, as illustrated in FIG. 12. Other possible means for attaching the end cap to the support base will be apparent to those in the art, and can include snap rings, spring tabs, and bayonet connectors, among others. The end cap 24, has one or more slots, bores, or recesses 32 formed in its outer surface to facilitate removal or replacement, with the user's fingers and/or by use of an appropriate tool. For the example illustrated, a spanner wrench having pegs spaced at the same separation as the recesses 32 can be used by inserting the pegs into the recesses. For a single slot, removal and replacement of the end cap could be achieved by using a screwdriver. Protruding tabs, rims, knurled edges or other means to enhance the ability to grasp the end cap can be used for manual assembly/disassembly of the microvessel. The cap assembly 42 at the opposite end of the microvessel can be permanently sealed using an adhesive or heat treatment to attach the support base 28 to the end cap 30, or the cap assembly 42 can be molded as a single piece, combining the support base 28 and the end cap 30.

Retained within the microvessel 20 are particle matrix materials 40 and a memory device 34. The recording device 34, in the preferred embodiment illustrated, includes a data storage unit(s) 38 and a shell 36 30 that protects the recording device 38 from the processing steps and/or solutions to which the microvessel are subjected. This shell 36 is preferably constructed of material that is non-reactive with and impervious to the solutions with which the microvessel may come into contact, and which is penetrable by the electromagnetic radiation, or similar means, used to read from and write to the memory device. The preferred device is presently a modified form of the IPTT-100 [Bio Medic Data Systems, Inc. ("BMDS"), Maywood, N.J.; see, also U.S. Pat. Nos. 5,422,636, 5,420,579, 5,262,772, 5,252, 962 and 5,250,962], which generally contains an electrically programmable memory chip 130 and decoding and power conversion circuitry 132 mounted on an elongated ceramic circuit board 134 and connected to an LC oscillator, comprising capacitor 138 and coil 136 wound around a ferrite core, which inductively receives and responds to a frequency-modulated magnetic signal generated by a similar LC oscillator in the write device, allowing the device to be remotely encoded and remotely read at a distance on the order of 1 cm or less. The device has been modified from the supplier's standard commercially-available form to provide physical dimensions to facilitate placement in the microvessel 20. The modification involves application of the simple and well-known relationship between inductor core area and length, the permeability of the core material, and the number of windings, i.e., L (inductance)=$N^2$ $\mu A/l$, where N is the number of windings, $\mu$ the permeability of the core, A is the core area and $l$ is the core length.

Other remotely programmable and readable tags are commercially available which may be used in the inventive system, such as those manufactured by Identification Device Technology, UK. These devices have circuitry and operational parameters similar to the device described above, but it may be necessary to modify the coil to reduce the access range to less than or equal to 1 cm. It is generally preferred that the responder, i.e., the memory device, and the transceiver in the control system be from the same manufacturer to assure complete compatibility.

The illustrated microvessel, as illustrated in FIGS. 11–13, is of a size sufficient to contain at least one recording device and one matrix particle, such as a TENTAGEL™ bead. The device is typically 20 mm in length [i.e., the largest dimension] or smaller, with a diameter of approximately 5 mm or less, although other sizes are also contemplated. These sizes are sufficient to contain form about 1 mg up to about 1 g of matrix particle, and thus range from about 1 mm up 100 mm in the largest dimension, typically about 5 mm to about 50 mm, preferably 10 mm to 30 mm, and most preferably about 15 to 25 mm. The size, of course can be smaller than those specified or larger. The wall material of the microvessel is PTFE mesh having a preferably about 50 $\mu$M to 100 $\mu$M, generally 50 to 70 $\mu$M hole size that is commercially available. The size of course is selected to be sufficiently small to retain the matrix particles. The cap apparatus is machined rod PTFE [commercially available from McMaster Carr, as Part #8546K11].

The matrix material is selected based upon the particular use of the microvessel; for example, a functionalized resin, such as TENTAGEL™ resin, commercially available from Rapp Polymere, Tubingen, Germany, is preferred for use in peptide synthesis and similar processes. The matrix material may also include fluophores or scintillants as described herein.

Alternative embodiments of the microvessel will be appreciated and include, for example, a pouch, including porous or semi-permeable material, which is permanently sealed to itself and contains matrix material and one or more memories.

B. FIGS. 14–16

Figure 14:
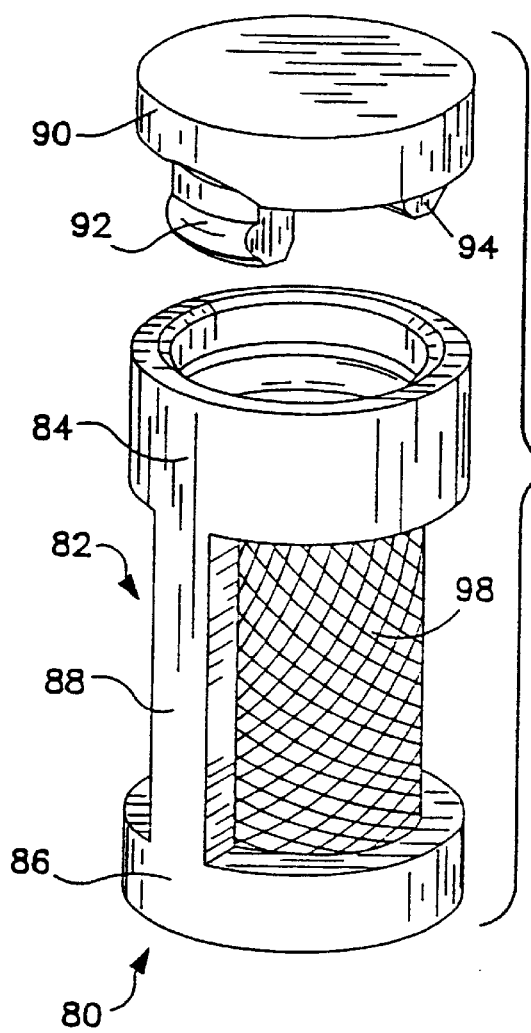
FIG. 14 is a perspective view of an alternative embodiment of a microvessel, with the end cap separated.
Figure 15:
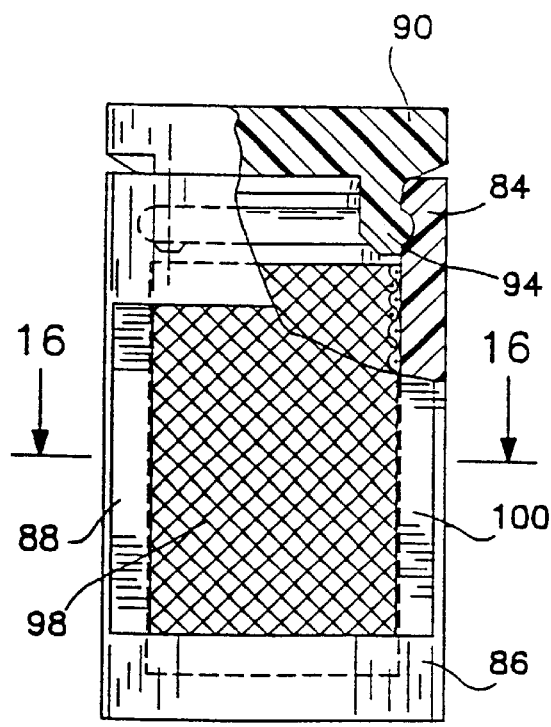
FIG. 15 is a side elevation view of the microvessel of FIG. 14, with a portion cut away.
Figure 16:
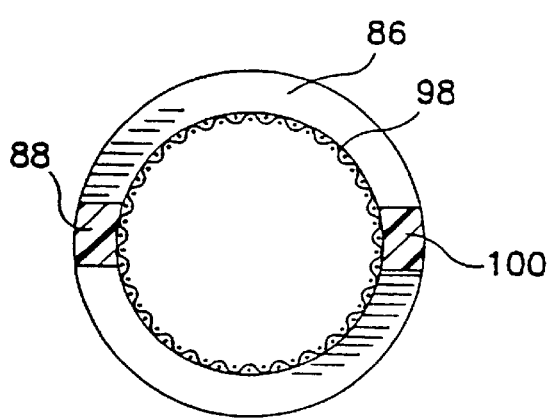
FIG. 16 is a sectional view taken along line 16—16 of FIG. 15.

FIGS. 14–16 illustrate an alternate embodiment of a microvessel provided herein. Like the microvessel described in Example 3, this embodiment of the microvessel also retains particulate matrix materials and one or more recording devices (not illustrated). The microvessel has a single-piece solid material frame 82, including a top ring 84, two support ribs 88, 100 disposed diametrically opposite each other and a bottom cap 86. The solid material frame 82 may be constructed of any material which is non-reactive with the solutions with which the microvessel will come into contact. Such appropriate materials include, for example, plastic, polytetrafluoroethylene (hereinafter, PTFE), TEFLON or polypropylene, and formation may be by molding or machining of the selected material, with the former being preferred for economy of manufacture.

The sidewall of the microvessel 98 is formed of porous or semi-permeable non-reactive material, such as PTFE mesh, preferably having a 70 $\mu$M pore size. The sidewall is preferably attached to the top ring 84 and bottom cap 86 of the solid material frame 82. Such attachment may be by known means such as bonding with appropriate glues or other chemicals or heat, with heat being preferred.

In the embodiment of FIGS. 14–16, the two support ribs 88, 100 are positioned opposite one another, however, any number of support ribs, i.e., one or more, may be provided. The microvessel sidewall 98 need not be fully attached to the support ribs 88, 100, however, the molding process by which the microvessels are formed may result in attachment at all contact points between the frame and the sidewall.

In the preferred manufacturing process, the sidewall material, a flat sheet of mesh, is rolled into a cylinder and placed inside the mold. The frame material is injected into the mold around the mesh, causing the frame to fuse to the mesh at all contact points, and sealing the edges of the mesh to close the cylinder.

In the embodiment illustrated in FIGS. 14–15, the microvessel is configured with a removable end cap 90. The end cap 90 is preferably constructed of the same material as the solid material frame 82. A snap ring, or, as illustrated, projections 92, 94 extend downward from the inside surface of the end cap 90. The projections 92, 94 have a flange which mates with a groove 96 formed in the inner wall of top ring 84 when pressed into the top ring to releasable secure the end cap 90 to the microvessel 80. As will be apparent, other means for releasably securing the end cap 90 to the top ring 84 can be used, including, but not limited to, those alternatives stated for the embodiment of FIGS. 11–13. The dimensions vary as described for the microvessel of FIGS. 11–13 and elsewhere herein.

In other embodiments, these vessels fabricated in any desired or convenient geometry, such as conical shapes. They can be solid at one end, and only require a single cap or sealable end.

These microvessels are prefereably fabricated as follows. The solid portions, such as the solid cap and body, are fabricated from a polypropylene resin, Moplen resin [e.g., V29G PP resin from Montell, Newark Del., a distributor for Himont, Italy]. The mesh portion is fabricated from a polypropylene, polyester, polyethylene or fluorphore-containing mesh [e.g., PROPYLTEX®, FLUORTEX®, and other such meshes, including cat. no. 9-70/22 available from TETKO® Inc, Briarcliff Manor, N.Y., which prepares woven screening media, polypropylene mesh, ETF mesh, PTFE mesh, polymers from W. L. Gore. The pores are any suitable size [typically about 50–100 $\mu$M, depending upon the size of the particulate matrix material] that permits contact with the synthetic components in the medium, but retains the particulate matrix particles.

EXAMPLE 4

Manual System

Illustrated in FIG. 17 is a program/read station for writing to and reading from the memory devices in the microvessel. The electronic components are commercially available from the same supplier of the memory devices, e.g., BMDS or ID TAG [Bracknell Berks RG12 3XQ, UK], so that the basic operations and frequency are compatible. The basic controller 170 and the transceiver 172 are disposed within a housing 174 which has a recessed area 176 positioned within the transmission range of coil 178. The microvessel 180 may be placed anywhere within recessed area 176, in any orientation, for both programming and reading functions. Basic controller 170 is connected to the system controller 182, illustrated here as a functional block, which provides the commands and encoded data for writing to the memory device in the microvessel and which receives and decodes data from the memory device during the read function. System controller 182 is typically a PC or lap top computer which has been programmed with control software 184 for the various write and read functions.

An example of the operation of the system of FIG. 17 is illustrated in FIG. 18. When power is supplied to the system, transceiver 172 emits an interrogation signal 185 to test for the presence of a memory device, i.e., a responder, within its detection range. The interrogation signal 185 is essentially a read signal that is continuously transmitted until a response 186 is received. The user manually places a microvessel 180 within the recessed area 176 so that the interrogation signal 185 provides a response to the controllers indicating the presence on the microvessel. The system receives the interrogation signal and performs a decode operation 187 to determine the data on the memory device within the microvessel, which data may include identification of the device and data concerning prior operations to which the microvessel has been exposed. Based upon the data obtained, the system makes a determination 188 of whether additional information is to be written. The system then performs a write operation 189 to record the immediately preceding operation. The write operation 189 involves modulating the transmitted signal as a series of "0's" and "1's", which are recorded on the memory chip, which typically has a 128 bit capacity. After completion of the programming step 189, an error check 190 is performed wherein a second read signal is emitted to verify the data that was written for integrity and correct content. If the correct data is not verified, the system may attempt to perform the write operation 189 again. After verification of the correct data, if the microvessel is one that should proceed to another operation, the system controller 182 will display instructions 192 for direction of the microvessel to the next process step.

The read operation is the same as the beginning of the write operation, with the interrogation signal being continuously transmitted, or transmitted at regular intervals, until a response is received. The response signal from the memory device in the microvessel 180 is conducted to system controller 182 for decoding and output of the data that is stored on the memory device. Software within the system controller 182 includes a data base mapping function which provides an index for identifying the process step associated with data written at one or more locations in the memory device. The system memory within the system controller 182 will retain the identification and process steps for each microvessel, and an output display of the information relating to each microvessel can indicate both where the microvessel has been, and where it should go in subsequent steps, if any. After the data stored within the microvessel has been read, it is removed from the interrogation field and advanced to its next process step.

EXAMPLE 5

Preparation of a Library and Encoding the Matrices with Memories

A pool of the matrices with memories prepared as in EXAMPLE 2 was split into two equal groups. Each group was then addressed and write-encoded with a unique radio frequency signal corresponding to the building block, in this instance an amino acid, to be added to that group The matrices with memories were then pooled, and common reactions and manipulations such as washing and drying, were performed. The pool was then re-split and each group was encoded with a second set of radio frequency signals corresponding to the next set of building blocks to be introduced, and the reactions were performed accordingly. This process was repeated until the synthesis was completed. The semiconductor devices also recorded temperature and can be modified to record other reaction conditions and parameters for each synthetic step for storage and future retrieval.

Ninety-six matrices with memories were used to construct a 24-member peptide library using a 3×2×2×2 "split and pool" strategy. The reactions, standard Fmoc peptide syntheses [see, e.g., Barany et al. (1987) *Int. J. Peptide Protein Res.* 30:705–739] were carried out separately with each group. All reactions were performed at ambient temperature; fmoc deprotection steps were run for 0.5 h; coupling steps were run for 1 h; and cleavage for 2 h. This number was selected to ensure the statistical formation of a 24-member library [see, Burgess et al. (1994) *J. Med. Chem.* 37:2985].

Each matrix with memory in the 96-member pool was decoded using a specifically designed radio frequency memory retrieving device [Bio Medic Data Systems Inc. DAS-5001 CONSOLE™ System, see, also U.S. Pat. No. 5,252,962 and U.S. Pat. No. 5,262,772] the identity of the peptide on each matrix with memory [Table 2]. The structural identity of each peptide was confirmed by mass spectrometry and $^1$H NMR spectroscopy. The content of peptide in each crude sample was determined by HPLC to be higher than 90% prior to any purification and could be increased further by standard chromatographic techniques.

TABLE 2

Radio frequency Encoded Combinatorial 24-member peptide library

| Entry (SEQ ID) | RF code | Peptide | # of matrices with memories[a,b] | Mass (Actual)[e] |
|---|---|---|---|---|
| 1 | LAGD | Leu-Ala-Gly-Asp | 3 | 372 (372.2) |
| 2 | LEGD | Leu-Glu-Gly-Asp | 4 | 432 (432.2) |
| 3 | SAGD | Ser-Ala-Gly-Asp | 5 | 348 (348.1) |
| 4 | SEGD | Ser-Glu-Gly-Asp | 5 | 406 (406.1) |
| 5 | LAVD | Leu-Ala-Val-Asp | 4 | 416 (416.2) |
| 6 | LEVD | Leu-Glu-Val-Asp | 6 | 474 (474.2) |
| 7 | SAVD | Ser-Ala-Val-Asp | 2 | 390 (390.2) |
| 8 | SEVD | Ser-Glu-Val-Asp | 3 | 446 (446.2) |
| 9 | LAGF | Leu-Ala-Gly-Phe | 5 | 406 (406.2) |
| 10 | LEGF | Leu-Glu-Gly-Phe | 5 | 464 (464.2) |
| 11 | SAGF | Ser-Ala-Gly-Phe | 5 | 380 (380.2) |
| 12 | SEGF | Ser-Glu-Gly-Phe | 6 | 438 (438.2) |
| 13 | LAVF | Leu-Ala-Val-Phe | 6 | 448 (448.3) |
| 14 | LEVF | Leu-Glu-Val-Phe | 2 | xxx |
| 15 | SAVF | Ser-Ala-Val-Phe | 2 | xxx |
| 16 | SEVF | Ser-Glu-Val-Phe | 1 | 480 (480.2) |
| 17 | LAGK | Leu-Ala-Gly-Lys | 2 | 387 (387.3) |
| 18 | LEGK | Leu-Glu-Gly-Lys | 1 | 445 (445.3) |
| 19 | SAGK | Ser-Ala-Gly-Lys | 4 | 361 (361.2) |
| 20 | SEGK | Ser-Glu-Gly-Lys | 3 | 419 (419.2) |
| 21 | LAVK | Leu-Ala-Val-Lys | 4 | 429 (429.3) |
| 22 | LEVK | Leu-Glu-Val-Lys | 6 | 487 (487.3) |
| 23 | SAVK | Ser-Ala-Val-Lys | 6 | 403 (403.3) |
| 24 | SEVK | Ser-Glu-Val-Lys | 6 | 461 (461.3) |

[a]This is the number of packets of each matrix with memory containing the same peptide.
[b]The ambient temperature was recorded by the sensor device of the chip in the matrices with memories at various points during the synthetic pathway.
[c]Mass refers to (M + H) except entry 1 and 8 which refer to (M − H). Since each peptide has a unique mass, the mass spectrum confirms its structure.
[d]HPLC conditions: Shimadzu SCL 10A with a MICROSORB-MV ™ C-18 column (5 μM, 100 Å; isocratic elution with acetonitrile/water.

EXAMPLE 6

Synthesis of a Decapeptide Library

Materials and Methods (1) A memory device [IPTT-100, Bio Medic Data Systems, Inc., Maywood, N.J.], which is 8×1×1 mm, and TENTAGEL® beads (20 mg) were encapsulated using a porous membrane wall and sealed (final size≈10×2×2 mm) as described in Example 2. In particular, each memory with matrix microvessel 20 mg of TENTAGEL® resin carrying the acid-cleavable linker PAL.

(2) Solvents and reagents [DMF, DCM, MeOH, Fmoc-amino acids, PyBOP, HATU, DIEA, and other reagents] were used as received. Mass spectra were recorded on an API I Perkin Elmer SCIEX Mass Spectrometer employing electrospray sample introduction. HPLC was performed with a Shimadzu SCI 10A with an AXXiOM C-18 column 15 μm, 100 Å; gradient: 0–20 min, 25–100% acetonitrile/water (0.1% TFA]. UV spectra were recorded on a Shimadzu UV-1601 instrument. Peptide sequencing was performed using a Beckman model 6300 amino acid analyzer. Chemicals, solvents and reagents were obtained from the following companies: amino acid derivatives (CalBiochem); solvents (VWR; reagents (Aldrich-Sigma).

(3) General procedure for Fmoc-amino acid coupling

The matrix with memory microvessels were placed in a flat-bottomed flask. Enough DMF [$v_r$ ml, 0.75 ml per microvessel] was added to completely cover all the matrix with memory microvessels. Fmoc-amino acid, EDIA, and PYBOP [or HATU for the hindered amino acids Pro and Ile] were added sequentially with final concentrations of 0.1, 0.2, and 0.1 M, respectively. The flask was sealed and shaken gently at ambient temperature for 1 h. The solution was removed and the matrix with memory microvessels were washed with DMF [4×$v_r$], and re-subjected to the same coupling conditions with half the amount of reagents. They ere finally washed with DMF [4×$v_r$], MeOH [4×$v_4$], DCM [4×$v_4$], and dried under vacuum at ambient temperature.

(4) Fmoc-deprotection

The matrix with memory microvessels were placed in a flat bottomed flash. Enough 20% piperidine solution in DMF [$v_r$ ml, 0.75 ml/matrix with memory microvessel] was added to completely cover the microvessels. The flask was sealed and gently shaken at ambient temperature for 30 min. Aliquots were removed and the UV absorption of the solution was measured at 302 nm to determine the Fmoc number. The matrix with memory microvessels were then washed with DMF [6×$v_r$] and DCM [6×$v_r$] and dried under vacuum at ambient temperature.

(5) Procedure for peptide cleavage from solid support

The TENTAGEL® beads [20–120 mg] from each matrix with memory microvessel were treated with 1 ml of TFA cleavage mixture [EDT:thioanisole;H$_2$O:PhOH:TFA, 1.5:3:3:4.5:88, w/w] at ambient temperature for 1.5 hours. The resin beads were removed by filtration through a glass-wool plug, the solution was concentrated, diluted with water [2 ml], extracted with diethyl ether [8×2 ml], and lyophilized to yield the peptide as a white powder [4–20 mg].

(6) Preparation of polyclonal antibodies

The peptide (SEQUENCE ID No. 25) with a cysteine at the N-terminus, was synthesized by standard solid phase methods using an automated Applied Biosystems 430A peptide synthesizer [see, Sakakibara (1971) *Chemistry and Biochemistry of Amino Acids, Peptides and Proteins*, Weinstein, ed, Vol. 1, Marcel Dekker, N.Y., pp. 51–85]. The synthetic peptide was conjugated to keyhole limpet hemocyanin using maleimidohexanoyl-N-hydroxysuccinimide as a cross-linking agent [see, Ishikawa et al. (1983) *J. Immunoassay* 4:209–237]. Rabbits were injected at multiple dorsal intradermal sites with 500 μg peptide emulsified with complete Freund's adjuvant. The animals were boosted regularly at 3–6 week intervals with 200 μg of peptide conjugate emulsified in incomplete Freund's adjuvant. The titer of the antisera after a few booster injections was approximately 1:50,000 to 1:100,000 as determined by ELISA using the unconjugated peptide as the antigen.

(7) Enzyme Linked Immunosorbant Assay [ELISA]

Plates were coated with 100 μl/well of a 0.5 μg/μl solution of peptides diluted in phosphate buffered saline [PBS] by incubating them overnight at 4° C. The plates were washed extensively with PBS and incubated with 200 μl of 0.1% bovine serum albumin [BSA] in PBS for 1 h at room temperature. The plates were then washed with PBS and 100 μl of prebled or rabbit anti-peptide [peptide of SEQ ID No. 25] antibody [1:100,000] was added to the duplicate wells. After a 1 h incubation at ambient temperature, the plates were washed with PBS and 100 μl of peroxidase-goat-antirabbit IgG diluted in PBS supplemented with 0.1% BSA was added. After incubation for another hour at ambient temperature, the plates were extensively washed with PBS and 100 μl of peroxidase substrate solution was added to each well. The plates were then incubated for 15 minutes at ambient temperature. The peroxidase reaction was measured by the increase in absorbance at 405 nm.

The library

Figure 10:
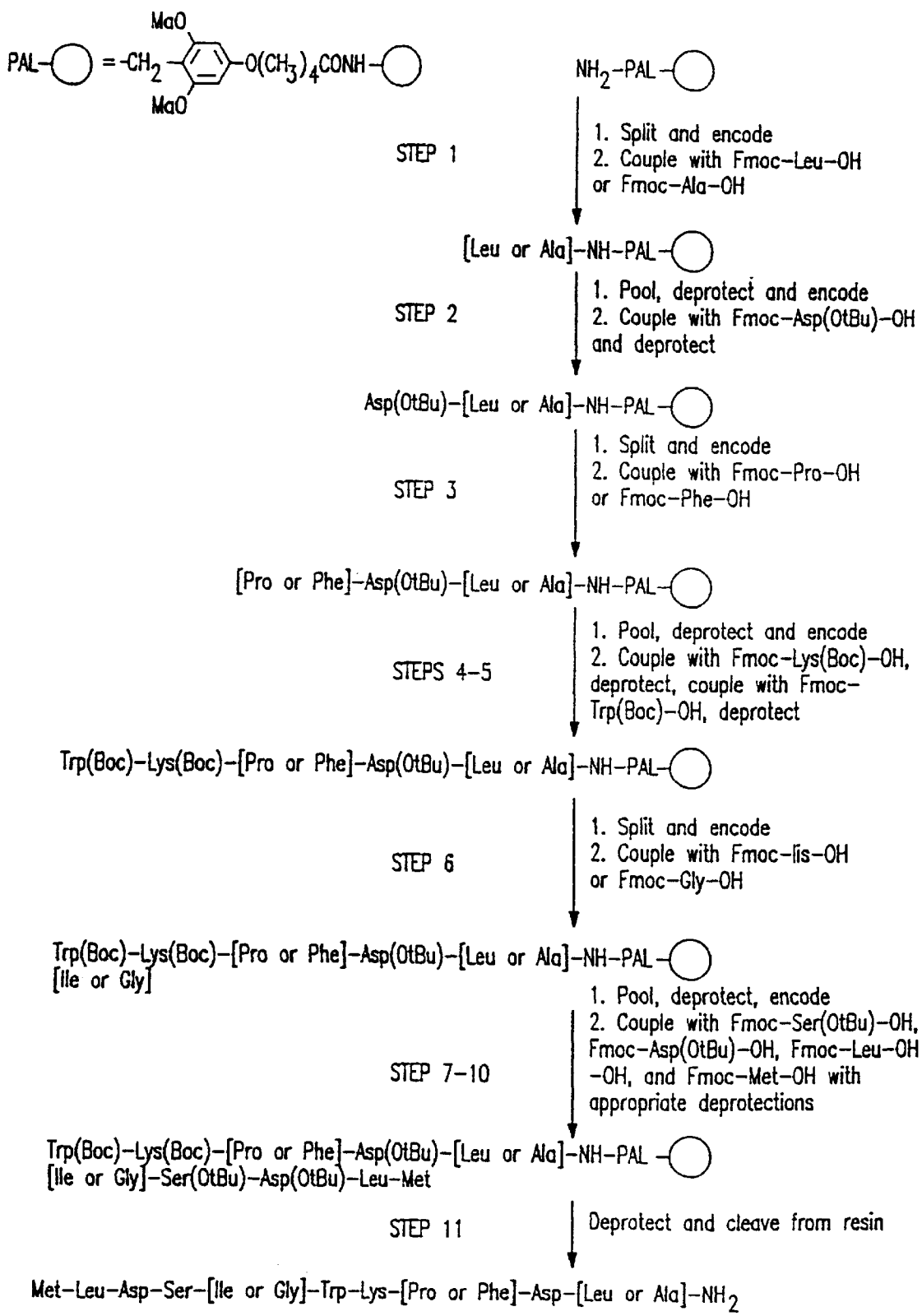
FIG. 10 is a scheme for the synthesis of the 8 member RF encoded combinatorial decameric peptide library described in EXAMPLE 4. All couplings were carried out in DMF at ambient temperature for 1 h [two couplings per amino acid], using PyBOP and EDIA or DIEA. Deprotection conditions: 20% piperidine in DMF, ambient temperature, 30 min; Cleavage conditions: 1,2-ethanedithiol:thioanisole:water:phenol:trifluoroacetic acid [1.5:3:3:4.5:88, w/w], ambient temperature, 1.5 h.

The library included the peptide having the sequence Met-Leu-Asp-Ser-Ile-Trp-Lys-Pro-Asp-Leu [MLDSIWKPDL; SEQ ID NO. 25], against which an antibody had been generated in rabbits [the peptide used for rabbits had an additional N-terminal Cys residue for linking], and seven other peptides differing at residues L, P, and/or I [SEQ ID NOs. 26–32 and the Scheme set forth in FIG. 10].

The matrix with memory microvessels loaded with TENTAGEL® beads carrying PAL linkers [20 mg each] were split into two equal groups. Each group was encoded with the radio frequency code L or A [the one-letter symbols for amino acids leucine and alanine, respectively] and the first coupling was carried out separately using Fmoc-Leu-OH or Fmoc-Ala-OH, respectively and ByBOP, or HATU for the sterically hindered amino acids [STEP 1, FIG. 10]. The microvessels were then pooled, deprotected with 20% piperidine in DMF [Fmoc removal], encoded with the code D and subjected to coupling with Fmoc-Asp(OtBu)-OH and deprotection as above [STEP 2]. The microvessels were then re-split into two equal and fully randomized groups and encoding was performed on each group with the codes P or F and amino acid derivatives Fmoc-Pro-OH or Fmoc-Phe-OH were coupled, respectively [STEP 3]. The microvessels were pooled again and amino acid derivatives Fmoc-Lys (Boc)-OH and Fmoc-Trp(Boc)-OH were coupled sequentially with appropriate encoding and deprotection procedures [STEPS 4 and 5], and then were re-split into two equal groups, encoded appropriately and the amino acid derivatives Fmoc-Ile-OH or Fmoc-Gly-OH were coupled separately [STEP 6]. The matrix with memory microvessels were pooled, the amino groups deprotected and the remaining amino acids [Ser, Asp, Leu and Met] were sequentially introduced with appropriate encoding and deprotections using suitably protected Fmoc derivatives [STEPS 7–10]. The introduction of each amino acid was performed by double couplings at every step. The coupling efficiency for each step was generally over 90% as measured by Fmoc number determination after Fmoc deprotection [UV spectroscopy].

Decoding each matrix with memory allowed identification of identical units. It was observed that a fairly even distribution of matrix with memories over the entire library space was obtained. It should be noted that sorting out the matrices with memories at each split by de-coding allows this random process to become an exact, "one compound-one matrix with memory method.

TENTAGEL® beads from matrices with memories with identical codes were pooled together and the peptides were cleaved from the resin separately with EDT:thioanisole:H$_2$O:PhOH:TFA [1.5:3:3:4.5:88m, w/w]. The work-up and isolation procedures involved filtration, evaporation, dilution with water, thorough extraction with diethyl ether, and lyophilization. The fully deprotected peptides were obtained as white solids, their structures were confirmed by mass spectroscopy, and their purity was determined by HPLC analysis. The peptide sequence in entry 2, [SEQ ID NO. 26] was confirmed by peptide amino acid sequence analysis. Ambient reactor temperature was also measured at specific synthesis steps by the on-board temperature thermistor.

Biological screening of the peptide library

A rabbit polyclonal antibody generated specifically against the peptide SEQ ID NO. 25 was used to detect this specific sequence in the REC™ peptide library by the ELISA method. The ELISA assay correctly identified the library member with the SEQ ID NO. 25 [100% binding]. The sequence of this peptide was also confirmed by the radio frequency code, mass spectroscopy, and amino acid sequence analysis.

It was also of interest to observe trends in the binding of the antibody to the other members of the library. It was observed that the binding of each peptide was dependent on the type, position, and number of modifications from the parent sequence. Thus, replacement of I with G did not change significantly the antigenicity of the peptide. Substitution of L with A reduced antibody binding by ≈40% and replacement of P with F essentially converted a peptide to a non-recognizable sequence. Replacement of two amino acids resulted in significant loss of binding. Thus the concurrent substitutions [I→G and P→F], [I→G and L→A], and [P→F and L→A] reduced antibody binding by ≈40, 60, and 92%, respectively. Finally, the peptide library member in which I, P and L were replaced with G, F and A, respectively, was not recognized by the antibody. Collectively, these results suggest that amino acids at the C-terminus of the peptide, especially P play an important role in this particular antibody-peptide recognition.

EXAMPLE 7

Procedures for Coating Glass-enclosed Memory Devices with Silylated Polystyrene

A procedure for coating glass-enclosed memory devics, such as the IPTT-100, is represented schematically as follows:

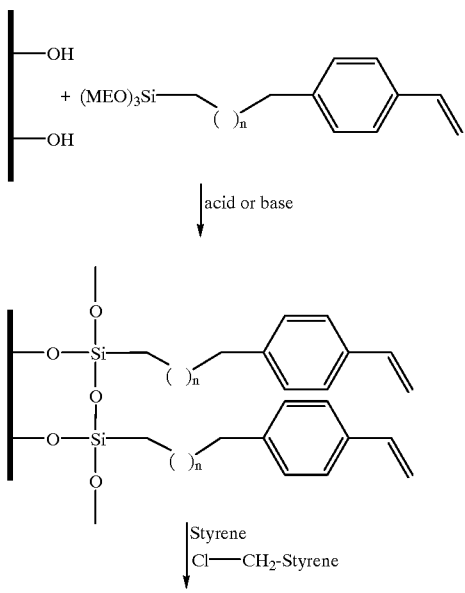

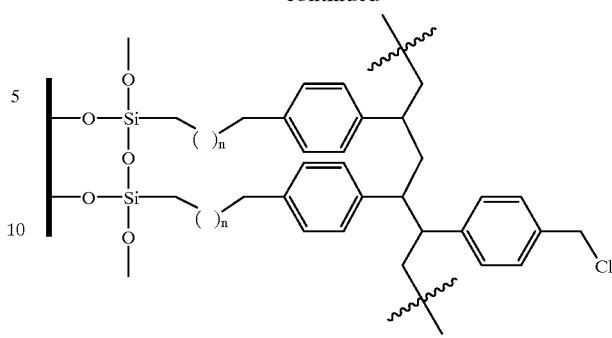

A. Procedure A

1. Before coating, the glass surface of the IPTT-100 transponder was cleaned using base, chloroform, ethanol and water, sequentially, and, then heated to 200° C. [or 300° C.] to remove water.

2. The residue from the solvents in step 1 were removed under vacuum.

3. N-styrylethyltrimethoxy silane HCl, chloromethyl styrene, divinyl benzene and benzoyl peroxide 19:1:0.1:0.2 moll is stirred for 10 minutes.

4. The resulting mixture was coated on the cleaned glass, which was then baked at 150–200° C. for 5 to 10 minutes in air or under nitrogen.

5. The coated glass was then sequentially washed with DCM, DMF and water. The resulting coating was stable in DCM, DMF, acid and base for at two weeks at 70° C.

B. Procedure B

1. Before coating, the glass surface is cleaned using base, chloroform, ethanol and water, sequentially, and, then heating to 200° C. [or 300° C.] to remove water.

2. The residue from the solvents in step 1 are removed under vacuum.

3. N-styrylethyltrimethoxy silane HCl [10–15%] is refluxed in toluene with the cleaned glass surface.

4. After reaction, the glass surface is washed with toluene, DCM, ethanol and water sequentially.

5. A mixture of chloromethyl styrene, divinyl benzene and benzoyl peroxide [molar ratio of N-styrylethyltrimethoxy silane HCl to the other compounds is 9:1:0.1:0.2 mol] is coated on the glass, which is then baked at 150–200° C. for 10 to 60 minutes.

6. The coated glass is then sequentially washed with toluene, DCM, DMF and water.

EXAMPLE 8

Preparation of Scintillant-encased Glass Beads and Chips

Materials:

POPOP [Aldrich] or PPO [concentrations about 5 to 6 g/l], and/or p-bis-o-methylstyrylbenzene [bis-MSB] or di-phenylanthracene [DPA] [concentrations about 1 g/l], or scintillation wax [FlexiScint from Packard]. Precise concentrations may be determined empirically depending upon the selected mixture of components.

Porous glass beads [Sigma]

IPTT-100 transponders [see, Examples 2–4].

A. Preparation of scintillant coated beads

Porous glass beads are soaked in a mixture of PPO [22–25% by weight] and bis-MSB [up to 1% by weight] in a monomer solution, such styrene or vinyltoluene, or in hot liquified scintillation wax 13–5 volume/volume of bead]. A layer of polystyrene [about 2 to 4 µM] is then applied. A peptide is either synthesized on the polystyrene, as described above, or is coated [adsorbed] or linked via a cleavable linker to the polystyrene.

B. Preparation of scintillant coated matrix with memory beads

1. The porous glass beads are replaced with glass encased [etched prior to use] transponders and are treated as in A. The resulting beads are sealed with polystyrene [2 to 5 µM] and then coated with a selected acceptor molecule, such as an antigen, antibody or receptor, to which a radiolabeled ligand or antibody selectively binds. The identity of the linked peptides or protein is encoded into each memory. After reactionn and counting in a liquid scintillation counter, the beads that have bound acceptor molecule are read to identify the linked protein.

2. The porous glass beads are replaced with glass encased [etched prior to use] transponders and are treated as in A and sealed as in A with polystyrene. A peptide, small organic or other library is synthesized on the polystyrene surface of each bead, and the identity of each member of the library encoded into the memory. The beads with linked molecules are reacted with labeled receptor and counted in a liquid scintillation counter. After counting in a liquid scintillation counter, the beads that have bound receptor are read to identify the molecule that bound to the receptor.

EXAMPLE 9

Use of the Scintillant Coated or Encased Particles in Assays

In experiments 1–3, as model system, the binding of biotin to functional amine groups was detected using $^{125}$I-strepavidin. In experiment 4, the binding of [Met$^5$] enkephalin to the functional amine groups was detected using $^{125}$I-antibody.

Experiment #1

1. Scintillant [PPO % 2 and DPA % 0.05] was introduced [Emerald Diagnostics, Eugene, Oreg.] and incorporated on the interior surface of polystyrene beads [Bang Laboratories]. The polystyrene beads were 3.1 µM, with 20% crosslinking and were derivatized with amine groups.

2. The concentration of the functional amine groups on the bead surfaces was estimated to be about 0.04125 µmol/mg. The amine groups were covalently linked to the N-hydroxy succinimide derivative of Biotin [Calbiochem 203112] at molecular ratio of 1:10, respectively. This was done by resuspending the beads in a 50% acetonitrile: water, Hepes [pH 8.0] buffered solution containing biotin for 2 hours at room temperature. After 2 hours, the beads were washed 6 times with 10 ml of 50% acetonitrile in water. Beads were resuspended in PBS [pH 7.2] and stored overnight at 4° C.

3. Using an SPA format, biotin was detected using $^{125}$I-streptavidin to the biotin was detected. This was done by diluting beads to a 20 mg/ml and addding them to 96 well plates at 4, 2, 1. 0.5, 0.25, and 0.125 mg per well. Volumes were adjusted to 100 ul per well. $^{125}$I-strepavidin was added to final concentration of 0.1 µCi per well. Plates were counted in a Wallac MicroBeta Trilux scintillation counter after 2 hours. Bound biotin was detected.

Experiment #2

1. Scintillants [pyrenebutyric acid and 9-anthracenepropionic acid] were covalently linked to the TENTAGEL® beads, with 0.25 mmol/g available functional amine groups, at 2%: 0.05% ratio, respectively. The fluorophore was linked to 15% of these sites.

2. The functional amine group on the TENTAGEL® beads were covalently linked to the N-hydroxy succinimide derivative of biotin. The free functional amine groups on beads [0.21 µmol/mg] were covalently linked to biotin [Calbiochem 203112]. Briefly, Biotin was mixed with the beads at a molecular ratio of 10:1 in 6 ml of 50% acetonitrile with Hepes [pH 8.0] and incubated for 2 hours at room temperature. At the end of incubation period, the beads were washed 3 times with 10 ml of 100% acetonitrile followed by 3 washes with 50% acetonitrile in water. The beads were resuspended in PBS [pH 7.2] and stored overnight at 4° C.

3. Biotin was detected using $^{125}$I-streptavidin detected in a SPA format. This was done by diluting beads to a 20 mg/ml, and introducing them into wells in 96 well plats at 4, 2, 1, 0.5, 0.25, and 0.125 mg per well. Volumes were adjusted to 100 µl per well. $^{125}$I-streptavidin [Amersham IM236] was added to each well at a concentration of 0.05 µCi/well. After approximately 2 hours, additional $^{125}$I-strepavidin was added for a final concentration of 0.1 uCi per well. Plates were counted in a Wallac MicroBeta Trilux scintillation counter after 2 hours. Bound biotin was detected.

Experiment #3

1. BMDS chips [and also similar chips ID TAG available from Identification Technologies Inc.] were coated with scintillant [PPO % 2 and DPA 0.5% in polystyrene [10% in dichloromethane].

2. The chip was then coated with a layer of derivatized silane.

3. The functional amine groups were covalently linked to the N-hydroxy succinimide derivative of Biotin. The free functional amine groups on the silane [375 nmol/chip] were covalently linked to Biotin [Calbiochem 203112]. Briefly, biotin was dissolved in 1 ml of 30% acetonitrile with Hepes [pH 8.0] and incubated with the chip for 2 hours at room temperature. At the end of incubation period, the chip was washed 3 times with 50% acetonitrile in water, resuspended in PBS [pH 7.2] and stored overnight at 4° C.

4. Biotin was detected in a SPA format by $^{125}$I-streptavidin. The chips were placed in 24-well plate with 500 µl $^{125}$I-streptavidin [0.1 µCi/well, Amersham IM236]). After a 2 hour incubation, the plates were counted in Wallac MicroBeta Trilux scintillation counter. Binding was detected.

Experiment #4

1. The chips were coated with scintillant IPPO % 2 and DPA] 0.05% in polystyrene [10% in dichloromethane].

2. The functional amine group was derivatized for spontaneous covalent binding to amine group [Xenopore, N.J.].

3. [Met$^5$]Enkephalin [tyr-gly-gly-phe-met; SEQ ID No. 33] peptide [R&D Antibodies] were covalently linked to the amine group by incubating the coagted chip with the peptide in 500 µl of PBS [160 µg peptide/ml, pH 8]) overnight at room temperature.

4. At the end of the incubation, the chips were washed and then incubated in 3% bovine serum albumin for 2 hours.

5. Linked peptide was detected in a SPA format. The chips were was placed in 24-well plate containing 500 µl of $^{125}$I-anti-[Met5]Enkephalin antibody [0.1 µCi/well, R&D Antibodies]. The antibody is a rabbit polyclonal against the C-terminal region of the peptide. After a 2 hour incubation, the plates were counted in Wallac MicroBeta Trilux scintillation counter and linked peptide was detected.

EXAMPLE 10

Synthesis of Oligonucleotide Libraries on OMDs

Oligonucleotide libraries are synthesis on OMDS [described above, see, e.g., FIG. 22]. Referring to FIG. 33, polypropylene sheets [(10×10×1 mm) the Moplen resin e.g., V29G PP resin from Montell, Newark Del., a distributor for Himont, Italy] are radiation grafted with polystyrene to give the surface modified devices1 [MACROCUBES™ or MACROBEADS™]. Each such device is imprinted with a unique symbology, such as the two-dimensional optical bar code using the methods described herein. The bar-coded devices are functionalized with amino groups to give functionalized OMDs devices3. The first set of nucleosides modified with a succinic acid linker are then coupled onto the matrices using DNA synthesizer with modified reaction vessels [suitable for use with the OMD-linked nascent oligonucleotides]. Five cycles of TCA de-blocking, sorting, tetrazole activation, coupling, capping, and oxidation are performed automatically on the machine [except the sorting] to yield oligonucleotides [hexamers] on the matrices 6. Cleavage and deprotection under standard conditions give the oligonucleotide hexamer library 7. The identity of each oligonucleotide is associated with the unique code in a remote memory, such as by manually entry before, during or after synthesis.

Since modifications will be apparent to those of skill in this art, it is intended that this invention be limited only by the scope of the appended claims.

What is claimed:

1. A method for tagging molecules comprising a target product produced in a synthesis comprising at least one synthesis step, the method comprising:

(a) first linking a first molecule to a matrix material;

(b) either prior to, during or after first linking, imprinting an optically-readable symbol on a surface of the matrix material or on a microvessel containing the matrix material, wherein the optically-readable symbol provides a unique identifier corresponding to each first molecule;

(c) first programming a remote memory with a first data point that creates a first record correlating the optically-readable symbol to the first molecule;

(d) second linking at least one second molecule to the first linked molecule in a first synthesis step;

(e) second programming the memory with a second data point that creates a second record correlating the optically-readable symbol and the at least one second linked molecule; and (f) if the synthesis comprises a plurality of synthesis steps, repeating steps (d) and (e) until the synthesis is complete.

2. The method of claim 1, wherein the matrix material is continuous and is in the form of a container, microvessel or laboratory glassware or chromatography column.

3. The method of claim 1, wherein the matrix material is continuous and is in the form of a container or microplate or test tube, culture dish, vial or beaker.

4. The method of claim 1, wherein:
the container is a plate with a plurality of wells; and
one or more of the wells is (are) imprinted with the optically-readable symbol.

5. The method of claim 1, wherein the matrix material is in the form of a cube or other parallelepiped having at least one outer surface adapted for linkage of biological particles or molecules.

6. The method of claim 1, wherein the matrix material is selected from the group consisting of a polystyrene, a cellulose, a glass, a polyacrylamide, a polysaccharide, a rubber, silicon, a plastic, sand, pumice, agarose, halogenated hydrocarbon polymers, polyvinyltoluene, and any polymer used as a matrix in solid phase syntheses, wherein at least a portion of the surface of the matrix material has been activated or derivatized for linkage of biological particles or molecules.

7. The method of claim 1, wherein the matrix material contains a scintillating material suitable for use in a scintillation proximity assay (SPA).

8. The method of claim 7, wherein the scintillating material is selected from the group consisting of doped glass and calcium fluoride.

9. The method of claim 8, wherein the scintillating material is a doped glass and a dopant within the doped glass is selected from the group consisting of Mn, Cu, Pb, Sn, Au, Ag, Sm and Ce.

10. The method of claim 7, wherein the scintillating material is yttrium silicate.

11. The method of claim 1, further comprising directing the sequence of steps (a) and (c) through (f) using a computer program.

12. The method of claim 1, wherein the matrix material comprises a luminescent moiety.

13. The method of claim 12, wherein the luminescent moiety is selected from among fluorophores.

14. The method of claim 12, wherein the luminescent moiety is selected from the group consisting of 2,5-diphenyloxazole (PPO), anthracene, 2-(4'-tert-butylphenyl)-5-(4"-biphenyl)-1,3,4-oxadiazole (butyl-PBD); 1-phenyl-3-mesityl-2-pyrazoline (PMP).

15. The method of claim 12, wherein the luminescent moiety is selected from the group consisting of rare earth metal cryptate allopycocyanin (APC), allophycocyanin B, phycocyanin C or phycocyanin R, a rhodamine, thiomine, phycocyanin R, phycoerythrocyanin, phycoerythrin C, phycoerythrin B, phycoerythrin R.

16. The method of claim 12, wherein the luminescent moiety is selected from the group consisting of Eu trisbipyridine diamine (EuTBP) and Tb tribipyridine diamine (TbTBP).

17. The method of claim 1, wherein a target product is an organic molecule.

18. The method of claim 1, wherein the synthesis is repeated using a plurality of matrices to produce a library of target products linked to matrices, wherein each matrix of the plurality of matrices is tagged with a unique optically-readable symbol.

19. The method of claim 18, wherein the memory is in a computer.

20. The method of claim 1, wherein the target product is an oligonucleotide.

21. The method of claim 20, wherein the oligonucleotide contains 6, 7 or 8 nucleotide base pairs.

22. The method of claim 1, further comprising screening the target product for activity or analyzing a structure of the target product or assessing an activity of the target product.

23. The method of claim 1, wherein the target product is a peptide and each added molecule is an amino acid.

24. The method of claim 1, wherein the target product is an oligonucleotide and each added molecule is an nucleotide.

25. The method of claim 1, wherein the target product is an oligomer and each added molecule is a monomer.

26. The method of claim 1, the target product is an organic molecule and each added molecule is a substituent on the organic molecule.

27. A multiplexed method for high throughput screening of synthesized compounds, comprising:

preparing a library of synthesized compounds comprising molecules or biological particles linked to a solid support matrix in combination with an optically-readable symbol, wherein the optically-readable symbol uniquely identifies each linked synthesized compound; and screening test compounds by contacting samples of test compounds with the library.

28. The method of claim 27, wherein the library is synthesized on the solid support matrix and during synthesis the identity of the synthesized compounds, or a component of the synthesized compound is written to memory.

29. The method of claim 27 wherein the library is a combinatorial library.

30. The method of claim 27, wherein the components of the library are molecules that are peptides, peptoids or organic molecules.

31. The method of claim 27, wherein the library is a phage display library.

32. In a non-radioactive energy transfer proximity assay, the improvement comprising adding a combination to the assay, the combination comprising:

a) an optically-readable symbol comprising a unique identifier;

b) a matrix comprising a matrix material selected from the group consisting of a solid continuous surface, wherein a first portion of the surface is for linking biological particles or molecules and a second portion of the surface is imprinted with the optically-readable symbol, and a plurality of particles for linking biological particles or molecules contained inside a microvessel, wherein an outer surface of the microvessel is imprinted with the optically-readable symbol;

c) at least one moiety linked to the first portion of the surface of the solid continuous surface or to the plurality of particles, the at least one moiety selected from a molecule, a biological particle, a mixture of molecules, a mixture of biological particles, or a mixture of molecules and biological particles, wherein the at least one moiety comprises at least one fluorescent moiety.

33. In a non-radioactive energy transfer proximity assay, the improvement comprising adding a combination to the assay, wherein the combination comprises:

a) a matrix material that forms a continuous surface, a first portion of the continuous surface adapted for use as a support matrix to which biological particles or molecules can be linked; and b) an optically-readable symbol imprinted on a second portion of the continuous surface, wherein the optically-readable comprises a unique identifier;

wherein at least one fluorescent moiety is linked to the first portion of the continuous surface.

34. In a scintillation proximity assay, the improvement comprising, including an optical memory as part of the matrix material, wherein the matrix material contains a scintillant.

35. In a scintillation proximity assay, the improvement comprising:

(a) adding a radiolabel to the matrix material in a combination comprising:

(i) an optically-readable symbol that comprises a unique identifier;

(ii) a matrix comprising a matrix material selected from the group consisting of a solid continuous surface, wherein a first portion of the surface is for linking biological particles or molecules and a second portion of the surface is imprinted with the optically-readable symbol, and a plurality of particles for linking biological particles or molecules contained inside a microvessel, wherein an outer surface of the microvessel is imprinted with the optically-readable symbol;

(iii) at least one moiety linked to the first portion of the surface of the solid continuous surface or to the plurality of particles, the at least one moiety selected from a molecule, a biological particle, a mixture of molecules, a mixture of biological particles, or a mixture of molecules and biological particles;

(b) coating the matrix with a ligand and recording an association between an identity of the ligand and the optically-readable symbol imprinted on the matrix;

(c) linking a receptor to a second matrix particle that contains a scintillant; and (d) reacting the receptor with the radio-labeled matrix, whereby light is produced.

36. In the scintillation proximity assay of claim 35, further comprising using a computer program to direct a sequence of steps (b) through (d).

37. In a scintillation proximity assay, the improvement comprising:

(a) adding a radiolabel to a matrix material in a combination comprising:

(i) a matrix material that forms a continuous surface, a first portion of the continuous surface adapted for use as a support matrix to which biological particles or molecules can be linked; and (ii) an optically-readable memory comprising a optically-readable symbol imprinted on a second portion of the continuous surface; wherein the optically-readable memory is readable by an optical detector;

(b) coating the matrix material with a receptor and recording an association between an identity of the receptor with data contained within the optically-readable memory imprinted on the matrix material;

(c) linking a ligand to a second matrix that contains a scintillant; and (d) reacting the ligand with the radio-labeled matrix, whereby light is produced.

38. In the scintillation proximity assay of claim 37, further comprising using a computer program to direct a sequence of steps (b) through (d).

39. In a scintillation proximity assay, the improvement comprising:
(a) adding a radiolabel to the matrix material in a combination comprising:
(i) a matrix material that forms a continuous surface, a first portion of the continuous surface adapted for use as a support matrix to which biological particles or molecules can be linked; and
(ii) an optically-readable memory comprising a optically-readable symbol imprinted on a second portion of the continuous surface; wherein the optically-readable memory is readable by an optical detector;
(b) coating the matrix material with a ligand and recording an association between an identity of the ligand with data contained within the optically-readable memory imprinted on the matrix material;
(c) linking a receptor to a second matrix that contains a scintillant; and
(d) reacting the receptor with the radio-labeled matrix, whereby light is produced.

40. In the scintillation proximity assay of claim 39, further comprising using a computer program to direct a sequence of steps (b) through (d).

41. The method of claim 1 wherein the matrix material comprises a plurality of matrix particles contained within a microvessel and the microvessel comprises a substantially rigid structure which is partially porous.

42. The method of claim 41, wherein the optically-readable symbol is imprinted on the microvessel.

43. The method of claim 42, wherein the optically-readable symbol is a two-dimensional bar code.

44. The method of claim 1, wherein the optically-readable symbol is a two-dimensional bar code.

* * * * *